(12) United States Patent
Gardner et al.

(10) Patent No.: US 8,603,800 B2
(45) Date of Patent: Dec. 10, 2013

(54) PRODUCTION OF ACETYL-COENZYME A DERIVED ISOPRENOIDS

(71) Applicant: Amyris, Inc., Emeryville, CA (US)

(72) Inventors: Timothy Stevens Gardner, Emeryville, CA (US); Kristy Michelle Hawkins, Emeryville, CA (US); Adam Leon Meadows, Emeryville, CA (US); Annie Ening Tsong, Emeryville, CA (US); Yoseph Tsegaye, Emeryville, CA (US)

(73) Assignee: AMYRIS, Inc., Emeryville, CA (US)

( * ) Notice: Subject to any disclaimer, the term of this patent is extended or adjusted under 35 U.S.C. 154(b) by 0 days.

(21) Appl. No.: 13/752,293

(22) Filed: Jan. 28, 2013

(65) Prior Publication Data

US 2013/0236942 A1 Sep. 12, 2013

Related U.S. Application Data

(63) Continuation of application No. 13/673,819, filed on Nov. 9, 2012, now Pat. No. 8,415,136.

(60) Provisional application No. 61/557,893, filed on Nov. 9, 2011.

(51) Int. Cl.
*C12N 1/19* (2006.01)
*C12P 1/00* (2006.01)

(52) U.S. Cl.
USPC .................................. 435/254.2; 435/41

(58) Field of Classification Search
None
See application file for complete search history.

(56) References Cited

U.S. PATENT DOCUMENTS

| 7,253,001 B2 | 8/2007 | Wahlbom et al. |
| 7,659,097 B2 | 2/2010 | Renninger et al. |
| 7,785,858 B2 | 8/2010 | Kozlov et al. |
| 8,012,722 B2 | 9/2011 | Chinen et al. |
| 2010/0248233 A1 | 9/2010 | Müller et al. |
| 2011/0275130 A1* | 11/2011 | Pronk et al. ............... 435/165 |
| 2011/0287476 A1 | 11/2011 | Renninger et al. |

FOREIGN PATENT DOCUMENTS

| WO | WO 2009/005704 A1 | 1/2009 |
| WO | WO 2010/141452 A1 | 12/2010 |
| WO | WO 2011/159853 A1 | 12/2011 |
| WO | WO 2013/020118 A1 | 2/2013 |

OTHER PUBLICATIONS

International Seach Report and Written Opinion, in PCT/US2012/064532, mailed Mar. 5, 2013, 11 pages.
Chandran et al., "Microbial production of isoprenoids", XP028254556, *Process Biochemistry* (2011) 46:1703-1710.
Ma et al., "Optimization of a heterologous mevalonate pathway through the use of variant HMG-CoA reductases", XP028274826, *Metabolic Engineering* (2011) 3:588-597.
Martin et al., "Engineering a mevalonate pathway in *Escherichia coli* for production of terpenoids", XP002420804, *Nature Biotechnology* (2003) 21:796-802.
Pitera et al., "Balancing a heterologous mevalonate pathway for improved isoprenoid production in *Escherichia coli*", XP005888126, *Metabolic Engineering* (2007) 9:193-207.
Chinen, et al., Innovative metabolic pathway design for efficient L-glutamate production by suppressing $CO_2$ emission. *J Biosci Bioeng.* (2007) 103(3):262-269.
Hedl, et al., Class II 3-hydroxy-3-methylglutaryl coenzyme A reductases. *J. Bacteriol.* (2004) 186(7):1927-1932.
Lan, et al., ATP drives direct photosynthetic production of 1-butanol in cyanobacteria. *Proc Natl Acad Sci USA*. (2012) 109(16):6018-6023.
Matsumoto, et al., A new pathway for poly(3-hydroxybutyrate) production in *Escherichia coli* and *Corynebacterium glutamicum* by functional expression of a new acetoacetyl-coenzyme A synthase. *Biosci Biotechnol Biochem.* (2011) 75(2):364-366.
Okamura, et al., Unprecedented acetoacetyl-coenzyme A synthesizing enzyme of the thiolase superfamily involved in the mevalonate pathway. *Proc Natl Aced Sci USA*. (2010) 107(25):11265-11270.
Sonderegger, et al., Metabolic engineering of a phosphoketolase pathway for pentose catabolism in *Saccharomyces cerevisiae*. *Appl Environ Microbiol.* (2004) 70(5):2892-2897.

* cited by examiner

*Primary Examiner* — Suzanne M Noakes
*Assistant Examiner* — Jae W Lee
(74) *Attorney, Agent, or Firm* — Squire Sanders (US) LLP

(57) ABSTRACT

Provided herein are compositions and methods for the heterologous production of acetyl-CoA-derived isoprenoids in a host cell. In some embodiments, the host cell is genetically modified to comprise a heterologous nucleotide sequence encoding an acetaldehyde dehydrogenase, acetylating (ADA, E.C. 1.2.1.10) and an MEV pathway comprising an NADH-using HMG-CoA reductase. In some embodiments, the host cell is genetically modified to comprise a heterologous nucleotide sequence encoding an ADA and an MEV pathway comprising an acetoacetyl-CoA synthase. In some embodiments, the genetically modified host cell further comprises one or more heterologous nucleotide sequences encoding a phosphoketolase and a phosphotransacetylase. In some embodiments, the genetically modified host cell further comprises a functional disruption of the native PDH-bypass. The compositions and methods described herein provide an energy-efficient yet redox balanced route for the heterologous production of acetyl-CoA-derived isoprenoids.

30 Claims, 14 Drawing Sheets

SEQUENCE LISTING

```
<160> NUMBER OF SEQ ID NOS: 54

<210> SEQ ID NO 1
<211> LENGTH: 1380
<212> TYPE: DNA
<213> ORGANISM: Dickeya zeae
<220> FEATURE:
<221> NAME/KEY: misc_feature
<222> LOCATION: (1)..(1380)
<223> OTHER INFORMATION: Dickeya zeae eutE gene sequence

<400> SEQUENCE: 1
atggagcatt cagttatcga accgacagtg cccatgccgc tgccagccat gtttgacgcg      60
ccatctggaa tcttttctag cctggacgat gcagtccagg cggcaaccct ggcacaacaa     120
cagttgtcgt ctgtggagtt acgccagcaa gttattaaag caattagagt tgcaggcgaa     180
cgctatgcac aggttctggc ggaaatggcg gtggctgaaa caggtatggg tcgggtagtg     240
gataaataca ttaaaaatgt ttcacaggct cgccatacac ccggcattga atgtctgagc     300
gcggaagttc tgacaggcga caatggcctg acactgattg aaaatgcccc ttggggagtg     360
gtggcttccg tgacgccaag cacgaaccca gccgccacag tcatcaataa tgcaatttcc     420
atgattgcgg cagggaattc agtcgttttt gcaccgcacc catccgccaa aaatgtgtcc     480
ttacgcacaa tatcgcttct taacaaagca attgtggcga caggtgggcc agaaaatctg     540
ctggtatccg tcgcaaatcc caacatcgaa acagctcaac gcctgttccg ttatccaggt     600
attggattac tcgtcgtaac aggtggtgag gcggtggtgg aagcggcgcg caaacacact     660
```

```
gataaacgtt taattgccgc aggcgccgga aaccccccag tagtcgttga cgaaacagcg      720
gatataccga aagccgctcg cgcaatagta aagggcgctt cgtttgacaa caatattatt      780
tgtgccgacg agaaagtatt aatcgtggtt gatcgcgtag ccgacgcctt attagccgaa      840
atgcaacgca acaatgctgt tttactgacg cctgaacaga cagaacgact tctgcccgct      900
ttgctgagcg atatagatga gcaggggaag ggacgcgtga accgcgatta tgtggggagg      960
gatgccgcta aactagcggc ggccattggt ttagaagtgt cagaacacac aagattatta     1020
cttgctgaaa cagatgctga tcatcctttt gcagtaaccg aattaatgat gcccgtattg     1080
cctgttatcc gtgtaaaaaa cgttgatgac gccattgccc tcgctgtaaa acttgagagt     1140
ggttgtcgtc acactgcagc aatgcattcg acaaacatta ggaacctgaa tcggatggca     1200
aatgctataa atacatcaat ttttgttaaa aatggtccgt gtatcgctgg gctgggcctg     1260
ggtggcgagg gctggacgtc gatgactata tctacaccca caggggaagg agttacctca     1320
gcacgcacct tcgtacgttt acgtagatgt gtattggttg acatgttcag aatcgcgtaa     1380
```

<210> SEQ ID NO 2
<211> LENGTH: 459
<212> TYPE: PRT
<213> ORGANISM: Dickeya zeae
<220> FEATURE:
<221> NAME/KEY: misc_feature
<222> LOCATION: (1)..(459)
<223> OTHER INFORMATION: Dickeya zeae eutE protein sequence

<400> SEQUENCE: 2

```
Met Glu His Ser Val Ile Glu Pro Thr Val Pro Met Pro Leu Pro Ala
1               5                   10                  15

Met Phe Asp Ala Pro Ser Gly Ile Phe Ser Ser Leu Asp Asp Ala Val
            20                  25                  30

Gln Ala Ala Thr Leu Ala Gln Gln Leu Ser Ser Val Glu Leu Arg
        35                  40                  45

Gln Gln Val Ile Lys Ala Ile Arg Val Ala Gly Glu Arg Tyr Ala Gln
    50                  55                  60

Val Leu Ala Glu Met Ala Val Ala Glu Thr Gly Met Gly Arg Val Val
65                  70                  75                  80

Asp Lys Tyr Ile Lys Asn Val Ser Gln Ala Arg His Thr Pro Gly Ile
                85                  90                  95

Glu Cys Leu Ser Ala Glu Val Leu Thr Gly Asp Asn Gly Leu Thr Leu
            100                 105                 110

Ile Glu Asn Ala Pro Trp Gly Val Val Ala Ser Val Thr Pro Ser Thr
        115                 120                 125

Asn Pro Ala Ala Thr Val Ile Asn Asn Ala Ile Ser Met Ile Ala Ala
    130                 135                 140

Gly Asn Ser Val Val Phe Ala Pro His Pro Ser Ala Lys Asn Val Ser
145                 150                 155                 160

Leu Arg Thr Ile Ser Leu Leu Asn Lys Ala Ile Val Ala Thr Gly Gly
                165                 170                 175

Pro Glu Asn Leu Leu Val Ser Val Ala Asn Pro Asn Ile Glu Thr Ala
            180                 185                 190

Gln Arg Leu Phe Arg Tyr Pro Gly Ile Gly Leu Leu Val Val Thr Gly
        195                 200                 205

Gly Glu Ala Val Val Glu Ala Ala Arg Lys His Thr Asp Lys Arg Leu
    210                 215                 220

Ile Ala Ala Gly Ala Gly Asn Pro Pro Val Val Val Asp Glu Thr Ala
```

```
                       225                 230                 235                 240
Asp Ile Pro Lys Ala Ala Arg Ala Ile Val Lys Gly Ala Ser Phe Asp
                    245                 250                 255

Asn Asn Ile Ile Cys Ala Asp Glu Lys Val Leu Ile Val Val Asp Arg
                260                 265                 270

Val Ala Asp Ala Leu Leu Ala Glu Met Gln Arg Asn Asn Ala Val Leu
            275                 280                 285

Leu Thr Pro Glu Gln Thr Glu Arg Leu Leu Pro Ala Leu Leu Ser Asp
        290                 295                 300

Ile Asp Glu Gln Gly Lys Gly Arg Val Asn Arg Asp Tyr Val Gly Arg
305                 310                 315                 320

Asp Ala Ala Lys Leu Ala Ala Ile Gly Leu Glu Val Ser Glu His
                325                 330                 335

Thr Arg Leu Leu Leu Ala Glu Thr Asp Ala Asp His Pro Phe Ala Val
                340                 345                 350

Thr Glu Leu Met Met Pro Val Leu Pro Val Ile Arg Val Lys Asn Val
            355                 360                 365

Asp Asp Ala Ile Ala Leu Ala Val Lys Leu Glu Ser Gly Cys Arg His
        370                 375                 380

Thr Ala Ala Met His Ser Thr Asn Ile Arg Asn Leu Asn Arg Met Ala
385                 390                 395                 400

Asn Ala Ile Asn Thr Ser Ile Phe Val Lys Asn Gly Pro Cys Ile Ala
                405                 410                 415

Gly Leu Gly Leu Gly Gly Glu Gly Trp Thr Ser Met Thr Ile Ser Thr
            420                 425                 430

Pro Thr Gly Glu Gly Val Thr Ser Ala Arg Thr Phe Val Arg Leu Arg
        435                 440                 445

Arg Cys Val Leu Val Asp Met Phe Arg Ile Ala
    450                 455

<210> SEQ ID NO 3
<211> LENGTH: 2728
<212> TYPE: DNA
<213> ORGANISM: Saccharomyces cerevisiae
<220> FEATURE:
<221> NAME/KEY: misc_feature
<222> LOCATION: (1)..(2728)
<223> OTHER INFORMATION: Saccharomyces cerevisiae ACS1 nucleotide
      sequence

<400> SEQUENCE: 3
acctcccgcg acctccaaaa tcgaactacc ttcacaatgt cgccctctgc cgtacaatca      60
tcaaaactag aagaacagtc aagtgaaatt gacaagttga agcaaaaat gtcccagtct     120 gcctccactg cgcagcagaa gaaggaacat gagtatgaac atttgaccct ggtcaagatc     180
gtgccacaac ggcccatctc agatagactg cagcccgcaa ttgctaccca ctattctcca     240
cacttggacg ggttgcagga ctatcagcgc ttgcacaagg agtctattga agaccctgct     300
aagttcttcg gttctaaagc tacccaattt ttaaactggt ctaagccatt cgataaggtg     360
ttcatcccag actctaaaac gggtaggccc tccttccaga acaatgcatg gttcctcaac     420
ggccaattaa acgcctgtta caactgtgtt gacagacatg ccttgaagac ccctaacaag     480
aaagccatta ttttcgaagg tgacgagcct ggccaaggct attccattac ctacaaggaa     540
ctacttgaag aagtttgtca gtggcacaa gtgctgactt actctatggg cgttcgcaag     600
ggcgatactt tgccgtgta catgcctatg gtcccagaag caatcataac cttgttggcc     660
atttcccgta tcggcgccat tcactccgta gtctttgccg gtttttcttc caactccttg     720
```

```
agagatcgta tcaacgatgg ggactctaaa gttgtcatca ctacagatga atccaacaga    780
ggtggtaaag tcattgagac taaaagaatt gttgatgacg cgctaagaga accccaggc    840
gtgagacacg tcttggttta tagaaagacc aacaatccat ctgttgcttt ccatgccccc    900
agagatttag attgggcaac agaaaagaag aaatacaaga cctactatcc atgcacaccc    960
gttgattctg aggatccatt attcttgttg tatacgtctg gttctactgg tgccccaag   1020
ggtgttcaac attctaccgc aggttacttg ctgggagctt gttgaccat gcgctacact   1080
tttgacactc accaagaaga cgttttcttc acagctggag acattggctg gattacaggc   1140
cacacttatg tggtttatgg tcccttacta tatggttgtg ccactttggt ctttgaaggg   1200
actcctgcgt acccaaatta ctcccgttat tgggatatta ttgatgaaca caaagtcacc   1260
caatttatg ttgccccaac tgctttgcgt ttgttgaaaa gagctggtga ttcctacatc   1320
gaaaatcatt ccttaaaatc tttgcgttgc ttgggttcgg tcggtgaacc aattgctgct   1380
gaagtttggg agtggtactc tgaaaaaata ggtaaaaatg aaatcccat gtagacacc   1440
tactggcaaa cagaatctgg ttcgcatctg tcaccccgc tggctggtgg tgtcacacca   1500
atgaaaccgg ttctgcctc attccccttc ttcggtattg atgcagttgt tcttgaccct   1560
aacactggtg aagaacttaa taccagccac gcagagggtg tccttgccgt caaagctgca   1620
tggccatcat ttgcaagaac tatttggaaa atcatgata ggtatctaga cacttatttg   1680
aacccttacc ctggctacta tttcactggt gatggtgctg caaggataa ggatggttat   1740
atctggattt tgggtcgtgt agacgatgtg gtgaacgtct ctggtcaccg tctgtctacc   1800
gctgaaattg aggctgctat tatcgaagat ccaattgtgg ccgagtgtgc tgttgtcgga   1860
ttcaacgatg acttgactgg tcaagcagtt gctgcatttg tggtgttgaa aaacaaatct   1920
aattggtcca ccgcaacaga tgatgaatta caagatatca agaagcattt ggtctttact   1980
gttagaaaag acatcgggcc atttgccgca ccaaaattga tcattttagt ggatgacttg   2040
cccaagacaa gatctggcaa aattatgaga cgtatttaa gaaaaatcct agcaggagaa   2100
agtgaccaac taggcgacgt ttctacattg tcaaaccctg gcattgttag acatctaatt   2160
gattcggtca agttgtaatg atgatttctt tcctttttat attgacgact tttttttttt   2220
cgtgtgtttt tgttctctta taaccgagct gcttacttat tattatttca ccttctcttt   2280
ttatttatac ttataattat ttattcttta catactgtta caagaaactc ttttctacat   2340
taattgcata aagtgtcaat cagcacatcc tctatatcgc tatcaacaac aaatttgaca   2400
aacctgccta tcttcagg aacaactgcc gcatcgctac caccactact tgtgaagtcc   2460
ctggagttta atatgcactg aaatttacct agccgtttta cacaagacca taatccatcc   2520
atgctatcgc agtatatgat tttgtgttcg ttttcgtct tgcgaaaggc atcctcaatg   2580
gcttgtttca ttgatccatc agtgtggctc gtaggtacca gcaaaaccac ttcatcagcg   2640
gcgtactcct cccactttat gggcagtcct tgtatcgact tgctcattat aatacatttg   2700
ctctatcccc gcgtgcttgg ccggccgt                                     2728
```

<210> SEQ ID NO 4
<211> LENGTH: 713
<212> TYPE: PRT
<213> ORGANISM: Saccharomyces cerevisiae
<220> FEATURE:
<221> NAME/KEY: misc_feature
<222> LOCATION: (1)..(713)
<223> OTHER INFORMATION: Saccharomyces cerevisiae ACS1 protein sequence

<400> SEQUENCE: 4

-continued

```
Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ser Thr Ala
                20                  25                  30

Gln Gln Lys Lys Glu His Glu Tyr Glu His Leu Thr Ser Val Lys Ile
            35                  40                  45

Val Pro Gln Arg Pro Ile Ser Asp Arg Leu Gln Pro Ala Ile Ala Thr
50                  55                  60

His Tyr Ser Pro His Leu Asp Gly Leu Gln Asp Tyr Gln Arg Leu His
65                  70                  75                  80

Lys Glu Ser Ile Glu Asp Pro Ala Lys Phe Phe Gly Ser Lys Ala Thr
                85                  90                  95

Gln Phe Leu Asn Trp Ser Lys Pro Phe Asp Lys Val Phe Ile Pro Asp
                100                 105                 110

Ser Lys Thr Gly Arg Pro Ser Phe Gln Asn Asn Ala Trp Phe Leu Asn
            115                 120                 125

Gly Gln Leu Asn Ala Cys Tyr Asn Cys Val Asp Arg His Ala Leu Lys
        130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
```

```
                420                 425                 430
Leu Lys Ser Leu Arg Cys Leu Gly Ser Val Gly Glu Pro Ile Ala Ala
            435                 440                 445
Glu Val Trp Glu Trp Tyr Ser Glu Lys Ile Gly Lys Asn Glu Ile Pro
        450                 455                 460
Ile Val Asp Thr Tyr Trp Gln Thr Glu Ser Gly Ser His Leu Val Thr
465                 470                 475                 480
Pro Leu Ala Gly Gly Val Thr Pro Met Lys Pro Gly Ser Ala Ser Phe
                485                 490                 495
Pro Phe Phe Gly Ile Asp Ala Val Val Leu Asp Pro Asn Thr Gly Glu
            500                 505                 510
Glu Leu Asn Thr Ser His Ala Glu Gly Val Leu Ala Val Lys Ala Ala
        515                 520                 525
Trp Pro Ser Phe Ala Arg Thr Ile Trp Lys Asn His Asp Arg Tyr Leu
            530                 535                 540
Asp Thr Tyr Leu Asn Pro Tyr Pro Gly Tyr Tyr Phe Thr Gly Asp Gly
545                 550                 555                 560
Ala Ala Lys Asp Lys Asp Gly Tyr Ile Trp Ile Leu Gly Arg Val Asp
                565                 570                 575
Asp Val Val Asn Val Ser Gly His Arg Leu Ser Thr Ala Glu Ile Glu
            580                 585                 590
Ala Ala Ile Ile Glu Asp Pro Ile Val Ala Glu Cys Ala Val Val Gly
        595                 600                 605
Phe Asn Asp Asp Leu Thr Gly Gln Ala Val Ala Ala Phe Val Val Leu
            610                 615                 620
Lys Asn Lys Ser Asn Trp Ser Thr Ala Thr Asp Asp Glu Leu Gln Asp
625                 630                 635                 640
Ile Lys Lys His Leu Val Phe Thr Val Arg Lys Asp Ile Gly Pro Phe
                645                 650                 655
Ala Ala Pro Lys Leu Ile Ile Leu Val Asp Asp Leu Pro Lys Thr Arg
            660                 665                 670
Ser Gly Lys Ile Met Arg Arg Ile Leu Arg Lys Ile Leu Ala Gly Glu
        675                 680                 685
Ser Asp Gln Leu Gly Asp Val Ser Thr Leu Ser Asn Pro Gly Ile Val
690                 695                 700
Arg His Leu Ile Asp Ser Val Lys Leu
705                 710

<210> SEQ ID NO 5
<211> LENGTH: 2287
<212> TYPE: DNA
<213> ORGANISM: Saccharomyces cerevisiae
<220> FEATURE:
<221> NAME/KEY: misc_feature
<222> LOCATION: (1)..(2287)
<223> OTHER INFORMATION: Saccharomyces cerevisiae ACS2 nucleotide
      sequence

<400> SEQUENCE: 5
acctcccgcg acctccaaaa tcgaactacc ttcacaatga caatcaagga acataaagta      60
gtttatgaag ctcacaacgt aaaggctctt aaggctcctc aacattttta caacagccaa     120
cccggcaagg gttacgttac tgatatgcaa cattatcaag aaatgtatca acaatctatc     180
aatgagccag aaaaattctt tgataagatg gctaaggaat acttgcattg ggatgctcca     240
tacaccaaag ttcaatctgg ttcattgaac aatggtgatg ttgcatggtt tttgaacggt     300
aaattgaatg catcatacaa ttgtgttgac agacatgcct ttgctaatcc cgacaagcca     360
```

```
gctttgatct atgaagctga tgacgaatcc gacaacaaaa tcatcacatt tggtgaatta    420
ctcagaaaag tttcccaaat cgctggtgtc ttaaaaagct ggggcgttaa gaaaggtgac    480
acagtggcta tctatttgcc aatgattcca gaagcggtca ttgctatgtt ggctgtggct    540
cgtattggtg ctattcactc tgttgtcttt gctgggttct ccgctggttc gttgaaagat    600
cgtgtcgttg acgctaattc taaagtggtc atcacttgtg atgaaggtaa agaggtggt     660 aagaccatca acactaaaaa aattgttgac gaaggtttga cggagtcga tttggtttcc    720 cgtatcttgg ttttccaaag aactggtact gaaggtattc caatgaaggc cggtagagat    780
tactggtggc atgaggaggc cgctaagcag agaacttacc tacctcctgt tcatgtgac    840 gctgaagatc tctatttttt attatacact tccggttcca ctggttctcc aaagggtgtc    900
gttcacacta caggtggtta tttattaggt gccgctttaa caactagata cgttttgat     960 attcacccag aagatgttct cttcactgcc ggtgacgtcg gctggatcac gggtcacacc   1020
tatgctctat atggtccatt aaccttgggt accgcctcaa taattttcga atccactcct   1080
gcctacccag attatggtag atattggaga attatccaac gtcacaaggc tacccatttc   1140
tatgtggctc caactgcttt aagattaatc aaacgtgtat gtgaagccga aattgccaaa   1200
tatgacactt cctcattacg tgtcttgggt tccgtcggtg aaccaatctc tccagactta   1260
tgggaatggt atcatgaaaa agtgggtaac aaaaactgtg tcatttgtga cactatgtgg   1320
caaacagagt ctggttctca tttaattgct cctttggcag gtgctgtccc aacaaaacct   1380
ggttctgcta ccgtgccatt ctttggtatt aacgcttgta tcattgaccc tgttacaggt   1440
gtggaattag aaggtaatga tgtcgaaggt gtccttgccg ttaaatcacc atggccatca   1500
atggctagat ctgtttggaa ccaccacgac cgttacatgg atacttactt gaaaccttat   1560
cctggtcact atttcacagg tgatggtgct ggtagagatc atgatggtta ctactggatc   1620 agggggtagag ttgacgacgt tgtaaatgtt tccggtcata gattatccac atcagaaatt   1680
gaagcatcta tctcaaatca cgaaaacgtc tcggaagctg ctgttgtcgg tattccagat   1740
gaattgaccg tcaaaccgt cgttgcatat gtttccctaa agatggtta tctacaaaac    1800 aacgctactg aaggtgatgc agaacacatc acaccagata atttacgtag agaattgatc   1860
ttacaagtta ggggtgagat tggtccttc gcctcaccaa aaaccattat tctagttaga   1920
gatctaccaa gaacaaggtc aggaaagatt atgagaagag ttctaagaaa ggttgcttct   1980
aacgaagccg aacagctagg tgacctaact actttggcca acccagaagt tgtacctgcc   2040
atcatttctg ctgtagagaa ccaatttttc tctcaaaaaa agaaataact taaatgagaa   2100
aaatttcgta atgagataaa atttcgctcc ttttctgttt tctattttct attttcccaa   2160
cttttgctct attcagttat aaattactat ttatccatca gttaaaaaac aagatctttt   2220
actggtcagc taggaaagcg aaaatacaaa gactttatgc actatccccg cgtgcttggc   2280
cggccgt                                                            2287
```

<210> SEQ ID NO 6
<211> LENGTH: 683
<212> TYPE: PRT
<213> ORGANISM: Saccharomyces cerevisiae
<220> FEATURE:
<221> NAME/KEY: misc_feature
<222> LOCATION: (1)..(683)
<223> OTHER INFORMATION: Saccharomyces cerevisiae ACS2 protein sequence

<400> SEQUENCE: 6

Met Thr Ile Lys Glu His Lys Val Val Tyr Glu Ala His Asn Val Lys

-continued

```
1               5                   10                  15
Ala Leu Lys Ala Pro Gln His Phe Tyr Asn Ser Gln Pro Gly Lys Gly
                20                  25                  30

Tyr Val Thr Asp Met Gln His Tyr Gln Glu Met Tyr Gln Gln Ser Ile
                35                  40                  45

Asn Glu Pro Glu Lys Phe Phe Asp Lys Met Ala Lys Glu Tyr Leu His
    50                  55                  60

Trp Asp Ala Pro Tyr Thr Lys Val Gln Ser Gly Ser Leu Asn Asn Gly
65                  70                  75                  80

Asp Val Ala Trp Phe Leu Asn Gly Lys Leu Asn Ala Ser Tyr Asn Cys
                85                  90                  95

Val Asp Arg His Ala Phe Ala Asn Pro Asp Lys Pro Ala Leu Ile Tyr
                100                 105                 110

Glu Ala Asp Asp Glu Ser Asp Asn Lys Ile Ile Thr Phe Gly Glu Leu
                115                 120                 125

Leu Arg Lys Val Ser Gln Ile Ala Gly Val Leu Lys Ser Trp Gly Val
                130                 135                 140

Lys Lys Gly Asp Thr Val Ala Ile Tyr Leu Pro Met Ile Pro Glu Ala
145                 150                 155                 160

Val Ile Ala Met Leu Ala Val Ala Arg Ile Gly Ala Ile His Ser Val
                165                 170                 175

Val Phe Ala Gly Phe Ser Ala Gly Ser Leu Lys Asp Arg Val Val Asp
                180                 185                 190

Ala Asn Ser Lys Val Val Ile Thr Cys Asp Glu Gly Lys Arg Gly Gly
                195                 200                 205

Lys Thr Ile Asn Thr Lys Lys Ile Val Asp Glu Gly Leu Asn Gly Val
                210                 215                 220

Asp Leu Val Ser Arg Ile Leu Val Phe Gln Arg Thr Gly Thr Glu Gly
225                 230                 235                 240

Ile Pro Met Lys Ala Gly Arg Asp Tyr Trp Trp His Glu Glu Ala Ala
                245                 250                 255

Lys Gln Arg Thr Tyr Leu Pro Pro Val Ser Cys Asp Ala Glu Asp Pro
                260                 265                 270

Leu Phe Leu Leu Tyr Thr Ser Gly Ser Thr Gly Ser Pro Lys Gly Val
                275                 280                 285

Val His Thr Thr Gly Gly Tyr Leu Leu Gly Ala Ala Leu Thr Thr Arg
                290                 295                 300

Tyr Val Phe Asp Ile His Pro Glu Asp Val Leu Phe Thr Ala Gly Asp
305                 310                 315                 320

Val Gly Trp Ile Thr Gly His Thr Tyr Ala Leu Tyr Gly Pro Leu Thr
                325                 330                 335

Leu Gly Thr Ala Ser Ile Ile Phe Glu Ser Thr Pro Ala Tyr Pro Asp
                340                 345                 350

Tyr Gly Arg Tyr Trp Arg Ile Ile Gln Arg His Lys Ala Thr His Phe
                355                 360                 365

Tyr Val Ala Pro Thr Ala Leu Arg Leu Ile Lys Arg Val Gly Glu Ala
                370                 375                 380

Glu Ile Ala Lys Tyr Asp Thr Ser Ser Leu Arg Val Leu Gly Ser Val
385                 390                 395                 400

Gly Glu Pro Ile Ser Pro Asp Leu Trp Glu Trp Tyr His Glu Lys Val
                405                 410                 415

Gly Asn Lys Asn Cys Val Ile Cys Asp Thr Met Trp Gln Thr Glu Ser
                420                 425                 430
```

Gly Ser His Leu Ile Ala Pro Leu Ala Gly Ala Val Pro Thr Lys Pro
        435                 440                 445

Gly Ser Ala Thr Val Pro Phe Phe Gly Ile Asn Ala Cys Ile Ile Asp
    450                 455                 460

Pro Val Thr Gly Val Glu Leu Glu Gly Asn Asp Val Glu Gly Val Leu
465                 470                 475                 480

Ala Val Lys Ser Pro Trp Pro Ser Met Ala Arg Ser Val Trp Asn His
            485                 490                 495

His Asp Arg Tyr Met Asp Thr Tyr Leu Lys Pro Tyr Pro Gly His Tyr
        500                 505                 510

Phe Thr Gly Asp Gly Ala Gly Arg Asp His Asp Gly Tyr Tyr Trp Ile
        515                 520                 525

Arg Gly Arg Val Asp Asp Val Val Asn Val Ser Gly His Arg Leu Ser
    530                 535                 540

Thr Ser Glu Ile Glu Ala Ser Ile Ser Asn His Glu Asn Val Ser Glu
545                 550                 555                 560

Ala Ala Val Val Gly Ile Pro Asp Glu Leu Thr Gly Gln Thr Val Val
            565                 570                 575

Ala Tyr Val Ser Leu Lys Asp Gly Tyr Leu Gln Asn Asn Ala Thr Glu
        580                 585                 590

Gly Asp Ala Glu His Ile Thr Pro Asp Asn Leu Arg Arg Glu Leu Ile
        595                 600                 605

Leu Gln Val Arg Gly Glu Ile Gly Pro Phe Ala Ser Pro Lys Thr Ile
    610                 615                 620

Ile Leu Val Arg Asp Leu Pro Arg Thr Arg Ser Gly Lys Ile Met Arg
625                 630                 635                 640

Arg Val Leu Arg Lys Val Ala Ser Asn Glu Ala Glu Gln Leu Gly Asp
            645                 650                 655

Leu Thr Thr Leu Ala Asn Pro Glu Val Val Pro Ala Ile Ile Ser Ala
        660                 665                 670

Val Glu Asn Gln Phe Phe Ser Gln Lys Lys Lys
        675                 680

<210> SEQ ID NO 7
<211> LENGTH: 1798
<212> TYPE: DNA
<213> ORGANISM: Saccharomyces cerevisiae
<220> FEATURE:
<221> NAME/KEY: misc_feature
<222> LOCATION: (1)..(1798)
<223> OTHER INFORMATION: Saccharomyces cerevisiae ALD4 nucleotide
      sequence

<400> SEQUENCE: 7
gcacccaggg acacacagca gcgaagtatt ttcagaatgt tcagtagatc tacgctctgc      60
ttaaagacgt ctgcatcctc cattgggaga cttcaattga gatatttctc acaccttcct    120
atgacagtgc ctatcaagct gcccaatggg ttggaatatg agcaaccaac ggggttgttc    180
atcaacaaca agtttgttcc ttctaaacag aacaagacct tcgaagtcat taacccttcc    240
acggaagaag aaatatgtca tatttatgaa ggtagagagg acgatgtgga agaggccgtg    300
caggccgccg accgtgcctt ctctaatggg tcttggaacg gtatcgaccc tattgacagg    360
ggtaaggctt tgtacaggtt agccgaatta attgaacagg acaaggatgt cattgcttcc    420
atcgagactt tggataacgg taaagctatc tcttcctcga gaggagatgt tgatttagtc    480
atcaactatt tgaaatcttc tgctggcttt gctgataaaa ttgatggtag aatgattgat    540
actggtagaa cccatttttc ttacactaag agacagcctt gggtgtttg tgggcagatt    600

-continued

```
attccttgga atttcccact gttgatgtgg gcctggaaga ttgcccctgc tttggtcacc    660
ggtaacaccg tcgtgttgaa gactgccgaa tccacccat tgtccgcttt gtatgtgtct    720
aaatacatcc cacaggcggg tattccacct ggtgtgatca acattgtatc cgggtttggt    780
aagattgtgg gtgaggccat tacaaaccat ccaaaaatca aaaggttgc cttcacaggg     840 tccacggcta cgggtagaca catttaccag tccgcagccg caggcttgaa aaaagtgact    900
ttggagctgg gtggtaaatc accaaacatt gtcttcgcgg acgccgagtt gaaaaaagcc    960
gtgcaaaaca ttatccttgg tatctactac aattctggtg aggtctgttg tgcgggttca   1020
agggtgtatg ttgaagaatc tatttacgac aaattcattg aagagttcaa agccgcttct   1080
gaatccatca aggtgggcga cccattcgat gaatctactt ccaaggtgc acaaacctct    1140 caaatgcaac taaacaaaat cttgaaatac gttgacattg taagaatga aggtgctact    1200 ttgattaccg gtggtgaaag attaggtagc aagggttact tcattaagcc aactgtcttt   1260
ggtgacgtta aggaagacat gagaattgtc aaagaggaaa tctttggccc tgttgtcact   1320
gtaaccaaat tcaaatctgc cgacgaagtc attaacatgg cgaacgattc tgaatacggg   1380
ttggctgctg gtattcacac ctctaatatt aataccgcct aaaagtggc tgatagagtt    1440 aatgcgggta cggtctggat aaacacttat aacgatttcc accacgcagt tcctttcggt   1500
gggttcaatg catctggttt gggcagggaa atgtctgttg atgctttaca aaactacttg   1560
caagttaaag cggtccgtgc caaattggac gagtaaggtc atcaataagc tggtgtcca    1620 atcgatgctt acatacataa aattaaatat tctgtctctg ttatatttcc acatgtcatc   1680
atttcaaata tatgtacttt aaagaaaata aaataaaaaa taaaattttt ttctcccgat   1740
aatcaatttt cttaattaat taattgcgtt acgaaacgcg atcgccgacg ccgccgat    1798
```

<210> SEQ ID NO 8
<211> LENGTH: 519
<212> TYPE: PRT
<213> ORGANISM: Saccharomyces cerevisiae
<220> FEATURE:
<221> NAME/KEY: misc_feature
<222> LOCATION: (1)..(519)
<223> OTHER INFORMATION: Saccharomyces cerevisiae ALD4 protein sequence

<400> SEQUENCE: 8

```
Met Phe Ser Arg Ser Thr Leu Cys Leu Lys Thr Ser Ala Ser Ser Ile
1               5                  10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140
```

```
Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
            165                 170                 175

Thr Lys Arg Gln Pro Leu Gly Val Cys Gly Gln Ile Ile Pro Trp Asn
        180                 185                 190

Phe Pro Leu Leu Met Trp Ala Trp Lys Ile Ala Pro Ala Leu Val Thr
    195                 200                 205

Gly Asn Thr Val Val Leu Lys Thr Ala Glu Ser Thr Pro Leu Ser Ala
210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
            245                 250                 255

Asn His Pro Lys Ile Lys Lys Val Ala Phe Thr Gly Ser Thr Ala Thr
        260                 265                 270

Gly Arg His Ile Tyr Gln Ser Ala Ala Ala Gly Leu Lys Lys Val Thr
    275                 280                 285

Leu Glu Leu Gly Gly Lys Ser Pro Asn Ile Val Phe Ala Asp Ala Glu
290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
            325                 330                 335

Tyr Asp Lys Phe Ile Glu Glu Phe Lys Ala Ala Ser Glu Ser Ile Lys
        340                 345                 350

Val Gly Asp Pro Phe Asp Glu Ser Thr Phe Gln Gly Ala Gln Thr Ser
    355                 360                 365

Gln Met Gln Leu Asn Lys Ile Leu Lys Tyr Val Asp Ile Gly Lys Asn
370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
            405                 410                 415

Ile Val Lys Glu Glu Ile Phe Gly Pro Val Val Thr Val Thr Lys Phe
        420                 425                 430

Lys Ser Ala Asp Glu Val Ile Asn Met Ala Asn Asp Ser Glu Tyr Gly
    435                 440                 445

Leu Ala Ala Gly Ile His Thr Ser Asn Ile Asn Thr Ala Leu Lys Val
450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
            485                 490                 495

Arg Glu Met Ser Val Asp Ala Leu Gln Asn Tyr Leu Gln Val Lys Ala
        500                 505                 510

Val Arg Ala Lys Leu Asp Glu
    515
```

<210> SEQ ID NO 9
<211> LENGTH: 2744
<212> TYPE: DNA
<213> ORGANISM: Saccharomyces cerevisiae
<220> FEATURE:
<221> NAME/KEY: misc_feature
<222> LOCATION: (1)..(2744)

<223> OTHER INFORMATION: Saccharomyces cerevisiae cytosolic aldehyde dehydrogenase 6 (ALD6) nucleotide sequence

<400> SEQUENCE: 9

```
catatggcgt atccaagccg aaaccctttg cctcatcccc acggaataag gcagccgaca      60
aaagaaaaac gaccgaaaag gaaccagaaa gaaaaaagag ggtgggcgcg ccgcggacgt     120
gtaaaaagat atgcatccag cttctatatc gctttaactt taccgttttg ggcatcggga    180
acgtatgtaa cattgatctc ctcttgggaa cggtgagtgc aacagatgcg atatagcacc    240
gaccatgtgg gcaaattcgt aataaattcg gggtgagggg gattcaagac aagcaacctt    300
gttagtcagc tcaaacagcg atttaacggt tgagtaacac atcaaaacac cgttcgaggt    360
caagcctggc gtgtttaaca agttcttgat atcatatata aatgtaataa gaagtttggt    420
aatattcaat tcgaagtgtt cagtctttta cttctcttgt tttatagaag aaaaaacatc    480
aagaaacatc tttaacatac acaaacacat actatcagaa tacaatgact aagctacact    540
ttgacactgc tgaaccagtc aagatcacac ttccaaatgg tttgacatac gagcaaccaa    600
ccggtctatt cattaacaac aagtttatga agctcaagac cggtaagacc tatcccgtcg    660
aagatccttc cactgaaaac accgtttgtg aggtctcttc tgccaccact gaagatgttg    720
aatatgctat cgaatgtgcc gaccgtgctt ccacgacac tgaatgggct acccaagacc    780
caagagaaag aggccgtcta ctaagtaagt tggctgacga attggaaagc caaattgact    840
tggtttcttc cattgaagct ttggacaatg gtaaaacttt ggcctttaag gcccgtgggg    900
atgttaccat tgcaatcaac tgtctaagag atgctgctgc ctatgccgac aaagtcaacg    960
gtagaacaat caacaccggt gacggctaca tgaacttcac caccttagag ccaatcggtg   1020
tctgtggtca aattattcca tggaactttc caataatgat gttggcttgg aagatcgccc   1080
cagcattggc catgggtaac gtctgtatct tgaaacccgc tgctgtcaca ccttaaatg    1140
ccctatactt tgcttcttta tgtaagaagg ttggtattcc agctggtgtc gtcaacatcg   1200
ttccaggtcc tggtagaact gttggtgctg cttttgaccaa cgacccaaga atcagaaagc   1260
tggcttttac cggttctaca gaagtcggta agagtgttgc tgtcgactct tctgaatcta   1320
acttgaagaa aatcactttg gaactaggtg gtaagtccgc ccatttggtc tttgacgatg   1380
ctaacattaa gaagactta ccaaatctag taaacggtat tttcaagaac gctggtcaaa   1440
tttgttcctc tggttctaga atttacgttc aagaaggtat ttacgacgaa ctattggctg   1500
ctttcaaggc ttacttggaa accgaaatca agttggtaa tccatttgac aaggctaact   1560
tccaaggtgc tatcactaac cgtcaacaat tcgacacaat tatgaactac atcgatatcg   1620
gtaagaaaga aggcgccaag atcttaactg gtggcgaaaa agttggtgac aagggttact   1680
tcatcagacc aaccgttttc tacgatgtta atgaagacat gagaattgtt aaggaagaaa   1740
tttttggacc agttgtcact gtcgcaaagt tcaagacttt agaagaaggt gtcgaaatgg   1800
ctaacagctc tgaattcggt ctaggttctg gtatcgaaac agaatctttg agcacaggtt   1860
tgaaggtggc caagatgttg aaggccggta ccgtctggat caacacatac aacgattttg   1920
actccagagt tccattcggt ggtgttaagc aatctggtta cggtagagaa atgggtgaag   1980
aagtctacca tgcatacact gaagtaaaag ctgtcagaat taagttgtaa tgtaccaacc   2040
tgcatttctt tccgtcatat acacaaaata ctttcatata aacttacttg gtcttacgtc   2100
ataaataaat atgtatacat ataaattaaa aaatttggtt ttatattttt acaaaaagaa   2160
tcgtttactt catttctccc ttttaagcga tacaatccat gaaaaagag aaaaagagag   2220
aacaggcttg tgccttcttt aaaacatccc acacaaaatc atattgaatt gaattttaca   2280
```

```
tcttaagcta gtgtacaaca actgctatat ccaaagaaaa ctaacgtgga ccgcttttag    2340
agttgagaaa aaggtttgaa aaaaatagca atacaaagac ttgtttcata tataaaatac    2400
agggagcaca ttgagctaat ataacataaa cactgcgaac caattccaat caaaaggtac    2460
acatgagagc attcccccga gtactgccat tcgccatca gagatcatat aataacatcc     2520
ttcttcgaac agtaaggctt tttggttcat cactttcttc ttttgatttc tctaggcaaa    2580
tgcctaaggt ggaccctgac aataccgctg caatgctact acagaaaaac ttgatccaaa    2640
gaaacaacat gctctatggg tatggatcag ggacaatacg atgtactttg ctagactcaa    2700
ctggacgagc caaatcacca ttagtagaga taaaacgtga ggat                     2744
```

<210> SEQ ID NO 10
<211> LENGTH: 500
<212> TYPE: PRT
<213> ORGANISM: Saccharomyces cerevisiae
<220> FEATURE:
<221> NAME/KEY: misc_feature
<222> LOCATION: (1)..(500)
<223> OTHER INFORMATION: Saccharomyces cerevisiae cytosolic aldehyde
      dehydrogenase 6 (ALD6) protein sequence

<400> SEQUENCE: 10

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270
```

Leu Gly Gly Lys Ser Ala His Leu Val Phe Asp Asp Ala Asn Ile Lys
            275                 280                 285

Lys Thr Leu Pro Asn Leu Val Asn Gly Ile Phe Lys Asn Ala Gly Gln
        290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500

<210> SEQ ID NO 11
<211> LENGTH: 2749
<212> TYPE: DNA
<213> ORGANISM: Leuconostoc mesenteroides
<220> FEATURE:
<221> NAME/KEY: misc_feature
<222> LOCATION: (1)..(2749)
<223> OTHER INFORMATION: Leuconostoc mesenteroides Phosphoketolase (PK)
      gene sequence

<400> SEQUENCE: 11
gttacggaag aagtcgtggt ttacggtgtt tatgattctt gcaaaaaata aggagtactt      60
aatctcatgg cagatttcga ttcaaaagag tacttggaac ttgttgataa gtggtggcgc     120
gcaactaact atttgtcagc tgggatgatc tttttgaaga gcaacccatt gttctcagtt     180
actaatacac ctatcaaggc tgaagatgta aagttaagc caatcggaca ctggggtact     240
atctcaggtc agacattctt gtatgcacat gctaaccgtt tgatcaacaa gtatggtttg     300
aacatgtttt acgttggtgg tcctggtcac ggtggccaag ttatggttac taacgcttac     360
ttagacggcg catatactga agattatcct gaaattactc aagatatcga aggtatgagc     420
cacttgttca agcgtttctc attccctggc ggtattggat cacacatgac agctcaaaca     480
cctggttcat tacacgaagg tggtgaattg ggctattcat tgagccacgc ttttggtgcc     540
gttttggaca atcctgacca agttgctttc gcagttgttg gtgatggtga agctgaaaca     600
ggtccttcaa tggcttcatg gcactcaatt aagttttga atgctaagaa tgatggtgcc     660

```
gttttgcctg tcttggattt gaacggattc aagatttcaa acccaactat cttctcacgt      720
atgagtgatg aagaaatcac aaagttcttt gaaggtttgg gttattcacc tcgcttcatc      780
gaaaacgatg atattcatga ctacgcaaca tatcaccaac ttgcagcaaa cattttggat      840
caagctattg aagatattca agctattcaa aatgatgcac gtgaaaatgg taagtatcaa      900
gatggtgaaa tccctgcatg ccagtaatt attgctcgct tgccaaaggg ctggggtgga       960
ccaacgcacg atgcaagtaa caatcctatt gaaaactcat tccgtgcgca ccaagtgcca     1020
ttgcctcttg aacaacacga tcttgcaaca ttgcctgaat cgaagactg gatgaactca      1080 tacaagcctg aagaattatt caatgctgat ggttctttga aggatgaatt gaaagctatc     1140
gctcctaagg gtgacaagcg tatgtcagct aaccctatta caaatggtgg tgctgatcgt     1200
tcagacttga agttgcctaa ctggagagaa ttcgctaacg atatcaatga tgatacacgt     1260
ggtaaggaat cgctgatag caagcgcaat atggacatgg caacattgtc aaactacttg      1320
ggtgctgttt cacaattgaa cccaactcgt ttccgcttct tcggtcctga tgaaacaatg     1380
tcaaaccgtt tgtgggggatt gttcaatgtt acaccacgtc aatggatgga agaaatcaag     1440
gaaccacaag atcaattgtt gagccctacg ggtcgcatta ttgattcaca attgtctgaa     1500
catcaagctg aaggttggct tgaaggatat actttgactg tcgtgttgg aatcttcgca      1560 tcatacgagt cattcttgcg tgttgtcgat acaatggtta cgcaacactt caagtggttg     1620
cgtcacgctt cagaacaagc atggcgtaat gactatccat cattgaactt gattgcaact     1680
tcaactgctt ccaacaaga tcacaatgga tatactcacc aagatccagg tatgttgact     1740
cacttggctg aaaagaagtc taactttatt cgtgaatatt tgccagctga tggtaactca     1800
ttgttggctg ttcaagaacg tgcttttctca gaacgtcata aggttaactt gttgattgct     1860
tctaagcaac cacgtcaaca atggtttaca gttgaagaag ctgaagtatt ggctaacgaa     1920 ggttttgaaga tcattgattg ggcttctact gcaccttcta gtgatgttga tattacattc     1980
gcatctgctg gtactgaacc aacaattgaa actttggctg ctttgtggtt gattaaccaa     2040
gcattcccag atgttaagtt ccgttatgtt aacgttgttg aattactacg tttgcaaaag     2100
aagtcagaac ctaacatgaa tgatgaacgt gaattatcag ccgaagaatt caacaagtat     2160
ttccaagctg atacaccagt tatcttcggt ttccatgctt atgaaaactt gattgaatca     2220
ttcttcttcg aacgtaagtt cacgggtgat gtatacgttc atggatatcg tgaagatggt     2280
gacatcacaa cgacatatga tatgcgtgta tattcacact tggatcgctt ccatcaagct     2340
aaggaagctg ctgaaatctt gtctgcaaat ggtaagattg atcaagctgc tgctgataca     2400
ttcatcgcta agatggatga tactttggca aagcatttcc aagttactcg taacgaaggt     2460
cgtgatatcg aagaattcac tgactggaca tggtcaccac ttaagtaatt taaaattatt     2520
ttatcaaaac caactattat tttaatagt tggtttttt atggctaaat tgactacata      2580
ctaaacgaaa ccatgtaaaa gtgccacata gttttactta ataagttcct tttattttt      2640 gatttgcaat gcaaaattgt aagcgtaata tgaataataa aaaccccaa ttagttagct      2700 aattgggggt tttgtaaatc accatatcag ccgctcatag tcttagacg                 2749
```

<210> SEQ ID NO 12
<211> LENGTH: 813
<212> TYPE: PRT
<213> ORGANISM: Leuconostoc mesenteroides
<220> FEATURE:
<221> NAME/KEY: misc_feature
<222> LOCATION: (1)..(813)
<223> OTHER INFORMATION: Leuconostoc mesenteroides Phosphoketolase (PK)

protein sequence

<400> SEQUENCE: 12

Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Lys Ala Glu Asp Val
        35                  40                  45

Lys Val Lys Pro Ile Gly His Trp Gly Thr Ile Ser Gly Gln Thr Phe
    50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gly Gln Val Met Val Thr Asn
                85                  90                  95

Ala Tyr Leu Asp Gly Ala Tyr Thr Glu Asp Tyr Pro Glu Ile Thr Gln
            100                 105                 110

Asp Ile Glu Gly Met Ser His Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Val Ala Phe Ala Val Val Gly Asp Gly Glu Ala
                165                 170                 175

Glu Thr Gly Pro Ser Met Ala Ser Trp His Ser Ile Lys Phe Leu Asn
            180                 185                 190

Ala Lys Asn Asp Gly Ala Val Leu Pro Val Leu Asp Leu Asn Gly Phe
        195                 200                 205

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
                245                 250                 255

Leu Asp Gln Ala Ile Glu Asp Ile Gln Ala Ile Gln Asn Asp Ala Arg
            260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
    290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
            325                 330                 335

Asn Ser Tyr Lys Pro Glu Glu Leu Phe Asn Ala Asp Gly Ser Leu Lys
        340                 345                 350

Asp Glu Leu Lys Ala Ile Ala Pro Lys Gly Asp Lys Arg Met Ser Ala
    355                 360                 365

Asn Pro Ile Thr Asn Gly Gly Ala Asp Arg Ser Asp Leu Lys Leu Pro
370                 375                 380

Asn Trp Arg Glu Phe Ala Asn Asp Ile Asn Asp Thr Arg Gly Lys
385                 390                 395                 400

Glu Phe Ala Asp Ser Lys Arg Asn Met Asp Met Ala Thr Leu Ser Asn

```
            405                 410                 415
Tyr Leu Gly Ala Val Ser Gln Leu Asn Pro Thr Arg Phe Arg Phe Phe
            420                 425                 430

Gly Pro Asp Glu Thr Met Ser Asn Arg Leu Trp Gly Leu Phe Asn Val
            435                 440                 445

Thr Pro Arg Gln Trp Met Glu Glu Ile Lys Glu Pro Gln Asp Gln Leu
            450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
            485                 490                 495

Phe Ala Ser Tyr Glu Ser Phe Leu Arg Val Val Asp Thr Met Val Thr
            500                 505                 510

Gln His Phe Lys Trp Leu Arg His Ala Ser Glu Gln Ala Trp Arg Asn
            515                 520                 525

Asp Tyr Pro Ser Leu Asn Leu Ile Ala Thr Ser Thr Ala Phe Gln Gln
            530                 535                 540

Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
            565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
            595                 600                 605

Val Glu Glu Ala Glu Val Leu Ala Asn Glu Gly Leu Lys Ile Ile Asp
            610                 615                 620

Trp Ala Ser Thr Ala Pro Ser Ser Asp Val Asp Ile Thr Phe Ala Ser
625                 630                 635                 640

Ala Gly Thr Glu Pro Thr Ile Glu Thr Leu Ala Ala Leu Trp Leu Ile
            645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
            675                 680                 685

Glu Leu Ser Ala Glu Glu Phe Asn Lys Tyr Phe Gln Ala Asp Thr Pro
            690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
            725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Glu Ile Leu Ser Ala Asn
            755                 760                 765

Gly Lys Ile Asp Gln Ala Ala Asp Thr Phe Ile Ala Lys Met Asp
            770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
            805                 810

<210> SEQ ID NO 13
<211> LENGTH: 1002
```

```
<212> TYPE: DNA
<213> ORGANISM: Clostridium kluyveri
<220> FEATURE:
<221> NAME/KEY: misc_feature
<222> LOCATION: (1)..(1002)
<223> OTHER INFORMATION: Clostridium kluyveri Phosphotransacetylase
      (PTA) gene sequence

<400> SEQUENCE: 13
atgaaattaa tggaaaatat ttttggttta gccaaagcag ataagaaaaa aattgttttg      60
gcagaaggag aagaagaaag gaacattaga gcttccgaag aaataataag ggatggtatt     120
gcagatataa ttttagtagg aagtgaaagt gtaataaaag agaatgcagc taaatttggg     180
gttaacttag ctggagtgga aatagtagat cctgaaactt caagtaaaac tgcaggctat     240
gccaatgctt tttatgaaat tagaaagaat aaaggagtta cactggaaaa agcagataaa     300
atagttagag atcctatata ttttgcaaca atgatggtga acttggaga tgcagatggt      360 ttagtttcag gtgcaataca tacaacggga gatcttttga gaccaggact tcaaatagtg     420
aagacagttc aggtgcttc tgtggtttcc agtgtatttt taatgagtgt accagattgt      480
gaatatggag aagatggatt cttgttattt gctgattgtg ctgtaaatgt atgtcctact     540
gctgaagaat tatcttcaat gcaataact acagcagaaa ctgcaaaaaa tttgtgtaaa     600
atagaaccaa gagttgccat gctttcattt tctactatgg aagtgctag tcatgaattg     660 gtagataaag ttacaaaagc aacaaaactt gctaagaag ctagacctga tttggatata      720
gatggagaac ttcaattgga tgcttcccta gtaaaaaaag ttgcagactt aaaagctccg     780
ggcagtaaag tggcaggaaa agccaatgta cttatattcc ctgatataca agcaggaaat     840
ataggatata agttagttca aagatttgca aaagctgagg ctataggacc tatatgtcag     900
ggatttgcaa agcctataaa tgatttatca agaggctgca gcgttgatga tatagtaaag     960
gtagtggctg taactgcagt tcaagcacag gcacagggtt ag                       1002

<210> SEQ ID NO 14
<211> LENGTH: 333
<212> TYPE: PRT
<213> ORGANISM: Clostridium kluyveri
<220> FEATURE:
<221> NAME/KEY: misc_feature
<222> LOCATION: (1)..(333)
<223> OTHER INFORMATION: Clostridium kluyveri Phosphotransacetylase
      (PTA) protein sequence

<400> SEQUENCE: 14

Met Lys Leu Met Glu Asn Ile Phe Gly Leu Ala Lys Ala Asp Lys Lys
1               5                   10                  15

Lys Ile Val Leu Ala Glu Gly Glu Glu Arg Asn Ile Arg Ala Ser
            20                  25                  30

Glu Glu Ile Ile Arg Asp Gly Ile Ala Asp Ile Ile Leu Val Gly Ser
        35                  40                  45

Glu Ser Val Ile Lys Glu Asn Ala Ala Lys Phe Gly Val Asn Leu Ala
    50                  55                  60

Gly Val Glu Ile Val Asp Pro Glu Thr Ser Ser Lys Thr Ala Gly Tyr
65                  70                  75                  80

Ala Asn Ala Phe Tyr Glu Ile Arg Lys Asn Lys Gly Val Thr Leu Glu
                85                  90                  95

Lys Ala Asp Lys Ile Val Arg Asp Pro Ile Tyr Phe Ala Thr Met Met
            100                 105                 110

Val Lys Leu Gly Asp Ala Asp Gly Leu Val Ser Gly Ala Ile His Thr
        115                 120                 125
```

```
Thr Gly Asp Leu Leu Arg Pro Gly Leu Gln Ile Val Lys Thr Val Pro
    130                 135                 140

Gly Ala Ser Val Val Ser Ser Val Phe Leu Met Ser Val Pro Asp Cys
145                 150                 155                 160

Glu Tyr Gly Glu Asp Gly Phe Leu Leu Phe Ala Asp Cys Ala Val Asn
            165                 170                 175

Val Cys Pro Thr Ala Glu Glu Leu Ser Ser Ile Ala Ile Thr Thr Ala
            180                 185                 190

Glu Thr Ala Lys Asn Leu Cys Lys Ile Glu Pro Arg Val Ala Met Leu
        195                 200                 205

Ser Phe Ser Thr Met Gly Ser Ala Ser His Glu Leu Val Asp Lys Val
    210                 215                 220

Thr Lys Ala Thr Lys Leu Ala Lys Glu Ala Arg Pro Asp Leu Asp Ile
225                 230                 235                 240

Asp Gly Glu Leu Gln Leu Asp Ala Ser Leu Val Lys Lys Val Ala Asp
            245                 250                 255

Leu Lys Ala Pro Gly Ser Lys Val Ala Gly Lys Ala Asn Val Leu Ile
            260                 265                 270

Phe Pro Asp Ile Gln Ala Gly Asn Ile Gly Tyr Lys Leu Val Gln Arg
        275                 280                 285

Phe Ala Lys Ala Glu Ala Ile Gly Pro Ile Cys Gln Gly Phe Ala Lys
290                 295                 300

Pro Ile Asn Asp Leu Ser Arg Gly Cys Ser Val Asp Asp Ile Val Lys
            310                 315                 320

Val Val Ala Val Thr Ala Val Gln Ala Gln Ala Gln Gly
                325                 330

<210> SEQ ID NO 15
<211> LENGTH: 2137
<212> TYPE: DNA
<213> ORGANISM: Streptomyces sp. CL190
<220> FEATURE:
<221> NAME/KEY: misc_feature
<222> LOCATION: (1)..(2137)
<223> OTHER INFORMATION: Streptomyces sp. CL190 nphT7 gene sequence

<400> SEQUENCE: 15
cctgcaggcc gtcgagggcg cctggaagga ctacgcggag caggacggcc ggtcgctgga      60
ggagttcgcg gcgttcgtct accaccagcc gttcacgaag atggcctaca aggcgcaccg     120
ccacctgctg aacttcaacg gctacgacac cgacaaggac gccatcgagg cgccctcgg     180 ccagacgacg gcgtacaaca acgtcatcgg caacagctac accgcgtcgg tgtacctggg     240
cctggccgcc ctgctcgacc aggcggacga cctgacgggc cgttccatcg gcttcctgag     300
ctacggctcg ggcagcgtcg ccgagttctt ctcgggcacc gtcgtcgccg gtaccgcga     360 gcgtctgcgc accgaggcga accaggaggc gatcgcccgg cgcaagagcg tcgactacgc     420
cacctaccgc gagctgcacg agtacacgct cccgtccgac ggcggcgacc acgccacccc     480
ggtgcagacc accggcccct tccggctggc cgggatcaac gaccacaagc gcatctacga     540
ggcgcgctag cgacacccct cggcaacggg gtgcgccact gttcggcgca ccccgtgccg     600
ggctttcgca cagctattca cgaccatttg aggggcgggc agccgcatga ccgacgtccg     660
attccgcatt atcggtacgg gtgcctacgt accggaacgg atcgtctcca acgatgaagt     720
cggcgcgccg gccggggtgg acgacgactg gatcacccgc aagaccggta tccggcagcg     780
tcgctgggcc gccgacgacc aggccacctc ggacctggcc acggccgcgg ggcgggcagc     840
```

-continued

```
gctgaaagcg gcgggcatca cgcccgagca gctgaccgtg atcgcggtcg ccacctccac    900
gccggaccgg ccgcagccgc ccacggcggc ctatgtccag caccacctcg gtgcgaccgg    960
cactgcggcg ttcgacgtca acgcggtctg ctccggcacc gtgttcgcgc tgtcctcggt   1020
ggcgggcacc ctcgtgtacc ggggcggtta cgcgctggtc atcggcgcgg acctgtactc   1080
gcgcatcctc aacccggccg accgcaagac ggtcgtgctg ttcggggacg gcgccggcgc   1140
aatggtcctc gggccgacct cgaccggcac gggccccatc gtccggcgcg tcgccctgca   1200
caccttcggc ggcctcaccg acctgatccg tgtgcccgcg ggcggcagcc gccagccgct   1260
ggacacggat ggcctcgacg cgggactgca gtacttcgcg atggacgggc gtgaggtgcg   1320
ccgcttcgtc acggagcacc tgccgcagct gatcaagggc ttcctgcacg aggccggggt   1380
cgacgccgcc gacatcagcc acttcgtgcc gcatcaggcc aacggtgtca tgctcgacga   1440
ggtcttcggc gagctgcatc tgccgcgggc gaccatgcac cggacggtcg agacctacgg   1500
caacacggga gcggcctcca tcccgatcac catggacgcg gccgtgcgcg ccggttcctt   1560
ccggccgggc gagctggtcc tgctggccgg gttcggcggc ggcatggccg cgagcttcgc   1620
cctgatcgag tggtagtcgc ccgtaccacc acagcggtcc ggcgccacct gttccctgcg   1680
ccgggccgcc ctcggggcct ttaggcccca caccgcccca gccgacggat tcagtcgcgg   1740
cagtacctca gatgtccgct gcgacggcgt cccggagagc ccgggcgaga tcgcgggccc   1800
ccttctgctc gtccccggcc cctcccgcga gcaccacccg cggcggacgg ccgccgtcct   1860
ccgcgatacg ccgggcgagg tcgcaggcga gcacgccgga cccggagaag ccccccagca   1920
ccagcgaccg gccgactccg tgcgcggcca gggcaggctg cgcgccgtcg acgtcggtga   1980
gcagcaccag gagctcctgc ggcccggcgt agaggtcggc cagccggtcg tagcaggtcg   2040
cgggcgcgcc cggcggcggg atcagacaga tcgtgcccgc ccgctcgtgc ctcgccgccc   2100
gcagcgtgac cagcggaatg tcccgcccag ctccgga                           2137
```

<210> SEQ ID NO 16
<211> LENGTH: 325
<212> TYPE: PRT
<213> ORGANISM: Streptomyces sp. CL190
<220> FEATURE:
<221> NAME/KEY: misc_feature
<222> LOCATION: (1)..(325)
<223> OTHER INFORMATION: Streptomyces sp. CL190 acetyl-CoA:malonyl-CoA
      acyltransferase protein sequence

<400> SEQUENCE: 16

```
Arg Phe Arg Ile Ile Gly Thr Gly Ala Tyr Val Pro Glu Arg Ile Val
1               5                   10                  15

Ser Asn Asp Glu Val Gly Ala Pro Ala Gly Val Asp Asp Trp Ile
            20                  25                  30

Thr Arg Lys Thr Gly Ile Arg Gln Arg Arg Trp Ala Ala Asp Asp Gln
        35                  40                  45

Ala Thr Ser Asp Leu Ala Thr Ala Ala Gly Arg Ala Ala Leu Lys Ala
    50                  55                  60

Ala Gly Ile Thr Pro Glu Gln Leu Thr Val Ile Ala Val Ala Thr Ser
65                  70                  75                  80

Thr Pro Asp Arg Pro Gln Pro Pro Thr Ala Ala Tyr Val Gln His His
                85                  90                  95

Leu Gly Ala Thr Gly Thr Ala Ala Phe Asp Val Asn Ala Val Cys Ser
            100                 105                 110

Gly Thr Val Phe Ala Leu Ser Ser Val Ala Gly Thr Leu Val Tyr Arg
        115                 120                 125
```

```
Gly Gly Tyr Ala Leu Val Ile Gly Ala Asp Leu Tyr Ser Arg Ile Leu
    130                 135                 140
Asn Pro Ala Asp Arg Lys Thr Val Val Leu Phe Gly Asp Gly Ala Gly
145                 150                 155                 160
Ala Met Val Leu Gly Pro Thr Ser Thr Gly Thr Gly Pro Ile Val Arg
                165                 170                 175
Arg Val Ala Leu His Thr Phe Gly Gly Leu Thr Asp Leu Ile Arg Val
                180                 185                 190
Pro Ala Gly Gly Ser Arg Gln Pro Leu Asp Thr Asp Gly Leu Asp Ala
                195                 200                 205
Gly Leu Gln Tyr Phe Ala Met Asp Gly Arg Glu Val Arg Arg Phe Val
    210                 215                 220
Thr Glu His Leu Pro Gln Leu Ile Lys Gly Phe Leu His Glu Ala Gly
225                 230                 235                 240
Val Asp Ala Ala Asp Ile Ser His Phe Val Pro His Gln Ala Asn Gly
                245                 250                 255
Val Met Leu Asp Glu Val Phe Gly Glu Leu His Leu Pro Arg Ala Thr
                260                 265                 270
Met His Arg Thr Val Glu Thr Tyr Gly Asn Thr Gly Ala Ala Ser Ile
                275                 280                 285
Pro Ile Thr Met Asp Ala Ala Val Arg Ala Gly Ser Phe Arg Pro Gly
                290                 295                 300
Glu Leu Val Leu Leu Ala Gly Phe Gly Gly Gly Met Ala Ala Ser Phe
305                 310                 315                 320
Ala Leu Ile Glu Trp
                325

<210> SEQ ID NO 17
<211> LENGTH: 1287
<212> TYPE: DNA
<213> ORGANISM: Pseudomonas mevalonii
<220> FEATURE:
<221> NAME/KEY: misc_feature
<222> LOCATION: (1)..(1287)
<223> OTHER INFORMATION: Pseudomonas mevalonii HMG-CoA reductase (mvaA)
      gene sequence

<400> SEQUENCE: 17
atgagcctcg attcccgcct gcccgctttc cgtaacctgt cccctgccgc gcgcctggac      60
cacatcggcc agttgctcgg cctgagccac gacgatgtca gcctgctggc caacgccggt     120
gccctgccga tggacatcgc caacggcatg atcgaaaacg tcatcggcac cttcgagctg     180
ccctatgccg tggccagcaa cttccagatc aatggccgtg atgtgctggt gccgctggtg     240
gtggaagagc cctcgatcgt cgccgctgct tcgtacatgg ccaagctggc ccgtgccaac     300
ggcggcttca ccacctccag cagcgccccg ctgatgcatg cccaggtaca gatcgtcggc     360
atacaggacc cgctcaatgc acgcctgagc ctgctgcgcc gcaaagacga aatcattgaa     420
ctggccaacc gcaaggacca gttgctcaac agcctcggcg gcggctgccg cgacatcgaa     480
gtgcacacct tcgccgatac cccgcgtggc ccgatgctgg tggcgcacct gatcgtcgat     540
gtacgcgatg ccatgggcgc caacaccgtc aataccatgg ccgaggccgt tgcgccgctg     600
atggaagcca tcaccggggg ccaggtacgc ctgcgcattc tgtccaacct ggccgacctg     660
cgcctggcca gggcccaggt gcggattact ccgcagcaac tggaaacggc cgaattcagt     720
ggcgaggcag tgatcgaagg catcctcgac gcctacgcct cgctgcggt cgacccttac     780 cgcgcggcca cccacaacaa gggcatcatg aatggcatcg acccactgat cgtcgccact     840
```

```
ggcaacgact ggcgtgcagt ggaagccggc gcccatgcgt atgcctgccg cagtggtcac      900
tacggctcgc tgaccacctg ggaaaaggac aacaacggcc atttggtcgg caccctggaa      960
atgccgatgc ccgtaggcct ggtcggcggc gccaccaaaa cccatccgct ggcgcaactg     1020
tcgctgcgca tcctcggcgt gaaaacagcc caggcgctcg ctgagattgc cgtggccgta     1080
ggcctggcga aaacctcgg ggccatgcgc ccctggcca ccgaaggcat ccagcgcggc       1140
cacatggccc tgcatgcgcg caatattgcc gtggtggcgg gcgcccgagg cgatgaggtg     1200
gactgggttg cccggcagtt ggtggaatac cacgacgtgc gcgccgaccg cgccgtagca     1260
ctgctgaaac aaaagcgcgg ccaatga                                         1287
```

<210> SEQ ID NO 18
<211> LENGTH: 428
<212> TYPE: PRT
<213> ORGANISM: Pseudomonas mevalonii
<220> FEATURE:
<221> NAME/KEY: misc_feature
<222> LOCATION: (1)..(428)
<223> OTHER INFORMATION: Pseudomonas mevalonii hydroxymethylglutaryl-
      CoA reductase protein sequence

<400> SEQUENCE: 18

```
Met Ser Leu Asp Ser Arg Leu Pro Ala Phe Arg Asn Leu Ser Pro Ala
1               5                   10                  15

Ala Arg Leu Asp His Ile Gly Gln Leu Leu Gly Leu Ser His Asp Asp
                20                  25                  30

Val Ser Leu Leu Ala Asn Ala Gly Ala Leu Pro Met Asp Ile Ala Asn
            35                  40                  45

Gly Met Ile Glu Asn Val Ile Gly Thr Phe Glu Leu Pro Tyr Ala Val
        50                  55                  60

Ala Ser Asn Phe Gln Ile Asn Gly Arg Asp Val Leu Val Pro Leu Val
65                  70                  75                  80

Val Glu Glu Pro Ser Ile Val Ala Ala Ser Tyr Met Ala Lys Leu
                85                  90                  95

Ala Arg Ala Asn Gly Gly Phe Thr Thr Ser Ser Ala Pro Leu Met
            100                 105                 110

His Ala Gln Val Gln Ile Val Gly Ile Gln Asp Pro Leu Asn Ala Arg
        115                 120                 125

Leu Ser Leu Leu Arg Arg Lys Asp Glu Ile Ile Glu Leu Ala Asn Arg
    130                 135                 140

Lys Asp Gln Leu Leu Asn Ser Leu Gly Gly Gly Cys Arg Asp Ile Glu
145                 150                 155                 160

Val His Thr Phe Ala Asp Thr Pro Arg Gly Pro Met Leu Val Ala His
                165                 170                 175

Leu Ile Val Asp Val Arg Asp Ala Met Gly Ala Asn Thr Val Asn Thr
            180                 185                 190

Met Ala Glu Ala Val Ala Pro Leu Met Glu Ala Ile Thr Gly Gly Gln
        195                 200                 205

Val Arg Leu Arg Ile Leu Ser Asn Leu Ala Asp Leu Arg Leu Ala Arg
    210                 215                 220

Ala Gln Val Arg Ile Thr Pro Gln Gln Leu Glu Thr Ala Glu Phe Ser
225                 230                 235                 240

Gly Glu Ala Val Ile Glu Gly Ile Leu Asp Ala Tyr Ala Phe Ala Ala
                245                 250                 255

Val Asp Pro Tyr Arg Ala Ala Thr His Asn Lys Gly Ile Met Asn Gly
            260                 265                 270
```

```
Ile Asp Pro Leu Ile Val Ala Thr Gly Asn Asp Trp Arg Ala Val Glu
            275                 280                 285

Ala Gly Ala His Ala Tyr Ala Cys Arg Ser Gly His Tyr Gly Ser Leu
        290                 295                 300

Thr Thr Trp Glu Lys Asp Asn Asn Gly His Leu Val Gly Thr Leu Glu
305                 310                 315                 320

Met Pro Met Pro Val Gly Leu Val Gly Gly Ala Thr Lys Thr His Pro
                325                 330                 335

Leu Ala Gln Leu Ser Leu Arg Ile Leu Gly Val Lys Thr Ala Gln Ala
            340                 345                 350

Leu Ala Glu Ile Ala Val Ala Val Gly Leu Ala Gln Asn Leu Gly Ala
        355                 360                 365

Met Arg Ala Leu Ala Thr Glu Gly Ile Gln Arg Gly His Met Ala Leu
    370                 375                 380

His Ala Arg Asn Ile Ala Val Val Ala Gly Ala Arg Gly Asp Glu Val
385                 390                 395                 400

Asp Trp Val Ala Arg Gln Leu Val Glu Tyr His Asp Val Arg Ala Asp
                405                 410                 415

Arg Ala Val Ala Leu Leu Lys Gln Lys Arg Gly Gln
            420                 425

<210> SEQ ID NO 19
<211> LENGTH: 1302
<212> TYPE: DNA
<213> ORGANISM: Silicibacter pomeroyi
<220> FEATURE:
<221> NAME/KEY: misc_feature
<222> LOCATION: (1)..(1302)
<223> OTHER INFORMATION: Silicibacter pomeroyi hydroxymethylglutaryl-
      CoA reductase gene sequence

<400> SEQUENCE: 19
atgacaggca agacgggtca catcgatggt ttgaactcgc gcattgaaaa gatgcgagat      60
ctcgaccccg cacaacggct ggtgcgcgtt gccgaggcgg cgggcctcga gcccgaggcg     120
atcagcgcgc tggcgggtaa cggcgccctg cccctctcgc tggccaacgg gatgatcgag     180
aacgtcatcg gcaaattcga actgccgctg ggcgtggcca cgaatttcac tgtgaacggc     240
cgcgactatc tgatcccgat gcggtcgaa gagccctcgg tggtggcggc gcgtccctat      300
atggcgcgta tcgcgcgcga gaatggcgga ttcaccgcgc atggcaccgc gcccttgatg     360
cgcgcccaga tccaggtggt cgggttgggt gatcccgagg cgcccggca gcgtctcctc     420 gcccacaagg ccgcgttcat ggaggcggcg gacgctgtcg atccggtgct tgtcgggctg     480
ggtggcggct gccgcgatat cgaggttcac gtgttccggg atacgccggt gggcgcgatg     540
gtcgtcctgc acctgatcgt cgatgtgcgc gacgcgatgg gggccaatac ggtcaacacg     600
atggccgaac ggctggcccc cgaggtcgag cggattgccg tggcaccgt gcggctgcgc      660 atcctgtcga acctcgccga cctgcgattg gtccgggcgc gggtggaact ggccccggaa     720
acactgacaa cgcagggcta tgacggcgcc gacgtgcgc ggggcatggt cgaggcctgc      780
gcgcttgcca tcgtcgaccc ctatcgcgcg gcgacccata caagggat catgaacggc       840 atcgaccggg tcgtcgtcgc caccggcaat gactggcgcg cgatcgaggc gggtgcccat     900
gcctatgccg cccgcacggg tcattatacc tcgctgaccc gctgggaact ggcgaatgac     960
gggcggcttg tgggcacgat cgaactgccc ctggcgcttg ccttgtcgg cggcgcgacc     1020 aagacgcacc cgaccgcacg ggcggcgctg gccctgatgc aggtagagac tgcaaccgaa    1080
```

```
ctggcccagg tcaccgccgc cgtgggtctg gcgcagaaca tggccgccat ccgcgcgctg   1140
gcgaccgaag gcatccagcg cggtcacatg acccttcatg cgcgcaacat cgcgatcatg   1200
gccggcgcaa caggcgccga tatcgaccgc gtcacccggg tcattgtcga agcgggcgac   1260
gtcagcgtgg cccgtgcaaa acaggtgctg gaaaacacct ga                      1302
```

<210> SEQ ID NO 20
<211> LENGTH: 433
<212> TYPE: PRT
<213> ORGANISM: Silicibacter pomeroyi
<220> FEATURE:
<221> NAME/KEY: misc_feature
<222> LOCATION: (1)..(433)
<223> OTHER INFORMATION: Silicibacter pomeroyi hydroxymethylglutaryl-
      CoA reductase protein sequence

<400> SEQUENCE: 20

```
Met Thr Gly Lys Thr Gly His Ile Asp Gly Leu Asn Ser Arg Ile Glu
1               5                   10                  15

Lys Met Arg Asp Leu Asp Pro Ala Gln Arg Leu Val Arg Val Ala Glu
                20                  25                  30

Ala Ala Gly Leu Glu Pro Glu Ala Ile Ser Ala Leu Ala Gly Asn Gly
            35                  40                  45

Ala Leu Pro Leu Ser Leu Ala Asn Gly Met Ile Glu Asn Val Ile Gly
        50                  55                  60

Lys Phe Glu Leu Pro Leu Gly Val Ala Thr Asn Phe Thr Val Asn Gly
65                  70                  75                  80

Arg Asp Tyr Leu Ile Pro Met Ala Val Glu Pro Ser Val Val Ala
                85                  90                  95

Ala Ala Ser Tyr Met Ala Arg Ile Ala Arg Glu Asn Gly Gly Phe Thr
            100                 105                 110

Ala His Gly Thr Ala Pro Leu Met Arg Ala Gln Ile Gln Val Val Gly
        115                 120                 125

Leu Gly Asp Pro Glu Gly Ala Arg Gln Arg Leu Leu Ala His Lys Ala
    130                 135                 140

Ala Phe Met Glu Ala Ala Asp Ala Val Asp Pro Val Leu Val Gly Leu
145                 150                 155                 160

Gly Gly Gly Cys Arg Asp Ile Glu Val His Val Phe Arg Asp Thr Pro
                165                 170                 175

Val Gly Ala Met Val Val Leu His Leu Ile Val Asp Val Arg Asp Ala
            180                 185                 190

Met Gly Ala Asn Thr Val Asn Thr Met Ala Glu Arg Leu Ala Pro Glu
        195                 200                 205

Val Glu Arg Ile Ala Gly Gly Thr Val Arg Leu Arg Ile Leu Ser Asn
    210                 215                 220

Leu Ala Asp Leu Arg Leu Val Arg Ala Arg Val Glu Leu Ala Pro Glu
225                 230                 235                 240

Thr Leu Thr Thr Gln Gly Tyr Asp Gly Ala Asp Val Ala Arg Gly Met
                245                 250                 255

Val Glu Ala Cys Ala Leu Ala Ile Val Asp Pro Tyr Arg Ala Ala Thr
            260                 265                 270

His Asn Lys Gly Ile Met Asn Gly Ile Asp Pro Val Val Val Ala Thr
        275                 280                 285

Gly Asn Asp Trp Arg Ala Ile Glu Ala Gly Ala His Ala Tyr Ala Ala
    290                 295                 300

Arg Thr Gly His Tyr Thr Ser Leu Thr Arg Trp Glu Leu Ala Asn Asp
305                 310                 315                 320
```

```
Gly Arg Leu Val Gly Thr Ile Glu Leu Pro Leu Ala Leu Gly Leu Val
            325                 330                 335

Gly Gly Ala Thr Lys Thr His Pro Thr Ala Arg Ala Ala Leu Ala Leu
            340                 345                 350

Met Gln Val Glu Thr Ala Thr Glu Leu Ala Gln Val Thr Ala Ala Val
            355                 360                 365

Gly Leu Ala Gln Asn Met Ala Ala Ile Arg Ala Leu Ala Thr Glu Gly
        370                 375                 380

Ile Gln Arg Gly His Met Thr Leu His Ala Arg Asn Ile Ala Ile Met
385                 390                 395                 400

Ala Gly Ala Thr Gly Ala Asp Ile Asp Arg Val Thr Arg Val Ile Val
            405                 410                 415

Glu Ala Gly Asp Val Ser Val Ala Arg Ala Lys Gln Val Leu Glu Asn
            420                 425                 430

Thr

<210> SEQ ID NO 21
<211> LENGTH: 1290
<212> TYPE: DNA
<213> ORGANISM: Delftia acidovorans
<220> FEATURE:
<221> NAME/KEY: misc_feature
<222> LOCATION: (1)..(1290)
<223> OTHER INFORMATION: Delftia acidovorans hydroxymethylglutaryl-
      CoA reductase nucleotide sequence

<400> SEQUENCE: 21
atggttgccg attcgcgact gcccaatttc cgcgccctca caccggccca gcgccgggat      60
ttcctggccg atgcctgcgg cctgtccgat gccgagcgcg ccctgctcgc tgccccggt     120 gccctgcccc tggcgctggc cgacggcatg atcgagaacg tgttcggcag cttcgagctg    180
ccgctgggcg tggccggcaa cttccgcgtc aacggccgcg acgtgctggt gcccatggcg    240
gtggaggagc cctcggtggt ggccgccgcc tcgtacatgg ccaagctggc gcgcgaggac    300
gggggctttc agacctcaag cacgctgccg ctgatgcgcg cccaggtcca ggtgctgggc    360
gtgaccgatc acacggcgc gcgcctggcc gtgctgcagg cgcgtgcgca gatcatcgag    420
cgcgccaaca gccgcgacaa ggtgctgatc ggcctgggcg gcggctgcaa ggacatcgag    480
gtccatgtct tccccgacac gccgcgcggc cccatgctgg tggtccacct gatcgtggac    540
gtgcgcgacg ccatgggcgc caacaccgtc aacaccatgg ccgaatcggt ggcgcccctg    600
gtcgagaaga tcacgggcgg cagcgtgcgg ctgcgcatcc tgtccaacct ggccgacctg    660
cggctggccc gcgcccgcgt gcggctcacg ccgcagaccc tggccacgca ggatcgcagc    720
ggcgaggaga tcatcgaagg cgtgctggac gcctatacct tcgcggccat cgaccctac    780 cgcgcggcca cgcacaacaa gggaatcatg aacggcatcg accccgtcat cgtggccacg    840
ggcaacgact ggcgcgcggt cgaggccggc gccatgcct atgccagccg cagcggcagc    900
tacacctcgc tgacgcgctg gaaaaggat gccggcggcg ccctggtcgg cagcatcgag    960
ctgcccatgc cggtgggcct tgtcggcggc gccaccaaga cccatccgct ggcacgcctg   1020
gcgctgaaga tcatggacct gcagtccgcc cagcagctgg gcgagatcgc cgccgccgtg   1080
ggcctggcgc agaacctggg cgccctgcgc gccctggcca ccgaaggcat tcagcgcggc   1140
cacatggccc tgcacgcccg caacatcgcc ctggtggccg gcgccacggg cgacgaggtc   1200
gatgccgtgg cgcgccagct ggccgccgag cacgacgtgc gcaccgaccg cgcgctggaa   1260
gtgctggccg cgctgcgcgc cagggcctga                                     1290
```

<210> SEQ ID NO 22
<211> LENGTH: 429
<212> TYPE: PRT
<213> ORGANISM: Delftia acidovorans
<220> FEATURE:
<221> NAME/KEY: misc_feature
<222> LOCATION: (1)..(429)
<223> OTHER INFORMATION: Delftia acidovorans hydroxymethylglutaryl-
    CoA reductase protein sequence

<400> SEQUENCE: 22

Met Val Ala Asp Ser Arg Leu Pro Asn Phe Arg Ala Leu Thr Pro Ala
1               5                   10                  15

Gln Arg Arg Asp Phe Leu Ala Asp Ala Cys Gly Leu Ser Asp Ala Glu
            20                  25                  30

Arg Ala Leu Leu Ala Ala Pro Gly Ala Leu Pro Leu Ala Leu Ala Asp
        35                  40                  45

Gly Met Ile Glu Asn Val Phe Gly Ser Phe Glu Leu Pro Leu Gly Val
    50                  55                  60

Ala Gly Asn Phe Arg Val Asn Gly Arg Asp Val Leu Val Pro Met Ala
65                  70                  75                  80

Val Glu Glu Pro Ser Val Val Ala Ala Ser Tyr Met Ala Lys Leu
                85                  90                  95

Ala Arg Glu Asp Gly Gly Phe Gln Thr Ser Ser Thr Leu Pro Leu Met
            100                 105                 110

Arg Ala Gln Val Gln Val Leu Gly Val Thr Asp Pro His Gly Ala Arg
        115                 120                 125

Leu Ala Val Leu Gln Ala Arg Ala Gln Ile Ile Glu Arg Ala Asn Ser
    130                 135                 140

Arg Asp Lys Val Leu Ile Gly Leu Gly Gly Gly Cys Lys Asp Ile Glu
145                 150                 155                 160

Val His Val Phe Pro Asp Thr Pro Arg Gly Pro Met Leu Val Val His
                165                 170                 175

Leu Ile Val Asp Val Arg Asp Ala Met Gly Ala Asn Thr Val Asn Thr
            180                 185                 190

Met Ala Glu Ser Val Ala Pro Leu Val Glu Lys Ile Thr Gly Gly Ser
        195                 200                 205

Val Arg Leu Arg Ile Leu Ser Asn Leu Ala Asp Leu Arg Leu Ala Arg
    210                 215                 220

Ala Arg Val Arg Leu Thr Pro Gln Thr Leu Ala Thr Gln Asp Arg Ser
225                 230                 235                 240

Gly Glu Glu Ile Ile Glu Gly Val Leu Asp Ala Tyr Thr Phe Ala Ala
                245                 250                 255

Ile Asp Pro Tyr Arg Ala Ala Thr His Asn Lys Gly Ile Met Asn Gly
            260                 265                 270

Ile Asp Pro Val Ile Val Ala Thr Gly Asn Asp Trp Arg Ala Val Glu
        275                 280                 285

Ala Gly Ala His Ala Tyr Ala Ser Arg Ser Gly Ser Tyr Thr Ser Leu
    290                 295                 300

Thr Arg Trp Glu Lys Asp Ala Gly Gly Ala Leu Val Gly Ser Ile Glu
305                 310                 315                 320

Leu Pro Met Pro Val Gly Leu Val Gly Gly Ala Thr Lys Thr His Pro
                325                 330                 335

Leu Ala Arg Leu Ala Leu Lys Ile Met Asp Leu Gln Ser Ala Gln Gln
            340                 345                 350

-continued

```
Leu Gly Glu Ile Ala Ala Ala Val Gly Leu Ala Gln Asn Leu Gly Ala
        355                 360                 365
Leu Arg Ala Leu Ala Thr Glu Gly Ile Gln Arg Gly His Met Ala Leu
    370                 375                 380
His Ala Arg Asn Ile Ala Leu Val Ala Gly Ala Thr Gly Asp Glu Val
385                 390                 395                 400
Asp Ala Val Ala Arg Gln Leu Ala Ala Glu His Asp Val Arg Thr Asp
                405                 410                 415
Arg Ala Leu Glu Val Leu Ala Ala Leu Arg Ala Arg Ala
            420                 425

<210> SEQ ID NO 23
<211> LENGTH: 5726
<212> TYPE: DNA
<213> ORGANISM: Artificial Sequence
<220> FEATURE:
<223> OTHER INFORMATION: Synthetic construct: pAM70 plasmid

<400> SEQUENCE: 23
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accataccac agcttttcaa ttcaattcat cattttttt ttattctttt ttttgatttc    240
ggtttctttg aaattttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat tgtttactaa aaacacatg    600 tggatatctt gactgatttt tccatggagg gcacagttaa gccgctaaag gcattatccg   660
ccaagtacaa tttttactc ttcgaagaca gaaaatttgc tgacattggt aatacagtca    720
aattgcagta ctctgcgggt gtatacagaa tagcagaatg ggcagacatt acgaatgcac   780
acggtgtggt gggcccaggt attgttagcg gtttgaagca ggcggcagaa gaagtaacaa   840
aggaacctag aggcctttg atgttagcag aattgtcatg caagggctcc ctatctactg    900
gagaatatac taagggtact gttgacattg cgaagagcga caaagatttt gttatcggct   960
ttattgctca agagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaagggaa   1140 gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga ataccgcac    1320 agatgcgtaa ggagaaaata ccgcatcagg aaattgtaaa cgttaatatt ttgttaaat    1380 tcgcgttaaa ttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatgcccc actacgtgaa ccatcaccct aatcaagttt ttggggtcg aggtgccgta    1620 aagcactaaa tcggaaccct aaagggagcc cccgatttag agcttgacgg ggaaagccgg   1680
```

```
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg ggccccccct cgaggtcgac ggtatcgata    2040
agcttgatat cgaattcctg cagcccgggg gatccactag ttctagagcg gccgccaccg    2100
cggtggagct ccagcttttg ttcccttag tgagggttaa ttgcgcgctt ggcgtaatca    2160
tggtcatagc tgtttcctgt gtgaaattgt tatccgctca caattccaca acataggga    2220
gccggaagca taaagtgtaa agcctggggt gcctaatgag tgaggtaact cacattaatt    2280
gcgttgcgct cactgcccgc tttccagtcg gaaacctgt cgtgccagct gcattaatga    2340
atcggccaac gcgcgggag aggcggtttg cgtattgggc gctcttccgc ttcctcgctc    2400
actgactcgc tgcgctcggt cgttcggctg cggcgagcgg tatcagctca ctcaaaggcg    2460
gtaatacggt tatccacaga atcagggat aacgcaggaa agaacatgtg agcaaaaggc    2520
cagcaaaagg ccaggaaccg taaaaaggcc gcgttgctgg cgttttccca taggctccgc    2580
ccccctgacg agcatcacaa aaatcgacgc tcaagtcaga ggtggcgaaa cccgacagga    2640
ctataaagat accaggcgtt ccccctgga agctccctcg tgcgctctcc tgttccgacc    2700
ctgccgctta ccggatacct gtccgccttt ctcccttcgg gaagcgtggc gctttctcat    2760
agctcacgct gtaggtatct cagttcggtg taggtcgttc gctccaagct gggctgtgtg    2820
cacgaaccc ccgttcagcc cgaccgctgc gccttatccg gtaactatcg tcttgagtcc    2880
aacccggtaa gacacgactt atcgccactg gcagcagcca ctggtaacag gattagcaga    2940
gcgaggtatg taggcggtgc tacagagttc ttgaagtggt ggcctaacta cggctacact    3000
agaaggacag tatttggtat ctgcgctctg ctgaagccag ttaccttcgg aaaaagagtt    3060
ggtagctctt gatccggcaa acaaaccacc gctggtagcg gtggtttttt tgtttgcaag    3120
cagcagatta cgcgcagaaa aaaggatct caagaagatc ctttgatctt ttctacgggg    3180
tctgacgctc agtggaacga aaactcacgt taagggattt tggtcatgag attatcaaaa    3240
aggatcttca cctagatcct tttaaattaa aaatgaagtt ttaaatcaat ctaaagtata    3300
tatgagtaaa cttggtctga cagttaccaa tgcttaatca gtgaggcacc tatctcagcg    3360
atctgtctat ttcgttcatc catagttgcc tgactccccg tcgtgtagat aactacgata    3420
cgggagggct taccatctgg ccccagtgct gcaatgatac gcgagaccc acgctcaccg    3480
gctccagatt tatcagcaat aaaccagcca gccggaaggg ccgagcgcag aagtggtcct    3540
gcaactttat ccgcctccat ccagtctatt aattgttgcc gggaagctag agtaagtagt    3600
tcgccagtta atagtttgcg caacgttgtt gccattgcta caggcatcgt ggtgtcacgc    3660
tcgtcgtttg gtatggcttc attcagctcc ggttcccaac gatcaaggcg agttacatga    3720
tcccccatgt tgtgcaaaaa agcggttagc tccttcggtc ctccgatcgt tgtcagaagt    3780
aagttggccg cagtgttatc actcatggtt atggcagcac tgcataattc tcttactgtc    3840
atgccatccg taagatgctt ttctgtgact ggtgagtact caaccaagtc attctgagaa    3900
tagtgtatgc ggcgaccgag ttgctcttgc ccggcgtcaa tacgggataa taccgcgcca    3960
catagcagaa ctttaaaagt gctcatcatt ggaaaacgtt cttcggggcg aaaactctca    4020
aggatcttac cgctgttgag atccagttcg atgtaaccca ctcgtgcacc caactgatct    4080
```

```
tcagcatctt ttactttcac cagcgtttct gggtgagcaa aacaggaag gcaaaatgcc      4140
gcaaaaaagg gaataagggc gacacggaaa tgttgaatac tcatactctt cctttttcaa      4200
tattattgaa gcatttatca gggttattgt ctcatgagcg gatacatatt tgaatgtatt      4260
tagaaaaata aacaaatagg ggttccgcgc acatttcccc gaaaagtgcc acctgaacga      4320
agcatctgtg cttcattttg tagaacaaaa atgcaacgcg agagcgctaa ttttttcaaac     4380
aaagaatctg agctgcattt ttacagaaca gaaatgcaac gcgaaagcgc tattttacca     4440
acgaagaatc tgtgcttcat ttttgtaaaa caaaaatgca acgcgagagc gctaattttt     4500
caaacaaaga atctgagctg cattttttaca gaacagaaat gcaacgcgag agcgctattt    4560
taccaacaaa gaatctatac ttcttttttg ttctacaaaa atgcatcccg agagcgctat     4620
ttttctaaca aagcatctta gattactttt tttctccttt gtgcgctcta taatgcagtc     4680
tcttgataac ttttttgcact gtaggtccgt taaggttaga agaaggctac tttggtgtct    4740
atttttctctt ccataaaaaa agcctgactc cacttcccgc gttactgat tactagcgaa    4800
gctgcgggtg catttttttca agataaaggc atccccgatt atattctata ccgatgtgga   4860
ttgcgcatac tttgtgaaca gaaagtgata gcgttgatga ttcttcattg gtcagaaaat     4920
tatgaacggt ttcttctatt ttgtctctat atactacgta taggaaatgt ttacattttc    4980
gtattgtttt cgattcactc tatgaatagt tcttactaca atttttttgt ctaaagtaga    5040
atactagaga taaacataaa aaatgtagag gtcgagttta gatgcaagtt caaggagcga    5100
aaggtggatg ggtaggttat atagggatat agcacagaga tatatagcaa agagatactt    5160
ttgagcaatg tttgtggaag cggtattcgc aatatttttag tagctcgtta cagtccggtg  5220
cgttttttggt tttttgaaag tgcgtcttca gagcgctttt ggttttcaaa agcgctctga  5280
agttcctata ctttctagag aataggaact tcggaatagg aacttcaaag cgtttccgaa  5340
aacgagcgct tccgaaaatg caacgcgagc tgcgcacata cagctcactg ttcacgtcgc   5400
acctatatct gcgtgttgcc tgtatatata tatacatgag aagaacggca tagtgcgtgt   5460
ttatgcttaa atgcgtactt atatgcgtct atttatgtag gatgaaaggt agtctagtac   5520
ctcctgtgat attatcccat tccatgcggg gtatcgtatg cttccttcag cactacccctt  5580
tagctgttct atatgctgcc actcctcaat tggattagtc tcatccttca atgctatcat   5640
ttcctttgat attggatcat actaagaaac cattattatc atgacattaa cctataaaaa   5700
taggcgtatc acgaggccct ttcgtc                                         5726
```

<210> SEQ ID NO 24
<211> LENGTH: 8125
<212> TYPE: DNA
<213> ORGANISM: Artificial Sequence
<220> FEATURE:
<223> OTHER INFORMATION: Synthetic construct: pAM01147 plasmid

<400> SEQUENCE: 24

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat cattttttttt ttattctttt ttttgatttc   240
ggtttctttg aaatttttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt  420
```

```
cgaaagctac atataaggaa cgtgctgcta ctcatcctag tcctgttgct gccaagctat      480
ttaatatcat gcacgaaaag caaacaaact tgtgtgcttc attggatgtt cgtaccacca      540
aggaattact ggagttagtt gaagcattag gtcccaaaat ttgtttacta aaaacacatg      600
tggatatctt gactgatttt tccatggagg gcacagttaa gccgctaaag gcattatccg      660
ccaagtacaa ttttttactc ttcgaagaca gaaaatttgc tgacattggt aatacagtca      720
aattgcagta ctctgcgggt gtatacagaa tagcagaatg ggcagacatt acgaatgcac      780
acggtgtggt gggcccaggt attgttagcg gtttgaagca ggcggcagaa gaagtaacaa      840
aggaacctag aggccttttg atgttagcag aattgtcatg caagggctcc ctatctactg      900
gagaatatac taagggtact gttgacattg cgaagagcga caaagatttt gttatcggct      960
ttattgctca aagagacatg ggtggaagag atgaaggtta cgattggttg attatgacac     1020
ccggtgtggg tttagatgac aagggagacg cattgggtca acagtataga accgtggatg     1080
atgtggtctc tacaggatct gacattatta ttgttggaag aggactattt gcaaagggaa     1140
gggatgctaa ggtagagggt gaacgttaca gaaaagcagg ctgggaagca tatttgagaa     1200
gatgcggcca gcaaaactaa aaaactgtat tataagtaaa tgcatgtata ctaaactcac     1260
aaattagagc ttcaatttaa ttatatcagt tattacccta tgcggtgtga aataccgcac     1320
agatgcgtaa ggagaaaata ccgcatcagg aaattgtaaa cgttaatatt ttgttaaaat     1380
tcgcgttaaa tttttgttaa atcagctcat tttttaacca ataggccgaa atcggcaaaa     1440
tcccttataa atcaaagaa tagaccgaga tagggttgag tgttgttcca gtttggaaca     1500
agagtccact attaaagaac gtggactcca acgtcaaagg gcgaaaaacc gtctatcagg     1560
gcgatggccc actacgtgaa ccatcaccct aatcaagttt ttggggtcg aggtgccgta     1620 aagcactaaa tcggaacccct aaagggagcc cccgatttag agcttgacgg ggaaagccgg     1680
cgaacgtggc gagaaaggaa gggaagaaag cgaaaggagc gggcgctagg gcgctggcaa     1740
gtgtagcggt cacgctgcgc gtaaccacca cacccgccgc gcttaatgcg ccgctacagg     1800
gcgcgtcgcg ccattcgcca ttcaggctgc gcaactgttg ggaagggcga tcggtgcggg     1860
cctcttcgct attacgccag ctggcgaaag ggggatgtgc tgcaaggcga ttaagttggg     1920
taacgccagg gttttcccag tcacgacgtt gtaaaacgac ggccagtgag cgcgcgtaat     1980
acgactcact ataggggcgaa ttgggtaccg gccccccct cgaggtcgac ggtatcgata     2040
agcttgatat cgaattcctg cagcccgggg gatccactag ttctagagcg gccgcttatt     2100
gcagaagatt agacttttt tgttgcaagt gggatgagct tggagcagga agaatacact     2160
atactggatc taaagagtac aatagatgga taagaatatt ggcagcgcaa aaaggcttca     2220
agcttacaca acacggttta tttcgaaata atatccttct cgaaagcttt aacgaacgca     2280
gaattttcga gttattaaac ttaaaatacg ctgaacccga acatagaaat atcgaatggg     2340
aaaaaaaaac tgcataaagg cattaaaaga ggagcgaatt tttttttaat aaaaatctta     2400
ataatcatta aaagataaat aatagtctat atatacgtat ataaataaaa aatattcaaa     2460
aaataaaata aactattatt ttagcgtaaa ggatggggaa agagaaaaga aaaaattga     2520 tctatcgatt tcaattcaat tcaattcagt ggtgatggtg atgatgccct ttatcgtcat     2580
cgtccttata atcgaattcc tggcctctct tttgttttag aagtgcgacg gcacgatctg     2640
ctctgacatc gtgatattca actaattgtc tggcaaccca atcgacttcg tcgcccttg     2700 cacctgctac aaccgctata ttcctcgcat gcaaggccat gtgacccctt gaataccttt     2760
cagttgctaa agccctcatt gcacccaaat tttgagcaag accaacagcc acagcgatct     2820
```

```
ctgccaaggc ttgggcagtt ttaactccta atattcttaa agataattga gccagagggt    2880
gggtcttcgt tgcaccacct actaatccaa ccggcatcgg catctccaga gtaccgacta    2940
aatgaccatt attatccttc tcccaagtag ttagagaacc ataatgtccg gacctacaag    3000
cgtacgcgtg agccccagcc tctacggctc tccaatcgtt accagtagca acaattagtg    3060
gatctatgcc gttcataata cctttattat gtgtagcggc tctgtatggg tcaacagcgg    3120
cgaaagcata agcgtctaga ataccttcaa tcacagcctc ccccgaaaat tccgctgttt    3180
ccaattgctg tggggttatt cttacttgtg cacgagctaa tcttagatca gctaaattag    3240
acaagatcct tagacgcact tgaccgccag taattgcctc cattaatggt gcgacggctt    3300
cagccattgt gtttactgtg ttcgccccca ttgcatcacg aacatctacg attaagtgag    3360
caactaacat aggtcctcta ggagtgtcag cgaatgtatg cacttcgatg tctctacaac    3420
caccacctaa cgaatttaac aattgatctt ttctattagc caattctatt atctcatctt    3480
ttcttctcaa caatgaaagt ctggcgttta aggatcttg tataccaacg atttgtactt    3540
gagcatgcat aagtggggct gaactgctgg tggtgaaacc tccgttcgct cttgccaatt    3600
tagccatgta tgatgctgct gcaactatag atggttcctc aacgactagt gggaccaaaa    3660
catccctacc attaatttga aaattcgaag caacggcgta cggaagttcg aaagtaccta    3720
taacattttc gatcatacca ttagcgatgt ccataggcaa tgctccagcg ttggccaaca    3780
aagaaacgtc atcatggctt aatcccaata gttgtcctat gtgatctaaa cgagcagccg    3840
gactcaggtt tctgaatgct ggcaatctgc tatctaaaga catatgtttt gagggaatat    3900
tcaactgttt ttttttatca tgttgatgct ctgcataata atgcccataa atatttccga    3960
cctgctttta tatctttgct agccaaacta actgaacata gctacacatt attttcagct    4020
tggctatttt gtgaacactg tatagccagt ccttcggatc acggtcaaca gttgtccgag    4080
cgcttttttgg acccttttccc ttattttttgg gttaaggaaa atgacagaaa atatatctaa    4140
tgagccttcg ctcaacagtg ctccgaagta tagcttttcca aaaggagagg caaagcaatt    4200
taagaatgta tgaacaaaat aaaggggaaa aattacccccc tctactttac caaacgaata    4260
ctaccaataa tatttacaac ttttccttat gattttttca ctgaagcgct tcgcaatagt    4320
tgtgagcgat atcaaaagta acgaaatgaa cttcgcggct cgtgctatat tcttgttgct    4380
accgtccata tctttccata gattttcaat cttttgatgtc tccatggtgg tacagagaac    4440
ttgtaaacaa ttcggtccct acatgtgagg aaattcgctg tgacacgcgg ccgccaccgc    4500
ggtggagctc cagcttttgt tccctttagt gagggttaat tgcgcgcttg gcgtaatcat    4560
ggtcatagct gtttcctgtg tgaaattgtt atccgctcac aattccacac aacataggag    4620
ccggaagcat aaagtgtaaa gcctggggtg cctaatgagt gaggtaactc acattaattg    4680
cgttgcgctc actgcccgct ttccagtcgg gaaacctgtc gtgccagctg cattaatgaa    4740
tcggccaacg cgcggggaga ggcggtttgc gtattgggcg ctcttccgct tcctcgctca    4800
ctgactcgct gcgctcggtc gttcggctgc ggcgagcggt atcagctcac tcaaaggcgg    4860
taatacggtt atccacagaa tcaggggata acgcaggaaa gaacatgtga gcaaaaggcc    4920
agcaaaaggc caggaaccgt aaaaaggccg cgttgctggc gttttttccat aggctccgcc    4980
cccctgacga gcatcacaaa aatcgacgct caagtcagag gtggcgaaac ccgacaggac    5040
tataaagata ccaggcgttt ccccctggaa gctccctcgt gcgctctcct gttccgaccc    5100
tgccgcttac cggatacctg tccgcctttc tcccttcggg aagcgtggcg ctttctcata    5160
gctcacgctg taggtatctc agttcggtgt aggtcgttcg ctccaagctg ggctgtgtgc    5220
```

```
acgaaccccc cgttcagccc gaccgctgcg ccttatccgg taactatcgt cttgagtcca   5280
acccggtaag acacgactta tcgccactgg cagcagccac tggtaacagg attagcagag   5340
cgaggtatgt aggcggtgct acagagttct tgaagtggtg gcctaactac ggctacacta   5400
gaaggacagt atttggtatc tgcgctctgc tgaagccagt taccttcgga aaaagagttg   5460
gtagctcttg atccggcaaa caaaccaccg ctggtagcgg tggttttttt gtttgcaagc   5520
agcagattac gcgcagaaaa aaggatctca agaagatcc tttgatcttt tctacggggt   5580
ctgacgctca gtggaacgaa aactcacgtt aagggatttt ggtcatgaga ttatcaaaaa   5640
ggatcttcac ctagatcctt ttaaattaaa aatgaagttt taaatcaatc taaagtatat   5700
atgagtaaac ttggtctgac agttaccaat gcttaatcag tgaggcacct atctcagcga   5760
tctgtctatt tcgttcatcc atagttgcct gactccccgt cgtgtagata actacgatac   5820
gggagggctt accatctggc cccagtgctg caatgatacc gcgagaccca cgctcaccgg   5880
ctccagattt atcagcaata aaccagccag ccggaagggc cgagcgcaga agtggtcctg   5940
caactttatc cgcctccatc cagtctatta attgttgccg ggaagctaga gtaagtagtt   6000
cgccagttaa tagtttgcgc aacgttgttg ccattgctac aggcatcgtg gtgtcacgct   6060
cgtcgtttgg tatggcttca ttcagctccg gttcccaacg atcaaggcga gttacatgat   6120
cccccatgtt gtgcaaaaaa gcggttagct ccttcggtcc tccgatcgtt gtcagaagta   6180
agttggccgc agtgttatca ctcatggtta tggcagcact gcataattct cttactgtca   6240
tgccatccgt aagatgcttt tctgtgactg gtgagtactc aaccaagtca ttctgagaat   6300
agtgtatgcg gcgaccgagt tgctcttgcc cggcgtcaat acgggataat accgcgccac   6360
atagcagaac tttaaaagtg ctcatcattg gaaaacgttc ttcggggcga aaactctcaa   6420
ggatcttacc gctgttgaga tccagttcga tgtaacccac tcgtgcaccc aactgatctt   6480
cagcatcttt tactttcacc agcgtttctg ggtgagcaaa aacaggaagg caaaatgccg   6540
caaaaaaggg aataagggcg acacggaaat gttgaatact catactcttc ctttttcaat   6600
attattgaag catttatcag ggttattgtc tcatgagcgg atacatattt gaatgtattt   6660
agaaaaataa acaaataggg gttccgcgca catttccccg aaaagtgcca cctgaacgaa   6720
gcatctgtgc ttcattttgt agaacaaaaa tgcaacgcga gagcgctaat ttttcaaaca   6780
aagaatctga gctgcatttt tacagaacag aaatgcaacg cgaaagcgct attttaccaa   6840
cgaagaatct gtgcttcatt tttgtaaaac aaaaatgcaa cgcgagagcg ctaattttc   6900 aaacaaagaa tctgagctgc atttttacag aacagaaatg caacgcgaga cgctatttt   6960 accaacaaag aatctatact ctttttttgt tctacaaaaa tgcatcccga gagcgctatt   7020
tttctaacaa agcatcttag attacttttt ttctcctttg tgcgctctat aatgcagtct   7080
cttgataact ttttgcactg taggtccgtt aaggttagaa gaaggctact ttggtgtcta   7140
ttttctcttc cataaaaaaa gcctgactcc acttcccgcg tttactgatt actagcgaag   7200
ctgcgggtgc attttttcaa gataaaggca tccccgatta tattctatac cgatgtggat   7260
tgcgcatact ttgtgaacag aaagtgatag cgttgatgat tcttcattgg tcagaaaatt   7320
atgaacggtt tcttctattt tgtctctata tactacgtat aggaaatgtt tacattttcg   7380
tattgttttc gattcactct atgaatagtt cttactacaa tttttttgtc taaagagtaa   7440
tactagagat aaacataaaa aatgtagagg tcgagtttag atgcaagttc aaggagcgaa   7500
aggtggatgg gtaggttata tagggatata gcacagagat atatagcaaa gagatacttt   7560
tgagcaatgt ttgtggaagc ggtattcgca atattttagt agctcgttac agtccggtgc   7620
```

```
gtttttggtt ttttgaaagt gcgtcttcag agcgcttttg gttttcaaaa gcgctctgaa   7680
gttcctatac tttctagaga ataggaactt cggaatagga acttcaaagc gtttccgaaa   7740
acgagcgctt ccgaaaatgc aacgcgagct gcgcacatac agctcactgt tcacgtcgca   7800
cctatatctg cgtgttgcct gtatatatat atacatgaga agaacggcat agtgcgtgtt   7860
tatgcttaaa tgcgtactta tatgcgtcta tttatgtagg atgaaaggta gtctagtacc   7920
tcctgtgata ttatcccatt ccatgcgggg tatcgtatgc ttccttcagc actaccettt   7980 agctgttcta tatgctgcca ctcctcaatt ggattagtct catccttcaa tgctatcatt   8040
tcctttgata ttggatcata ctaagaaacc attattatca tgacattaac ctataaaaat   8100
aggcgtatca cgaggccctt tcgtc                                         8125
```

<210> SEQ ID NO 25
<211> LENGTH: 10881
<212> TYPE: DNA
<213> ORGANISM: Artificial Sequence
<220> FEATURE:
<223> OTHER INFORMATION: Synthetic construct: ERG10-ERG13 integration
      construct

<400> SEQUENCE: 25

```
agcgcccaat acgcaaaccg cctctccccg cgcgttggcc gattcattaa tgcagctggc   60
acgacaggtt tcccgactgg aaagcgggca gtgagcgcaa cgcaattaat gtgagttagc  120
tcactcatta ggcaccccag gctttacact ttatgcttcc ggctcgtatg ttgtgtggaa  180
ttgtgagcgg ataacaattt cacacaggaa acagctatga ccatgattac gccaagctat  240
ttaggtgaca ctatagaata ctcaagctat gcatcaagct tggtaccgag ctcggatcca  300
ctagtaacgg ccgccagtgt gctggaattc gcccttaaat atgaccccca atatgagaaa  360
ttaaggctag attattctca ggaaaaagct tttcatcttg aaatgctgca attatgtcgg  420
gtcccatttc tccacactta gcatctctct tataatgccc acagactaag ttccaatctc  480
ttagaaaagt ttcaccctga aaccttgtaa gctttctatg atgcacttca tgaacctgtt  540
gggaagcctt ggccttaccg cttaaataat cctggaagga tagctttggt gcttgaatag  600
ctccttcatc taaaaagat gcaaattcct cgatgtccgt ttccttaatt acataaagct  660
tcatgtcagg aataacaaaa aaataaagcc attcatcgtg ttgttttggc cttgaataa  720 attcattttg caaatgcacc gcatttatta gtattcctgg agaaccacct aaatgggagc  780
gcaatttact aatggcatta tatggccgat tgtattagt atccaaatta tgattccatg  840
ctaccttcca tggttgagca aacctatcac ccggtgataa cagcaaaaca tgcttattgt  900
aattgggcgt tctatgagga agcttgatat gaggatctaa tggatcagtt tttgaaggca  960
gccttgcgtt tatttcttgg caataacagt ttgtttgatc attttgagca cgggtatgaa 1020
gatcaggaac gctaatatgt ttgaagctat gatggaagga tgcccgctgc tgcaaagttt 1080
tgacagttat acgtagcatt ttatttttg tgtcagtgca ccttctctca cttttctact 1140
aaggaaattt gatatttcaa atgtagtatg ctaataaata agaacacccg catgcacgaa 1200
aaagggaaat ttaaaactag ttaggtaaac aaagttcaga acaagaaatg atatggttgt 1260
tttacataga tatatactca gtattcgttt ttataacgtt cgctgcactg ggggtctaa  1320 ggcgcctgat tcaagaaata tcttgaccgc agttaactgt gggaatactc aggtatcgta 1380
agatgcaaga gttcgaatct cttagcaacc attatttttt tcctcaacat aacgagaaca 1440
cacaggggcg ctatcgcaca gaatcaaatt cgatgactgg aaatttttg ttaatttcag 1500
```

-continued

```
aggtcgcctg acgcatatac cttttctcaac tgaaaaattg ggagaaaaag gaaaggtgag   1560
agcgccggaa ccggctttc atatagaata gagaagcgtt catgactaaa tgcttgcatc    1620
acaatacttg aagttgacaa tattatttaa ggacctattg ttttttccaa taggtggtta   1680
gcaatcgtct tactttctaa cttttcttac cttttacatt tcagcaatat atatatatat    1740
atttcaagga tataccattc taatgtctgc ccctaagaag atcgtcgttt tgccaggtga   1800
ccacgttggt caagaaatca cagccgaagc cattaaggtt cttaaagcta tttctgatgt    1860
tcgttccaat gtcaagttcg atttcgaaaa tcatttaatt ggtggtgctg ctatcgatgc    1920
tacaggtgtt ccacttccag atgaggcgct ggaagcctcc aagaaggctg atgccgtttt    1980
gttaggtgct gtgggtggtc ctaaatgggg taccggtagt gttagacctg aacaaggttt    2040
actaaaaatc cgtaaagaac ttcaattgta cgccaactta agaccatgta actttgcatc    2100
cgactctctt ttagacttat ctccaatcaa gccacaattt gctaaaggta ctgacttcgt    2160
tgttgtcaga gaattagtgg gaggtattta ctttggtaag agaaaggaag acgatggtga    2220
tggtgtcgct tgggatagtg aacaatacac cgttccagaa gtgcaaagaa tcacaagaat    2280
ggccgctttc atggcccctac aacatgagcc accattgcct atttggtcct tggataaagc    2340
taatgttttg gcctcttcaa gattatggag aaaaactgtg gaggaaacca tcaagaacga    2400
attccctaca ttgaaggttc aacatcaatt gattgattct gccgccatga tcctagttaa    2460
gaacccaacc cacctaaatg gtattataat caccagcaac atgtttggtg atatcatctc    2520
cgatgaagcc tccgttatcc caggttcctt gggtttgttg ccatctgcgt ccttggcctc    2580
tttgccagac aagaacaccg catttggttt gtacgaacca tgccacggtt ctgctccaga    2640
tttgccaaag aataaggtca accctatcgc cactatcttg tctgctgcaa tgatgttgaa    2700
attgtcattg aacttgcctg aagaaggtaa ggccattgaa gatgcagtta aaaaggtttt    2760
ggatgcaggt atcagaactg gtgatttagg tggttccaac agtaccaccg aagtcggtga    2820
tgctgtcgcc gaagaagtta agaaaatcct tgcttaaaaa gattctcttt ttttatgata    2880
tttgtacata aactttataa atgaaattca taatagaaac gacacgaaat tacaaaatgg    2940
aatatgttca tagggtagac gaaactatat acgcaatcta catacattta tcaagaagga    3000
gaaaaaggag gatgtaaagg aatacaggta agcaaattga tactaatggc tcaacgtaaa    3060
agtaagtcaa aaggcacacc tcagcgtttg agtacctgaa aaacgatgaa tcgcaaataa    3120
aactttaaat tatgcctgtt atacataaag ccatttatat atttatgtat tttatgaaaa    3180
agatcatgag aaaatcgcag aacgtaatca tatcttttca atgacaatag aggaagcacc    3240
accaccacca ttacaaatgg cggcaacacc gatcttacct ccttcttgct gtaagatgga    3300
tagcagtgta acaaccactc tagcaccaga acaacccaat gggtgaccta gagcaacagc    3360
accaccatat acattaacct tagatgggtc tagcttcaaa atcttagtgt tcaccaaacc    3420
gacaaccgaa aaggcttcat tgaattcaaa gtaatcaaca gaattgatgt cttcgatgcc    3480
agcatgtttc aaagcctttg gaactgcaag agatggagcc catgtaaaat cagctggttg    3540
atgagcggcc tcaccccaac ctttgataat agccaaaggc ttcaaattct tttccttcaa    3600
aactttttcg gaaaccaaga tgacggctgc agcaccatcg ttgattggag aagcgttagc    3660
ggcagtaaca gtaccgtttt cttttttggaa aacagtcctt gcagatctca attttctcaac    3720
gtgtaatcta gcaggttcct cgtccttcgt gacttgagta tcaggcttac ctctaaatcc    3780
cttaatggta acaggtacaa tttcattgtc gaatttacct tccttttgag attttttgaga    3840
tttttggtag gattcgatgg caaaattgtc ttgttgttct ctagtaatat cccaatcacg    3900
```

```
ggcacacttt tctgcgtgta cacccatggc tagaccatcg tacgcatcgt tcaacccatc     3960
tctttcgaca ccatcaacaa gaacagtttg gccaaatttg gcacccgcac gggctgctgg     4020
catgtagtat ggtgcgttag tcatagattc acaaccacca gctacgacaa catcagcatt     4080
accacatttg atggattgag cacccaaaat gattgccttc atagcggatg cacagacctt     4140
gttaactgtg cttgcaacga tatgattact caaaccggca gccaaagcaa cttgtctggc     4200
cggagcttgg cccaaattgg cagaaagaac gttaccaaaa ataatttcgt caaaatcctt     4260
ggatgcatcc aattctggaa ccttagccaa ggcgcctttt aaagcaacag cacccaattc     4320
cactgctgtc ttggaggata gagaaccctg gaatgaacca attggggttc tggcagtcga     4380
tacaatgtaa acgttctgag acattatagt ttttctcct tgacgttaaa gtatagaggt       4440
atattaacaa tttttgttg atacttttat gacatttgaa taagaagtaa tacaaaccga       4500
aaatgttgaa agtattagtt aaagtggtta tgcagctttt gcatttatat atctgttaat     4560
agatcaaaaa tcatcgcttc gctgattaat taccccagaa ataaggctaa aaaactaatc     4620
gcattattat cctatggttg ttaatttgat tcgttgattt gaaggtttgt ggggccaggt     4680
tactgccaat ttttcctctt cataaccata aaagctagta ttgtagaatc tttattgttc     4740
ggagcagtgc ggcgcgaggc acatctgcgt ttcaggaacg cgaccggtga agaccaggac     4800
gcacggagga gagtcttccg tcggagggct gtcgcccgct cggcggcttc taatccgtac     4860
ttcaatatag caatgagcag ttaagcgtat tactgaaagt tccaaagaga aggttttttt     4920
aggctaagat aatggggctc tttacatttc cacaacatat aagtaagatt agatatggat     4980
atgtatatgg tggtattgcc atgtaatatg attattaaac ttctttgcgt ccatccaaaa     5040
aaaaagtaag aattttttgaa aattcaatat aaatgaaact ctcaactaaa ctttgttggt     5100
gtggtattaa aggaagactt aggccgcaaa agcaacaaca attacacaat acaaacttgc     5160
aaatgactga actaaaaaaa caaaagaccg ctgaacaaaa aaccagacct caaaatgtcg     5220
gtattaaagg tatccaaatt tacatcccaa ctcaatgtgt caaccaatct gagctagaga     5280
aatttgatgg cgtttctcaa ggtaaataca caattggtct gggccaaacc aacatgtctt     5340
ttgtcaatga cagagaagat atctactcga tgtccctaac tgttttgtct aagttgatca     5400
agagttacaa catcgacacc aacaaaattg gtagattaga agtcggtact gaaactctga     5460
ttgacaagtc caagtctgtc aagtctgtct tgatgcaatt gtttggtgaa acactgacg     5520 tcgaaggtat tgacacgctt aatgcctgtt acggtggtac caacgcgttg ttcaactctt     5580
tgaactggat tgaatctaac gcatgggatg gtagagacgc cattgtagtt tgcggtgata     5640
ttgccatcta cgataagggt gccgcaagac caaccggtgg tgccggtact gttgctatgt     5700
ggatcggtcc tgatgctcca attgtatttg actctgtaag agcttcttac atggaacacg     5760
cctacgattt ttacaagcca gatttcacca gcgaatatcc ttacgtcgat ggtcattttt     5820
cattaacttg ttacgtcaag gctcttgatc aagtttacaa gagttattcc aagaaggcta     5880
tttctaaagg gttggttagc gatcccgctg gttcggatgc tttgaacgtt ttgaaatatt     5940
tcgactacaa cgtttttccat gttccaacct gtaaattggt cacaaaatca tacggtagat     6000
tactatataa cgatttcaga gccaatcctc aattgttccc agaagttgac gccgaattag     6060
ctactcgcga ttatgacgaa tctttaaccg ataagaacat tgaaaaaact tttgttaatg     6120
ttgctaagcc attccacaaa gagagagttg cccaatcttt gattgttcca acaaacacag     6180
gtaacatgta caccgcatct gtttatgccg cctttgcatc tctattaaac tatgttggat     6240
ctgacgactt acaaggcaag cgtgttggtt tattttctta cggttccggt ttagctgcat     6300
```

```
ctctatattc ttgcaaaatt gttggtgacg tccaacatat tatcaaggaa ttagatatta    6360
ctaacaaatt agccaagaga atcaccgaaa ctccaaagga ttacgaagct gccatcgaat    6420
tgagagaaaa tgcccatttg aagaagaact tcaaacctca aggttccatt gagcatttgc    6480
aaagtggtgt ttactacttg accaacatcg atgacaaatt tagaagatct tacgatgtta    6540
aaaaataatc ttcccccatc gattgcatct tgctgaaccc ccttcataaa tgctttattt    6600
ttttggcagc ctgcttttt tagctctcat ttaatagagt agtttttaa tctatatact    6660 aggaaaactc tttatttaat aacaatgata tatatataga cgggagtgga agaacggga    6720 aaccaactat cgagattgta tacgctggtc ggcaaggacc agcagtgaca tgtgatgtat    6780
atatattcag gttcaaaaaa aaagttatg agcttttggt tattatgaat gtagcagaca     6840
ttttgaggtc gttcgggcga gagtgcgccg gtaaatgaag aaaatatagg atattattaa    6900
tattagaatt aaactattat attgcagggg agagaagaaa ggggtataaa tatatattac    6960
aaagcggaaa acttgcgcca tttaaacaga gacatcgtcc gggcgctcgt gtgattttct    7020
tatagtgaag aagttaatac ctttaggttg gttttccgta gcagcagtgg cagtgaccgg    7080
attagcattg gaagaaggcc ccactatgct tgcactttgt tgcatgtctt caggtccagt    7140
ggcagtcaat attgggtcag ttgcttgctc cttctctcta tggaagggat tccatctgga    7200
ggaggttctg tatcttgaat tgtcgatgga gtaagtagag gccaaccttg ccctaacaga    7260
ccagaagacc agcaggataa attccacgat acataaaaag acacttgccc aagccatacc    7320
catcatagag gcacccaatt gggcactacg atgatcgtca tggaaagcat tctttgccat    7380
ggcagaggcg gccgtttgca agacaacggc tgccgtattg aagacaaacc caaaagacat    7440
gaggataagc accatctctg aaagcatctt cgagcaccaa gtcaaaacgt aaaggataaa    7500
cgacacacct acaaaggcaa gcgcaatcca aaagaaacaa aatgaaaatc tagtcaggta    7560
gtaaaaagcg tctcttttgg aaataaactg tgagggaca ttgatgtgtg tgttgaagtt     7620
atctactggg gaaatggggt atgcaggtgc caaattgctt gtgcaggtat ccgacccgtc    7680
tttatcctgt agacaggcaa gggcgaattc tgcagatatc catcacactg gcggccgctc    7740
gagcatgcat ctagagggcc caattcgccc tatagtgagt cgtattacaa ttcactggcc    7800
gtcgttttac aacgtcgtga ctgggaaaac cctggcgtta cccaacttaa tcgccttgca    7860
gcacatcccc ctttcgccag ctggcgtaat agcgaagagg cccgcaccga tcgcccttcc    7920
caacagttgc gcagcctata cgtacggcag tttaaggttt acacctataa aagagagagc    7980
cgttatcgtc tgtttgtgga tgtacagagt gatattattg acacgccggg gcgacggatg    8040
gtgatccccc tggccagtgc acgtctgctg tcagataaag tctcccgtga actttacccg    8100
gtggtgcata tcgggatga aagctggcgc atgatgacca ccgatatggc cagtgtgccg    8160
gtctccgtta tcggggaaga agtggctgat ctcagccacc gcgaaaatga catcaaaaac    8220
gccattaacc tgatgttctg gggaatataa atgtcaggca tgagattatc aaaaaggatc    8280
ttcacctaga tccttttcac gtagaaagcc agtccgcaga aacggtgctg acccccggatg   8340 aatgtcagct actgggctat ctggacaagg gaaaacgcaa gcgcaaagag aaagcaggta    8400
gcttgcagtg ggcttacatg gcgatagcta gactgggcgg ttttatggac agcaagcgaa    8460
ccggaattgc cagctgggc gccctctggt aaggttggga agccctgcaa agtaaactgg    8520
atggctttct cgccgccaag atctgatgg cgcagggat caagctctga tcaagagaca     8580
ggatgaggat cgtttcgcat gattgaacaa gatggattgc acgcaggttc tccggccgct    8640
tgggtggaga ggctattcgg ctatgactgg gcacaacaga caatcggctg ctctgatgcc    8700
```

```
gccgtgttcc ggctgtcagc gcaggggcgc ccggttcttt ttgtcaagac cgacctgtcc    8760
ggtgccctga atgaactgca agacgaggca gcgcggctat cgtggctggc cacgacgggc    8820
gttccttgcg cagctgtgct cgacgttgtc actgaagcgg aagggactg gctgctattg     8880
ggcgaagtgc cggggcagga tctcctgtca tctcaccttg ctcctgccga aaagtatcc     8940
atcatggctg atgcaatgcg gcggctgcat acgcttgatc cggctacctg cccattcgac    9000
caccaagcga aacatcgcat cgagcgagca cgtactcgga tggaagccgg tcttgtcgat    9060
caggatgatc tggacgaaga gcatcagggg ctcgcgccag ccgaactgtt cgccaggctc    9120
aaggcgagca tgcccgacgg cgaggatctc gtcgtgaccc atggcgatgc ctgcttgccg    9180
aatatcatgg tggaaaatgg ccgcttttct ggattcatcg actgtggccg gctgggtgtg    9240
gcggaccgct atcaggacat agcgttggct acccgtgata ttgctgaaga gcttggcggc    9300
gaatgggctg accgcttcct cgtgctttac ggtatcgccg ctcccgattc gcagcgcatc    9360
gccttctatc gccttcttga cgagttcttc tgaattatta cgcttacaa tttcctgatg     9420
cggtattttc tccttacgca tctgtgcggt atttcacacc gcatacaggt ggcacttttc    9480
ggggaaatgt gcgcggaacc cctatttgtt tattttttcta aatacattca aatatgtatc    9540
cgctcatgag acaataaccc tgataaatgc ttcaataata gcacgtgagg agggccacca    9600
tggccaagtt gaccagtgcc gttccggtgc tcaccgcgcg cgacgtcgcc ggagcggtcg    9660
agttctggac cgaccggctc gggttctccc gggacttcgt ggaggacgac ttcgccggtg    9720
tggtccggga cgacgtgacc ctgttcatca gcgcggtcca ggaccaggtg gtgccggaca    9780
acaccctggc ctgggtgtgg gtgcgcggcc tggacgagct gtacgccgag tggtcggagg    9840
tcgtgtccac gaacttccgg gacgcctccg ggccggccat gaccgagatc ggcgagcagc    9900
cgtggggggcg ggagttcgcc ctgcgcgacc cggccggcaa ctgcgtgcac ttcgtggccg    9960
aggagcagga ctgacacgtg ctaaaacttc attttttaatt taaaaggatc taggtgaaga   10020
tccttttttga taatctcatg accaaaatcc cttaacgtga gttttcgttc cactgagcgt   10080
cagaccccgt agaaaagatc aaaggatctt cttgagatcc ttttttttctg cgcgtaatct   10140
gctgcttgca aacaaaaaaa ccaccgctac cagcggtggt ttgtttgccg gatcaagagc   10200
taccaactct ttttccgaag gtaactggct tcagcagagc gcagatacca aatactgtcc   10260
ttctagtgta gccgtagtta ggccaccact tcaagaactc tgtagcaccg cctacatacc   10320
tcgctctgct aatcctgtta ccagtggctg ctgccagtgg cgataagtcg tgtcttaccg   10380
ggttggactc aagacgatag ttaccggata aggcgcagcg gtcgggctga acggggggtt   10440
cgtgcacaca gcccagcttg gagcgaacga cctacaccga actgagatac ctacagcgtg   10500
agctatgaga aagcgccacg cttcccgaag ggagaaaggc ggacaggtat ccggtaagcg   10560
gcagggtcgg aacaggagag cgcacgaggg agcttccagg gggaaacgcc tggtatcttt   10620
atagtcctgt cgggtttcgc cacctctgac ttgagcgtcg atttttgtga tgctcgtcag   10680
gggggcggag cctatggaaa aacgccagca acgcggcctt tttacggttc ctggccttt    10740
gctggccttt tgctcacatg ttctttcctg cgttatcccc tgattctgtg gataaccgta   10800
ttaccgcctt tgagtgagct gataccgctc gccgcagccg aacgaccgag cgcagcgagt   10860
cagtgagcga ggaagcggaa g                                              10881
```

<210> SEQ ID NO 26
<211> LENGTH: 24
<212> TYPE: DNA
<213> ORGANISM: Artificial Sequence
<220> FEATURE:

<223> OTHER INFORMATION: Synthetic primer YT_164_36_001

<400> SEQUENCE: 26
gcctgtctac aggataaaga cggg                                                    24

<210> SEQ ID NO 27
<211> LENGTH: 44
<212> TYPE: DNA
<213> ORGANISM: Artificial Sequence
<220> FEATURE:
<223> OTHER INFORMATION: Synthetic primer YT_164_36_002

<400> SEQUENCE: 27
tcccgttctt tccactcccg tctatatata tatcattgtt atta                              44

<210> SEQ ID NO 28
<211> LENGTH: 44
<212> TYPE: DNA
<213> ORGANISM: Artificial Sequence
<220> FEATURE:
<223> OTHER INFORMATION: Synthetic primer YT_164_36_003

<400> SEQUENCE: 28
taataacaat gatatatata tagacgggag tggaaagaac ggga                              44

<210> SEQ ID NO 29
<211> LENGTH: 54
<212> TYPE: DNA
<213> ORGANISM: Artificial Sequence
<220> FEATURE:
<223> OTHER INFORMATION: Synthetic primer YT_164_36_004

<400> SEQUENCE: 29
ccaacaaagt ttagttgaga gtttcattta tattgaattt tcaaaaattc ttac                   54

<210> SEQ ID NO 30
<211> LENGTH: 54
<212> TYPE: DNA
<213> ORGANISM: Artificial Sequence
<220> FEATURE:
<223> OTHER INFORMATION: Synthetic primer YT_164_36_005

<400> SEQUENCE: 30
gtaagaattt ttgaaaattc aatataaatg aaactctcaa ctaaactttg ttgg                   54

<210> SEQ ID NO 31
<211> LENGTH: 60
<212> TYPE: DNA
<213> ORGANISM: Artificial Sequence
<220> FEATURE:
<223> OTHER INFORMATION: Synthetic primer YT_164_36_006

<400> SEQUENCE: 31
gtcaaggaga aaaactata atgtctcaga acgtttacat tgtatcgact gccagaaccc              60

<210> SEQ ID NO 32
<211> LENGTH: 60
<212> TYPE: DNA
<213> ORGANISM: Artificial Sequence
<220> FEATURE:
<223> OTHER INFORMATION: Synthetic primer YT_164_36_007

<400> SEQUENCE: 32
gggttctggc agtcgataca atgtaaacgt tctgagacat tatagttttt tctccttgac             60

<210> SEQ ID NO 33

```
<211> LENGTH: 42
<212> TYPE: DNA
<213> ORGANISM: Artificial Sequence
<220> FEATURE:
<223> OTHER INFORMATION: Synthetic primer YT_164_36_008

<400> SEQUENCE: 33
gtgtgccttt tgacttactt ttacgttgag ccattagtat ca                    42

<210> SEQ ID NO 34
<211> LENGTH: 42
<212> TYPE: DNA
<213> ORGANISM: Artificial Sequence
<220> FEATURE:
<223> OTHER INFORMATION: Synthetic primer YT_164_36_009

<400> SEQUENCE: 34
tgatactaat ggctcaacgt aaaagtaagt caaaaggcac ac                    42

<210> SEQ ID NO 35
<211> LENGTH: 56
<212> TYPE: DNA
<213> ORGANISM: Artificial Sequence
<220> FEATURE:
<223> OTHER INFORMATION: Synthetic primer YT_164_36_010

<400> SEQUENCE: 35
gatatttctt gaatcaggcg ccttagaccc cccagtgcag cgaacgttat aaaaac     56

<210> SEQ ID NO 36
<211> LENGTH: 56
<212> TYPE: DNA
<213> ORGANISM: Artificial Sequence
<220> FEATURE:
<223> OTHER INFORMATION: Synthetic primer YT_164_36_011

<400> SEQUENCE: 36
gtttttataa cgttcgctgc actgggggt ctaaggcgcc tgattcaaga aatatc      56

<210> SEQ ID NO 37
<211> LENGTH: 31
<212> TYPE: DNA
<213> ORGANISM: Artificial Sequence
<220> FEATURE:
<223> OTHER INFORMATION: Synthetic construct: Linker YT_164_36_012

<400> SEQUENCE: 37
aaatatgacc cccaatatga gaaattaagg c                                31

<210> SEQ ID NO 38
<211> LENGTH: 54
<212> TYPE: DNA
<213> ORGANISM: Artificial Sequence
<220> FEATURE:
<223> OTHER INFORMATION: Synthetic primer YT_164_30_Gal3F

<400> SEQUENCE: 38
gagctcgcgg ccgcgtacat acctctctcc gtatcctcgt aatcattttc ttgt       54

<210> SEQ ID NO 39
<211> LENGTH: 46
<212> TYPE: DNA
<213> ORGANISM: Artificial Sequence
<220> FEATURE:
<223> OTHER INFORMATION: Synthetic primer YT_164_30_Gal3R

<400> SEQUENCE: 39
```

```
catatgacta tgtgttgccc tacctttta cttttatttt ctcttt              46
```

<210> SEQ ID NO 40
<211> LENGTH: 54
<212> TYPE: DNA
<213> ORGANISM: Artificial Sequence
<220> FEATURE:
<223> OTHER INFORMATION: Synthetic primer YT_164_30_Gal7F

<400> SEQUENCE: 40

```
gagctcgcgg ccgcgtgtca cagcgaatttt cctcacatgt agggaccgaa ttgt   54
```

<210> SEQ ID NO 41
<211> LENGTH: 46
<212> TYPE: DNA
<213> ORGANISM: Artificial Sequence
<220> FEATURE:
<223> OTHER INFORMATION: Synthetic primer YT_164_30_Gal7R

<400> SEQUENCE: 41

```
catatgtttt gagggaatat tcaactgttt tttttatca tgttga              46
```

<210> SEQ ID NO 42
<211> LENGTH: 28
<212> TYPE: DNA
<213> ORGANISM: Artificial Sequence
<220> FEATURE:
<223> OTHER INFORMATION: Synthetic construct: RYSE Linker 0

<400> SEQUENCE: 42

```
gacggcacgg ccacgcgttt aaaccgcc                                 28
```

<210> SEQ ID NO 43
<211> LENGTH: 27
<212> TYPE: DNA
<213> ORGANISM: Artificial Sequence
<220> FEATURE:
<223> OTHER INFORMATION: Synthetic construct: RYSE Linker 19

<400> SEQUENCE: 43

```
cccgccaggc gctggggttt aaacacc                                  27
```

<210> SEQ ID NO 44
<211> LENGTH: 2738
<212> TYPE: DNA
<213> ORGANISM: Artificial Sequence
<220> FEATURE:
<223> OTHER INFORMATION: Synthetic construct: Kan A-ADH1 disruption
      construct

<400> SEQUENCE: 44

```
gacggcacgg ccacgcgttt aaaccgccaa tgggctaaac aagactacac caattacact   60
gcctcattga tgtggtaca taacgaacta atactgtagc cctagacttg atagccatca  120
tcatatcgaa gtttcactac cctttttcca tttgccatct attgaagtaa taataggcgc  180
atgcaacttc ttttcttttt ttttcttttc tctctccccc gttgttgtct caccatatcc  240
gcaatgacaa aaaatgatg gaagacacta aggaaaaaa ttaacgacaa agacagcacc  300
aacagatgtc gttgttccag agctgatgag gggtatctcg aagcacacga aacttttcc  360
ttccttcatt cacgcacact actctctaat gagcaacggt atacgccctt ccttccagtt  420
acttgaattt gaaataaaaa aaagtttgct gtcttgctat caagtataaa tagacctgca  480
attattaatc ttttgtttcc tcgtcattgt tctcgctcac acgcggccag ggggagcctc  540
gacactagta atacacatca tcgtcctaca agttcatcaa agtgttggac agacaactat  600
```

```
accagcatgg atctcttgta tcggttcttt tctcccgctc tctcgcaata acaatgaaca    660
ctgggtcaat catagcctac acaggtgaac agagtagcgt ttatacaggg tttatacggt    720
gattcctacg gcaaaaattt ttcatttcta aaaaaaaaaa gaaaaatttt tctttccaac    780
gctagaagga aagaaaaat ctaattaaat tgatttggtg attttctgag agttcccttt    840
ttcatatatc gaattttgaa tataaaagga gatcgaaaaa attttctat tcaatctgtt    900 ttctggtttt atttgatagt ttttttgtgt attattatta tggattagta ctggtttata    960 tgggttttc tgtataactt cttttttattt tagtttgttt aatcttattt tgagttacat   1020
tatagttccc taactgcaag agaagtaaca ttaaaaatgg gtaaggaaaa gactcacgtt   1080
tcgaggccgc gattaaattc caacatggat gctgatttat atgggtataa atgggctcgc   1140
gataatgtcg ggcaatcagg tgcgacaatc tatcgattgt atgggaagcc cgatgcgcca   1200
gagttgtttc tgaaacatgg caaaggtagc gttgccaatg atgttacaga tgagatggtc   1260 agactaaaact ggctgacgga atttatgcct cttccgacca tcaagcattt tatccgtact   1320
cctgatgatg catggttact caccactgcg atccccggca aaacagcatt ccaggtatta   1380
gaagaatatc ctgattcagg tgaaaatatt gttgatgcgc tggcagtgtt cctgcgccgg   1440
ttgcattcga ttcctgtttg taattgtcct tttaacagcg atcgcgtatt tcgtctcgct   1500
caggcgcaat cacgaatgaa taacggttg gttgatgcga gtgattttga tgacgagcgt   1560
aatggctggc ctgttgaaca gtctggaaa gaaatgcata agcttttgcc attctcaccg   1620
gattcagtcg tcactcatgg tgatttctca cttgataacc ttattttga cgaggggaaa   1680 ttaataggtt gtattgatgt tggacgagtc ggaatcgcag accgatacca ggatcttgcc   1740
atcctatgga actgcctcgg tgagttttct ccttcattac agaaacggct ttttcaaaaa   1800
tatggtattg ataatcctga tatgaataaa ttgcagtttc atttgatgct cgatgagttt   1860
ttctaagttt aacttgatac tactagattt tttctcttca tttataaaat ttttggttat   1920
aattgaagct ttagaagtat gaaaaaatcc ttttttttca ttctttgcaa ccaaaataag   1980
aagcttcttt tattcattga aatgatgaat ataaacctaa caaagaaaa agactcgaat   2040 atcaaacatt aaaaaaaaat aaaagaggtt atctgttttc ccatttagtt ggagtttgca   2100
ttttctaata gatagaactc tcaattaatg tggatttagt ttctctgttc gttttttttt   2160
gttttgttct cactgtattt acatttctat ttagtattta gttattcata taatcttaac   2220
ttctcgagga gctccgctcg tccaacgccg gcggaccttt taaaacgaaa attcttattc   2280
ttgagtaact ctttcctgta ggtcaggttg ctttctcagg tatagcatga ggtcgctctt   2340
attgaccaca cctctaccgg catgccgagc aaatgcctgc aaatcgctcc ccatttcacc   2400
caattgtaga tatgctaact ccagcaatga gttgatgaat ctcggtgtgt attttatgtc   2460
ctcagaggac aacacctgtt gtaatcgttc ttccacacgg atccacagcc tagccttcag   2520
ttgggctcta tcttcatcgt cattcattgc atctactagc cccttacctg agcttcaaga   2580
cgttatatcg cttttatgta tcatgatctt atcttgagat atgaatacat aaatatattt   2640
actcaagtgt atacgtgcat gctttttta cggcagcatt ttttttttcaa ctctgatcgc   2700 cccttactg cggtgtttaa accccagcgc ctggcggg                             2738
```

<210> SEQ ID NO 45
<211> LENGTH: 3059
<212> TYPE: DNA
<213> ORGANISM: Artificial Sequence
<220> FEATURE:
<223> OTHER INFORMATION: Synthetic construct: i2235 integration construct

<400> SEQUENCE: 45

```
gacggcacgg ccacgcgttt aaaccgcctc gatatttcct gtgagaagtt taaatccact    60
aaggtttttc attgttgctg cagatgtgtt tttccattca tcctgaaata tgcactgcta   120
ttccgcattc cattcccta gtctttttta gttctttccg ttcgaccttc atcgaaaaat   180
gacaaaacgc gttaggaaca acaaccaatt gcaaacaagc agtgaaacaa aaccatcaag   240
gcccgaaaat acaagtgtgt actaatacag taagtaggtc aaatacgcaa tgaccaaaga   300
tgccgtgaat ctagatgctt acaccgtgag cttcatgcct ttctataccg agtatcaagg   360
accaaccgaa gagtttaagg attacaaatt cgaagatact atttactttc gtggcaagga   420
actgaagagg gaaagtctg cgacgccttc cagtagcgat aacacaacta gtaatacctt   480
cagtaatggc gccatcctct cgggaaacac aataactggc aagatagttt cagtgaataa   540
ttacgaaaga gagggcactg atcgcaacga attggcgcga ttgcaagaat tgatctccct   600
catcgatgtc ataaatcagt aaatataagc tcacacgcgg ccaggggag cccgttgagc   660
cattagtatc aatttgctta cctgtattcc tttactatcc tcctttttct ccttcttgat   720
aaatgtatgt agattgcgta tatagtttcg tctaccctat gaacatattc cattttgtaa   780
tttcgtgtcg tttctattat gaatttcatt tataaagttt atgtacaaat atcataaaaa   840
aagagaatct ttttaagcaa ggattttctt aacttcttcg gcgacagcat caccgacttc   900
ggtggtactg ttggaaccac ctaaatcacc agttctgata cctgcatcca aaaccttttt   960
aactgcatct tcaatggcct taccttcttc aggcaagttc aatgacaatt tcaacatcat  1020
tgcagcagac aagatagtgg cgatagggtc aaccttattc tttggcaaat ctggagcaga  1080
accgtggcat ggttcgtaca aaccaaatgc ggtgttcttg tctggcaaag aggccaagga  1140
cgcagatggc aacaaaccca aggaacctgg gataacggag gcttcatcgg agatgatatc  1200
accaaacatg ttgctggtga ttataatacc atttaggtgg gttgggttct taactaggat  1260
catggcggca gaatcaatca attgatgttg aaccttcaat gtagggaatt cgttcttgat  1320
ggtttcctcc acagttttt tccataatct tgaagaggcc aaaacattag ctttatccaa  1380
ggaccaaata ggcaatggtg gctcatgttg tagggccatg aaagcggcca ttcttgtgat  1440
tctttgcact tctggaacgg tgtattgttc actatcccaa gcgacaccat caccatcgtc  1500
ttcctttctc ttaccaaagt aaatacctcc cactaattct ctgacaacaa cgaagtcagt  1560
acctttagca aattgtggct tgattggaga taagtctaaa agagagtcgg atgcaaagtt  1620
acatggtctt aagttggcgt acaattgaag ttctttacgg atttttagta aaccttgttc  1680
aggtctaaca ctaccggtac cccatttagg accacccaca gcacctaaca aaacggcatc  1740
aaccttcttg gaggcttcca gcgcctcatc tggaagtggg acacctgtag catcgatagc  1800
agcaccacca attaaatgat tttcgaaatc gaacttgaca ttggaacgaa catcagaaat  1860
agctttaaga accttaatgg cttcggctgt gatttcttga ccaacgtggt cacctggcaa  1920
aacgacgatc ttcttagggg cagacatagg ggcagacatt agaatggtat atccttgaaa  1980
tatatatata tattgctgaa atgtaaaagg taagaaaagt tagaaagtaa gacgattgct  2040
aaccacctat tggaaaaaac aataggtcct taaataatat tgtcaacttc aagtattgtg  2100
atgcaagcat ttagtcatga acgcttctct attctatatg aaaagccggt tccggcctct  2160
cacctttcct ttttctccca attttcagt tgaaaaaggt atatgcgtca ggcgacctct  2220
gaaattaaca aaaaatttcc agtcatcgaa tttgattctg tgcgatagcg ccctgtgtg   2280
```

-continued

```
ttctcgttat gttgaggaaa aaaataatgg ttgctaagag attcgaactc ttgcatctta    2340
cgatacctga gtattcccac agttaactgc ggtcaagata tttcttgaat caggcgcctc    2400
gctcgtccaa cgccggcgga cctcttaaat gagaaaaatt tcgtaatgag ataaaatttc    2460 gctcctttc tgttttctat tttctatttt cccaacttt gctctattca gttataaatt     2520
actatttatc catcagttaa aaaacaagat cttttactgg tcagctagga aagcgaaaat    2580
acaaagactt tatgcactta gtgatatata tgtatagata tatccatttt tacgcactta   2640
tcatatatct tagttatcta aatacaatct agttattcgt acacaatcgc ccctgttatc    2700
cctatagtgg gaataaagta atgcactgtg acggggttct tcgcccggga tagggtaaaa    2760
ggatattgcc gtttcaagaa acttcgggga taatcgaata agataccgag aaagctattg    2820
ttcgttgtgc acgtaggatg tatattgaac aagcatgacc agaatctgat gcattacgag    2880
aaggttacgg gatgatatca gacctccgaa gtccatgttg caaaatgtgc cgactttccg    2940
cggcgctatt tggcacaaat ttcaggagaa acatcactgt cggtgttata gaattccatc    3000
tatattgttt tccccgtagg catacgtcga gcggtgttta accccagcg cctggcggg     3059
```

<210> SEQ ID NO 46
<211> LENGTH: 8106
<212> TYPE: DNA
<213> ORGANISM: Artificial Sequence
<220> FEATURE:
<223> OTHER INFORMATION: Synthetic construct: i74804 integration
      construct

<400> SEQUENCE: 46

```
gacggcacgg ccacgcgttt aaaccgcccg ctcgcctcat ccccacggga ataaggcagc      60
cgacaaaaga aaacgaccg aaaaggaacc agaaagaaaa aagagggtgg gcgcgccgcg     120
gacgtgtaaa aagatatgca tccagcttct atatcgcttt aactttaccg ttttgggcat    180
cgggaacgta tgtaacattg atctcctctt gggaacggtg agtgcaacga atgcgatata    240
gcaccgacca tgtgggcaaa ttcgtaataa attcggggtg aggggattc aagacaagca    300 accttgttag tcagctcaaa cagcgattta acggttgagt aacacatcaa acaccgttc    360 gaggtcaagc ctggcgtgtt taacaagttc ttgatatcat atataaatgt aataagaagt    420
ttggtaatat tcaattcgaa gtgttcagtc ttttacttct cttgttttat agaagaaaaa    480
acatcaagaa acatctttaa catacacaaa cacatactat cagaatacac gctcgtccaa    540
cgccggcgga cctttcagac gcgactgcct catcagtaag acccgttgaa aagaacttac    600
ctgaaaaaaa cgaatatata ctagcgttga atgttagcgt caacaacaag aagtttaatg    660
acgcggaggc caaggcaaaa agattccttg attacgtaag ggagttagaa tcattttgaa    720
taaaaaacac gcttttcag ttcgagttta tcattatcaa tactgccatt tcaaagaata    780
cgtaaataat taatagtagt gattttccta actttattta gtcaaaaaat tagcctttta    840
attctgctgt aacccgtaca tgcccaaaat aggggcggg ttacacagaa tatataacat    900
cgtaggtgtc tgggtgaaca gtttattcct ggcatccact aaatataatg gagcccgctt    960
tttaagctgg catccagaaa aaaaagaat cccagcacca aatatattgt ttcttcacca   1020
accatcagtt cataggtcca ttctcttagc gcaactacag agaacagggg cacaaacagg   1080
caaaaaacgg gcacaacctc aatggagtga tgcaacctgc ctggagtaaa tgatgacaca   1140
aggcaattga cccacgcatg tatctatctc attttcttac accttctatt accttctgct   1200
ctctctgatt tggaaaagc tgaaaaaaa ggttgaaacc agttccctga aattattccc    1260
ctacttgact aataagtata taagacggt aggtattgat tgtaattctg taaatctatt    1320
```

```
tcttaaactt cttaaattct acttttatag ttagtctttt ttttagtttt aaaacaccaa   1380
gaacttagtt tcgacctccc gcgacctcca aaatcgaact accttcacaa tggaacattc   1440
tgtaatcgaa ccaactgtgc ccatgccgct accagccatg tttgacgctc catctggtat   1500
ttttagctct ttggacgacg ctgtgcaagc agccacctta gcccaacaac aactaagttc   1560
agttgagttg cgtcagcaag taatcaaagc cataagagtg gccggagaaa ggtatgcaca   1620
agttttggct gaaatggcag ttgctgaaac tggtatgggt agggtggtgg ataagtacat   1680
taagaatgtc tctcaagctc gtcatacgcc tggtatagaa tgtttatcgg ccgaggttct   1740
tacgggtgat aatggcctaa cattgattga aaatgcccct tggggagtcg tagcttcagt   1800
cacgccaagc acaaatccag cagctacggt aattaataat gcaatctcaa tgattgcagc   1860
ggggaattca gtcgtgttcg caccacatcc ttctgccaaa aacgtctcac taaggactat   1920
ttctttactc aacaaggcca ttgtcgctac cggcggccca gaaaatttac tagttagtgt   1980
ggcaaaccct aacatcgaaa ctgcacagag attattcaga tatccgggta ttggattgtt   2040
agttgtgaca ggtggtgaag ccgtcgttga agccgctagg aagcatacag ataaaaggtt   2100
aattgcagcc ggcgctggta atcctcctgt tgttgtggac gaaactgctg atatacctaa   2160
agccgcaaga gcaattgtca agggtgcttc tttcgacaac aacataattt gtgctgatga   2220
aaaagttttg attgtggtag acagagttgc agatgcacta ttggcagaaa tgcaaagaaa   2280
taacgccgtc ttacttacac ccgaacagac cgaaagacta ctacccgctc ttttgtccga   2340
tattgacgaa cagggcaaag gacgtgtgaa tagagattat gttggaagag atgcggctaa   2400
attagcagcg gctattggtc tggaagttag cgaacatact cgtctactcc tggcagagac   2460
agacgctgat catccattcg ccgtgacgga gctgatgatg ccagtgttac cagtaataag   2520
agtcaagaat gtagatgatg caatcgcatt ggcagttaag ctagagtcag gctgcagaca   2580
cacagctgcg atgcactcta ctaatataag aaacttaaat agaatggcta atgccatcaa   2640
tacctctatc tttgtaaaaa atggtccatg tattgcaggt ttgggtttag gcggtgaagg   2700
ttggacttca atgactatta gcactccgac cggtgaaggt gttacaagcg ctcgtacctt   2760
tgtcagatta agaaggtgtg tcttagtcga catgtttcgg attgcttaag cggccgcgag   2820
taataattat tgcttccata taatattttt atatacctct tattttatg tattagttaa   2880 ttaagtatt ttatctatct gcttatcatt ttcttttcat atagggggg ttggtgtttt   2940 cttgcccatc agattgatgt cctccaactc ggcactattt tacaaagggt ttttttgtaa   3000
gagaaggaga agacagatac taaaccatac gttactcgaa acaaaaaaaa aaaaatgga   3060 aaaagctgct atcaacaaaa gacggcctca tcaaacctaa agaaccatg tcagcgtatg   3120 tatatacctt gtaatttacg tttccttaaa tcttctttct actaacgttt tcattattct   3180
atactctatg accaataaaa acagactgta ctttcaaaat ttacccagta ggccagcaaa   3240
taaagaaaat tataccagat tacttctgaa acacattaat cccaacaaca agtatgccat   3300
taatccgtcg ctaccccatc cccgcgtgct tggccggccg tacactgagt aatggtagtt   3360
ataagaaaga gaccgagtta gggacagtta gaggcggtgg agatattcct tatggcatgt   3420
ctggcgatga taaaactttt caaacggcag ccccgatcta aaagagctga cagggaaatg   3480
gtcagaaaaa gaaacgtgca cccgcccgtc tggacgcgcc gctcacccgc acggcagaga   3540
ccaatcagta aaaatcaacg gttaacgaca ttactatata tataatatag gaagcattta   3600
atagaacagc atcgtaatat atgtgtactt tgcagttatg acgccagatg gcagtagtgg   3660
aagatattct ttattgaaaa atagcttgtc accttacgta caatcttgat ccggagcttt   3720
```

```
tcttttttg ccgattaaga attcggtcga aaaagaaaa ggagagggcc aagagggagg    3780
gcattggtga ctattgagca cgtgagtata cgtgattaag cacacaaagg cagcttggag    3840
tatgtctgtt attaatttca caggtagttc tggtccattg gtgaaagttt gcggcttgca    3900
gagcacagag gccgcagaat gtgctctaga ttccgatgct gacttgctgg gtattatatg    3960
tgtgcccaat agaaagagaa caattgaccc ggttattgca aggaaaattt caagtcttgt    4020
aaaagcatat aaaaatagtt caggcactcc gaaatacttg gttggcgtgt ttcgtaatca    4080
acctaaggag gatgttttgg ctctggtcaa tgattacggc attgatatcg tccaactgca    4140
tggagatgag tcgtggcaag aataccaaga gttcctcggt ttgccagtta ttaaaagact    4200
cgtatttcca aaagactgca acatactact cagtgcagct tcacagaaac ctcattcgtt    4260
tattcccttg tttgattcag aagcaggtgg gacaggtgaa cttttggatt ggaactcgat    4320
ttctgactgg gttggaaggc aagagagccc cgaaagctta cattttatgt tagctggtgg    4380
actgacgcca gaaaatgttg gtgatgcgct tagattaaat ggcgttattg gtgttgatgt    4440
aagcggaggt gtggagacaa atggtgtaaa agactctaac aaaatagcaa atttcgtcaa    4500
aaatgctaag aaataggtta ttactgagta gtatttattt aagtattgtt tgtgcacttg    4560
cctgcaggcc ttttgaaaag caagcataaa agatctaaac ataaaatctg taaaataaca    4620
agatgtaaag ataatgctaa atcatttggc tttttgattg attgtacagg aaaatataca    4680
tcgcagggggg ttgacttta ccatttcacc gcaatggaat caaacttgtt gaagagaatg    4740
ttcacaggcg catacgctac aatgacacgg ccggccaagc acgcggggat ggggtagcga    4800
cggattaatg gcatacttgt tgttgggatt aatgtgtttc agaagtaatc tggtataatt    4860
ttctttattt gctggcctac tgggtaaatt ttgaaagtac agtctgtttt tattggtcat    4920
agagtataga ataatgaaaa cgttagtaga agaagattt aaggaaacgt aaattacaag    4980
gtatatacat acgctgacat ggtttcttta ggtttgatga ggccgtcttt tgttgatagc    5040
agcttttcc attttttttt ttttttgttc gagtaacgta tggtttagta tctgtcttct    5100
ccttctctta caaaaaaacc ctttgtaaaa tagtgccgag ttggaggaca tcaatctgat    5160
gggcaagaaa acaccaaccc cccctatatg aaaagaaaat gataagcaga tagataaaaa    5220
tacttaatta actaatacat aaaaataaga ggtatataaa aatattatat ggaagcaata    5280
attattactc gcggccgctt aagcaatccg aaacatgtcg actaagacac accttcttaa    5340
tctgacaaag gtacgagcgc ttgtaacacc ttcaccggtc ggagtgctaa tagtcattga    5400
agtccaacct tcaccgccta aacccaaacc tgcaatacat ggaccatttt ttacaaagat    5460
agaggtattg atggcattag ccattctatt taagtttctt atattagtag agtgcatcgc    5520
agctgtgtgt ctgcagcctg actctagctt aactgccaat gcgattgcat catctacatt    5580
cttgactctt attactggta acactggcat catcagctcc gtcacggcga atggatgatc    5640
agcgtctgtc tctgccagga gtagacgagt atgttcgcta acttccagac caatagccgc    5700
tgctaattta gccgcatctc ttccaacata atctctattc acacgtcctt tgccctgttc    5760
gtcaatatcg gacaaaagag cgggtagtag tctttcggtc tgttcgggtg taagtaagac    5820
ggcgttattt ctttgcattt ctgccaatag tgcatctgca actctgtcta ccacaatcaa    5880
aacttttca tcagcacaaa ttatgttgtt gtcgaaagaa gcacccttga caattgctct    5940
tgcggcttta ggtatgtcag cagtttcgtc cacaacaaca ggaggattac cagcgccggc    6000
tgcaattaac cttttatctg tatgcttcct agcggcttca acgacggctt caccacctgt    6060
cacaactaac aatccaatac ccggatatct gaataatctc tgtgcagttt cgatgttagg    6120
```

```
gtttgccaca ctaactagta aattttctgg gccgccggta gcgacaatgg ccttgttgag    6180
taaagaaata gtccttagtg agacgttttt ggcagaagga tgtggtgcga acacgactga    6240
attccccgct gcaatcattg agattgcatt attaattacc gtagctgctg gatttgtgct    6300
tggcgtgact gaagctacga ctccccaagg ggcattttca atcaatgtta ggccattatc    6360
acccgtaaga acctcggccg ataaacattc tataccaggc gtatgacgag cttgagagac    6420
attcttaatg tacttatcca ccaccctacc cataccagtt tcagcaactg ccatttcagc    6480
caaaacttgt gcataccttt ctccggccac tcttatggct ttgattactt gctgacgcaa    6540
ctcaactgaa cttagttgtt gttgggctaa ggtggctgct gcacagcgt cgtccaaaga    6600
gctaaaaata ccagatggag cgtcaaacat ggctggtagc ggcatgggca cagttggttc    6660
gattacagaa tgttccattg tgaaggtagt tcgattttgg aggtcgcggg aggtcgaaac    6720
taagttcttg gtgttttaaa actaaaaaaa agactaacta taaagtaga atttaagaag    6780
tttaagaaat agatttacag aattacaatc aatacctacc gtctttatat acttattagt    6840
caagtagggg aataatttca gggaactggt ttcaaccttt ttttttcagct ttttccaaat    6900
cagagagagc agaaggtaat agaaggtgta agaaaatgag atagatacat gcgtgggtca    6960
attgccttgt gtcatcattt actccaggca ggttgcatca ctccattgag gttgtgcccg    7020
ttttttgcct gtttgtgccc ctgttctctg tagttgcgct aagagaatgg acctatgaac    7080
tgatggttgg tgaagaaaac aatattttgg tgctgggatt cttttttttt ctggatgcca    7140
gcttaaaaag cgggctccat tatatttagt ggatgccagg aataaactgt tcacccagac    7200
acctacgatg ttatatattc tgtgtaaccc gcccctatt ttgggcatgt acgggttaca    7260
gcagaattaa aaggctaatt ttttgactaa ataaagttag gaaaatcact actattaatt    7320
atttacgtat tctttgaaat ggcagtattg ataatgataa actcgaactg aaaaagcgtg    7380
tttttttattc aaaatgattc taactcccctt acgtaatcaa ggaatctttt tgccttggcc    7440
tccgcgtcat taaacttctt gttgttgacg ctaacattca acgctagtat atattcgttt    7500
ttttcaggta agttctttttc aacgggtctt actgatgagg cagtcgcgtc tgaaaggtcc    7560
gccggcgttg gacgagcgtg taccaacctg catttctttc cgtcatatac acaaaatact    7620
ttcatataaa cttacttggt cttacgtcat aaataaatat gtatacatat aaattaaaaa    7680
atttggtttt atattttttac aaaaagaatc gtttacttca tttctcccctt ttaagcgata    7740
caatccatga aaaagagaa aaagagagaa caggcttgtg ccttctttaa aacatcccac    7800
acaaaatcat attgaattga attttacatc ttaagctagt gtacaacaac tgctatatcc    7860
aaagaaaact aacgtggacc gcttttagag ttgagaaaaa ggtttgaaaa aaatagcaat    7920
acaaagactt gtttcatata taaaaatacag ggagcacatt gagctaatat aacataaaca    7980
ctgcgaacca attccaatca aaggtacac atgagagcat tccccgagt actgccattt    8040
cgccatcaga gatcatataa taacatcctt cttcgaacgg cggtttaaac gcgtggccgt    8100
gccgtc                                                                8106
```

<210> SEQ ID NO 47
<211> LENGTH: 2404
<212> TYPE: DNA
<213> ORGANISM: Artificial Sequence
<220> FEATURE:
<223> OTHER INFORMATION: Synthetic construct: i76220 integration construct

<400> SEQUENCE: 47

```
gacggcacgg ccacgcgttt aaaccgccgc acgtgtatgt acggctgtgt aaatatgata    60
atcatctcgg acgaacggcg tagtactctc catcccctaa aaatgttcac gtgtgactgc   120
tccatttcgc cggatgtcga gatgaccccc ccccctcaaa aggcactcac ctgctgacat   180
gccgtggcaa atgattgggg tcatcctttt tttctgttat ctctaagatc caagaaaaag   240
taaaaaaaaa aggttggggt acgaattgcc gccgagcctc cgatgccatt attcaatggg   300
tattgcagtt ggggtatagt tcctcggtgg caaatagttc tcccttcatt ttgtatataa   360
actgggcggc tattctaagc atatttctcc cttaggttat ctggtagtac gttatatctt   420
gttcttatat tttctatcta taagcaaaac caaacatatc aaaactacta gaaagacatt   480
gccccactgt gttcgctcgt ccaacgccgg cggacctttc tcgacgtggg cctttttctt   540
gccatatgga tccgctgcac ggtcctgttc cctagcatgt acgtgagcgt atttcctttt   600
aaaccacgac gctttgtctt cattcaacgt ttcccattgt ttttttctac tattgctttg   660
ctgtgggaaa aacttatcga aagatgacga cttttttctta attctcgttt taagagcttg   720
gtgagcgcta ggagtcactg ccaggtatcg tttgaacacg gcattagtca gggaagtcat   780
aacacagtcc tttcccgcaa ttttcttttt ctattactct tggcctcctc tagtacactc   840
tatatttttt tatgcctcgg taatgatttt cattttttttt tttccaccta gcggatgact   900
cttttttttt cttagcgatt ggcattatca cataatgaat tatacattat ataaagtaat   960
gtgatttctt cgaagaatat actaaaaaat gagcaggcaa gataaacgaa ggcaaagatg  1020
acagagcaga aagccctagt aaagcgtatt acaaatgaaa ccaagattca gattgcgatc  1080
tctttaaagg gtggtcccct agcgatagag cactcgatct tcccagaaaa agaggcagaa  1140
gcagtagcag aacaggccac acaatcgcaa gtgattaacg tccacacagg tatagggttt  1200
ctggaccata tgatacatgc tctggccaag cattccggct ggtcgctaat cgttgagtgc  1260
attggtgact tacacataga cgaccatcac accactgaag actgcgggat tgctctcggt  1320
caagctttta aagaggccct aggggccgtg cgtggagtaa aaaggtttgg atcaggattt  1380 gcgccttttgg atgaggcact tccagagcg gtggtagatc tttcgaacag gccgtacgca  1440
gttgtcgaac ttggtttgca aagggagaaa gtaggagatc tctcttgcga gatgatcccg  1500
cattttcttg aaagctttgc agaggctagc agaattaccc tccacgttga ttgtctgcga  1560
ggcaagaatg atcatcaccg tagtgagagt gcgttcaagg ctcttgcggt tgccataaga  1620
gaagccacct cgcccaatgg taccaacgat gttccctcca ccaaaggtgt tcttatgtag  1680
tgacaccgat tatttaaagc tgcagcatac gatatatata catgtgtata tatgtatacc  1740
tatgaatgtc agtaagtatg tatacgaaca gtatgatact gaagatgaca aggtaatgca  1800
tcattctata cgtgtcattc tgaacggagc gcgctttcct tttttctttt tgcttttttct  1860 tttttttttct cttgaactcg aggtccgccg gcgttggacg agcgtgatga tttctttcct  1920
ttttatattg acgactttttt ttttttcgtg tgttttttgtt ctcttataac cgagctgctt  1980
acttattatt atttcaccttt ctcttttttat ttatacttat aattatttat tctttacata  2040
ctgttacaag aaactctttt ctacattaat tgcataaagt gtcaatcagc acatcctcta  2100
tatcgctatc aacaacaaat ttgacaaacc tgcctatatc ttcaggaaca actgccgcat  2160
cgctaccacc actacttgtg aagtccctgg agtttaatat gcactgaaat ttacctagcc  2220
gttttacaca agaccataat ccatccatgc tatcgcagta tatgattttg tgttcgtttt  2280
tcgtcttgcg aaaggcatcc tcaatggctt gtttcattga tccatcagtg tggctcgtag  2340
gtaccagcaa aaccacttca tcagcggcgt actcctggcg gtttaaacgc gtggccgtgc  2400
```

-continued

| | |
|---|---|
| cgtc | 2404 |

<210> SEQ ID NO 48
<211> LENGTH: 8536
<212> TYPE: DNA
<213> ORGANISM: Artificial Sequence
<220> FEATURE:
<223> OTHER INFORMATION: Synthetic construct: i73830 integration construct

<400> SEQUENCE: 48

| | |
|---|---|
| gacggcacgg ccacgcgttt aaaccgccac ccagccaagg tagtctaaaa gctaatttct | 60 |
| ctaaaaggga gaaagttggt gattttttat ctcgcattat tatatatgca agaatagtta | 120 |
| aggtatagtt ataaagtttt atcttaattg ccacatacgt acattgacac gtagaaggac | 180 |
| tccattattt ttttcattct agcatactat tattccttgt aacgtccag agtattccat | 240 |
| ttaattgtcc tccatttctt aacggtgacg aaggatcacc atacaacaac tactaaagat | 300 |
| tatagtacac tctcaccttg caactattta tctgacattt gccttacttt tatctccagc | 360 |
| ttcccctcga ttttattttt caatttgatt tctaaagctt tttgcttagg cataccaaac | 420 |
| catccactca tttaacacct tatttttttt ttcgaagaca gcatccaact ttatacgttc | 480 |
| actacctttt tttttacaac aatttcattc ttcatcctat gaacgctcgt ccaacgccgg | 540 |
| cggacctttc agacgcgact gcctcatcag taagacccgt tgaaagaac ttacctgaaa | 600 |
| aaaacgaata tatactagcg ttgaatgtta gcgtcaacaa caagaagttt aatgacgcgg | 660 |
| aggccaaggc aaaagattc cttgattacg taagggagtt agaatcattt tgaataaaaa | 720 |
| acacgctttt tcagttcgag tttatcatta tcaatactgc catttcaaag aatacgtaaa | 780 |
| taattaatag tagtgatttt cctaacttta tttagtcaaa aaattagcct tttaattctg | 840 |
| ctgtaacccg tacatgccca aaatagggg cgggttacac agaatatata acatcgtagg | 900 |
| tgtctgggtg aacagtttat tcctggcatc cactaaatat aatggagccc gcttttaag | 960 |
| ctggcatcca gaaaaaaaaa gaatcccagc accaaaatat tgttttcttc accaaccatc | 1020 |
| agttcatagg tccattctct tagcgcaact acagagaaca ggggcacaaa caggcaaaaa | 1080 |
| acgggcacaa cctcaatgga gtgatgcaac ctgcctggag taaatgatga cacaaggcaa | 1140 |
| ttgacccacg catgtatcta tctcattttc ttacaccttc tattaccttc tgctctctct | 1200 |
| gatttggaaa aagctgaaaa aaaaggttga aaccagttcc ctgaaattat tcccctactt | 1260 |
| gactaataag tatataaaga cggtaggtat tgattgtaat tctgtaaatc tatttcttaa | 1320 |
| acttcttaaa ttctactttt atagttagtc tttttttag ttttaaaaca ccaagaactt | 1380 |
| agtttcgacc tcccgcgacc tccaaaatcg aactaccttc acaatggctg atttcgattc | 1440 |
| taaagaatac ttggagttag ttgacaagtg gtggcgtgcc accaactact tgtccgctgg | 1500 |
| tatgattttc ttgaagtcca acccattatt ctctgttact aatacccaa tcaaggccga | 1560 |
| agatgtcaaa gttaaaccaa ttggtcactg gggtactatt tccggtcaaa ctttcttata | 1620 |
| cgcccacgct aaccgtttga ttaacaagta cggtctcaac atgttttacg ttggtggtcc | 1680 |
| aggtcacggt ggtcaagtca tggttactaa cgccctactta gacggtgcct acaccgaaga | 1740 |
| ttacccagaa attactcaag acatcgaagg tatgtctcat ttgttcaagc gtttctcttt | 1800 |
| ccctggtggt attggttccc atatgaccgc tcaaactcca ggttccttgc acgaaggtgg | 1860 |
| tgaattgggt tactctttgt cccatgcttt cggtgctgtt ttggacaacc cagaccaagt | 1920 |
| tgcttttgct gtcgttggtg atggtgaagc tgaaactggt ccatcatgg cctcttggca | 1980 |
| ttccattaag ttcttaaatg ccaagaacga tggtgccgtt ttgccagttt tggatttaaa | 2040 |

```
cggtttcaag atttccaatc caaccatttt ttctagaatg tctgatgaag aaattactaa    2100
gttcttcgaa ggtttgggtt attcccctag attcattgaa aatgatgaca ttcacgacta    2160
cgccacctac caccaattgg ccgctaacat cttagatcaa gccatcgaag acattcaagc    2220
tattcaaaat gacgccagag agaatggtaa atatcaagat ggtgaaattc cagcttggcc    2280
tgttattatc gctagattgc caaagggttg gggtggtcca acccacgatg cttctaataa    2340
tccaattgaa aactctttca gagctcacca agttccatta ccattggaac aacacgattt    2400
ggccaccttg ccagaattcg aagattggat gaactcttac aagccagaag aattattcaa    2460
cgctgatggt tccttgaagg atgagttgaa agctattgcc ccaaagggtg ataagagaat    2520
gtctgctaac ccaatcacca acggtggtgc tgacagatcc gacttgaaat tgccaaattg    2580
gagagaattc gctaacgaca tcaacgacga taccagaggt aaggaattcg ctgactctaa    2640
gagaaacatg gatatggcta ctttatccaa ctatttaggt gccgtttctc aattgaaccc    2700
aaccagattc agattcttcg gtccagatga aaccatgtcc aacagattgt ggggtttgtt    2760
taatgttacc ccacgtcaat ggatggaaga aatcaaggaa ccacaagatc aattgttgtc    2820
tccaactggt cgtatcatcg attcccaatt gtctgaacac caagctgaag gttggttgga    2880
aggttacact ttgactggta gagttggtat ctttgcctct tacgaatctt tcttgagagt    2940
tgttgatacc atggtcactc aacatttcaa gtggttgcgt cacgcttccg aacaagcttg    3000
gagaaatgac tatccatcct taaatttgat cgctacctct accgctttcc aacaagatca    3060
taacggttat actcaccaag accctggtat gttaactcat ttggccgaga agaagtctaa    3120
cttcattaga gaatatttgc cagccgacgg taactctttg ttagccgttc aagagagagc    3180
tttctctgaa agacataagg ttaacttatt gatcgcttct aaacaaccaa gacaacaatg    3240
gttcactgtt gaagaagctg aagtcttagc taacgaaggt ttgaagatta tcgattgggc    3300
ttctactgct ccatcttccg atgttgatat tacttttgct tctgccggta ctgaaccaac    3360
cattgagact ttggccgcct tatggttgat taatcaagct ttccctgacg ttaagtttag    3420
atacgttaac gttgttgaat tgttaagatt gcaaaagaaa tctgaaccaa acatgaacga    3480
cgaaagagaa ttatctgccg aagaatttaa taagtacttc caagccgaca ctccagttat    3540
cttcggtttc cacgcttacg aaaacttgat tgaatctttc tttttcgaga gaaagttcac    3600
cggtgatgtc tatgttcacg gttatagaga agatggtgat atcactacca cctacgatat    3660
gagagtctat tcccacttgg atcgtttcca tcaagccaag gaagccgccg aaatcttgtc    3720
tgctaacggt aaaatcgacc aagccgctgc cgacaccttt attgctaaga tggacgacac    3780
tttggccaaa cacttccaag ttactagaaa tgaaggtaga gatattgaag aattcactga    3840
ctggacttgg tctccattga agtaagtgaa tttactttaa atcttgcatt taaataaatt    3900 ttcttttat agctttatga cttagtttca atttatatac tattttaatg acattttcga    3960
ttcattgatt gaaagctttg tgtttttttct tgatgcgcta ttgcattgtt cttgtctttt    4020 tcgcccacatg taatatctgt agtagatacc tgatacattg tggatgctga gtgaaatttt    4080
agttaataat ggaggcgctc ttaataattt tggggatatt ggcttatccc cgcgtgcttg    4140
gccggccgta cgaaaatcgt tattgtcttg aaggtgaaat ttctactctt attaatggtg    4200
aacgttaagc tgatgctatg atggaagctg attggtctta acttgcttgt catcttgcta    4260
atggtcattg gctcgtgtta ttacttaagt tatttgtact cgttttgaac gtaatgctaa    4320
tgatcatctt atgaataat agtgagtggt ttcagggtcc ataaagcttt tcaattcatc    4380 ttttttttt ttgttctttt ttttgattcc ggtttctttg aaattttttt gattcggtaa    4440
```

```
tctccgagca gaaggaagaa cgaaggaagg agcacagact tagattggta tatatacgca   4500
tatgtggtgt tgaagaaaca tgaaattgcc cagtattctt aacccaactg cacagaacaa   4560
aaacctgcag gaaacgaaga taatcatgt cgaaagctac atataaggaa cgtgctgcta    4620
ctcatcctag tcctgttgct gccaagctat ttaatatcat gcacgaaaag caaacaaact   4680
tgtgtgcttc attggatgtt cgtaccacca aggaattact ggagttagtt gaagcattag   4740
gtcccaaaat ttgtttacta aaaacacatg tggatatctt gactgatttt tccatggagg   4800
gcacagttaa gccgctaaag gcattatccg ccaagtacaa ttttttactc ttcgaagaca   4860
gaaaatttgc tgacattggt aatacagtca aattgcagta ctctgcgggt gtatacagaa   4920
tagcagaatg ggcagacatt acgaatgcac acggtgtggt gggcccaggt attgttagcg   4980
gtttgaagca ggcggcggaa gaagtaacaa aggaacctag aggcctttg atgttagcag    5040 aattgtcatg caagggctcc ctagctactg gagaatatac taagggtact gttgacattg   5100
cgaagagtga caaagatttt gttatcggct ttattgctca aagagacatg ggtggaagag   5160
atgaaggtta cgattggttg attatgacac ccggtgtggg tttagatgac aagggagacg   5220
cattgggtca acagtataga accgtggatg atgtggtctc tacaggatct gacattatta   5280
ttgttggaag aggactattt gcaaagggaa gggatgctaa ggtagagggt gaacgttaca   5340
gaaaagcagg ctgggaagca tatttgagaa gatgcggcca gcaaaactaa aaaactgtat   5400
tataagtaaa tgcatgtata ctaaactcac aaattagagc ttcaatttaa ttatatcagt   5460
tattaccacg aaaatcgtta ttgtcttgaa ggtgaaattt ctactcttat taatggtgaa   5520
cgttaagctg atgctatgat ggaagctgat tggtcttaac ttgcttgtca tcttgctaat   5580
ggtcatatgg ctcgtgttat tacttaagtt atttgtactc gttttgaacg taatgctaat   5640
gatcatctta tggaataata gtgaacggcc ggccaagcac gcgggatgg gatgagcttg    5700 gagcaggaag aatacactat actggatcta aagagtacaa tagatggata agaatattgg   5760
cagcgcaaaa aggcttcaag cttacacaac acggtttatt tcgaaataat atccttctcg   5820
aaagctttaa cgaacgcaga attttcgagt tattaaactt aaaatacgct gaacccgaac   5880
atagaaatat cgaatgggaa aaaaaaactg cataaaggca ttaaagagg agcgaatttt    5940 tttttaataa aaatcttaat aatcattaaa agataaataa tagtctatat atacgtatat   6000
aaataaaaaa tattcaaaaa ataaaataaa ctattatttt agcgtaaagg atggggaaag   6060
agaaaagaaa aaaattgatc tatcgatttc aattcaattc aatagatctt tatccttgtg   6120
cttgtgcctg aactgcggta acggcaacaa ctttgacgat gtcgtcgact gaacatcccc   6180
ttgacaaatc gttgataggt ttggcaaatc cctgacatat aggaccgatg gcttcggcct   6240
ttgcgaatct ttggaccaac ttgtatccga tgtttcctgc ctggatgtct gggaagatca   6300
agacatttgc cttaccagcg actttagatc caggggcttt caaatctgcg accttcttaa   6360
ccaatgaggc gtctaactgc aattcaccgt cgatgtctaa gtcaggccta gcctccttag   6420
ccaattttgt tgcctttgta accttgtcga ctaattcatg tgaggctgat cccatggttg   6480
agaatgacaa catggctacc cttggctcga tcttgcacaa attctttgca gtctcagcag   6540
tggtaattgc gattgaagat aactcttcag cggtaggaca aacatttaca gcgcagtcag   6600 cgataacaa aaaaccgtcc tctccatact cgcagtcagg tactgacatc aagaagactg    6660
atgagacgac agatgcacct ggtactgttt tgacaatctg caaaccaggc cttaacaagt   6720
ctcctgtagt atgtatagca ccagatacca aaccgtcagc gtcacctaac ttgaccatca   6780
ttgttgcgaa gtagattggg tccctgacga ttttgtcagc cttctccaag gtgactccct   6840
```

```
tgtttttttct gatctcgtag aaagcgttgg cgtaaccggc ggtcttagaa gaagtttctg    6900
ggtcgactat ctctactccg gccaaattta ctccgaattt tgcggcgttt tccttaatga    6960
cagactctga accgaccaag attatgtcgg caataccgtc cctaataatc tcctctgaag    7020
ccctgatgtt cctctcttcc tcaccctctg ccaaaacgat tttcttcttg tcggccttgg    7080
ccaatccgaa gatattctcc atcaatttca ttgtgaaggt agttcgattt tggaggtcgc    7140
gggaggtcga aactaagttc ttggtgtttt aaaactaaaa aaaagactaa ctataaaagt    7200
agaatttaag aagtttaaga aatagattta cagaattaca atcaatacct accgtcttta    7260
tatacttatt agtcaagtag gggaataatt tcagggaact ggtttcaacc ttttttttca    7320
gcttttccca aatcagagag agcagaaggt aatagaaggt gtaagaaaat gagatagata    7380
catgcgtggg tcaattgcct tgtgtcatca tttactccag gcaggttgca tcactccatt    7440
gaggttgtgc ccgttttttg cctgtttgtg cccctgttct ctgtagttgc gctaagagaa    7500
tggacctatg aactgatggt tggtgaagaa acaatatttt tggtgctggg attctttttt    7560
tttctggatg ccagcttaaa aagcgggctc cattatattt agtggatgcc aggaataaac    7620
tgttcaccca gacacctacg atgttatata ttctgtgtaa cccgcccct attttgggca    7680 tgtacgggtt acagcagaat taaaaggcta atttttttgac taaataaagt taggaaaatc    7740
actactatta attatttacg tattctttga aatggcagta ttgataatga taaactcgaa    7800
ctgaaaaagc gtgtttttta ttcaaaatga ttctaactcc cttacgtaat caaggaatct    7860
ttttgccttg gcctccgcgt cattaaactt cttgttgttg acgctaacat tcaacgctag    7920
tatatattcg ttttttttcag gtaagttctt ttcaacgggt cttactgatg aggcagtcgc    7980
gtctgaaagg tccgccggcg ttggacgagc gctccatgct ggacttactc gtcgaagatt    8040
tcctgctact ctctatataa ttagacaccc atgttataga tttcagaaaa caatgtaata    8100
atatatggta gcctcctgaa actaccaagg gaaaaatctc aacaccaaga gctcatattc    8160
gttggaatag cgataatatc tctttacctc aatcttatat gcatgttatt tgctcttata    8220
attggtctct atttagggaa aaagtcggt ttgagagctt ctcgcgatgt gaaatctcaa    8280
tttgaactgc acgccaaagc tagcccattt cacgaacacc agaaagaaga atcccccaag    8340
gatcgcatga cagagtatgc tctctcatat cgttgagtat gaatgccaat acactgatca    8400
gctttacaag aaacgtaaaa tctggcacga tggtagactg aaatactttc agttaaacaa    8460
cagattcatg ctttatacgg aaaaggataa cgttttgtta gctagtgagg cggtttaaac    8520
gcgtggccgt gccgtc                                                    8536
```

<210> SEQ ID NO 49
<211> LENGTH: 9734
<212> TYPE: DNA
<213> ORGANISM: Artificial Sequence
<220> FEATURE:
<223> OTHER INFORMATION: Synthetic construct: i74810 integration
      construct

<400> SEQUENCE: 49

```
gacggcacgg ccacgcgttt aaaccgcccg ctcgcctcat ccccacggga ataaggcagc      60
cgacaaaaga aaaacgaccg aaaaggaacc agaaagaaaa aagagggtgg gcgcgccgcg     120
gacgtgtaaa aagatatgca tccagcttct atatcgcttt aactttaccg ttttgggcat    180
cgggaacgta tgtaacattg atctcctctt gggaacggtg agtgcaacga atgcgatata    240
gcaccgacca tgtgggcaaa ttcgtaataa attcggggtg aggggattc aagacaagca     300
```

```
accttgttag tcagctcaaa cagcgattta acggttgagt aacacatcaa acaccgttc      360
gaggtcaagc ctggcgtgtt taacaagttc ttgatatcat atataaatgt aataagaagt     420
ttggtaatat tcaattcgaa gtgttcagtc ttttacttct cttgttttat agaagaaaaa     480
acatcaagaa acatctttaa catacacaaa cacatactat cagaatacac gctcgtccaa     540
cgccggcgga cctttcagac gcgactgcct catcagtaag acccgttgaa aagaacttac     600
ctgaaaaaaa cgaatatata ctagcgttga atgttagcgt caacaacaag aagtttaatg     660
acgcggaggc caaggcaaaa agattccttg attacgtaag ggagttagaa tcattttgaa     720
taaaaaacac gcttttttcag ttcgagttta tcattatcaa tactgccatt tcaaagaata    780
cgtaaataat aatagtagt gattttccta actttattta gtcaaaaaat tagccttta      840
attctgctgt aacccgtaca tgcccaaaat aggggcggg ttacacagaa tataaacat      900
cgtaggtgtc tgggtgaaca gttattcct ggcatccact aaatataatg gagcccgctt    960
tttaagctgg catccagaaa aaaaagaat cccagcacca aaatattgtt ttcttcacca    1020
accatcagtt cataggtcca ttctcttagc gcaactacag agaacagggg cacaaacagg    1080
caaaaaacgg gcacaacctc aatggagtga tgcaacctgc ctggagtaaa tgatgacaca    1140
aggcaattga cccacgcatg tatctatctc attttcttac accttctatt accttctgct    1200
ctctctgatt tggaaaaagc tgaaaaaaaa ggttgaaacc agttccctga aattattccc    1260
ctacttgact aataagtata taaagacggt aggtattgat tgtaattctg taaatctatt    1320
tcttaaactt cttaaattct acttttatag ttagtctttt ttttagttt aaaacaccaa    1380
gaacttagtt tcgacctccc gcgacctcca aaatcgaact accttcacaa tggctgattt    1440
cgattctaaa gaatacttgg agttagttga caagtggtgg cgtgccacca actacttgtc    1500
cgctggtatg atttttcttga agtccaaccc attattctct gttactaata ccccaatcaa    1560
ggccgaagat gtcaaagtta aaccaattgg tcactgggt actatttccg gtcaaacttt     1620
cttatacgcc cacgctaacc gtttgattaa caagtacggt ctcaacatgt tttacgttgg    1680
tggtccaggt cacggtggtc aagtcatggt tactaacgcc tacttagacg gtgcctacac    1740
cgaagattac ccagaaatta ctcaagacat cgaaggtatg tctcatttgt tcaagcgttt    1800
ctctttccct ggtggtattg gttcccatat gaccgctcaa actccaggtt ccttgcacga    1860
aggtggtgaa ttgggttact cttgtccca tgctttcggt gctgttttgg acaacccaga    1920
ccaagttgct tttgctgtcg ttggtgatgg tgaagctgaa actggtccat ctatggcctc    1980
ttggcattcc attaagttct taaatgccaa gaacgatggt gccgttttgc cagttttgga    2040
tttaaacggt ttcaagattt ccaatccaac cattttttct agaatgtctg atgaagaaat    2100
tactaagttc ttcgaaggtt tgggttattc ccctagattc attgaaaatg atgacattca    2160
cgactacgcc acctaccacc aattggccgc taacatctta gatcaagcca tcgaagacat    2220
tcaagctatt caaaatgacg ccagagagaa tggtaaatat caagatggtg aaattccagc    2280
ttggcctgtt attatcgcta gattgccaaa gggttgggt ggtccaaccc acgatgcttc    2340
taataatcca attgaaaact cttttcagagc tcaccaagtt ccattaccat ggaacaaca    2400
cgatttggcc accttgccag aattcgaaga ttggatgaac tcttacaagc cagaagaatt    2460
attcaacgct gatggttcct tgaaggatga gttgaaagct attgccccaa agggtgataa    2520
gagaatgtct gctaacccaa tcaccaacgg tggtgctgac agatccgact tgaaattgcc    2580
aaattggaga gaattcgcta acgacatcaa cgacgatacc agaggtaagg aattcgctga    2640
ctctaagaga aacatggata tggctacttt atccaactat ttaggtgccg tttctcaatt    2700
```

-continued

```
gaacccaacc agattcagat tcttcggtcc agatgaaacc atgtccaaca gattgtgggg    2760
tttgtttaat gttaccccac gtcaatggat ggaagaaatc aaggaaccac aagatcaatt    2820
gttgtctcca actggtcgta tcatcgattc ccaattgtct gaacaccaag ctgaaggttg    2880
gttggaaggt tacactttga ctggtagagt tggtatcttt gcctcttacg aatctttctt    2940
gagagttgtt gataccatgg tcactcaaca tttcaagtgg ttgcgtcacg cttccgaaca    3000
agcttggaga aatgactatc catccttaaa tttgatcgct acctctaccg ctttccaaca    3060
agatcataac ggttatactc accaagaccc tggtatgtta actcatttgg ccgagaagaa    3120
gtctaacttc attagagaat atttgccagc cgacggtaac tctttgttag ccgttcaaga    3180
gagagctttc tctgaaagac ataaggttaa cttattgatc gcttctaaac aaccaagaca    3240
acaatggttc actgttgaag aagctgaagt cttagctaac gaaggtttga agattatcga    3300
ttgggcttct actgctccat cttccgatgt tgatattact tttgcttctg ccggtactga    3360
accaaccatt gagactttgg ccgccttatg gttgattaat caagctttcc ctgacgttaa    3420
gtttagatac gttaacgttg ttgaattgtt aagattgcaa agaaatctg aaccaaacat    3480 gaacgacgaa agagaattat ctgccgaaga atttaataag tacttccaag ccgcactcc    3540 agttatcttc ggtttccacg cttacgaaaa cttgattgaa tctttctttt tcgagagaaa    3600
gttcaccggt gatgtctatg ttcacggtta tagagaagat ggtgatatca ctaccaccta    3660
cgatatgaga gtctattccc acttggatcg tttccatcaa gccaaggaag ccgccgaaat    3720
cttgtctgct aacggtaaaa tcgaccaagc cgctgccgac acctttattg ctaagatgga    3780
cgacactttg gccaaacact tccaagttac tagaaatgaa ggtagagata ttgaagaatt    3840
cactgactgg acttggtctc cattgaagta agtgaattta ctttaaatct tgcatttaaa    3900
taaattttct tttatagct ttatgactta gtttcaattt atatactatt ttaatgacat    3960
tttcgattca ttgattgaaa gctttgtgtt ttttcttgat gcgctattgc attgttcttg    4020 tcttttcgc cacatgtaat atctgtagta gatacctgat acattgtgga tgctgagtga    4080
aattttagtt aataatggag gcgctcttaa taattttggg gatattggct tatccccgcg    4140
tgcttggccg gccgtacact gagtaatggt agttataaga aagagaccga gttagggaca    4200
gttagaggcg gtggagatat tccttatggc atgtctggcg atgataaaac ttttcaaacg    4260
gcagccccga tctaaaagag ctgacaggga aatggtcaga aaaagaaacg tgcacccgcc    4320
cgtctggacg cgccgctcac ccgcacggca gagaccaatc agtaaaaatc aacggttaac    4380
gacattacta tatatataat ataggaagca tttaatagaa cagcatcgta atatatgtgt    4440
actttgcagt tatgacgcca gatggcagta gtggaagata ttctttattg aaaaatagct    4500
tgtcacctta cgtacaatct tgatccggag ctttctcttt tttgccgatt aagaattcgg    4560
tcgaaaaaag aaaaggagag ggccaagagg gagggcattg gtgactattg agcacgtgag    4620
tatacgtgat taagcacaca aaggcagctt ggagtatgtc tgttattaat ttcacaggta    4680
gttctggtcc attggtgaaa gtttgcggct tgcagagcac agaggccgca gaatgtgctc    4740
tagattccga tgctgacttg ctgggtatta tatgtgtgcc aatagaaag agaacaattg    4800 acccggttat tgcaaggaaa atttcaagtc ttgtaaaagc atataaaaat agttcaggca    4860
ctccgaaata cttggttggc gtgtttcgta atcaacctaa ggaggatgtt ttggctctgg    4920
tcaatgatta cggcattgat atcgtccaac tgcatggaga tgagtcgtgg caagaatacc    4980
aagagttcct cggtttgcca gttattaaaa gactcgtatt tccaaaagac tgcaacatac    5040
tactcagtgc agcttcacag aaacctcatt cgtttattcc cttgtttgat tcagaagcag    5100
```

```
gtgggacagg tgaacttttg gattggaact cgatttctga ctgggttgga aggcaagaga    5160
gccccgaaag cttacatttt atgttagctg gtggactgac gccagaaaat gttggtgatg    5220
cgcttagatt aaatggcgtt attggtgttg atgtaagcgg aggtgtggag acaaatggtg    5280
taaaagactc taacaaaata gcaaatttcg tcaaaaatgc taagaaatag gttattactg    5340
agtagtattt atttaagtat tgtttgtgca cttgcctgca ggccttttga aaagcaagca    5400
taaaagatct aaacataaaa tctgtaaaat aacaagatgt aaagataatg ctaaatcatt    5460 tggcttttg attgattgta caggaaaata tacatcgcag ggggttgact tttaccattt     5520
caccgcaatg gaatcaaact tgttgaagag aatgttcaca ggcgcatacg ctacaatgac    5580
acggccggcc aagcacgcgg ggataagcca atatccccaa aattattaag agcgcctcca    5640
ttattaacta aaatttcact cagcatccac aatgtatcag gtatctacta cagatattac    5700
atgtggcgaa aaagacaaga acaatgcaat agcgcatcaa gaaaaaacac aaagctttca    5760
atcaatgaat cgaaaatgtc attaaaatag tatataaatt gaaactaagt cataaagcta    5820 taaaagaaa atttatttaa atgcaagatt taaagtaaat tcacttactt caatggagac     5880
caagtccagt cagtgaattc ttcaatatct ctaccttcat ttctagtaac ttggaagtgt    5940
ttggccaaag tgtcgtccat cttagcaata aaggtgtcgg cagcggcttg gtcgatttta    6000
ccgttagcag acaagatttc ggcggcttcc ttggcttgat ggaaacgatc caagtgggaa    6060
tagactctca tatcgtaggt ggtagtgata tcaccatctt ctctataacc gtgaacatag    6120
acatcaccgg tgaactttct ctcgaaaaag aaagattcaa tcaagttttc gtaagcgtgg    6180
aaaccgaaga taactggagt gtcggcttgg aagtacttat taaattcttc ggcagataat    6240
tctctttcgt cgttcatgtt tggttcagat ttcttttgca atcttaacaa ttcaacaacg    6300
ttaacgtatc taaacttaac gtcagggaaa gcttgattaa tcaaccataa ggcggccaaa    6360
gtctcaatgg ttggttcagt accggcagaa gcaaaagtaa tatcaacatc ggaagatgga    6420
gcagtagaag cccaatcgat aatcttcaaa ccttcgttag ctaagacttc agcttcttca    6480
acagtgaacc attgttgtct tggttgttta gaagcgatca ataagttaac cttatgtctt    6540
tcagagaaag ctctctcttg aacggctaac aaagagttac cgtcggctgg caaatattct    6600
ctaatgaagt tagacttctt ctcggccaaa tgagttaaca taccagggtc ttggtgagta    6660
taaccgttat gatcttgttg gaaagcggta gaggtagcga tcaaatttaa ggatggatag    6720
tcatttctcc aagcttgttc ggaagcgtga cgcaaccact tgaaatgttg agtgaccatg    6780
gtatcaacaa ctctcaagaa agattcgtaa gaggcaaaga taccaactct accagtcaaa    6840
gtgtaacctt ccaaccaacc ttcagcttgg tgttcagaca attgggaatc gatgatacga    6900
ccagttggag acaacaattg atcttgtggt tccttgattt cttccatcca ttgacgtggg    6960
gtaacattaa acaaccccca caatctgttg gacatggttt catctggacc gaagaatctg    7020
aatctggttg ggttcaattg agaaacggca cctaaatagt tggataaagt agccatatcc    7080
atgtttctct tagagtcagc gaattcctta cctctggtat cgtcgttgat gtcgttagcg    7140
aattctctcc aatttggcaa tttcaagtcg gatctgtcag caccaccgtt ggtgattggg    7200
ttagcagaca ttctcttatc acccttgggg gcaatagctt tcaactcatc cttcaaggaa    7260
ccatcagcgt tgaataattc ttctggcttg taagagttca tccaatcttc gaattctggc    7320
aaggtggcca atcgtgttg ttccaatggt aatggaactt ggtgagctct gaaagagttt     7380
tcaattggat tattagaagc atcgtggggtt ggaccacccc aaccctttgg caatctagcg    7440
ataataacag gccaagctgg aatttcacca tcttgatatt taccattctc tctggcgtca    7500
```

-continued

```
ttttgaatag cttgaatgtc ttcgatggct tgatctaaga tgttagcggc caattggtgg    7560
taggtggcgt agtcgtgaat gtcatcattt tcaatgaatc tagggggaata acccaaacct   7620
tcgaagaact tagtaatttc ttcatcagac attctagaaa aaatggttgg attggaaatc    7680
ttgaaaccgt ttaaatccaa aactggcaaa acggcaccat cgttcttggc atttaagaac    7740
ttaatggaat gccaagaggc catagatgga ccagtttcag cttcaccatc accaacgaca    7800
gcaaaagcaa cttggtctgg gttgtccaaa acagcaccga agcatggga caaagagtaa     7860
cccaattcac caccttcgtg caaggaacct ggagtttgag cggtcatatg ggaaccaata    7920
ccaccaggga aagagaaacg cttgaacaaa tgagacatac cttcgatgtc ttgagtaatt    7980
tctgggtaat cttcggtgta ggcaccgtct aagtaggcgt tagtaaccat gacttgacca    8040
ccgtgacctg gaccaccaac gtaaaacatg ttgagaccgt acttgttaat caaacggtta    8100
gcgtgggcgt ataagaaagt ttgaccggaa atagtacccc agtgaccaat tggtttaact    8160
ttgacatctt cggccttgat tggggtatta gtaacagaga ataatgggtt ggacttcaag    8220
aaaatcatac cagcggacaa gtagttggtg gcacgccacc acttgtcaac taactccaag    8280
tattctttag aatcgaaatc agccattgtg aaggtagttc gattttggag gtcgcgggag    8340
gtcgaaacta agttcttggt gttttaaaac taaaaaaaag actaactata aagtagaat    8400
ttaagaagtt taagaaatag atttacagaa ttacaatcaa tacctaccgt ctttatatac    8460
ttattagtca agtaggggaa taatttcagg gaactggttt caaccttttt tttcagcttt    8520
ttccaaatca gagagagcag aaggtaatag aaggtgtaag aaaatgagat agatacatgc    8580
gtgggtcaat tgccttgtgt catcatttac tccaggcagg ttgcatcact ccattgaggt    8640
tgtgcccgtt ttttgcctgt ttgtgcccct gttctctgta gttgcgctaa gagaatggac    8700
ctatgaactg atggttggtg aagaaaacaa tattttggtg ctgggattct ttttttttct    8760
ggatgccagc ttaaaaagcg ggctccatta tatttagtgg atgccaggaa taaactgttc    8820
acccagacac ctacgatgtt atatattctg tgtaacccgc cccctatttt gggcatgtac    8880
gggttacagc agaattaaaa ggctaatttt ttgactaaat aaagttagga aaatcactac    8940
tattaattat ttacgtattc tttgaaatgg cagtattgat aatgataaac tcgaactgaa    9000
aaagcgtgtt ttttattcaa aatgattcta actcccttac gtaatcaagg aatcttttg     9060
ccttggcctc cgcgtcatta aacttcttgt tgttgacgct aacattcaac gctagtatat    9120
attcgttttt ttcaggtaag ttcttttcaa cgggtcttac tgatgaggca gtcgcgtctg    9180
aaaggtccgc cggcgttgga cgagcgtgta ccaacctgca tttctttccg tcatatacac    9240
aaaatacttt catataaact tacttggtct tacgtcataa ataaatatgt atacatataa    9300
attaaaaaat ttggttttat atttttacaa aaagaatcgt ttacttcatt tctcccttt     9360
aagcgataca atccatgaaa aaagagaaaa agagagaaca ggcttgtgcc ttctttaaaa    9420
catcccacac aaaatcatat tgaattgaat tttacatctt aagctagtgt acaacaactg    9480
ctatatccaa agaaaactaa cgtggaccgc ttttagagtt gagaaaaagg tttgaaaaaa    9540
atagcaatac aaagacttgt ttcatatata aaatacaggg agcacattga gctaatataa    9600
cataaacact gcgaaccaat tccaatcaaa aggtacacat gagagcattc ccccgagtac    9660
tgccatttcg ccatcagaga tcatataata acatccttct tcgaacggcg gtttaaacgc    9720
gtggccgtgc cgtc                                                      9734
```

<210> SEQ ID NO 50
<211> LENGTH: 7980
<212> TYPE: DNA

<213> ORGANISM: Artificial Sequence
<220> FEATURE:
<223> OTHER INFORMATION: Synthetic construct: i76221 integration
      construct

<400> SEQUENCE: 50

| | | | | | |
|---|---|---|---|---|---|
| gacggcacgg | ccacgcgttt | aaaccgccgc | acgtgtatgt | acggctgtgt | aaatatgata | 60 |
| atcatctcgg | acgaacggcg | tagtactctc | catcccctaa | aaatgttcac | gtgtgactgc | 120 |
| tccatttcgc | cggatgtcga | gatgaccccc | cccctcaaa | aggcactcac | ctgctgacat | 180 |
| gccgtggcaa | atgattgggg | tcatccttt | tttctgttat | ctctaagatc | caaagaaaag | 240 |
| taaaaaaaa | aggttggggt | acgaattgcc | gccgagcctc | cgatgccatt | attcaatggg | 300 |
| tattgcagtt | ggggtatagt | tcctcggtgg | caaatagttc | tcccttcatt | ttgtatataa | 360 |
| actgggcggc | tattctaagc | atatttctcc | cttaggttat | ctggtagtac | gttatatctt | 420 |
| gttcttatat | tttctatcta | aagcaaaac | caaacatatc | aaaactacta | gaaagacatt | 480 |
| gccccactgt | gttcgctcgt | ccaacgccgg | cggacctttc | agacgcgact | gcctcatcag | 540 |
| taagacccgt | tgaaaagaac | ttacctgaaa | aaacgaata | tatactagcg | ttgaatgtta | 600 |
| gcgtcaacaa | caagaagttt | aatgacgcgg | aggccaaggc | aaaaagattc | cttgattacg | 660 |
| taagggagtt | agaatcattt | tgaataaaaa | acacgctttt | tcagttcgag | tttatcatta | 720 |
| tcaatactgc | catttcaaag | aatacgtaaa | taattaatag | tagtgatttt | cctaacttta | 780 |
| tttagtcaaa | aaattagcct | tttaattctg | ctgtaacccg | tacatgccca | aaataggggg | 840 |
| cgggttacac | agaatatata | acatcgtagg | tgtctgggtg | aacagtttat | tcctggcatc | 900 |
| cactaaatat | aatggagccc | gcttttaag | ctggcatcca | gaaaaaaaa | gaatcccagc | 960 |
| accaaaatat | tgttttcttc | accaaccatc | agttcatagg | tccattctct | tagcgcaact | 1020 |
| acagagaaca | ggggcacaaa | caggcaaaaa | acgggcacaa | cctcaatgga | gtgatgcaac | 1080 |
| ctgcctggag | taaatgatga | cacaaggcaa | ttgacccacg | catgtatcta | tctcattttc | 1140 |
| ttacaccttc | tattaccttc | tgctctctct | gatttggaaa | aagctgaaaa | aaaaggttga | 1200 |
| aaccagttcc | ctgaaattat | tcccctactt | gactaataag | tatataaaga | cggtaggtat | 1260 |
| tgattgtaat | tctgtaaatc | tatttcttaa | acttcttaaa | ttctacttt | atagttagtc | 1320 |
| tttttttag | ttttaaaaca | ccaagaactt | agtttcgacc | tcccgcgacc | tccaaaatcg | 1380 |
| aactaccttc | acaatggaac | attctgtaat | cgaaccaact | gtgcccatgc | cgctaccagc | 1440 |
| catgtttgac | gctccatctg | gtattttag | ctctttggac | gacgctgtgc | aagcagccac | 1500 |
| cttagcccaa | caacaactaa | gttcagttga | gttgcgtcag | caagtaatca | aagccataag | 1560 |
| agtggccgga | gaaaggtatg | cacaagtttt | ggctgaaatg | gcagttgctg | aaactggtat | 1620 |
| gggtagggtg | gtggataagt | acattaagaa | tgtctctcaa | gctcgtcata | cgcctggtat | 1680 |
| agaatgttta | tcggccgagg | ttcttacggg | tgataatggc | ctaacattga | ttgaaaatgc | 1740 |
| cccttgggga | gtcgtagctt | cagtcacgcc | aagcacaaat | ccagcagcta | cggtaattaa | 1800 |
| taatgcaatc | tcaatgattg | cagcggggaa | ttcagtcgtg | ttcgcaccac | atccttctgc | 1860 |
| caaaaacgtc | tcactaagga | ctatttcttt | actcaacaag | gccattgtcg | ctaccggcgg | 1920 |
| cccagaaaat | ttactagtta | gtgtggcaaa | ccctaacatc | gaaactgcac | agagattatt | 1980 |
| cagatatccg | ggtattggat | tgttagttgt | gacaggtggt | gaagccgtcg | ttgaagccgc | 2040 |
| taggaagcat | acagataaaa | ggttaattgc | agccggcgct | ggtaatcctc | ctgttgttgt | 2100 |
| ggacgaaact | gctgacatac | ctaaagccgc | aagagcaatt | gtcaagggtg | cttcttcga | 2160 |
| caacaacata | atttgtgctg | atgaaaaagt | tttgattgtg | gtagacagag | ttgcagatgc | 2220 |

```
actattggca gaaatgcaaa gaaataacgc cgtcttactt acacccgaac agaccgaaag    2280
actactaccc gctcttttgt ccgatattga cgaacagggc aaaggacgtg tgaatagaga    2340
ttatgttgga agagatgcgg ctaaattagc agcggctatt ggtctggaag ttagcgaaca    2400
tactcgtcta ctcctggcag agacagacgc tgatcatcca ttcgccgtga cggagctgat    2460
gatgccagtg ttaccagtaa taagagtcaa gaatgtagat gatgcaatcg cattggcagt    2520
taagctagag tcaggctgca gacacacagc tgcgatgcac tctactaata taagaaactt    2580
aaatagaatg gctaatgcca tcaatacctc tatctttgta aaaaatggtc catgtattgc    2640
aggtttgggt ttaggcggtg aaggttggac ttcaatgact attagcactc cgaccggtga    2700
aggtgttaca agcgctcgta cctttgtcag attaagaagg tgtgtcttag tcgacatgtt    2760
tcggattgct taagcggccg cgagtaataa ttattgcttc catataatat ttttatatac    2820
ctcttatttt tatgtattag ttaattaagt attttttatct atctgcttat cattttcttt    2880
tcatataggg ggggttggtg ttttcttgcc catcagattg atgtcctcca actcggcact    2940
attttacaaa gggttttttt gtaagagaag gagaagacag atactaaacc atacgttact    3000
cgaaacaaaa aaaaaaaaaa tggaaaaagc tgctatcaac aaaagacggc ctcatcaaac    3060
ctaaagaaac catgtcagcg tatgtatata ccttgtaatt tacgtttcct taaatcttct    3120
ttctactaac gttttcatta ttctatactc tatgaccaat aaaaacagac tgtactttca    3180
aaatttaccc agtaggccag caaataaaga aaattatacc agattacttc tgaaacacat    3240
taatcccaac aacaagtatg ccattaatcc gtcgctaccc catccccgcg tgcttggccg    3300
gccgtttctc gacgtgggcc ttttttcttgc catatggatc cgctgcacgg tcctgttccc    3360
tagcatgtac gtgagcgtat ttccttttaa accacgacgc tttgtcttca ttcaacgttt    3420
cccattgttt ttttctacta ttgctttgct gtgggaaaaa cttatcgaaa gatgacgact    3480
ttttcttaat tctcgttttta agagcttggt gagcgctagg agtcactgcc aggtatcgtt    3540
tgaacacggc attagtcagg gaagtcataa cacagtcctt tcccgcaatt ttcttttttct    3600 attactcttg gcctcctcta gtacactcta tattttttta tgcctcggta atgattttca    3660
tttttttttt tccacctagc ggatgactct ttttttttct tagcgattgg cattatcaca    3720
taatgaatta tacattatat aaagtaatgt gatttcttcg aagaatatac taaaaaatga    3780
gcaggcaaga taaacgaagg caaagatgac agagcagaaa gccctagtaa agcgtattac    3840
aaatgaaacc aagattcaga ttgcgatctc tttaaagggt ggtcccctag cgatagagca    3900
ctcgatcttc ccagaaaaag aggcagaagc agtagcagaa caggccacac aatcgcaagt    3960
gattaacgtc cacacaggta tagggtttct ggaccatatg atacatgctc tggccaagca    4020
ttccggctgg tcgctaatcg ttgagtgcat tggtgactta cacatagacg accatcacac    4080
cactgaagac tgcgggattg ctctcggtca agcttttaaa gaggccctag ggccgtgcg    4140 tggagtaaaa aggtttggat caggatttgc gcctttggat gaggcacttt ccagagcggt    4200
ggtagatctt tcgaacaggc cgtacgcagt tgtcgaactt ggtttgcaaa gggagaaagt    4260
aggagatctc tcttgcgaga tgatcccgca tttttcttgaa agctttgcag aggctagcag    4320
aattaccctc cacgttgatt gtctgcgagg caagaatgat catcaccgta gtgagagtgc    4380
gttcaaggct cttgcggttg ccataagaga agccacctcg cccaatggta ccaacgatgt    4440
tccctccacc aaaggtgttc ttatgtagtg acaccgatta tttaaagctg cagcatacga    4500
tatatataca tgtgtatata tgtataccta tgaatgtcag taagtatgta tacgaacagt    4560
atgatactga agatgacaag gtaatgcatc attctatacg tgtcattctg aacgaggcgc    4620
```

```
gctttccttt tttcttttttg cttttttcttt tttttttctct tgaactcgac ggccggccaa   4680
gcacgcgggg atggggtagc gacggattaa tggcatactt gttgttggga ttaatgtgtt   4740
tcagaagtaa tctggtataa ttttctttat ttgctggcct actgggtaaa ttttgaaagt   4800
acagtctgtt tttattggtc atagagtata gaataatgaa aacgttagta gaaagaagat   4860
ttaaggaaac gtaaattaca aggtatatac atacgctgac atggtttctt taggtttgat   4920
gaggccgtct tttgttgata gcagcttttt ccattttttt tttttttgtt tcgagtaacg   4980
tatggtttag tatctgtctt ctccttctct tacaaaaaaa cccttttgtaa aatagtgccg   5040 agttggagga catcaatctg atgggcaaga aaacaccaac ccccctata tgaaaagaaa   5100 atgataagca gatagataaa aatacttaat taactaatac ataaaaataa gaggtatata   5160
aaaatattat atggaagcaa taattattac tcgcggccgc ttaagcaatc cgaaacatgt   5220
cgactaagac acaccttctt aatctgacaa aggtacgagc gcttgtaaca ccttcaccgg   5280
tcggagtgct aatagtcatt gaagtccaac cttcaccgcc taaacccaaa cctgcaatac   5340
atggaccatt ttttacaaag atagaggtat tgatggcatt agccattcta tttaagtttc   5400
ttatattagt agagtgcatc gcagctgtgt gtctgcagcc tgactctagc ttaactgcca   5460
atgcgattgc atcatctaca ttcttgactc ttattactgg taacactggc atcatcagct   5520
ccgtcacggc gaatggatga tcagcgtctg tctctgccag gagtagacga gtatgttcgc   5580
taacttccag accaatagcc gctgctaatt tagccgcatc tcttccaaca taatctctat   5640
tcacacgtcc tttgccctgt tcgtcaatat cggacaaaag agcgggtagt agtctttcgg   5700
tctgttcggg tgtaagtaag acggcgttat ttctttgcat ttctgccaat agtgcatctg   5760
caactctgtc taccacaatc aaaactttt catcagcaca aattatgttg ttgtcgaaag   5820 aagcacccctt gacaattgct cttgcggctt taggtatgtc agcagtttcg tccacaacaa   5880
caggaggatt accagcgccg gctgcaatta accttttatc tgtatgcttc ctagcggctt   5940
caacgacggc ttcaccacct gtcacaacta acaatccaat acccggatat ctgaataatc   6000
tctgtgcagt ttcgatgtta gggtttgcca cactaactag taaattttct gggccgccgg   6060
tagcgacaat ggccttgttg agtaaagaaa tagtccttag tgagacgttt ttggcagaag   6120
gatgtggtgc gaacacgact gaattccccg ctgcaatcat tgagattgca ttattaatta   6180
ccgtagctgc tggatttgtg cttggcgtga ctgaagctac gactccccaa ggggcatttt   6240
caatcaatgt taggccatta tcacccgtaa gaacctcggc cgataaacat tctataccag   6300
gcgtatgacg agcttgagag acattcttaa tgtacttatc caccacccta cccataccag   6360
tttcagcaac tgccatttca gccaaaactt gtgcatacct ttctccggcc actcttatgg   6420
ctttgattac ttgctgacgc aactcaactg aacttagttg ttgttgggct aaggtggctg   6480
cttgcacagc gtcgtccaaa gagctaaaaa taccagatgg agcgtcaaac atggctggta   6540
gcggcatggg cacagttggt tcgattacag aatgttccat tgtgaaggta gttcgatttt   6600
ggaggtcgcg ggaggtcgaa actaagttct tggtgtttta aaactaaaaa aaagactaac   6660
tataaaagta gaatttaaga agtttaagaa atagatttac agaattacaa tcaataccta   6720
ccgtctttat atacttatta gtcaagtagg ggaataattt cagggaactg gtttcaacct   6780
tttttttcag cttttttccaa atcagagaga gcagaaggta atagaaggtg taagaaaatg   6840
agatagatac atgcgtgggt caattgcctt gtgtcatcat ttactccagg caggttgcat   6900
cactccattg aggttgtgcc cgttttttgc ctgtttgtgc ccctgttctc tgtagttgcg   6960
ctaagagaat ggacctatga actgatggtt ggtgaagaaa acaatatttt ggtgctggga   7020
```

-continued

```
ttcttttttt ttctggatgc cagcttaaaa agcgggctcc attatattta gtggatgcca      7080
ggaataaact gttcacccag acacctacga tgttatatat tctgtgtaac ccgcccccta      7140
ttttgggcat gtacgggtta cagcagaatt aaaaggctaa ttttttgact aaataaagtt      7200
aggaaaatca ctactattaa ttatttacgt attctttgaa atggcagtat tgataatgat      7260
aaactcgaac tgaaaagcg tgtttttat tcaaaatgat tctaactccc ttacgtaatc        7320
aaggaatctt tttgccttgg cctccgcgtc attaaacttc ttgttgttga cgctaacatt      7380
caacgctagt atatattcgt ttttttcagg taagttcttt tcaacgggtc ttactgatga      7440
ggcagtcgcg tctgaaaggt ccgccggcgt tggacgagcg tgatgatttc tttccttttt      7500
atattgacga cttttttttt ttcgtgtgtt tttgttctct tataaccgag ctgcttactt      7560
attattattt caccttctct ttttatttat acttataatt atttattctt tacatactgt      7620
tacaagaaac tcttttctac attaattgca taaagtgtca atcagcacat cctctatatc      7680
gctatcaaca acaaatttga caaacctgcc tatatcttca ggaacaactg ccgcatcgct      7740
accaccacta cttgtgaagt ccctggagtt taatatgcac tgaaatttac ctagccgttt      7800
tacacaagac cataatccat ccatgctatc gcagtatatg attttgtgtt cgttttttcgt     7860 cttgcgaaag gcatcctcaa tggcttgttt cattgatcca tcagtgtggc tcgtaggtac      7920
cagcaaaacc acttcatcag cggcgtactc ctggcggttt aaacgcgtgg ccgtgccgtc      7980
```

<210> SEQ ID NO 51
<211> LENGTH: 13266
<212> TYPE: DNA
<213> ORGANISM: Artificial Sequence
<220> FEATURE:
<223> OTHER INFORMATION: Synthetic construct: i84022 integration
      construct

<400> SEQUENCE: 51

```
gacggcacgg ccacgcgttt aaaccgccaa gtgatgtaac taaatacacg attaccatgg        60
aaattaacgt acctttttg tgcgtgtatt gaaatattat gacatattac agaaagggtt       120
cgcaagtcct gtttctatgc cttttctctta gtaattcacg aaataaacct atggtttacg     180
aaatgatcca cgaaaatcat gttattattt acatcaacat atcgcgaaaa ttcatgtcat      240
gtccacatta acatcattgc agagcaacaa ttcattttca tagagaaatt tgctactatc     300
acccactagt actaccattg gtacctacta ctttgaattg tactaccgct gggcgttatt      360
aggtgtgaaa ccacgaaaag ttcaccataa cttcgaataa agtcgcggaa aaagtaaac      420 agctattgct actcaaatga ggtttgcaga agcttgttga agcatgatga agcgttctaa      480
acgcactatt catcattaaa tatttaaagc tcataaaatt gtattcaatt cctattctaa      540
atggctttta tttctattac aactattagc tctaaatcca tatcctcata agcagcaatc      600
aattctatct atactttaaa cgctcgtcca acgccggcgg acctgatgtg tattactagt      660
gtcgacgaca gcattcgccc agtattttt ttattctaca aaccttctat aatttcaaag       720
tatttacata attctgtatc agtttaatca ccataatatc gttttctttg tttagtgcaa      780
ttaatttttc ctattgttac ttcgggcctt tttctgtttt atgagctatt ttttccgtca      840
tccttccgga tccagatttt cagcttcatc tccagattgt gtctacgtaa tgcacgccat      900
cattttaaga gaggacctcc cgcgacctcc aaaatcgaac taccttcaca atgaaacttc      960
ttagtagtat tgagcaggcg tgtgacatct gtagattgaa gaaattgaaa tgtagtaagg     1020
agaagcccaa atgtgcgaaa tgccttaaaa ataattggga atgcagatat agtccgaaga    1080
```

-continued

```
cgaagcgcag tccccttacc cgcgcgcacc ttacggaggt cgagagtcgc cttgagcgcc    1140
ttgagcaact tttccttctt atcttcccca gagaggattt ggatatgatc cttaagatgg    1200
acagtcttca agacattaag gcgcttctta cggggctttt cgtgcaggac aacgtcaaca    1260
aggacgcggt gacggaccgc cttgccagtg tcgaaaccga catgccccct acgcttcgcc    1320
aacaccgcat ttccgccacg agtagtagtg aggaatcctc aataagggg cagcgccaac     1380 ttaccgtgag tatcgatagt gcggcccacc acgacaatag tacgatcccc cttgacttca    1440
tgccgcgcga cgccttgcac gggttcgact ggagtgagga agacgatatg agtgacggtc    1500
ttccgttcct taagaccgat ccgaataaca acggttttt cggtgatggg agtttgcttt     1560
gcatcttgag aagtatcggt ttcaagcccg agaactatac caatagtaat gtcaatcgct    1620
tgcccacgat gatcaccgac cgctataccc ttgccagtcg cagtacgacg agtagacttt    1680
tgcagtccta cttgaacaac ttccatccgt attgtcccat tgtccatagt cccacccta    1740 tgatgcttta caacaatcaa atcgagattg ccagtaaaga ccagtggcag attttgttca    1800
attgtattct tgcgatcggg gcgtggtgca ttgaaggtga gagtaccgac attgacgtct    1860
tctattacca gaacgccaag agtcaccta cctccaaagt gtttgaaagt gggagtatta    1920
tccttgtcac ggcgcttcac ttgcttagta gatacacgca atggcgccaa aagacgaaca    1980
cctcctacaa cttccattcc ttcagtattc gcatggcgat tagtcttggt cttaaccgcg    2040
atttgccgag tagttttcc gactcctcca tccttgagca gcgcagaaga atctggtgga    2100
gtgtgtatag ttgggaaatt cagcttagtc ttttgtacgg gagaagtatt caattgagtc    2160
aaaacacgat tagttttccc agtagtgtgg atgacgtcca aagaacgacg acggggccga    2220
cgatttacca cggtattatc gagacggcgc gcttgcttca ggtctttacg aagatttacg    2280
agcttgataa gacggtgacc gcggagaagt cccccattg cgcgaagaag tgtcttatga    2340
tctgcaacga aatcgaagaa gtcagtcgcc aagcgccgaa attccttcag atggacatca    2400
gtacgacggc ccttacgaac cttcttaaag agcatccctg gcttagtttc acgcgctttg    2460
agcttaaatg gaagcaactt agtttgatta tctacgtgct tcgcgacttc tttaccaact    2520
tcacgcaaaa gaaaagtcag cttgagcaag accagaacga ccaccagtcc tacgaggtca    2580
agagatgtag tattatgctt tccgacgcgg cgcagcgcac cgtcatgagt gtgtcctcct    2640
acatggataa ccacaacgtg acgccgtact tcgcgtggaa ctgcagttac tatctttta    2700 acgcggtgct tgtgccgatt aaaacccttt tgagtaatag taagagtaac gccgaaaaca    2760
atgaaacggc gcagcttctt cagcagatca ataccgtcct tatgcttctt aagaagcttg    2820
cgaccttcaa gattcaaacc tgcgagaagt atatccaggt gcttgaggaa gtgtgcgccc    2880
ccttccttct tagtcaatgc gcgattccgc ttcccccacat ttcctacaat aactccaacg    2940
ggtccgcgat caagaacatc gtggggagtg cgaccattgc gcagtatccc accttgcccg    3000
aagagaacgt gaataacatt tccgtcaagt acgtcagtcc cggtagtgtg ggtcccagtc    3060
ccgtcccgct taagagtggg gcgtcctttt ccgaccttgt gaaacttctt agtaatagac    3120
cgccgagtag aaatagtccg gtcacgattc gcgctccac gcccagtcac agaagtgtga    3180
cccccttcct tggtcagcaa cagcaacttc agagtcttgt cccgcttacg cccagtgccc    3240 ttttcgggg tgcgaacttc aaccagtccg gtaacatcgc cgactccagt cttagtttta    3300
cctttaccaa ttcctccaat gggcccaatt tgattacgac ccagacgaac agtcaggcct    3360
tgagtcagcc gatcgcgagt agtaatgtcc acgacaattt tatgaacaac gagattaccg    3420
cctccaagat cgacgacggg aacaacagta agccgcttag tcccgggtgg accgatcaga    3480
```

```
ccgcctacaa tgccttcggg attaccacgg gtatgttcaa cacgaccacg atggacgacg    3540
tgtacaatta ccttttttgac gacgaggaca cgccgccgaa tccgaagaag gaatgagcca   3600
attggtgcgg caattgataa taacgaaaat gtcttttaat gatctgggta taatgaggaa    3660
ttttccgaac gttttttactt tatatatata tatacatgta acatatattc tatacgctat   3720
atcgagaaaa cgcgatggtg gggtgacttt caactcggcg tatccccgcg tgcttggccg    3780
gccgtagtta tgacaattac aacaacagaa ttctttctat atatgcacga acttgtaata   3840
tggaagaaat tatgacgtac aaactataaa gtaaatattt tacgtaacac atggtgctgt    3900
tgtgcttctt tttcaagaga ataccaatga cgtatgacta agtttatgta ttttccaaaa   3960
cctgtttagc cctggcgaca gatacgtctc cggcttcaac gatgaccctg gtgaccctgt    4020
caatgtcggc tccggtggca ccggccatga ttgcgatgtt ccttgcgtgt aaggtcatgt   4080
gtccccttg gattccctcg gttgccaagg ccctaattgc ggccatattc tgagccaaac    4140
caacggcggc agtaacctgg gccaactcag tagcggtttc gacctgcatt aaggccaaag   4200
cggccctagc tgtagggtga gtcttggtgg ctcctcctac caaacccaag gccaaaggca    4260
attcaatggt accgaccaac ctaccgtcgt tggccaactc ccaccttgtc aaagaggtgt   4320
aatgtccggt cctggcggcg taggcgtggg ctccagcttc gatggccctc cagtcgttac    4380
ctgttgcgac gacgactggg tcaattccgt tcataattcc cttgttatgg gttgcggccc   4440
tgtaagggtc gactattgct aaggcgcagg cttcaaccat tccccttgca acgtcggcac    4500
catcgtatcc ctgggtggtc aaagtctcag gggctaactc aaccctggct cttaccaacc   4560
tcaagtcggc caagttagac aaaatcctca acctgacggt tccaccagcg atcctctcta    4620
cctctggagc taacctttca gccatggtgt taactgtgtt ggcacccatg cgtctctga   4680
catcaacaat caagtgcaat acgaccattg caccaacagg ggtgtcccta aaaacatgga    4740
cctcaatgtc tctgcaacca ccacctaaac caaccaaaac tggatctacg gcatctgctg   4800
cttccatgaa agcagcctta tgggccaaca acctttgcct agctccttct gggtctccta    4860
atccgacaac ttggatttgg gccctcatta aggtgcagt tccgtgtgcg gtgaatccac   4920
cgttctctct agctatcctt gccatatatg aggctgcggc aacaacagat ggttcctcga    4980
ctgccatagg tattaagtag tcccttccgt tgacggtgaa gttggtggcg acacccaatg   5040
gcaactcaaa ttttccgata acattctcga tcataccgtt ggccaatgac aaaggcaaag    5100
caccgttacc ggccaatgca gaaatggctt caggttccaa tcctgcggct tcggcaaccc   5160
taactaacct ctgagcagga tccaagtccc tcatcttctc gatccttgag ttcaatccgt    5220
cgatgtgacc tgtctttcca gtcattgtaa agttagttgg ttgcgcgact tcgggtgggg   5280
taagtataga ggtatattaa caattttttg ttgatacttt tatgacattt gaataagaag    5340
taatacaaac cgaaaatgtt gaaagtatta gttaaagtgg ttatgcagct tttgcattta   5400
tatatctgtt aatagatcaa aaatcatcgc ttcgctgatt aattacccca gaaataaggc    5460
taaaaaacta atcgcattat tatcctatgg ttgttaattt gattcgttga tttgaaggtt   5520
tgtggggcca ggttactgcc aattttttcct cttcataacc ataaaagcta gtattgtaga    5580
atctttattg ttcggagcag tgcggcgcga ggcacatctg cgtttcagga acgcgaccgg   5640
tgaagaccag gacgcacgga ggagagtctt ccgtcggagg gctgtcgccc gctcggcggc    5700
ttctaatccg tacttcaata tagcaatgag cagttaagcg tattactgaa agttccaaag   5760
agaaggtttt tttaggctaa gataatgggg ctctttacat ttccacaaca tataagtaag    5820
attagatatg gatatgtata tggtggtatt gccatgtaat atgattatta aacttctttg   5880
```

```
cgtccatcca aaaaaaaagt aacgcacgca cactcccgac agacaactag cttgataatg    5940
tctcagaacg tttacattgt atcgactgcc agaaccccaa ttggttcatt ccagggttct    6000
ctatcctcca agacagcagt ggaattgggt gctgttgctt taaaaggcgc cttggctaag    6060
gttccagaat tggatgcatc caaggatttt gacgaaatta ttttttggtaa cgttctttct    6120 gccaatttgg gccaagctcc ggccagacaa gttgctttgg ctgccggttt gagtaatcat    6180
atcgttgcaa gcacagttaa caaggtctgt gcatccgcta tgaaggcaat cattttgggt    6240
gctcaatcca tcaaatgtgg taatgctgat gttgtcgtag ctggtggttg tgaatctatg    6300
actaacgcac catactacat gccagcagcc cgtgcgggtg ccaaatttgg ccaaactgtt    6360
cttgttgatg gtgtcgaaag agatgggttg aacgatgcgt acgatggtct agccatgggt    6420
gtacacgcag aaaagtgtgc ccgtgattgg gatattacta gagaacaaca agacaatttt    6480
gccatcgaat cctaccaaaa atctcaaaaa tctcaaaagg aaggtaaatt cgacaatgaa    6540
attgtacctg ttaccattaa gggatttaga ggtaagcctg atactcaagt cacgaaggac    6600
gaggaacctg ctagattaca cgttgaaaaa ttgagatctg caaggactgt tttccaaaaa    6660
gaaaacggta ctgttactgc cgctaacgct tctccaatca cgatggtgc tgcagccgtc    6720 atcttggttt ccgaaaaagt tttgaaggaa aagaatttga agccttttggc tattatcaaa    6780 ggttggggtg aggccgctca tcaaccagct gattttacat gggctccatc tcttgcagtt    6840
ccaaaggctt tgaaacatgc tggcatcgaa gacatcaatt ctgttgatta ctttgaattc    6900
aatgaagcct tttcggttgt cggtttggtg aacactaaga ttttgaagct agacccatct    6960
aaggttaatg tatatggtgg tgctgttgct ctaggtcacc cattgggttg ttctggtgct    7020
agagtggttg ttacactgct atccatctta cagcaagaag gaggtaagat cggtgttgcc    7080
gccatttgta atggtggtgg tggtgcttcc tctattgtca ttgaaaagat atgattacgt    7140
tctgcgattt tctcatgatc ttttttcataa aatacataaa tatataaatg ctttatgta    7200 taacaggcat aatttaaagt tttatttgcg attcatcgtt tttcaggtac tcaaacgctg    7260
aggtgtgcct tttgacttac ttttccgcct tggcaagctg gccgaacctg caggccgcga    7320
gcgccgatac gaaaatcgtt attgtcttga aggtgaaatt tctactctta ttaatggtga    7380
acgttaagct gatgctatga tggaagctga ttggtcttaa cttgcttgtc atcttgctaa    7440
tggtcattgg ctcgtgttat tacttaagtt atttgtactc gttttgaacg taatgctaat    7500
gatcatctta tggaataata gtgagtggtt tcagggtcca taaagctttt caattcatct    7560
tttttttttt tgttctttt tttgattccg gtttctttga aattttttg attcggtaat    7620 ctccgagcag aaggaagaac gaaggaagga gcacagactt agattggtat atatacgcat    7680
atgtggtgtt gaagaaacat gaaattgccc agtattctta acccaactgc acagaacaaa    7740
aacctgcagg aaacgaagat aaatcatgtc gaaagctaca tataaggaac gtgctgctac    7800
tcatcctagt cctgttgctg ccaagctatt taatatcatg cacgaaaagc aaacaaactt    7860
gtgtgcttca ttgatgttc gtaccaccaa ggaattactg gagttagttg aagcattagg    7920
tcccaaaatt tgtttactaa aaacacatgt ggatatcttg actgatttt ccatggaggg    7980 cacagttaag ccgctaaagg cattatccgc caagtacaat ttttactct tcgaagacag    8040 aaaatttgct gacattggta atacagtcaa attgcagtac tctgcgggtg tatacagaat    8100
agcagaatgg gcagacatta cgaatgcaca cggtgtggtg ggcccaggta ttgttagcgg    8160
tttgaagcag gcgcggaag aagtaacaaa ggaacctaga ggccttttga tgttagcaga    8220
attgtcatgc aagggctccc tagctactgg agaatatact aagggtactg ttgacattgc    8280
```

```
gaagagtgac aaagattttg ttatcggctt tattgctcaa agagacatgg gtggaagaga    8340
tgaaggttac gattggttga ttatgacacc cggtgtgggt ttagatgaca agggagacgc    8400
attgggtcaa cagtatagaa ccgtggatga tgtggtctct acaggatctg acattattat    8460
tgttggaaga ggactatttg caaagggaag ggatgctaag gtagagggtg aacgttacag    8520
aaaagcaggc tgggaagcat atttgagaag atgcggccag caaaactaaa aaactgtatt    8580
ataagtaaat gcatgtatac taaactcaca aattagagct tcaatttaat tatatcagtt    8640
attaccacga aaatcgttat tgtcttgaag gtgaaatttc tactcttatt aatggtgaac    8700
gttaagctga tgctatgatg gaagctgatt ggtcttaact tgcttgtcat cttgctaatg    8760
gtcatatggc tcgtgttatt acttaagtta tttgtactcg ttttgaacgt aatgctaatg    8820
atcatcttat ggaataatag tgaacggccg gccaagcacg cggggattga atgagaaaaa    8880
aaatcggttg ggcttaactt taaagaaaaa agttgagatt agatttattg tgttataaat    8940
atagatatac aattctttat aaaaaaaata tatatatata tcattgttat taaataaaga    9000
gttttcctag tatatagatt aaaaaactac tctattaaat gagagctaaa aaaagcaggc    9060
tgccaaaaaa ataaagcatt tatgaagggg gttcagcaag atgcaatcga tgggggaaga    9120
ttatttttta acatcgtaag atcttctaaa tttgtcatcg atgttggtca agtagtaaac    9180
accactttgc aaatgctcaa tggaaccttg aggtttgaag ttcttcttca aatgggcatt    9240
ttctctcaat tcgatggcag cttcgtaatc ctttggagtt tcggtgattc tcttggctaa    9300
tttgttagta atatctaatt ccttgataat atgttggacg tcaccaacaa ttttgcaaga    9360
atatagagat gcagctaaac cggaaccgta agaaaataaa ccaacacgct tgccttgtaa    9420
gtcgtcagat ccaacatagt ttaatagaga tgcaaaggcg gcataaacag atgcggtgta    9480
catgttacct gtgtttgttg gaacaatcaa agattgggca actctctctt tgtggaatgg    9540
cttagcaaca ttaacaaaag ttttttcaat gttcttatcg gttaaagatt cgtcataatc    9600
gcgagtagct aattcggcgt caacttctgg gaacaattga ggattggctc tgaaatcgtt    9660
atatagtaat ctaccgtatg atttttgtgac caatttacag gttggaacat ggaaaacgtt    9720
gtagtcgaaa tatttcaaaa cgttcaaagc atccgaacca gcgggatcgc taaccaaccc    9780
tttagaaata gccttcttgg aataactctt gtaaacttga tcaagagcct tgacgtaaca    9840
agttaatgaa aaatgaccat cgacgtaagg atattcgctg gtgaaatctg gcttgtaaaa    9900
atcgtaggcg tgttccatgt aagaagctct tacagagtca aatacaattg gagcatcagg    9960
accgatccac atagcaacag taccggcacc accggttggt cttgcggcac ccttatcgta   10020
gatggcaata tcaccgcaaa ctacaatggc gtctctacca tcccatgcgt tagattcaat   10080
ccagttcaaa gagttgaaca acgcgttggt accaccgtaa caggcattaa gcgtgtcaat   10140
accttcgacg tcagtgtttt caccaaacaa ttgcatcaag acagacttga cagacttgga   10200
cttgtcaatc agagtttcag taccgacttc taatctacca attttgttgg tgtcgatgtt   10260
gtaactcttg atcaacttag acaaaacagt tagggacatc gagtagatat cttctctgtc   10320
attgacaaaa gacatgttgg tttggcccag accaattgtg tatttacctt gagaaacgcc   10380
atcaaatttc tctagctcag attggttgac acattgagtt gggatgtaaa tttggatacc   10440
tttaataccg acattttgag gtctggtttt ttgttcagcg gtcttttgtt tttttagttc   10500
agtcatttgc aagtttgtat tgtgtaattg ttgttgcttt tgcggcctaa gtcttccttt   10560
aataccacac caacaaagtt tagttgagag tttcattgtg aaggtagttc gattttggag   10620
gtcgcgggag gttactttttt ttttggatgg acgcaaagaa gtttaataat catattacat   10680
```

```
ggcaatacca ccatatacat atccatatct aatcttactt atatgttgtg gaaatgtaaa   10740
gagccccatt atcttagcct aaaaaaacct tctctttgga actttcagta atacgcttaa   10800
ctgctcattg ctatattgaa gtacggatta gaagccgccg agcgggcgac agccctccga   10860
cggaagactc tcctccgtgc gtcctggtct tcaccggtcg cgttcctgaa acgcagatgt   10920
gcctcgcgcc gcactgctcc gaacaataaa gattctacaa tactagcttt tatggttatg   10980
aagaggaaaa attggcagta acctggcccc acaaaccttc aaatcaacga atcaaattaa   11040
caaccatagg ataataatgc gattagtttt ttagccttat ttctggggta attaatcagc   11100
gaagcgatga tttttgatct attaacagat atataaatgc aaaagctgca taaccacttt   11160
aactaatact ttcaacattt tcggtttgta ttacttctta ttcaaatgtc ataaaagtat   11220
caacaaaaaa ttgttaatat acctctatac ttaccccacc cgaagtcgcg caaccaacta   11280
actttacaat gactggaaag acaggtcaca tcgacggatt gaactcaagg atcgagaaga   11340
tgagggactt ggatcctgct cagaggttag ttagggttgc cgaagccgca ggattggaac   11400
ctgaagccat ttctgcattg gccggtaacg gtgctttgcc tttgtcattg gccaacggta   11460
tgatcgagaa tgttatcgga aaatttgagt tgccattggg tgtcgccacc aacttcaccg   11520
tcaacggaag ggactactta atacctatgg cagtcgagga accatctgtt gttgccgcag   11580
cctcatatat ggcaaggata gctagagaga acgtggatt caccgcacac ggaactgcac   11640
ctttaatgag ggcccaaatc caagttgtcg gattaggaga cccagaagga gctaggcaaa   11700
ggttgttggc ccataaggct gctttcatgg aagcagcaga tgccgtagat ccagttttgg   11760
ttggtttagg tggtggttgc agagacattg aggtccatgt ttttagggac accctgttg    11820
gtgcaatggc cgtattgcac ttgattgttg atgtcagaga cgccatgggt gccaacacag   11880
ttaacaccat ggctgaaagg ttagctccag aggtagagag gatcgctggt ggaaccgtca   11940
ggttgaggat tttgtctaac ttggccgact tgaggttggt aagagccagg gttgagttag   12000
cccctgagac tttgaccacc cagggatacg atggtgccga cgttgcaagg ggaatggttg   12060
aagcctgcgc cttagcaata gtcgacccct acagggccgc aacccataac aagggaatta   12120
tgaacggaat tgacccagtc gtcgtcgcaa caggtaacga ctggagggcc atcgaagctg   12180
gagcccacgc ctacgccgcc aggaccggac attacacctc tttgacaagg tgggagttgg   12240
ccaacgacgg taggttggtc ggtaccattg aattgccttt ggccttgggt ttggtaggag   12300
gagccaccaa gactcaccct acagctaggg ccgctttggc cttaatgcag gtcgaaaccg   12360
ctactgagtt ggcccaggtt actgccgccg ttggttggc tcagaatatg gccgcaatta   12420
gggccttggc aaccgaggga atccaaaggg gacacatgac cttacacgca aggaacatcg   12480
caatcatggc cggtgccacc ggagccgaca ttgacagggt caccagggtc atcgttgaag   12540
ccggagacgt atctgtcgcc agggctaaac aggttttgga aaatacataa acttagtcat   12600
acgtcattgg tattctcttg aaaagaagc acaacagcac catgtgttac gtaaaatatt   12660
tactttatag tttgtacgtc ataatttctt ccatattaca agttcgtgca tatatagaaa   12720
gaattctgtt gttgtaattg tcataactag gtccgccggc gttggacgag cgaatgtgta   12780
tattagttta aaaagttgta tgtaataaaa gtaaaattta atattttgga tgaaaaaaac   12840
cattttaga ctttttctta actagaatgc tggagtagaa atacgccatc tcaagataca    12900
aaaagcgtta ccggcactga tttgtttcaa ccagtatata gattattatt gggtcttgat   12960
caactttcct cagacatatc agtaacagtt atcaagctaa atatttacgc gaaagaaaaa   13020
caaatatttt aattgtgata cttgtgaatt ttattttatt aaggatacaa agttaagaga   13080
```

-continued

| | |
|---|---|
| aaacaaaatt tatatacaat ataagtaata ttcatatata tgtgatgaat gcagtcttaa | 13140 |
| cgagaagaca tggccttggt gacaactctc ttcaaaccaa cttcagcctt tctcaattca | 13200 |
| tcagcagatg ggtcttcgat ttgcaaagca gccaaagcgg cggtttaaac gcgtggccgt | 13260 |
| gccgtc | 13266 |

<210> SEQ ID NO 52
<211> LENGTH: 13712
<212> TYPE: DNA
<213> ORGANISM: Artificial Sequence
<220> FEATURE:
<223> OTHER INFORMATION: Synthetic construct: i84024 integration construct

<400> SEQUENCE: 52

| | |
|---|---|
| gacggcacgg ccacgcgttt aaaccgccaa gtgatgtaac taaatacacg attaccatgg | 60 |
| aaattaacgt acctttttg tgcgtgtatt gaaatattat gacatattac agaaagggtt | 120 |
| cgcaagtcct gtttctatgc ctttctctta gtaattcacg aaataaacct atggtttacg | 180 |
| aaatgatcca cgaaaatcat gttattattt acatcaacat atcgcgaaaa ttcatgtcat | 240 |
| gtccacatta acatcattgc agagcaacaa ttcattttca tagagaaatt tgctactatc | 300 |
| acccactagt actaccattg gtacctacta ctttgaattg tactaccgct gggcgttatt | 360 |
| aggtgtgaaa ccacgaaaag ttcaccataa cttcgaataa agtcgcggaa aaagtaaac | 420 |
| agctattgct actcaaatga ggtttgcaga agcttgttga agcatgatga agcgttctaa | 480 |
| acgcactatt catcattaaa tatttaaagc tcataaaatt gtattcaatt cctattctaa | 540 |
| atggcttta tttctattac aactattagc tctaaatcca tatcctcata agcagcaatc | 600 |
| aattctatct atactttaaa cgtcgtcca acgccggcgg acctgatgtg tattactagt | 660 |
| gtcgacgaca gcattcgccc agtatttttt ttattctaca aaccttctat aatttcaaag | 720 |
| tatttacata attctgtatc agtttaatca ccataatatc gttttctttg tttagtgcaa | 780 |
| ttaattttc ctattgttac ttcgggcctt tttctgtttt atgagctatt ttttccgtca | 840 |
| tccttccgga tccagatttt cagcttcatc tccagattgt gtctacgtaa tgcacgccat | 900 |
| cattttaaga gaggacctcc cgcgacctcc aaaatcgaac taccttcaca atgaaacttc | 960 |
| ttagtagtat tgagcaggcg tgtgacatct gtagattgaa gaaattgaaa tgtagtaagg | 1020 |
| agaagcccaa atgtgcgaaa tgccttaaaa ataattggga atgcagatat agtccgaaga | 1080 |
| cgaagcgcag tccccttacc cgcgcgcacc ttacggaggt cgagagtcgc cttgagcgcc | 1140 |
| ttgagcaact tttccttctt atcttcccca gagaggattt ggatatgatc cttaagatgg | 1200 |
| acagtcttca agacattaag gcgcttctta cggggctttt cgtgcaggac aacgtcaaca | 1260 |
| aggacgcggt gacggaccgc cttgccagtg tcgaaaccga catgcccctt acgcttcgcc | 1320 |
| aacaccgcat ttccgccacg agtagtagtg aggaatcctc caataagggg cagcgccaac | 1380 |
| ttaccgtgag tatcgatagt gcggcccacc acgacaatag tacgatcccc cttgacttca | 1440 |
| tgccgcgcga cgccttgcac gggttcgact ggagtgagga agacgatatg agtgacggtc | 1500 |
| ttccgttct taagaccgat ccgaataaca acggttttt cggtgatggg agtttgcttt | 1560 |
| gcatcttgag aagtatcggt ttcaagcccg agaactatac caatagtaat gtcaatcgct | 1620 |
| tgcccacgat gatcaccgac cgctataccc ttgccagtcg cagtacgacg agtagacttt | 1680 |
| tgcagtccta cttgaacaac ttccatccgt attgtcccat tgtccatagt cccacccta | 1740 |
| tgatgcttta caacaatcaa atcgagattg ccagtaaaga ccagtggcag atttttgttca | 1800 |
| attgtattct tgcgatcggg gcgtggtgca ttgaaggtga gagtaccgac attgacgtct | 1860 |

```
tctattacca gaacgccaag agtcacctta cctccaaagt gtttgaaagt gggagtatta    1920
tccttgtcac ggcgcttcac ttgcttagta gatacacgca atggcgccaa aagacgaaca    1980
cctcctacaa cttccattcc ttcagtattc gcatggcgat tagtcttggt cttaaccgcg    2040
atttgccgag tagttttttcc gactcctcca tccttgagca gcgcagaaga atctggtgga   2100
gtgtgtatag ttgggaaatt cagcttagtc ttttgtacgg gagaagtatt caattgagtc    2160
aaaacacgat tagttttccc agtagtgtgg atgacgtcca aagaacgacg acggggccga    2220
cgatttacca cggtattatc gagacggcgc gcttgcttca ggtctttacg aagatttacg    2280
agcttgataa gacggtgacc gcggagaagt cccccatttg cgcgaagaag tgtcttatga    2340
tctgcaacga aatcgaagaa gtcagtcgcc aagcgccgaa attccttcag atggacatca    2400
gtacgacggc ccttacgaac cttcttaaag agcatccctg gcttagtttc acgcgcttttg   2460 agcttaaatg gaagcaactt agtttgatta tctacgtgct tcgcgacttc tttaccaact    2520
tcacgcaaaa gaaaagtcag cttgagcaag accagaacga ccaccagtcc tacgaggtca    2580
agagatgtag tattatgctt tccgacgcgg cgcagcgcac cgtcatgagt gtgtcctcct    2640
acatggataa ccacaacgtg acgccgtact tcgcgtggaa ctgcagttac tatcttttta    2700
acgcggtgct tgtgccgatt aaaacccttt tgagtaatag taagagtaac gccgaaaaca    2760
atgaaacggc gcagcttctt cagcagatca ataccgtcct tatgcttctt aagaagcttg    2820
cgaccttcaa gattcaaacc tgcgagaagt atatccaggt gcttgaggaa gtgtgcgccc    2880
ccttccttct tagtcaatgc gcgattccgc ttccccacat ttcctacaat aactccaacg    2940
ggtccgcgat caagaacatc gtggggagtg cgaccattgc gcagtatccc accttgcccg    3000
aagagaacgt gaataacatt tccgtcaagt acgtcagtcc cggtagtgtg ggtcccagtc    3060
ccgtcccgct taagagtggg gcgtccttttt ccgaccttgt gaaacttctt agtaatagac   3120
cgccgagtag aaatagtccg gtcacgattc gcgctccac gcccagtcac agaagtgtga    3180
cccccttcct tggtcagcaa cagcaacttc agagtcttgt cccgcttacg cccagtgccc    3240
ttttcggggg tgcgaacttc aaccagtccg gtaacatcgc cgactccagt cttagtttta   3300
cctttaccaa ttcctccaat gggcccaatt tgattacgac ccagacgaac agtcaggcct    3360
tgagtcagcc gatcgcgagt agtaatgtcc acgacaattt tatgaacaac gagattaccg    3420
cctccaagat cgacgacggg aacaacagta agccgcttag tcccgggtgg accgatcaga    3480
ccgcctacaa tgccttcggg attaccacgg gtatgttcaa cacgaccacg atggacgacg    3540
tgtacaatta ccttttttgac gacgaggaca cgccgccgaa tccgaagaag gaatgagcca    3600
attggtgcgg caattgataa taacgaaaat gtcttttaat gatctgggta taatgaggaa    3660
ttttccgaac gttttttactt tatatatata tatacatgta acatatattc tatacgctat    3720
atcgagaaaa cgcgatggtg gggtgacttt caactcggcg tatccccgcg tgcttggccg    3780
gccgtccgca tgactcaaga gaagcatgtg gttttttgagt tttttttcgtt gaattttcag   3840 gtaaagctca atagttatga caattacaac aacagaattc tttctatata tgcacgaact    3900
tgtaatatgg aagaaattat gacgtacaaa ctataaagta aatattttac gtaacacatg    3960
gtgctgttgt gcttcttttt caagagaata ccaatgacgt atgactaagt ttaggattta    4020
atgcaggtga cggacccatc tttcaaacga tttatcag tggcgtccaa attgttaggt      4080
tttgttggtt cagcaggttt cctgttgtgg gtcatatgac tttgaaccaa atggccggct    4140
gctagggcag cacataagga taattcacct gccaagacgg cacaggcaac tattcttgct    4200
aattgacgtg cgttggtacc aggagcggta gcatgtgggc ctcttacacc taataagtcc    4260
```

```
aacatggcac cttgtggttc tagaacagta ccaccaccga tggtacctac ttcgatggat    4320
ggcatggata cggaaattct caaatcaccg tccacttctt tcatcaatgt tatacagttg    4380
gaactttcga cattttgtgc aggatcttgt cctaatgcca agaaaacagc tgtcactaaa    4440
ttagctgcat gtgcgttaaa tccaccaaca gacccagcca ttgcagatcc aaccaaattc    4500
ttagcaatgt tcaactcaac caatgcggaa acatcacttt taacactttt tctgacaaca    4560
tcaccaggaa tagtagcttc tgcgacgaca ctcttaccac gaccttcgat ccagttgatg    4620
gcagctggtt ttttgtcggt acagtagtta ccagaaacgg agacaacctc catatcttcc    4680
cagccatact cttctaccat ttgctttaat gagtattcga cacccttaga aatcatattc    4740
atacccattg cgtcaccagt agttgttcta aatctcatga agagtaaatc tcctgctaga    4800
caagtttgaa tatgttgcag acgtgcaaat cttgatgtag agttaaaagc tttttttaatt    4860 gcgttttgtc cctcttctga gtctaaccat atcttacagg caccagatct tttcaaagtt    4920
gggaaacgga ctactgggcc tcttgtcata ccatccttag ttaaaacagt tgttgcacca    4980
ccgccagcat tgattgcctt acagccacgc atggcagaag ctaccaaaca accctctgta    5040
gttgccattg gtatatgata agatgtacca tcgataacca aggggcctat aacaccaacg    5100
ggcaaaggca tgtaacctat aacattttca caacaagcgc caaatacgcg gtcgtagtca    5160
taatttttat atggtaaacg atcagatgct aatacaggac cttctgccaa aattgaagaa    5220
gccttcctac gtaccgcaac cgctctcgta gtatcaccta attttttctc caaagcgtac    5280
aaaggtaact taccgtgaat aaccaaggca gcgacctctt tgttcttcaa ttgttttgta    5340
tttccactac ttaataatgc ttctaattct tctaaaggac gtattttctt atccaagctt    5400
tcaatatcgc gggaatcatc ttcctcacta gatgatgaag gtcctgatga gctcgattgc    5460
gcagatgata aacttttgac tttcgatcca gaaatgactg ttttattggt taaaactggt    5520
gtagaagcct tttgtacagg agcagtaaaa gacttcttgg tgacttcagt cttcaccaat    5580
tggtctgcag ccattgtaaa gttagttggt tgcgcgactt cgggtggggt aagtatagag    5640
gtatattaac aattttttgt tgatactttt atgacatttg aataagaagt aatacaaacc    5700
gaaaatgttg aaagtattag ttaaagtggt tatgcagctt ttgcatttat atatctgtta    5760
atagatcaaa aatcatcgct tcgctgatta attaccccag aaataaggct aaaaaactaa    5820
tcgcattatt atcctatggt tgttaatttg attcgttgat ttgaaggttt gtggggccag    5880
gttactgcca atttttcctc ttcataacca taaaagctag tattgtagaa tctttattgt    5940
tcggagcagt gcggcgcgag gcacatctgc gtttcaggaa cgcgaccggt gaagaccagg    6000
acgcacggag gagagtcttc cgtcggaggg ctgtcgcccg ctcggcggct tctaatccgt    6060
acttcaatat agcaatgagc agttaagcgt attactgaaa gttccaaaga gaaggttttt    6120
ttaggctaag ataatggggc tctttacatt tccacaacat ataagtaaga ttagatatgg    6180
atatgtatat ggtggtattg ccatgtaata tgattattaa acttctttgc gtccatccaa    6240
aaaaaaagta acgcacgcac actcccgaca gacaactagc ttgataatga ctgatgttcg    6300
tttcagaatc atcggtaccg gtgcctatgt tccagaaaga attgtttcta acgacgaagt    6360
tggtgctcca gctggtgttg atgacgactg gatcaccaga aagactggta tcagacaaag    6420
aagatgggct gctgatgacc aagctacttc tgacttagct actgctgctg gtagagccgc    6480
cttgaaggct gctggtatta ctccagaaca attgactgtt atcgctgttg ctacctccac    6540
tccagataga ccacaaccac ctaccgctgc ctacgttcaa caccacttgg gtgctactgg    6600
tactgctgct ttcgacgtta acgctgtttg ttccggtact gttttcgcct tatcttctgt    6660
```

```
cgccggtacc ttggtctaca gaggtggtta tgctttggtt atcggtgctg acttgtactc    6720
cagaatcttg aatccagctg acagaaagac cgttgttttg ttcggtgatg gtgctggtgc    6780
tatggttttg ggtccaactt ctactggtac tggtccaatc gttagaagag tcgctttaca    6840
cacctttggt ggtttaaccg atttgattag agttccagct ggtggttcta gacaaccatt    6900
ggacactgac ggtttggacg ccggtttgca atactttgcc atggacggta gagaagttag    6960
acgtttcgtc actgaacatt tgccacaatt gatcaaaggt ttcttgcatg aagctggtgt    7020
tgacgctgct gatatttctc atttcgtccc acatcaagcc aacggtgtta tgttggacga    7080 agttttggt  gaattgcatt tgccaagagc taccatgcac agaactgttg aaacttacgg    7140
taataccggt gctgcttcca ttccaattac tatggacgct gctgttagag ccggttcctt    7200
tagaccaggt gaattggtct tattggctgg ttttggtggt ggtatggccg cctctttcgc    7260
cttgattgaa tggtagatgc tatgtaatag acaataaaac catgtttata taaaaaaaat    7320
tcaaaataga aaacgattct gtacaaggag attttttttt ttgttctagt gtgtttatat    7380
tatccttggc taagaggcac taacctgcag gccgcgagcg ccgatacgaa aatcgttatt    7440
gtcttgaagg tgaaatttct actcttatta atggtgaacg ttaagctgat gctatgatgg    7500
aagctgattg gtcttaactt gcttgtcatc ttgctaatgg tcattggctc gtgttattac    7560
ttaagttatt tgtactcgtt ttgaacgtaa tgctaatgat catcttatgg aataatagtg    7620
agtggtttca gggtccataa agcttttcaa ttcatctttt tttttttgt  tctttttttt    7680 gattccggtt tctttgaaat ttttttgatt cggtaatctc cgagcagaag gaagaacgaa    7740
ggaaggagca cagacttaga ttggtatata tacgcatatg tggtgttgaa gaaacatgaa    7800
attgcccagt attcttaacc caactgcaca gaacaaaaac ctgcaggaaa cgaagataaa    7860
tcatgtcgaa agctacatat aaggaacgtg ctgctactca tcctagtcct gttgctgcca    7920
agctatttaa tatcatgcac gaaaagcaaa caaacttgtg tgcttcattg gatgttcgta    7980
ccaccaagga attactggag ttagttgaag cattaggtcc caaaatttgt ttactaaaaa    8040
cacatgtgga tatcttgact gatttttcca tggagggcac agttaagccg ctaaaggcat    8100
tatccgccaa gtacaatttt ttactcttcg aagacagaaa atttgctgac attggtaata    8160
cagtcaaatt gcagtactct gcgggtgtat acagaatagc agaatgggca gacattacga    8220
atgcacacgg tgtggtgggc ccaggtattg ttagcggttt gaagcaggcg gcggaagaag    8280
taacaaagga acctagaggc cttttgatgt tagcagaatt gtcatgcaag gctcccctag    8340
ctactggaga atatactaag ggtactgttg acattgcgaa gagtgacaaa gattttgtta    8400
tcggctttat tgctcaaaga gacatggggt gaagagatga aggttacgat tggttgatta    8460
tgacacccgg tgtgggttta gatgacaagg gagacgcatt gggtcaacag tatagaaccg    8520
tggatgatgt ggtctctaca ggatctgaca ttattattgt tggaagagga ctatttgcaa    8580
agggaaggga tgctaaggta gagggtgaac gttacagaaa agcaggctgg gaagcatatt    8640
tgagaagatg cggccagcaa aactaaaaaa ctgtattata agtaaatgca tgtatactaa    8700
actcacaaat tagagcttca atttaattat atcagttatt accacgaaaa tcgttattgt    8760
cttgaaggtg aaatttctac tcttattaat ggtgaacgtt aagctgatgc tatgatggaa    8820
gctgattggt cttaacttgc ttgtcatctt gctaatggtc atatggctcg tgttattact    8880
taagttattt gtactcgttt tgaacgtaat gctaatgatc atcttatgga ataatagtga    8940
acggccggcc aagcacgcgg ggattgaatg agaaaaaaaa tcggttgggc ttaacttta    9000 agaaaaaagt tgagattaga tttattgtgt tataaatata gatatacaat tctttataaa    9060
```

```
aaaaatatat atatatatca ttgttattaa ataaagagtt ttcctagtat atagattaaa   9120
aaactactct attaaatgag agctaaaaaa agcaggctgc caaaaaaata aagcatttat   9180
gaagggggtt cagcaagatg caatcgatgg gggaagatta tttttttaaca tcgtaagatc   9240 ttctaaattt gtcatcgatg ttggtcaagt agtaaacacc actttgcaaa tgctcaatgg   9300
aaccttgagg tttgaagttc ttcttcaaat gggcattttc tctcaattcg atggcagctt   9360
cgtaatcctt tggagtttcg gtgattctct tggctaattt gttagtaata tctaattcct   9420
tgataatatg ttggacgtca ccaacaattt tgcaagaata tagagatgca gctaaaccgg   9480
aaccgtaaga aaataaacca acacgcttgc cttgtaagtc gtcagatcca acatagttta   9540
atagagatgc aaaggcggca taaacagatg cggtgtacat gttacctgtg tttgttggaa   9600
caatcaaaga ttgggcaact ctctctttgt ggaatggctt agcaacatta acaaaagttt   9660
tttcaatgtt cttatcggtt aaagattcgt cataatcgcg agtagctaat tcggcgtcaa   9720
cttctgggaa caattgagga ttggctctga atcgttata tagtaatcta ccgtatgatt   9780
ttgtgaccaa tttacaggtt ggaacatgga aaacgttgta gtcgaaatat ttcaaaacgt   9840
tcaaagcatc cgaaccagcg ggatcgctaa ccaaccctttt agaaatagcc ttcttggaat   9900
aactcttgta aacttgatca agagccttga cgtaacaagt taatgaaaaa tgaccatcga   9960
cgtaaggata ttcgctggtg aaatctggct tgtaaaaatc gtaggcgtgt tccatgtaag  10020
aagctcttac agagtcaaat acaattggag catcaggacc gatccacata gcaacagtac  10080
cggcaccacc ggttggtctt gcggcaccct tatcgtagat ggcaatatca ccgcaaacta  10140
caatggcgtc tctaccatcc catgcgttag attcaatcca gttcaaagag ttgaacaacg  10200
cgttggtacc accgtaacag gcattaagcg tgtcaatacc ttcgacgtca gtgttttcac  10260
caaacaattg catcaagaca gacttgacag acttggactt gtcaatcaga gtttcagtac  10320
cgacttctaa tctaccaatt tgttggtgt cgatgttgta actcttgatc aacttagaca  10380
aaacagttag ggacatcgag tagatatctt ctctgtcatt gacaaaagac atgttggttt  10440
ggcccagacc aattgtgtat ttaccttgag aaacgccatc aaatttctct agctcagatt  10500
ggttgacaca ttgagttggg atgtaaattt ggataccttt aataccgaca ttttgaggtc  10560 tggtttttg ttcagcggtc ttttgttttt ttagttcagt catttgcaag tttgtattgt  10620
gtaattgttg ttgcttttgc ggcctaagtc ttcctttaat accacaccaa caaagtttag  10680
ttgagagttt cattgtgaag gtagttcgat tttggaggtc gcgggaggtt acttttttt  10740 tggatggacg caaagaagtt taataatcat attacatggc aataccacca tatacatatc  10800
catatctaat cttacttata tgttgtggaa atgtaaagag ccccattatc ttagcctaaa  10860
aaaaccttct ctttggaact ttcagtaata cgcttaactg ctcattgcta tattgaagta  10920
cggattagaa gccgccgagc gggcgacagc cctccgacgg aagactctcc tccgtgcgtc  10980
ctggtcttca ccggtcgcgt tcctgaaacg cagatgtgcc tcgcgccgca ctgctccgaa  11040
caataaagat tctacaatac tagcttttat ggttatgaag aggaaaaatt ggcagtaacc  11100 tggcccaca aaccttcaaa tcaacgaatc aaattaacaa ccataggata ataatgcgat  11160 tagttttta gccttatttc tggggtaatt aatcagcgaa gcgatgattt ttgatctatt  11220
aacagatata taaatgcaaa agctgcataa ccactttaac taatactttc aacattttcg  11280
gtttgtatta cttcttattc aaatgtcata aaagtatcaa caaaaaattg ttaatatacc  11340
tctatactta ccccaccga agtcgcgcaa ccaactaact ttacaatggc tgcagaccaa  11400
ttggtgaaga ctgaagtcac caagaagtct tttactgctc ctgtacaaaa ggcttctaca  11460
```

```
ccagttttaa ccaataaaac agtcatttct ggatcgaaag tcaaaagttt atcatctgcg    11520
caatcgagct catcaggacc ttcatcatct agtgaggaag atgattcccg cgatattgaa    11580
agcttggata agaaaatacg tcctttagaa gaattagaag cattattaag tagtggaaat    11640
acaaaacaat tgaagaacaa agaggtcgct gccttggtta ttcacggtaa gttacctttg    11700
tacgctttgg agaaaaaatt aggtgatact acgagagcgg ttgcggtacg taggaaggct    11760 cttttcaattt tggcagaagc tcctgtatta gcatctgatc gtttaccata taaaaattat    11820
gactacgacc gcgtatttgg cgcttgttgt gaaaatgtta taggttacat gcctttgccc    11880
gttggtgtta taggcccctt ggttatcgat ggtacatctt atcatatacc aatggcaact    11940
acagagggtt gtttggtagc ttctgccatg cgtggctgta aggcaatcaa tgctggcggt    12000
ggtgcaacaa ctgttttaac taaggatggt atgacaagag gcccagtagt ccgtttccca    12060
actttgaaaa gatctggtgc ctgtaagata tggttagact cagaagaggg acaaaacgca    12120
attaaaaaag cttttaactc tacatcaaga tttgcacgtc tgcaacatat tcaaacttgt    12180
ctagcaggag atttactctt catgagattt agaacaacta ctggtgacgc aatgggtatg    12240
aatatgattt ctaagggtgt cgaatactca ttaaagcaaa tggtagaaga gtatggctgg    12300
gaagatatgg aggttgtctc cgtttctggt aactactgta ccgacaaaaa accagctgcc    12360
atcaactgga tcgaaggtcg tggtaagagt gtcgtcgcag aagctactat tcctggtgat    12420
gttgtcagaa aagtgttaaa aagtgatgtt tccgcattgg ttgagttgaa cattgctaag    12480
aatttggttg gatctgcaat ggctgggtct gttggtggat ttaacgcaca tgcagctaat    12540
ttagtgacag ctgttttctt ggcattagga caagatcctg cacaaaatgt cgaaagttcc    12600
aactgtataa cattgatgaa agaagtggac ggtgatttga gaatttccgt atccatgcca    12660
tccatcgaag taggtaccat cggtggtggt actgttctag aaccacaagg tgccatgttg    12720
gacttattag gtgtaagagg cccacatgct accgctcctg gtaccaacgc acgtcaatta    12780
gcaagaatag ttgcctgtgc cgtcttggca ggtgaattat ccttatgtgc tgccctagca    12840
gccggccatt tggttcaaag tcatatgacc cacaacagga aacctgctga accaacaaaa    12900
cctaacaatt tggacgccac tgatataaat cgtttgaaag atgggtccgt cacctgcatt    12960
aaatcctaaa cttagtcata cgtcattggt attctcttga aaagaagca  caacagcacc    13020 atgtgttacg taaaatattt actttatagt ttgtacgtca taatttcttc catattacaa    13080
gttcgtgcat atatagaaag aattctgttg ttgtaattgt cataactatt gagctttacc    13140
tgaaaattca acgaaaaaaa ctcaaaaacc acatgcttct cttgagtcat gcggaggtcc    13200
gccggcgttg gacgagcgaa tgtgtatatt agtttaaaaa gttgtatgta ataaagtaa    13260 aatttaatat tttggatgaa aaaaaccatt tttagacttt ttcttaacta gaatgctgga    13320
gtagaaatac gccatctcaa gatacaaaaa gcgttaccgg cactgatttg tttcaaccag    13380
tatatagatt attattgggt cttgatcaac tttcctcaga catatcagta acagttatca    13440 agctaaaatat ttacgcgaaa gaaaaacaaa tattttaatt gtgatacttg tgaattttat    13500
tttattaagg atacaaagtt aagagaaaac aaaatttata tacaatataa gtaatattca    13560
tatatatgtg atgaatgcag tcttaacgag aagacatggc cttggtgaca actctcttca    13620
aaccaacttc agcctttctc aattcatcag cagatgggtc ttcgatttgc aaagcagcca    13680
aagcggcggt ttaaacgcgt ggccgtgccg tc                                  13712
```

<210> SEQ ID NO 53
<211> LENGTH: 13964

<212> TYPE: DNA
<213> ORGANISM: Artificial Sequence
<220> FEATURE:
<223> OTHER INFORMATION: Synthetic construct: i84026 integration construct

<400> SEQUENCE: 53

```
gacggcacgg ccacgcgttt aaaccgccaa gtgatgtaac taaatacacg attaccatgg      60
aaattaacgt acctttttg tgcgtgtatt gaaatattat gacatattac agaaagggtt     120
cgcaagtcct gtttctatgc ctttctctta gtaattcacg aaataaacct atggtttacg    180
aaatgatcca cgaaaatcat gttattattt acatcaacat atcgcgaaaa ttcatgtcat    240
gtccacatta acatcattgc agagcaacaa ttcattttca tagagaaatt tgctactatc    300
acccactagt actaccattg gtacctacta ctttgaattg tactaccgct gggcgttatt    360
aggtgtgaaa ccacgaaaag ttcaccataa cttcgaataa agtcgcggaa aaaagtaaac    420
agctattgct actcaaatga ggtttgcaga agcttgttga agcatgatga agcgttctaa    480
acgcactatt catcattaaa tatttaaagc tcataaaatt gtattcaatt cctattctaa    540
atggctttta tttctattac aactattagc tctaaatcca tatcctcata agcagcaatc    600
aattctatct atactttaaa cgctcgtcca acgccggcgg acctgatgtg tattactagt    660
gtcgacgaca gcattcgccc agtattttt ttattctaca aaccttctat aatttcaaag    720
tatttacata attctgtatc agtttaatca ccataatatc gttttctttg tttagtgcaa    780
ttaattttc ctattgttac ttcgggcctt tttctgtttt atgagctatt ttttccgtca    840
tccttccgga tccagatttt cagcttcatc tccagattgt gtctacgtaa tgcacgccat    900
cattttaaga gaggacctcc cgcgacctcc aaaatcgaac taccttcaca atgaaacttc    960
ttagtagtat tgagcaggcg tgtgacatct gtagattgaa gaaattgaaa tgtagtaagg   1020
agaagcccaa atgtgcgaaa tgccttaaaa ataattggga atgcagatat agtccgaaga   1080
cgaagcgcag tccccttacc cgcgcgcacc ttacggaggt cgagagtcgc cttgagcgcc   1140
ttgagcaact tttccttctt atcttcccca gagaggattt ggatatgatc cttaagatgg   1200
acagtcttca agacattaag gcgcttctta cggggctttt cgtgcaggac aacgtcaaca   1260
aggacgcggt gacggaccgc cttgccagtg tcgaaaccga catgccccctt acgcttcgcc   1320
aacaccgcat ttccgccacg agtagtagtg aggaatcctc caataagggg cagcgccaac   1380
ttaccgtgag tatcgatagt gcggcccacc acgacaatag tacgatcccc cttgacttca   1440
tgccgcgcga cgccttgcac gggttcgact ggagtgagga agacgatatg agtgacggtc   1500
ttccgtttct aagaccgat ccgaataaca acggtttttt cggtgatggg agtttgcttt    1560
gcatcttgag aagtatcggt ttcaagcccg agaactatac caatagtaat gtcaatcgct   1620
tgcccacgat gatcaccgac cgctataccc ttgccagtcg cagtacgacg agtagacttt   1680
tgcagtccta cttgaacaac ttccatccgt attgtcccat tgtccatagt cccacccttta  1740
tgatgcttta caacaatcaa atcgagattg ccagtaaaga ccagtggcag attttgttca   1800
attgtattct tgcgatcggg gcgtggtgca ttgaaggtga gagtaccgac attgacgtct   1860
tctattacca gaacgccaag agtcacctta cctccaaagt gtttgaaagt gggagtatta   1920
tccttgtcac ggcgcttcac ttgcttagta gatacacgca atggcgccaa aagacgaaca   1980
cctcctacaa cttccattcc ttcagtattc gcatggcgat tagtcttggt cttaaccgcg   2040
atttgccgag tagttttttcc gactcctcca tccttgagca gcgcagaaga atctggtgga   2100
gtgtgtatag ttgggaaatt cagcttagtc ttttgtacgg gagaagtatt caattgagtc   2160
```

```
aaaacacgat tagttttccc agtagtgtgg atgacgtcca agaacgacg acggggccga    2220 cgatttacca cggtattatc gagacggcgc gcttgcttca ggtctttacg aagatttacg    2280
agcttgataa gacggtgacc gcggagaagt cccccatttg cgcgaagaag tgtcttatga    2340
tctgcaacga aatcgaagaa gtcagtcgcc aagcgccgaa attccttcag atggacatca    2400
gtacgacggc ccttacgaac cttcttaaag agcatccctg gcttagtttc acgcgctttg    2460
agcttaaatg gaagcaactt agtttgatta tctacgtgct tcgcgacttc tttaccaact    2520
tcacgcaaaa gaaaagtcag cttgagcaag accagaacga ccaccagtcc tacgaggtca    2580
agagatgtag tattatgctt tccgacgcgg cgcagcgcac cgtcatgagt gtgtcctcct    2640
acatggataa ccacaacgtg acgccgtact tcgcgtggaa ctgcagttac tatctttta    2700 acgcggtgct tgtgccgatt aaaccctttt tgagtaatag taagagtaac gccgaaaaca    2760
atgaaacggc gcagcttctt cagcagatca ataccgtcct tatgcttctt aagaagcttg    2820
cgaccttcaa gattcaaacc tgcgagaagt atatccaggt gcttgaggaa gtgtgcgccc    2880
ccttccttct tagtcaatgc gcgattccgc ttccccacat ttcctacaat aactccaacg    2940
ggtccgcgat caagaacatc gtggggagtg cgaccattgc gcagtatccc accttgcccg    3000
aagagaacgt gaataacatt tccgtcaagt acgtcagtcc cggtagtgtg ggtcccagtc    3060
ccgtcccgct taagagtggg gcgtcctttt ccgaccttgt gaaacttctt agtaatagac    3120
cgccgagtag aaatagtccg gtcacgattc cgcgctccac gcccagtcac agaagtgtga    3180 ccccttcct tggtcagcaa cagcaacttc agagtcttgt cccgcttacg cccagtgccc    3240
ttttcggggg tgcgaacttc aaccagtccg gtaacatcgc cgactccagt cttagtttta    3300
cctttaccaa ttcctccaat gggcccaatt tgattacgac ccagacgaac agtcaggcct    3360
tgagtcagcc gatcgcgagt agtaatgtcc acgacaattt tatgaacaac gagattaccg    3420
cctccaagat cgacgacggg aacaacagta agccgcttag tcccgggtgg accgatcaga    3480
ccgcctacaa tgccttcggg attaccacgg gtatgttcaa cacgaccacg atggacgacg    3540
tgtacaatta cctttttgac gacgaggaca cgccgccgaa tccgaagaag gaatgagcca    3600
attggtgcgg caattgataa taacgaaaat gtcttttaat gatctgggta taatgaggaa    3660
ttttccgaac gtttttactt tatatatata tatacatgta acatatattc tatacgctat    3720
atcgagaaaa cgcgatggtg gggtgacttt caactcggcg tatccccgcg tgcttggccg    3780
gccgtccgca tgactcaaga gaagcatgtg gtttttgagt ttttttcgtt gaattttcag    3840
gtaaagctca atagttatga caattacaac aacagaattc tttctatata tgcacgaact    3900
tgtaatatgg aagaaattat gacgtacaaa ctataaagta aatattttac gtaacacatg    3960
gtgctgttgt gcttcttttt caagagaata ccaatgacgt atgactaagt ttaggattta    4020
atgcaggtga cggacccatc tttcaaacga tttatatcag tggcgtccaa attgttaggt    4080
tttgttggtt cagcaggttt cctgttgtgg gtcatatgac tttgaaccaa atggccggct    4140
gctagggcag cacataagga taattcacct gccaagacgg cacaggcaac tattcttgct    4200
aattgacgtg cgttggtacc aggagcggta gcatgtgggc ctcttacacc taataagtcc    4260
aacatggcac cttgtggttc tagaacagta ccaccaccga tggtacctac ttcgatggat    4320
ggcatggata cggaaattct caaatcaccg tccacttctt tcatcaatgt tatacagttg    4380
gaactttcga cattttgtgc aggatcttgt cctaatgcca agaaaacagc tgtcactaaa    4440
ttagctgcat gtgcgttaaa tccaccaaca gacccagcca ttgcagatcc aaccaaattc    4500
ttagcaatgt tcaactcaac caatgcggaa acatcacttt ttaacacttt tctgacaaca    4560
```

```
tcaccaggaa tagtagcttc tgcgacgaca ctcttaccac gaccttcgat ccagttgatg    4620
gcagctggtt ttttgtcggt acagtagtta ccagaaacgg agacaacctc catatcttcc    4680
cagccatact cttctaccat ttgctttaat gagtattcga cacccttaga aatcatattc    4740
atacccattg cgtcaccagt agttgttcta aatctcatga agagtaaatc tcctgctaga    4800
caagtttgaa tatgttgcag acgtgcaaat cttgatgtag agttaaaagc ttttttaatt    4860
gcgttttgtc cctcttctga gtctaaccat atcttacagg caccagatct tttcaaagtt    4920
gggaaacgga ctactgggcc tcttgtcata ccatccttag ttaaaacagt tgttgcacca    4980
ccgccagcat tgattgcctt acagccacgc atggcagaag ctaccaaaca accctctgta    5040
gttgccattg gtatatgata agatgtacca tcgataacca aggggcctat aacaccaacg    5100
ggcaaaggca tgtaacctat aacattttca caacaagcgc caaatacgcg gtcgtagtca    5160 taattttat atggtaaacg atcagatgct aatacaggag cttctgccaa aattgaaaga    5220
gccttcctac gtaccgcaac cgctctcgta gtatcaccta attttttctc caaagcgtac    5280
aaaggtaact taccgtgaat aaccaaggca gcgacctctt tgttcttcaa ttgttttgta    5340
tttccactac ttaataatgc ttctaattct tctaaaggac gtattttctt atccaagctt    5400
tcaatatcgc gggaatcatc ttcctcacta gatgatgaag gtcctgatga gctcgattgc    5460
gcagatgata aacttttgac tttcgatcca gaaatgactg ttttattggt taaaactggt    5520
gtagaagcct tttgtacagg agcagtaaaa gacttcttgg tgacttcagt cttcaccaat    5580
tggtctgcag ccattgtaaa gttagttggt tgcgcgactt cgggtggggt aagtatagag    5640
gtatattaac aatttttgt tgatactttt atgacatttg aataagaagt aatacaaacc    5700
gaaaatgttg aaagtattag ttaaagtggt tatgcagctt ttgcatttat atatctgtta    5760
atagatcaaa aatcatcgct tcgctgatta attaccccag aaataaggct aaaaaactaa    5820
tcgcattatt atcctatggt tgttaatttg attcgttgat ttgaaggttt gtggggccag    5880
gttactgcca attttcctc ttcataacca taaaagctag tattgtagaa tctttattgt    5940
tcggagcagt gcggcgcgag gcacatctgc gtttcaggaa cgcgaccggt gaagaccagg    6000
acgcacggag gagagtcttc cgtcggaggg ctgtcgcccg ctcggcggct tctaatccgt    6060
acttcaatat agcaatgagc agttaagcgt attactgaaa gttccaaaga gaaggttttt    6120
ttaggctaag ataatggggc tctttacatt tccacaacat ataagtaaga ttagatatgg    6180
atatgtatat ggtggtattg ccatgtaata tgattattaa acttctttgc gtccatccaa    6240 aaaaaagta acgcacgcac actcccgaca gacaactagc ttgataatgt ctcagaacgt    6300
ttacattgta tcgactgcca gaaccccaat tggttcattc cagggttctc tatcctccaa    6360
gacagcagtg gaattgggtg ctgttgcttt aaaaggcgcc ttggctaagg ttccagaatt    6420
ggatgcatcc aaggattttg acgaaattat ttttggtaac gttctttctg ccaatttggg    6480
ccaagctccg gccagacaag ttgctttggc tgccggtttg agtaatcata tcgttgcaag    6540
cacagttaac aaggtctgtg catccgctat gaaggcaatc attttgggtg ctcaatccat    6600
caaatgtggt aatgctgatg ttgtcgtagc tggtggttgt gaatctatga ctaacgcacc    6660
atactacatg ccagcagccc gtgcgggtgc caaatttggc caaactgttc ttgttgatgg    6720
tgtcgaaaga gatgggttga acgatgcgta cgatggtcta gccatgggtg tacacgcaga    6780
aaagtgtgcc cgtgattggg atattactag agaacaacaa gacaattttg ccatcgaatc    6840
ctaccaaaaa tctcaaaaat ctcaaaagga aggtaaattc gacaatgaaa ttgtacctgt    6900
taccattaag ggatttagag gtaagcctga tactcaagtc acgaaggacg aggaacctgc    6960
```

-continued

```
tagattacac gttgaaaaat tgagatctgc aaggactgtt ttccaaaaag aaaacggtac    7020
tgttactgcc gctaacgctt ctccaatcaa cgatggtgct gcagccgtca tcttggtttc    7080
cgaaaaagtt ttgaaggaaa agaatttgaa gcctttggct attatcaaag gttggggtga    7140
ggccgctcat caaccagctg attttacatg ggctccatct cttgcagttc caaaggcttt    7200
gaaacatgct ggcatcgaag acatcaattc tgttgattac tttgaattca atgaagcctt    7260
ttcggttgtc ggtttggtga acactaagat tttgaagcta gacccatcta aggttaatgt    7320
atatggtggt gctgttgctc taggtcaccc attgggttgt tctggtgcta gagtggttgt    7380
tacactgcta tccatcttac agcaagaagg aggtaagatc ggtgttgccg ccatttgtaa    7440
tggtggtggt ggtgcttcct ctattgtcat tgaaaagata tgattacgtt ctgcgatttt    7500
ctcatgatct ttttcataaa atacataaat atataaatgg ctttatgtat aacaggcata    7560
atttaaagtt ttatttgcga ttcatcgttt ttcaggtact caaacgctga ggtgtgcctt    7620
ttgacttact tttccgcctt ggcaagctgg ccgaacctgc aggccgcgag cgccgatacg    7680
aaaatcgtta ttgtcttgaa ggtgaaattt ctactcttat taatggtgaa cgttaagctg    7740
atgctatgat ggaagctgat tggtcttaac ttgcttgtca tcttgctaat ggtcattggc    7800
tcgtgttatt acttaagtta tttgtactcg ttttgaacgt aatgctaatg atcatcttat    7860
ggaataatag tgagtggttt cagggtccat aaagctttc aattcatctt ttttttttt    7920
gttcttttt ttgattccgg tttctttgaa attttttga ttcggtaatc tccgagcaga    7980
aggaagaacg aaggaaggag cacagactta gattggtata tatacgcata tgtggtgttg    8040
aagaaacatg aaattgccca gtattcttaa cccaactgca cagaacaaaa acctgcagga    8100
aacgaagata aatcatgtcg aaagctacat ataaggaacg tgctgctact catcctagtc    8160
ctgttgctgc caagctattt aatatcatgc acgaaaagca aacaaacttg tgtgcttcat    8220
tggatgttcg taccaccaag gaattactgg agttagttga agcattaggt cccaaaattt    8280
gtttactaaa aacacatgtg gatatcttga ctgattttc catggagggc acagttaagc    8340
cgctaaaggc attatccgcc aagtacaatt ttttactctt cgaagacaga aaatttgctg    8400
acattggtaa tacagtcaaa ttgcagtact ctgcgggtgt atacagaata gcagaatggg    8460
cagacattac gaatgcacac ggtgtggtgg gcccaggtat tgttagcggt ttgaagcagg    8520
cggcggaaga agtaacaaag gaacctagag gccttttgat gttagcagaa ttgtcatgca    8580
agggctccct agctactgga gaatatacta agggtactgt tgacattgcg aagagtgaca    8640
aagattttgt tatcggcttt attgctcaaa gagacatggg tggaagagat gaaggttacg    8700
attggttgat tatgacaccc ggtgtgggtt tagatgacaa gggagacgca ttgggtcaac    8760
agtatagaac cgtggatgat gtggtctcta caggatctga cattattatt gttgaagag    8820
gactatttgc aaagggaagg gatgctaagg tagagggtga acgttacaga aaagcaggct    8880
gggaagcata tttgagaaga tgcggccagc aaaactaaaa aactgtatta taagtaaatg    8940
catgtatact aaactcacaa attagagctt caatttaatt atatcagtta ttaccacgaa    9000
aatcgttatt gtcttgaagg tgaaatttct actcttatta atggtgaacg ttaagctgat    9060
gctatgatgg aagctgattg gtcttaactt gcttgtcatc ttgctaatgg tcatatggct    9120
cgtgttatta cttaagttat ttgtactcgt tttgaacgta atgctaatga tcatcttatg    9180
gaataatagt gaacggccgg ccaagcacgc ggggattgaa tgagaaaaaa aatcggttgg    9240
gcttaacttt aagaaaaaaa gttgagatta gattttattgt gttataaata tagatataca    9300
attctttata aaaaaaatat atatatatat cattgttatt aaataaagag ttttcctagt    9360
```

```
atatagatta aaaaactact ctattaaatg agagctaaaa aaagcaggct gccaaaaaaa   9420
taaagcattt atgaaggggg ttcagcaaga tgcaatcgat gggggaagat tattttttaa   9480
catcgtaaga tcttctaaat ttgtcatcga tgttggtcaa gtagtaaaca ccactttgca   9540
aatgctcaat ggaaccttga ggtttgaagt tcttcttcaa atgggcattt tctctcaatt   9600
cgatggcagc ttcgtaatcc tttggagttt cggtgattct cttggctaat ttgttagtaa   9660
tatctaattc cttgataata tgttggacgt caccaacaat tttgcaagaa tatagagatg   9720
cagctaaacc ggaaccgtaa gaaaataaac caacacgctt gccttgtaag tcgtcagatc   9780
caacatagtt taatagagat gcaaaggcgg cataaacaga tgcggtgtac atgttacctg   9840
tgtttgttgg aacaatcaaa gattgggcaa ctctctcttt gtggaatggc ttagcaacat   9900
taacaaaagt ttttttcaatg ttcttatcgg ttaaagattc gtcataatcg cgagtagcta   9960
attcggcgtc aacttctggg aacaattgag gattggctct gaaatcgtta tatagtaatc  10020
taccgtatga ttttgtgacc aatttacagg ttggaacatg gaaaacgttg tagtcgaaat  10080
atttcaaaac gttcaaagca tccgaaccag cgggatcgct aaccaaccct ttagaaatag  10140
ccttcttgga ataactcttg taaacttgat caagagcctt gacgtaacaa gttaatgaaa  10200
aatgaccatc gacgtaagga tattcgctgg tgaaatctgg cttgtaaaaa tcgtaggcgt  10260
gttccatgta agaagctctt acagagtcaa atacaattgg agcatcagga ccgatccaca  10320
tagcaacagt accggcacca ccggttggtc ttgcggcacc cttatcgtag atggcaatat  10380
caccgcaaac tacaatggcg tctctaccat cccatgcgtt agattcaatc cagttcaaag  10440
agttgaacaa cgcgttggta ccaccgtaac aggcattaag cgtgtcaata ccttcgacgt  10500
cagtgttttc accaaacaat tgcatcaaga cagacttgac agacttggac ttgtcaatca  10560
gagtttcagt accgacttct aatctaccaa ttttgttggt gtcgatgttg taactcttga  10620
tcaacttaga caaaacagtt agggacatcg agtagatatc ttctctgtca ttgacaaaag  10680
acatgttggt ttggcccaga ccaattgtgt atttaccttg agaaacgcca tcaaatttct  10740
ctagctcaga ttggttgaca cattgagttg ggatgtaaat ttggatacct ttaataccga  10800
cattttgagg tctggttttt tgttcagcgg tcttttgttt tttagttca gtcatttgca   10860
agtttgtatt gtgtaattgt tgttgctttt gcggcctaag tcttcctta ataccacacc   10920
aacaaagttt agttgagagt ttcattgtga aggtagttcg attttggagg tcgcgggagg  10980
ttacttttttt tttggatgga cgcaaagaag tttaataatc atattacatg gcaataccac  11040
catatacata tccatatcta atcttactta tatgttgtgg aaatgtaaag agccccatta  11100
tcttagccta aaaaaccctt ctctttggaa cttttcagtaa tacgcttaac tgctcattgc  11160
tatattgaag tacggattag aagccgccga gcgggcgaca gccctccgac ggaagactct  11220
cctccgtgcg tcctggtctt caccggtcgc gttcctgaaa cgcagatgtg cctcgcgccg  11280
cactgctccg aacaataaag attctacaat actagctttt atggttatga agaggaaaaa  11340
ttggcagtaa cctggcccca caaaccttca aatcaacgaa tcaaattaac aaccatagga  11400
taataatgcg attagttttt tagccttatt tctggggtaa ttaatcagcg aagcgatgat  11460
ttttgatcta ttaacagata tataaatgca aaagctgcat aaccactttg actaatactt  11520
tcaacatttt cggtttgtat tacttcttat tcaaatgtca taaagtatc aacaaaaaat   11580
tgttaatata cctctatact taccccaccc gaagtcgcgc aaccaactaa ctttacaatg  11640
gctgcagacc aattggtgaa gactgaagtc accaagaagt cttttactgc tcctgtacaa  11700
aaggcttcta caccagtttt aaccaataaa acagtcattt ctggatcgaa agtcaaaagt  11760
```

```
ttatcatctg cgcaatcgag ctcatcagga ccttcatcat ctagtgagga agatgattcc    11820
cgcgatattg aaagcttgga taagaaaata cgtcctttag aagaattaga agcattatta    11880
agtagtggaa atacaaaaca attgaagaac aaagaggtcg ctgccttggt tattcacggt    11940
aagttacctt tgtacgcttt ggagaaaaaa ttaggtgata ctacgagagc ggttgcggta    12000
cgtaggaagg ctctttcaat tttggcagaa gctcctgtat tagcatctga tcgtttacca    12060
tataaaaatt atgactacga ccgcgtattt ggcgcttgtt gtgaaaatgt tataggttac    12120
atgcctttgc ccgttggtgt tataggcccc ttggttatcg atggtacatc ttatcatata    12180
ccaatggcaa ctacagaggg ttgtttggta gcttctgcca tgcgtggctg taaggcaatc    12240
aatgctggcg gtggtgcaac aactgtttta actaaggatg gtatgacaag aggcccagta    12300
gtccgtttcc caactttgaa aagatctggt gcctgtaaga tatggttaga ctcagaagag    12360
ggacaaaacg caattaaaaa agcttttaac tctacatcaa gatttgcacg tctgcaacat    12420
attcaaactt gtctagcagg agatttactc ttcatgagat ttagaacaac tactggtgac    12480
gcaatgggta tgaatatgat ttctaagggt gtcgaatact cattaaagca aatggtagaa    12540
gagtatggct gggaagatat ggaggttgtc tccgtttctg gtaactactg taccgacaaa    12600
aaaccagctg ccatcaactg gatcgaaggt cgtggtaaga gtgtcgtcgc agaagctact    12660
attcctggtg atgttgtcag aaaagtgtta aaaagtgatg tttccgcatt ggttgagttg    12720
aacattgcta agaatttggt tggatctgca atggctgggt ctgttggtgg atttaacgca    12780
catgcagcta atttagtgac agctgttttc ttggcattag acaagatcc tgcacaaaat    12840
gtcgaaagtt ccaactgtat aacattgatg aaagaagtgg acggtgattt gagaatttcc    12900
gtatccatgc catccatcga gtaggtacc atcggtggtg gtactgttct agaaccacaa    12960
ggtgccatgt tggacttatt aggtgtaaga ggcccacatg ctaccgctcc tggtaccaac    13020
gcacgtcaat tagcaagaat agttgcctgt gccgtcttgg caggtgaatt atccttatgt    13080
gctgccctag cagccggcca tttggttcaa agtcatatga cccacaacag gaaacctgct    13140
gaaccaacaa aacctaacaa tttggacgcc actgatataa atcgtttgaa agatgggtcc    13200
gtcacctgca ttaaatccta aacttagtca tacgtcattg gtattctctt gaaaagaag    13260
cacaacagca ccatgtgtta cgtaaaatat ttactttata gtttgtacgt cataatttct    13320
tccatattac aagttcgtgc atatatagaa agaattctgt tgttgtaatt gtcataacta    13380
ttgagcttta cctgaaaatt caacgaaaaa aactcaaaaa ccacatgctt ctcttgagtc    13440
atgcggaggt ccgccggcgt tggacagcg aatgtgtata ttagtttaaa agttgtatg    13500
taataaaagt aaaatttaat attttggatg aaaaaaacca tttttagact ttttcttaac    13560
tagaatgctg gagtagaaat acgccatctc aagatacaaa aagcgttacc ggcactgatt    13620
tgtttcaacc agtatataga ttattattgg gtcttgatca actttcctca gacatatcag    13680
taacagttat caagctaaat atttacgcga aagaaaaaca aatattttaa ttgtgatact    13740
tgtgaatttt attttattaa ggatacaaag ttaagagaaa acaaaattta tatacaatat    13800
aagtaatatt catatatatg tgatgaatgc agtcttaacg agaagacatg gccttggtga    13860
caactctctt caaaccaact tcagcctttc tcaattcatc agcagatggg tcttcgattt    13920
gcaaagcagc caaagcggcg gtttaaacgc gtggccgtgc cgtc                    13964
```

<210> SEQ ID NO 54
<211> LENGTH: 13963
<212> TYPE: DNA
<213> ORGANISM: Artificial Sequence
<220> FEATURE:

<223> OTHER INFORMATION: Synthetic construct: i85207 integration
      construct

<400> SEQUENCE: 54

```
gacggcacgg ccacgcgttt aaaccgccag ggcaaggttg gcctctactt actccatcga       60
caattcaaga tacagaacct cctccagatg gaatcccttc catagagaga aggagcaagc      120
aactgaccca atattgactg ccactggacc tgaagacatg caacaaagtg caagcatagt      180
ggggccttct tccaatgcta atccggtcac tgccactgct gctacggaaa accaacctaa      240
aggtattaac ttcttcacta taagaaaatc acacgagcgc ccggacgatg tctctgttta      300
aatggcgcaa gttttccgct ttgtaatata tatttatacc cctttcttct ctcccctgca      360
atataatagt ttaattctaa tattaataat atcctatatt ttcttcattt accggcgcac      420
tctcgcccga acgacctcaa aatgtctgct acattcataa taaccaaaag ctcataactt      480
tttttttttga acctgaatat atatacatca catgtcactg ctggtccttg ccgaccagcg      540
tatacaatct cgatagttgg tttccgttc tttccactcc cgtccgctcg tccaacgccg       600
gcggaccttc acatgtaggg accgaattgt ttacaagttc tctgtaccac catggagaca      660
tcaaagattg aaaatctatg gaaagatatg gacggtagca acaagaatat agcacgagcc      720
gcgaagttca tttcgttact tttgatatcg ctcacaacta ttgcgaagcg cttcagtgaa      780
aaaatcataa ggaaaagttg taaatattat tggtagtatt cgtttggtaa agtagagggg      840
gtaattttttc cccttttattt tgttcataca ttcttaaatt gctttgcctc tccttttgga      900
aagctatact tcggagcact gttgagcgaa ggctcattag atatatttttc tgtcattttc      960
cttaacccaa aaataaggga aagggtccaa aaagcgctcg acaactgtt gaccgtgatc      1020
cgaaggactg gctatacagt gttcacaaaa tagccaagct gaaaataatg tgtagctatg     1080
ttcagttagt ttggctagca aagatataaa agcaggtcgg aaatatttat gggcattatt     1140
atgcagagca tcaacatgat aaaaaaacct cccgcgacct ccaaaatcga actaccttca     1200
caatgactgc cgacaacaat agtatgcccc atggtgcagt atctagttac gccaaattag     1260
tgcaaaacca acacctgaa gacatttttgg aagagtttcc tgaaattatt ccattacaac     1320
aaagacctaa tacccgatct agtgagacgt caaatgacga aagcggagaa acatgttttt     1380
ctggtcatga tgaggagcaa attaagttaa tgaatgaaaa ttgtattgtt ttggattggg     1440
acgataatgc tattggtgcc ggtaccaaga aagtttgtca tttaatggaa aatattgaaa     1500
agggtttact acatcgtgca ttctccgtct ttattttcaa tgaacaaggt gaattacttt     1560
tacaacaaag agccactgaa aaaataactt tccctgatct ttggactaac acatgctgct     1620
ctcatccact atgtattgat gacgaattag gtttgaaggg taagctagac gataagatta     1680
agggcgctat tactgcggcg gtgagaaaac tagatcatga attaggtatt ccagaagatg     1740
aaactaagac aaggggtaag tttcactttt taaacagaat ccattacatg gcaccaagca     1800
atgaaccatg gggtgaacat gaaattgatt acatcctatt ttataagatc aacgctaaag     1860
aaaacttgac tgtcaaccca aacgtcaatg aagttagaga cttcaaatgg gtttcaccaa     1920
atgatttgaa aactatgttt gctgacccaa gttacaagtt tacgccttgg tttaagatta     1980
tttgcgagaa ttacttattc aactggtggg agcaattaga tgaccttttct gaagtggaaa     2040
atgacaggca aattcataga atgctataac aacgcgtcaa taatataggc tacataaaaaa    2100
tcataataac tttgttatca tagcaaaatg tgatataaaa cgtttcattt cacctgaaaa     2160
atagtaaaaa taggcgacaa aaatcctag taatatgtaa actttatttt ctttatttat     2220
ttacagaact ctgaatatac attgattgtt cacattttttt ttttctcttc tcaatttccc    2280
```

```
ttgattatat tcaaaaggtt attggcctct tgaatgtttc ccactgaatc cccgcgtgct    2340
tggccggccg tggagcgacc tcatgctata cctgagaaag caacctgacc tacaggaaag    2400
agttactcaa gaataagaat tttcgtttta aaacctaaga gtcactttaa aatttgtata    2460
cacttatttt ttttataact tatttaataa taaaaatcat aaatcataag aaattcgctc    2520
aaacgaccat tggatggaca aagaaggact tcatgtaaga tttcatgtca ccttcggcgt    2580
gagtgaaacc atcgttaaca gagtataaaa cttcacacat tctagccaag ttgatagctg    2640
gcattaacaa agggaatgga acggcggttg gtctcaaaga ttctctgtta ataaccttcc    2700
aggcgtcttc gacttttcta gagatgtatt cacaggcttc ttcttcagaa gcaccggatt    2760
ccttagaata acattcgatg gaggaggcaa catgacctct ttcttgttct tctttatgag    2820
agacaatatc atccatcaat ctaatgataa cacaagaagc ttcaacaata ggtgggtagg    2880
aagaaaccca tttaaaagtg tcctcgttaa caatgtcacc tctaccaacg taagatctag    2940
cagtgatcaa accgtaggta ccggtaacca tggaaacaga catgtactct tccaaagtag    3000
gcatgtaacc ttcttttcaac catctggctt caaccaagta gtttctgacc aattccttag    3060
ccatttcctt aacgtagtgg atttgataag ccttaccttc ctttttctaaa gattcttcca    3120
tttcaacgtg caagttaacc aattcttggt agatcaactt catgtattct ggcaacatgt    3180
ccaaacaaga aatggaccac ttctcaacgg cttgagtgaa aatttccaat tcttcgtagg    3240
taccgtagtt gtcgaaggta tcatccaaaa cgaccaacca catacaagac ttcatcaaga    3300
acattctggt tctggcatgt tgtggttcat agtaaataga caaatccag aagtaaccttt    3360
cgacaactct atcacgaacg aatggcaatt tgttttgcaa gtctaaatct ttccaccact    3420
tgcagatgtg agacaattct ttcttatgca tggattgcaa aacagagaaa tctaacttag    3480
ccaacttcaa caaaacctcg tcgtgagaag tttcttgttg gtaaattggc atatagtgta    3540
aagcttcgat tctggccaat cttcttctca atggttgctt caaggcttgg tggatttggg    3600
ttcttaagga agagtcacaa gatggatcct tggcaataat gtccaagtga accttagaga    3660
attccaaagc gttgtccaag atggtttcat cttcgactct catgaaagca gcttcgtaca    3720
aggccaagat accttgagcg tcgttacaca aagattcctt aaatttacct ttttcgtcca    3780
taaagtcctt gaaacaccca gaggagacat tgaaaccttg ttgacgcaac aaacgaaacc    3840
acaaggagat agattgtaaa ttttccttat cgacccattg ttcaccgtaa gtgacatgga    3900
tatgttgtaa agcttcttcg atttcttctt caaaatggta agcaatacct aaacgttgaa    3960
cagcattgat taattcgatc aacttaacat gttgcatagg ttcgttagaa cccttaatag    4020
taatcaattc cttcttaact tcctcccttta actcttcgac taattgcttc ttcataacca    4080
agtcctctgg ttcatcgtaa gtcaaaaatt gatcaccccca aatggaagcg ttgaagttag    4140
cggtatgtct aataacgtct ggcttggtag aatccttatc atcgacaaca attggggaag    4200
tagatggaga ggaagaaaca gaggaaatag gcaaagtgga cattgtaaag ttagttggtt    4260
gcgcgacttc gggtgggta agtatagagg tatattaaca attttttgtt gatactttta    4320
tgacatttga ataagaagta atacaaaccg aaaatgttga agtattagt taaagtggtt    4380
atgcagcttt tgcatttata tatctgttaa tagatcaaaa atcatcgctt cgctgattaa    4440
ttaccccaga aataaggcta aaaaactaat cgcattatta tcctatggtt gttaatttga    4500
ttcgttgatt tgaaggtttg tggggccagg ttactgccaa ttttttcctct tcataaccat    4560
aaaagctagt attgtagaat ctttattgtt cggagcagtg cggcgcgagg cacatctgcg    4620
tttcaggaac gcgaccggtg aagaccagga cgcacggagg agagtcttcc gtcggagggc    4680
```

```
tgtcgcccgc tcggcggctt ctaatccgta cttcaatata gcaatgagca gttaagcgta    4740
ttactgaaag ttccaaagag aaggttttt  taggctaaga taatggggct ctttacattt    4800
ccacaacata taagtaagat tagatatgga tatgtatatg gtggtattgc catgtaatat    4860
gattattaaa cttctttgcg tccatccaaa aaaaaagtaa cgcacgcaca ctcccgacag    4920
acaactagct tgataatggc ttcagaaaaa gaaattagga gagagagatt cttgaacgtt    4980
ttccctaaat tagtagagga attgaacgca tcgcttttgg cttacggtat gcctaaggaa    5040
gcatgtgact ggtatgccca ctcattgaac tacaacactc caggcggtaa gttaaataga    5100
ggtttgtccg ttgtggacac gtatgctatt ctctccaaca agaccgttga acaattgggg    5160
caagaagaat acgaaaaggt tgctattcta ggttggtgca ttgagttgtt gcaggcttac    5220
ttcttggtcg ccgatgatat gatggacaag tccattacca gaagaggcca accatgttgg    5280
tacaaggttc ctgaagttgg ggaaattgcc atcaatgacg cattcatgtt agaggctgct    5340
atctacaagc ttttgaaatc tcacttcaga acgaaaaat  actacataga tatcaccgaa    5400
ttgttccatg aagtcacctt ccaaaccgaa ttgggccaat tgatggactt aatcactgca    5460
cctgaagaca agtcgacttg agtaagttc  tccctaaaga agcactcctt catagttact    5520
ttcaagactg cttactattc tttctacttg cctgtcgcat tggctatgta cgttgccggt    5580
atcacagatg aaaaggattt gaacaagcc  agagatgtct tgattccatt gggtgaatat    5640
ttccaaattc aagatgacta cttagactgc ttcggtaccc cagaacagat cggtaagatc    5700
ggtacagata tccaagataa caatgttct  tgggtaatca acaaggcatt agaacttgct    5760
tccgcagaac aaagaaagac tttagacgaa aattacggta agaaggactc agtcgcagaa    5820
gccaaatgca aaagatttt  caatgacttg aaaatcgacc agttataccga cgaatatgaa    5880 gagtctgttg ccaaggattt gaaggccaag atctcccaag tcgacgagtc tcgtggcttc    5940
aaagccgacg tcttaactgc gttttgaac  aaggtttaca agagaagtaa atagaactaa    6000
cgctaatcga taaaacatta gatttcagat tagataagga ccatgtataa gaaatatata    6060
cttccactat aatatagtat aagcttacag atagtatctc tcgatctacc gttccacgtg    6120
actagtccaa gaacctgcag gccgcgagcg ccgatacgaa aatcgttatt gtcttgaagg    6180
tgaaatttct actcttatta atggtgaacg ttaagctgat gctatgatgg aagctgattg    6240
gtcttaactt gcttgtcatc ttgctaatgg tcattggctc gtgttattac ttaagttatt    6300
tgtactcgtt ttgaacgtaa tgctaatgat catcttatgg aataatagtg agtggtttca    6360
gggtccataa agcttttcaa ttcatctttt tttttttgt  tcttttttt  gattccggtt    6420 tctttgaaat ttttttgatt cggtaatctc cgagcagaag gaagaacgaa ggaaggagca    6480
cagacttaga ttggtatata tacgcatatg tggtgttgaa gaaacatgaa attgcccagt    6540
attcttaacc caactgcaca gaacaaaaac ctgcaggaaa cgaagataaa tcatgtcgaa    6600
agctacatat aaggaacgtg ctgctactca tcctagtcct gttgctgcca agctatttaa    6660
tatcatgcac gaaaagcaaa caaacttgtg tgcttcattg gatgttcgta ccaccaagga    6720
attactggag ttagttgaag cattaggtcc caaaatttgt ttactaaaaa cacatgtgga    6780
tatcttgact gatttttcca tggagggcac agttaagccg ctaaaggcat atccgccaa     6840 gtacaatttt ttactcttcg aagacagaaa atttgctgac attggtaata cagtcaaatt    6900
gcagtactct gcgggtgtat acagaatagc agaatgggca gacattacga atgcacacgg    6960
tgtggtgggc ccaggtattg ttagcggttt gaagcaggcg gcggaagaag taacaaagga    7020
acctagaggc cttttgatgt tagcagaatt gtcatgcaag ggctccctag ctactggaga    7080
```

```
atatactaag ggtactgttg acattgcgaa gagtgacaaa gattttgtta tcggctttat   7140
tgctcaaaga gacatgggtg gaagagatga aggttacgat tggttgatta tgacacccgg   7200
tgtgggttta gatgacaagg gagacgcatt gggtcaacag tatagaaccg tggatgatgt   7260
ggtctctaca ggatctgaca ttattattgt tggaagagga ctatttgcaa agggaaggga   7320
tgctaaggta gagggtgaac gttacagaaa agcaggctgg gaagcatatt tgagaagatg   7380
cggccagcaa aactaaaaaa ctgtattata agtaaatgca tgtatactaa actcacaaat   7440
tagagcttca atttaattat atcagttatt accacgaaaa tcgttattgt cttgaaggtg   7500
aaatttctac tcttattaat ggtgaacgtt aagctgatgc tatgatggaa gctgattggt   7560
cttaacttgc ttgtcatctt gctaatggtc atatggctcg tgttattact taagttattt   7620
gtactcgttt tgaacgtaat gctaatgatc atcttatgga ataatagtga atcggcgctc   7680
gcggcctgca ggtttcctca tcctagtatg tatagcttgt acccattaaa cgaattttat   7740
catgccgccg aaaggaacaa tttcaagtac tatcggaaga tgaatggtta gatgttaagc   7800
gcggtcactt caaacttcac atttataaag atgtcacatg gaccactatt atctaccttta  7860 agttatttat caagataagt ttccggatct ttttcttttcc taacacccca gtcagcctga   7920
gttacatcca gccattgaac cttagaaaat cttttgtcat cagcggtttg agccctaaga   7980
tcaacatctt gcttagcaat cactgcaatg gcgtcataac caccagcacc aggtattaag   8040
caagtaagaa ctccttttaa ggtctggcaa tcatccaata agctagtttg tacgggaggt   8100
tcgatatcgg caccagattc tttagttatt tttctaaagg aacgtctaat tgtggcaact   8160
gcatctctaa cttctgtgat ctcaggatac ttttgacagg tacagtcatt cctctcaaga   8220
gactcaaata tctgatcgct gtaatcgtca tgagtctcgt gtaagcgatc tagtttagat   8280
agtccatcca taaatctaga atttgcatga tcgagttctg tatatatttt caagctttcc   8340
ggcatatgcg aatcatacca attttttacc ttctggacca gttttactgt ttctgaacca   8400
ttcttaatat cgcccatcca taaagttaat cccgaaggta aatggttact tttaatcgtt   8460
atattccagt cttcttcatt aaccaaatgc gccagtttac tgccgtaagt agcacttcca   8520
atatctggca aattagagat taatgcgggt gggaatcttc tatatctgat agatccatat   8580
gctgccgccg ctacatcaaa cccgcttcca attttaccct gagcttgaca atgagcaact   8640
tgtgataaat tatgaataac ttctctatat ttgtctacat tattttccag gtccgataca   8700
aaaaaggagg ccaaagctgt agttaaaact gtgactaaac ctgccgagga gcccagccct   8760
gttttgggaa cttcttcaat tctgtgcgaa tgaaaactca atcttctgtt gccacgatgt   8820
tcggtaacgc tgtcctcctg agaatggtag gcatcatcag agaaaatatc aataacgaac   8880
aagtttctat tgcagtagtc gtccatgtta ggcttaaagt agctaaatac gttagcgata   8940
acttttccaa tgaaagggtt cttagatccg cctatcgaaa caggaatgaa gccagtttta   9000
ggacttatat ggtacagcca ctccccatct ttaaattgtt tacttttcac acgcacttca   9060
aacttatcag actcttgcaa tgaaccgtaa ggatgggcta cagcatgcat tcttgccgat   9120
aatccgacta caaatgcttc atatttcgga tctaaaacta aatatccacc agctagtaac   9180
gctttccctg gggcactgaa ggctctcaac tctgacatta tcaagctagt tgtctgtcgg   9240
gagtgtgcgt gcgttttttt atcatgttga tgctctgcat aataatgccc ataaatattt   9300
ccgacctgct tttatatctt tgctagccaa actaactgaa catagctaca cattatttttc  9360 agcttggcta ttttgtgaac actgtatagc cagtccttcg gatcacggtc aacagttgtc   9420
cgagcgcttt ttggacccctt tcccttattt ttgggttaag gaaaatgaca gaaaatatat   9480
```

```
ctaatgagcc ttcgctcaac agtgctccga agtatagctt tccaaaagga gaggcaaagc    9540
aatttaagaa tgtatgaaca aaataaaggg gaaaaattac cccctctact ttaccaaacg    9600
aatactacca ataatattta caacttttcc ttatgattt ttcactgaag cgcttcgcaa     9660
tagttgtgag cgatatcaaa agtaacgaaa tgaacttcgc ggctcgtgct atattcttgt    9720
tgctaccgtc catatctttc catagatttt caatctttga tgtctccatg gtggtacaga    9780
gaacttgtaa acaattcggt ccctacatgt gaacggccgg ccaagcacgc ggggatccga    9840
agcatgtagg gaggtcatga tatgaaaaag caaagagta ggcatcaaaa agtttctcat     9900
tcaagtggta actgctgtta aaattaagat atttataaat tgaagcttgg tcgttccgac    9960
caataccgta gggaaacgta aattagctat tgtaaaaaaa ggaaaagaaa agaaaagaaa   10020
aatgttacat atcgaattga tcttattcct ttggtagacc agtctttgcg tcaatcaaag   10080
attcgtttgt ttcttgtggg cctgaaccga cttgagttaa aatcactctg gcaacatcct   10140
tttgcaactc aagatccaat tcacgtgcag taaagttaga tgattcaaat tgatggttga   10200
aagcctcaag ctgctcagta gtaaatttct tgtcccatcc aggaacagag ccaaacaatt   10260
tatagataaa tgcaaagagt ttcgactcat tttcagctaa gtagtacaac acagcatttg   10320
gacctgcatc aaacgtgtat gcaacgattg tttctccgta aaactgatta atggtgtggc   10380
accaactgat gatacgcttg gaagtgtcat tcatgtagaa tattggaggg aaagagtcca   10440
aacatgtggc atggaaagag ttggaatcca tcattgtttc ctttgcaaag gtggcgaaat   10500
cttttttcaac aatggctta cgcatgactt caaatctctt tggtacgaca tgttcaattc    10560
tttctttaaa tagttcggag gttgccacgg tcaattgcat accctgagtg gaactcacat   10620
cctttttaat atcgctgaca actaggacac aagctttcat ctgaggccag tcagagctgt   10680
ctgcgatttg tactgccatg gaatcatgac catcttcagc tttcccatt tcccaggcca    10740
cgtatccgcc aaacaacgat ctacaagctg aaccagaccc ctttcttgct attctagata   10800
tttctgaagt tgactgtggt aattggtata acttagcaat tgcagagacc aatgcagcaa   10860
agccagcagc ggaggaagct aaaccagctg ctgtaggaaa gttattttcg gagacaatgt   10920
ggagtttcca ttgagataat gtgggcaatg aggcgtcctt cgattccatt tccttctta    10980
attggcgtag gtcgcgcaga caattttgag ttctttcatt gtcgatgctg tgtggttctc   11040
catttaacca caaagtgtcg cgttcaaact caggtgcagt agccgcagag gtcaacgttc   11100
tgaggtcatc ttgcgataaa gtcactgata tggacgaatt ggtgggcaga ttcaacttcg   11160
tgtcccttt ccccaataac ttaagggttg cgatgttgac gggtgcggta acggatgctg    11220
tgtaaacggt cattgtgaag gtagttcgat tttggaggtc gcgggaggtt actttttttt   11280
tggatggacg caaagaagtt taataatcat attacatggc aataccacca tatacatatc   11340
catatctaat cttacttata tgttgtggaa atgtaaagag ccccattatc ttagcctaaa   11400
aaaaccttct ctttggaact ttcagtaata cgcttaactg ctcattgcta tattgaagta   11460
cggattagaa gccgccgagc gggcgacagc cctccgacgg aagactctcc tccgtgcgtc   11520
ctggtcttca ccggtcgcgt tcctgaaacg cagatgtgcc tcgcgccgca ctgctccgaa   11580
caataaagat tctacaatac tagctttat ggttatgaag aggaaaaatt ggcagtaacc    11640
tggccccaca aaccttcaaa tcaacgaatc aaattaacaa ccataggata ataatgcgat   11700
tagttttta gccttatttc tggggtaatt aatcagcgaa gcgatgattt ttgatctatt   11760
aacagatata taaatgcaaa agctgcataa ccacttaac taatactttc aacatttcg     11820
gtttgtatta cttcttattc aaatgtcata aaagtatcaa caaaaaattg ttaatatacc   11880
```

```
tctatactta ccccacccga agtcgcgcaa ccaactaact ttacaatgtc attaccgttc   11940
ttaacttctg caccgggaaa ggttattatt tttggtgaac actctgctgt gtacaacaag   12000
cctgccgtcg ctgctagtgt gtctgcgttg agaacctacc tgctaataag cgagtcatct   12060
gcaccagata ctattgaatt ggacttccccg gacattagct ttaatcataa gtggtccatc   12120
aatgatttca atgccatcac cgaggatcaa gtaaactccc aaaaattggc caaggctcaa   12180
caagccaccg atggcttgtc tcaggaactc gttagtcttt tggatccgtt gttagctcaa   12240
ctatccgaat ccttccacta ccatgcagcg ttttgtttcc tgtatatgtt tgtttgccta   12300
tgcccccatg ccaagaatat taagtttcct ttaaagtcta ctttacccat cggtgctggg   12360
ttgggctcaa gcgcctctat ttctgtatca ctggccttag ctatggccta cttgggggggg   12420
ttaataggat ctaatgactt ggaaaagctg tcagaaaacg ataagcatat agtgaatcaa   12480
tgggccttca taggtgaaaa gtgtattcac ggtacccctt caggaataga taacgctgtg   12540
gccacttatg gtaatgccct gctatttgaa aaagactcac ataatggaac aataaacaca   12600
aacaatttta agttcttaga tgatttccca gccattccaa tgatcctaac ctatactaga   12660
attccaaggt ctacaaaaga tcttgttgct cgcgttcgtg tgttggtcac cgagaaattt   12720
cctgaagtta tgaagccaat tctagatgcc atgggtgaat gtgccctaca aggcttagag   12780
atcatgacta agttaagtaa atgtaaaggc accgatgacg aggctgtaga aactaataat   12840
gaactgtatg aacaactatt ggaattgata agaataaatc atggactgct tgtctcaatc   12900
ggtgtttctc atcctggatt agaacttatt aaaaatctga gcgatgattt gagaattggc   12960
tccacaaaac ttaccggtgc tggtggcggc ggttgctctt tgactttgtt acgaagagac   13020
attactcaag agcaaattga cagtttcaaa aagaaattgc aagatgattt tagttacgag   13080
acatttgaaa cagacttggg tgggactggc tgctgtttgt taagcgcaaa aaatttgaat   13140
aaagatctta aaatcaaatc cctagtattc caattatttg aaaataaaac taccacaaag   13200
caacaaattg acgatctatt attgccagga aacacgaatt taccatggac ttcataagct   13260
aatttgcgat aggcattatt tattagttgt ttttaatctt aactgtgtat gaagttttat   13320
gtaataaaga tagaaagaga aacaaaaaaa aatttttcgt agtatcaatt cagctttcga   13380
agacagaatg aaatttaagc agaccatagt atccttgata cattgactca ggtccgccgg   13440
cgttggacga gcgaagcatc ttgccctgtg cttggccccc agtgcagcga acgttataaa   13500
aacgaatact gagtatatat ctatgtaaaa caaccatatc atttcttgtt ctgaactttg   13560
tttacctaac tagtttaaa tttccctttt tcgtgcatgc gggtgttctt atttattagc   13620
atactacatt tgaaatatca aatttcctta gtagaaaagt gagagaaggt gcactgacac   13680
aaaaaataaa atgctacgta taactgtcaa aactttgcag cagcgggcat ccttccatca   13740
tagcttcaaa catattagcg ttcctgatct tcatacccgt gctcaaaatg atcaaacaaa   13800
ctgttattgc caagaaataa acgcaaggct gccttcaaaa actgatccat tagatcctca   13860
tatcaagctt cctcatagaa cgcccaatta caataagcat gttttgctgt tatcaccggg   13920
tgataggttt gctcaggcgg tttaaacgcg tggccgtgcc gtc                     13963
```

PRODUCTION OF ACETYL-COENZYME A DERIVED ISOPRENOIDS

Figure 1:
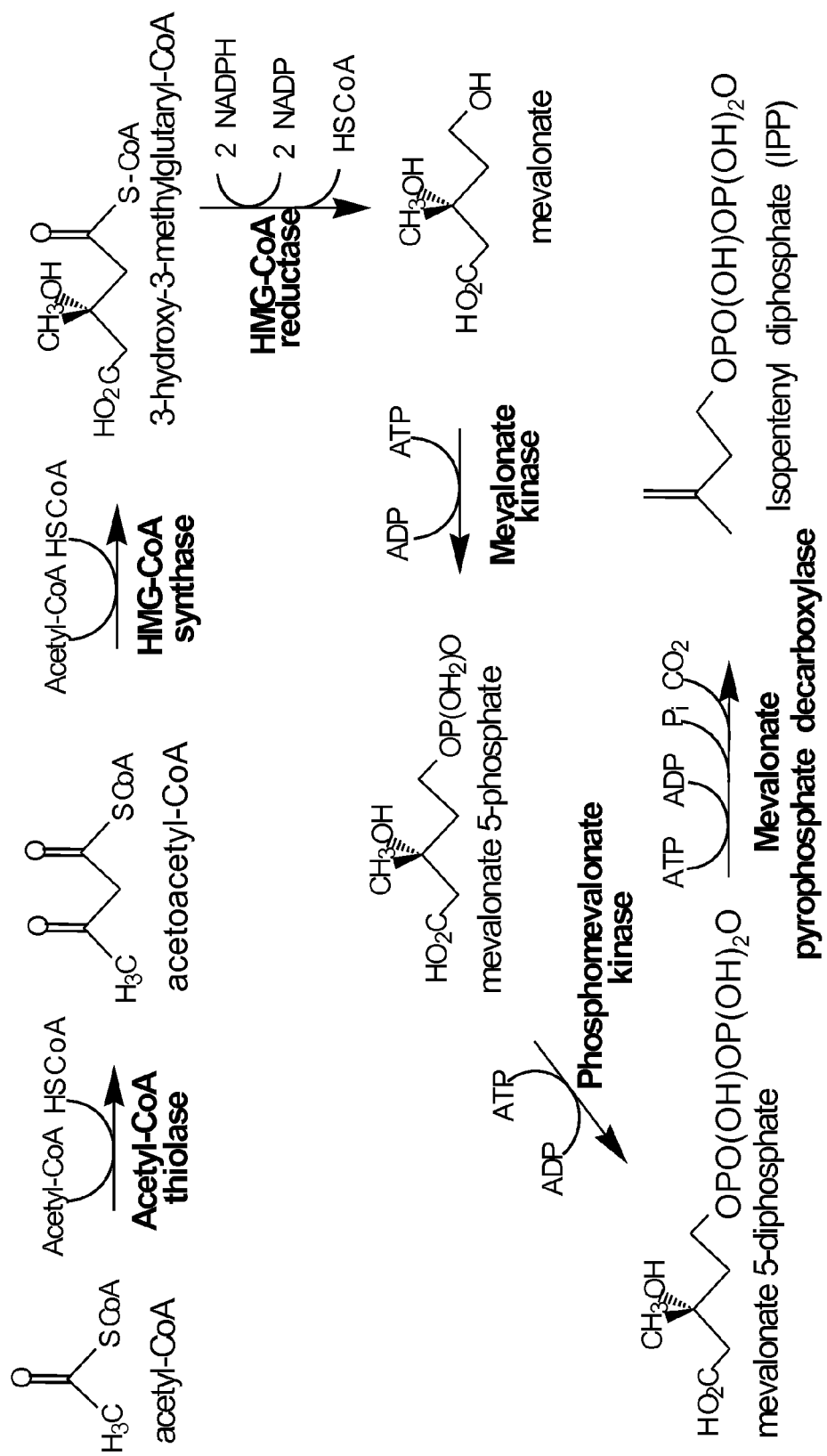

This application is a continuation of U.S. patent application Ser. No. 13/673,819 filed on Nov. 9, 2012, which in turn claims benefit of priority of U.S. Provisional Application No. 61/557,893, filed on Nov. 9, 2011, the contents of each of which are hereby incorporated by reference in their entirety.

1. FIELD OF THE INVENTION

The present disclosure relates to compositions and methods for producing acetyl-CoA derived isoprenoids in engineered host cells.

2. BACKGROUND

Acetyl coenzyme A (acetyl-CoA) is a key intermediate in the synthesis of essential biological compounds, including polyketides, fatty acids, isoprenoids, phenolics, alkaloids, vitamins, and amino acids. Among the metabolites derived from acetyl-CoA are primary and secondary metabolites, including compounds of industrial utility. Isoprenoids, for example, are used in pharmaceutical products and as biofuels, food additives, and other specialty chemicals. An isoprenoid product is typically composed of repeating five carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Prokaryotes, with some exceptions, typically employ the deoxyxylulose-5-phosphate (DXP) pathway to convert pyruvate and glyceraldehyde 3-phosphate (G3P) to IPP and DMAPP. Eukaryotes, with the exception of plants, generally use the mevalonate-dependent (MEV) pathway to convert acetyl-CoA to IPP, which is subsequently isomerized to DMAPP.

The unicellular fungus *Saccharomyces cerevisiae* and its close relatives use two endogenous pathways to generate acetyl-CoA. One pathway takes place in the mitochondrial matrix, where the PDH complex catalyzes the oxidative decarboxylation of pyruvate, generated from glucose via glycolysis, to acetyl CoA. The PDH complex consists of 60 polypeptide chains—24 chains of the lipoamide reductase-transacetylase, 12 chains of dihydrolipyl dehydrogenase, and 24 chains of pyruvate decarboxylase. This massive complex converts pyruvate to acetyl-CoA, generating NADH as a byproduct. The resulting acetyl-CoA can then be completely oxidized to $CO_2$ and $H_2O$ via the citric acid cycle for energy generation, or be used for biosynthetic reactions that are performed in the mitochondria.

The acetyl-CoA generated in the mitochondria is unable to cross the mitochondrial membrane into the cytosol. Thus, to generate cytosolic acetyl-CoA, which is needed for the biosynthesis of important primary and secondary metabolites, *S. cerevisiae* uses an independent mechanism located in the cytosol known as the "PDH-bypass." This multi-step pathway catalyzes: (1) the decarboxylation of pyruvate into acetaldehyde by pyruvate decarboxylase (PDC, EC 4.1.1.1); (2) the conversion of acetaldehyde into acetate by acetaldehyde dehydrogenase (ACDH, EC 1.2.1.5 and EC 1.2.1.4), which reduced one $NADP^+$ to one NADPH; and (3) the synthesis of acetyl-CoA from acetate and CoA by acetyl-CoA synthetase (ACS, EC 6.2.1.1), which hydrolyzes 1 ATP to 1 AMP, the energetic equivalent of hydrolyzing 2 ATP to 2 ADP.

Since nature provides only low yield sources for the extraction of many acetyl-CoA derived biomolecules, fermentative production using genetically modified microorganisms has become a promising alternative for their production. However, utilization of the native acetyl-CoA pathway for production of the acetyl-CoA intermediate has certain limitations. For example, isoprenoid production via the native MEV pathway requires three acetyl-CoA molecules and the oxidation of two NADPH for each molecule of mevalonate generated, as shown in FIG. 1. While the PDH-bypass generates one NADPH per acetyl-CoA produced, two ATP equivalents are expended in the process. Thus, while the generation of NADPH is beneficial with regard to the cofactor requirements of the native MEV pathway, the expenditure of six ATP equivalents per mevalonate generated results in an energetically inefficient reaction, as more carbon source must be diverted to ATP synthesis, e.g., via the TCA cycle and oxidative phosphorylation, at the expense of product yield.

Thus, one of the challenges in designing a production host that efficiently produces acetyl-CoA derived compounds is to optimize acetyl-CoA production such that the ATP requirements are minimized, while also meeting the co-factor and requirements of the biosynthetic pathway. The compositions and methods provided herein address this need and provide related advantages as well.

3. SUMMARY OF THE INVENTION

The compositions and methods described herein provide for the energetically efficient and co-factor balanced production of acetyl-CoA derived isoprenoids. By utilizing a heterologous acylating acetaldehyde dehydrogenase (alternately referred to as "acetylaldehyde dehydrogenase, acetylating," "acetylaldehyde dehydrogenase, acylating," or "ADA" (EC 1.2.1.10)) as an alternative to the PDH-bypass for cytosolic production of acetyl-CoA, two equivalents of ATP are saved per molecule of acetyl-CoA produced. ADA converts acetaldehyde directly to acetyl-CoA without expenditure of ATP, and reduces one $NAD^+$ to one NADH in the process.

While the ATP savings gained from replacement of the PDH-bypass with ADA can be utilized towards higher product yields, there are potential shortcomings associated with the use of ADA in combination with the native mevalonate pathway. First, inactivation of the native PDH-bypass removes one source of NADPH, while the reaction catalyzed by ADA produces NADH. Thus, the replacement of the PDH-bypass with ADA, without further pathway modification, introduces a redox imbalance in isoprenoid synthesis, which consumes NADPH.

Secondly, ADA catalyzes the following reversible reaction:

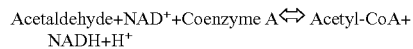

The native PDH-bypass reaction for forming acetyl-CoA is thermodynamically favorable because the reaction is coupled to the hydrolysis of ATP to AMP. In contrast, the ADA reaction is not coupled to ATP, and is much closer to equilibrium than the native PDH-bypass reactions for forming Acetyl-CoA. Thus, the reaction catalyzed by ADA has a lower a thermodynamic driving force behind the conversion of acetaldehyde to acetyl-CoA, and without further pathway modification, the theoretical energy gains of ADA may not be realized.

The compositions and methods described herein address these shortcomings. In some embodiments, to address the redox imbalance introduced by replacement of the PDH-bypass with ADA, the genetically modified host cells further utilize an NADH-using enzyme in the isoprenoid pathway to consume ADA-generated NADH. Thus, the pool of NADH generated by the ADA-mediated conversion of acetaldehyde to acetyl-CoA can be utilized directly towards isoprenoid synthesis. In some embodiments, the NADH-using enzyme is an enzyme that is non-native to the isoprenoid pathway. For example, the NADH-using enzyme can replace an NADPH-using enzyme that is native to the isoprenoid pathway. In particular embodiments, the NADH-using enzyme is an NADH-using 3-hydroxy-3-methylglutaryl-CoA reductase (HMG-CoA reductase) that converts HMG-CoA to mevalonate.

Figure 5:
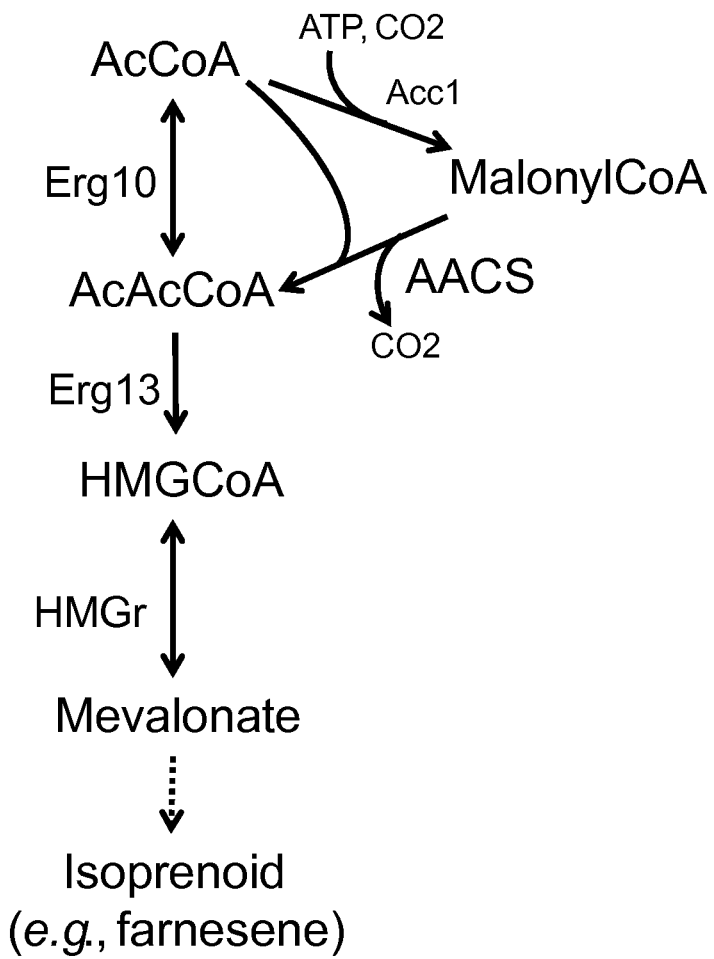

In some embodiments, to address the lower thermodynamic driving force behind the ADA reaction, the genetically modified host cells further utilize, as a first step in the mevalonate pathway, a thermodynamically favorable reaction immediately downstream of acetyl-CoA to provide a pull on the ADA reaction. In some embodiments, the formation of acetoacetyl-CoA from acetyl-CoA is catalyzed by an acetoacetyl-CoA synthase (AACS; alternately referred to as an acetyl-CoA:malonyl-CoA acyltransferase). The reaction catalyzed by AACS is thermodynamically more favorable than the reaction catalyzed by the acetyl-CoA thiolase of the native mevalonate pathway, due to the hydrolysis of 1 ATP resulting from the generation of malonyl-CoA by acetyl-CoA carboxylase (FIG. 5). Thus, AACS provides a stronger pull on acetyl-CoA to drive the ADA reaction forward.

Figure 2:
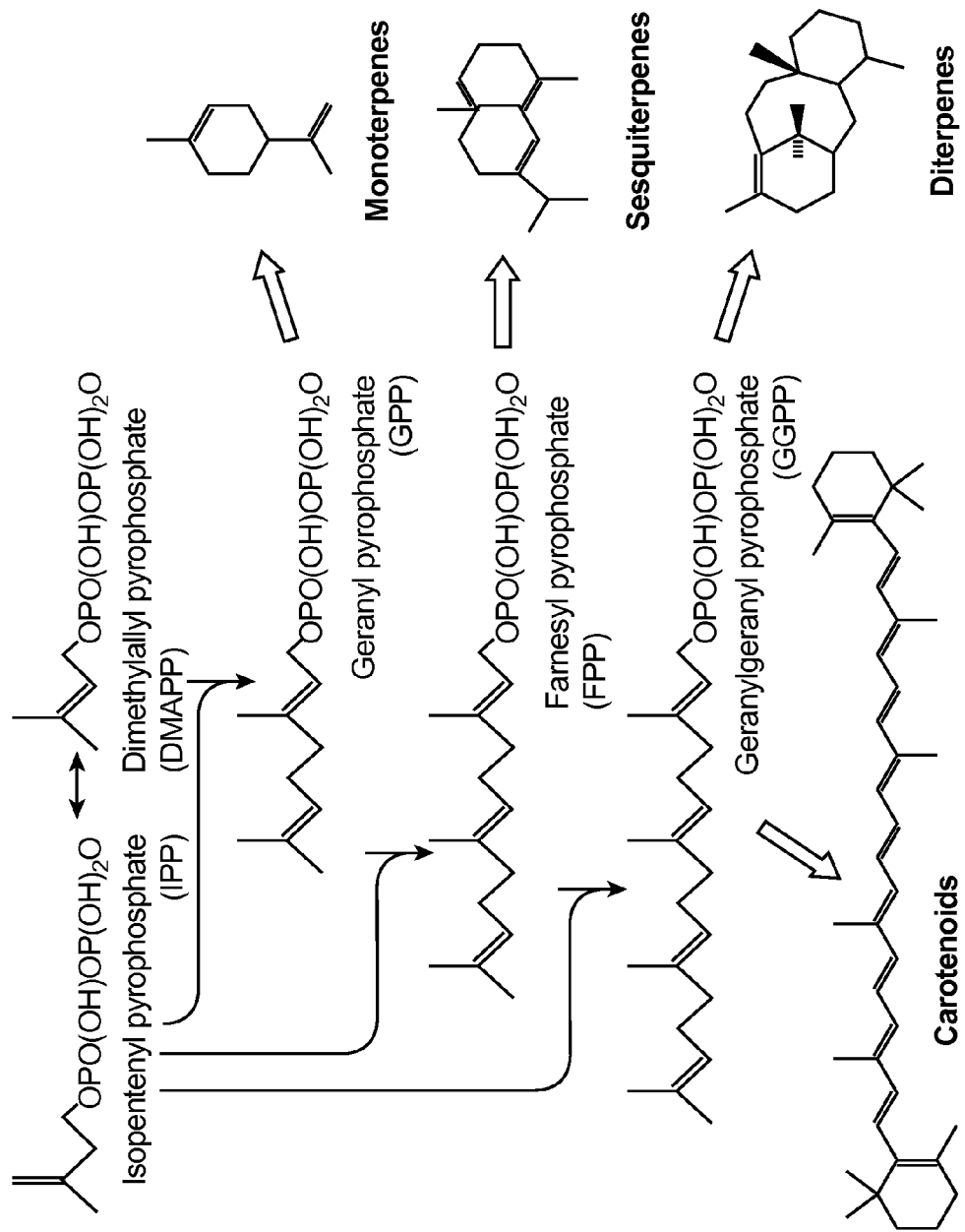
Figure 3:
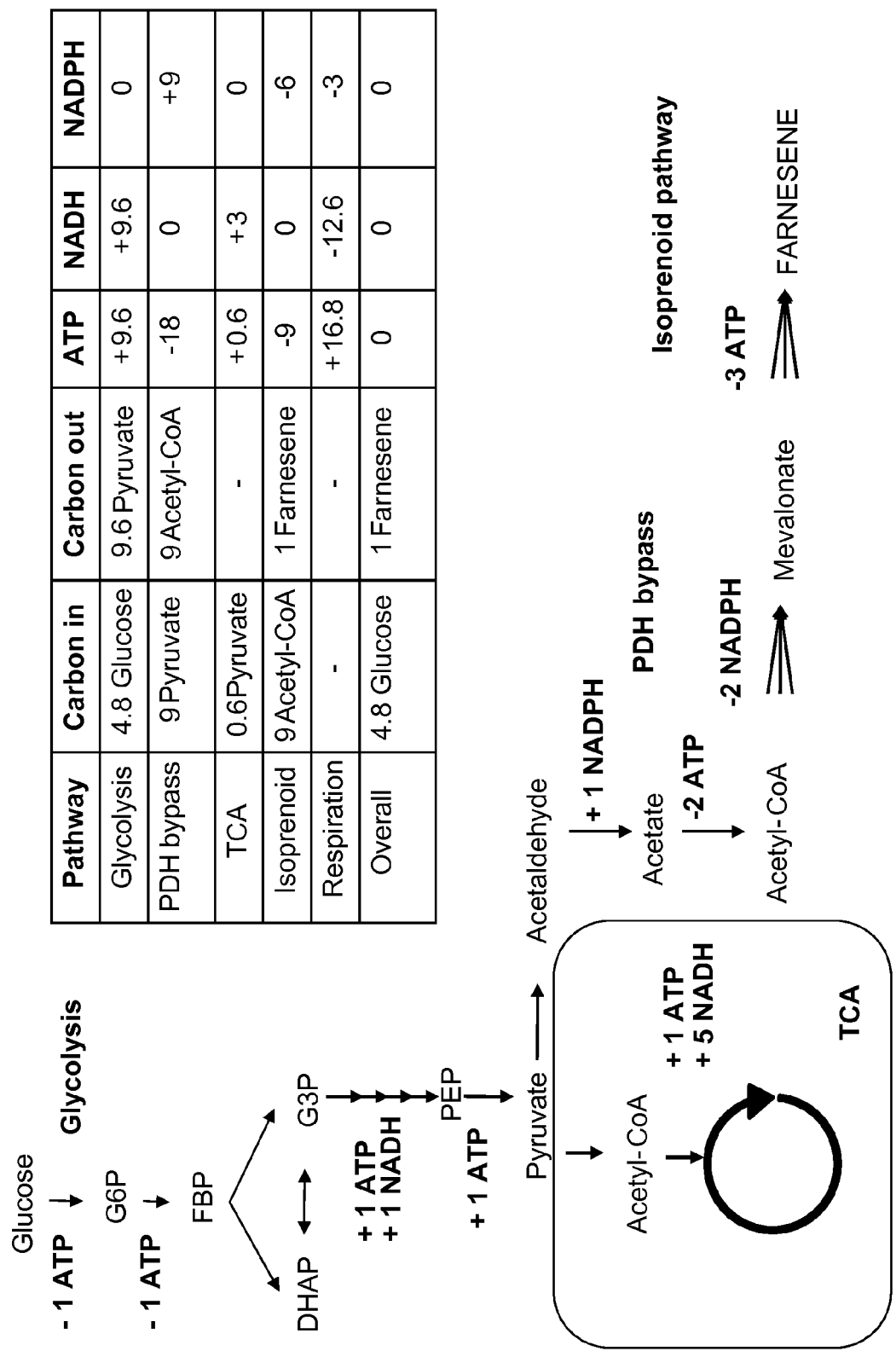
Figure 4:
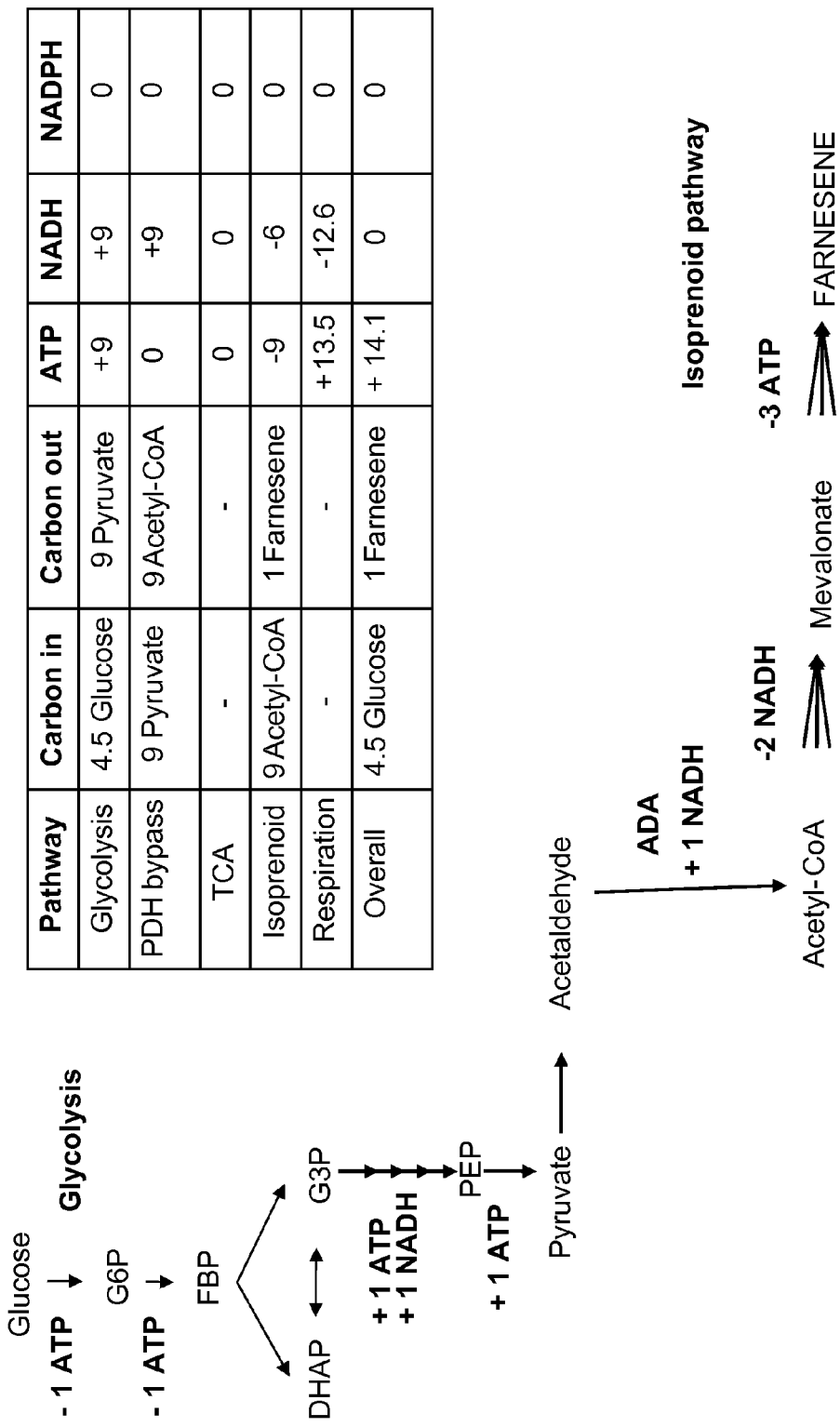

The advantages of utilizing a heterologous ADA in combination with these modifications are exemplified by the improved theoretical yield of the sesquiterpene farnesene in host cells comprising a MEV pathway. Isoprenoid production via the native mevalonate pathway is illustrated in FIG. 1 and FIG. 2. As indicated in FIG. 3, when cytosolic acetyl-CoA is synthesized from glucose using only the chemical reactions which occur in the native yeast metabolic network, the maximum possible stoichiometric yield for conversion of glucose to farnesene via the mevalonate pathway is 23.6 wt %, with 4.77 molecules of glucose being required for the synthesis of each molecule of farnesene. 27 ATP are required per molecule of farnesene, 18 of which are consumed in the synthesis of cytosolic acetyl-CoA from acetaldehyde via the PDH-bypass. However, by including the reactions catalyzed by ADA and NADH-using HMG-CoA reductase into the metabolic network for mevalonate production, as illustrated in FIG. 4, the maximum theoretical stoichiometric yield is improved to 25.2 wt %. In particular, ADA converts acetaldehyde to acetyl-CoA without any ATP input; this reduces the ATP equivalents required for farnesene synthesis to 9, resulting in a savings of 18 ATP equivalents per molecule of farnesene produced (2 ATP equivalents per acetyl-CoA×9 acetyl-CoAs per 1 farnesene). This savings in ATP usage during acetyl-CoA production eliminates the cell's need for oxygen to run the TCA cycle for farnesene production. The oxygen requirement for conversion of glucose to farnesene decreases from 7.8 molecules of $O_2$ per glucose consumed to 6, thereby reducing a major production cost of providing oxygen to fermenters at scale. In addition, redox imbalance is alleviated by co-introduction of an NADH-using HMG-CoA reductase, which consumes NADH generated by ADA.

Figure 6:
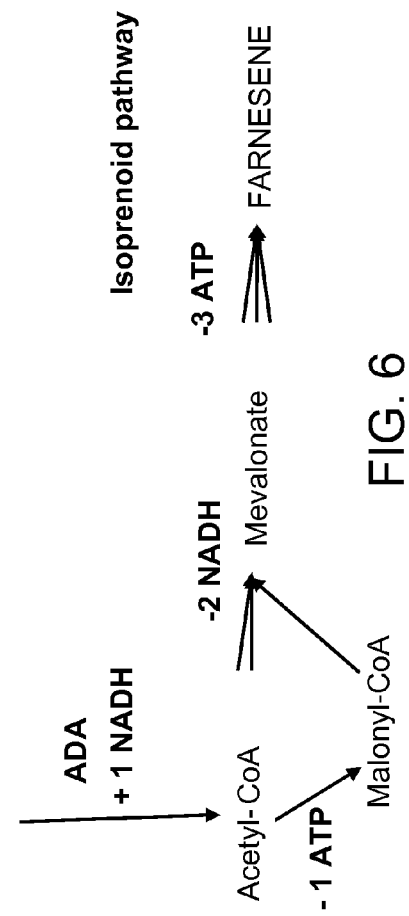
Figure 6:
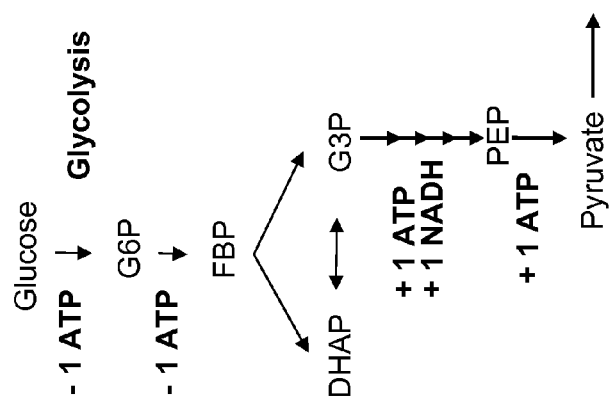

As indicated in FIG. 4, there remains a stoichiometric excess of ATP in a strain that comprises both an ADA and an NADH-using HMG-CoA reductase, which can be used by the cell for maintenance and growth. Alternatively, some of this excess ATP can be utilized towards improving the kinetics of acetoacetyl-CoA production, by introducing an acetoacetyl-CoA synthase (AACS). As illustrated in FIG. 5, AACS is an enzyme which synthesizes acetoacteyl-CoA from malonyl-CoA and acetyl-CoA. Malonyl-CoA synthesis requires an energetic input of 1 ATP per molecule of acetyl-CoA converted (catalyzed by acetyl-CoA carboxylase, thereby improving the thermodynamic driving force of acetoacetyl-CoA synthesis from acetyl-CoA. Importantly, this does not affect the maximum stoichiometric yield of farnesene from sugar or the oxygen demand of the pathway, as there is still excess ATP available in this strain design, as illustrated in FIG. 6.

Figure 7:
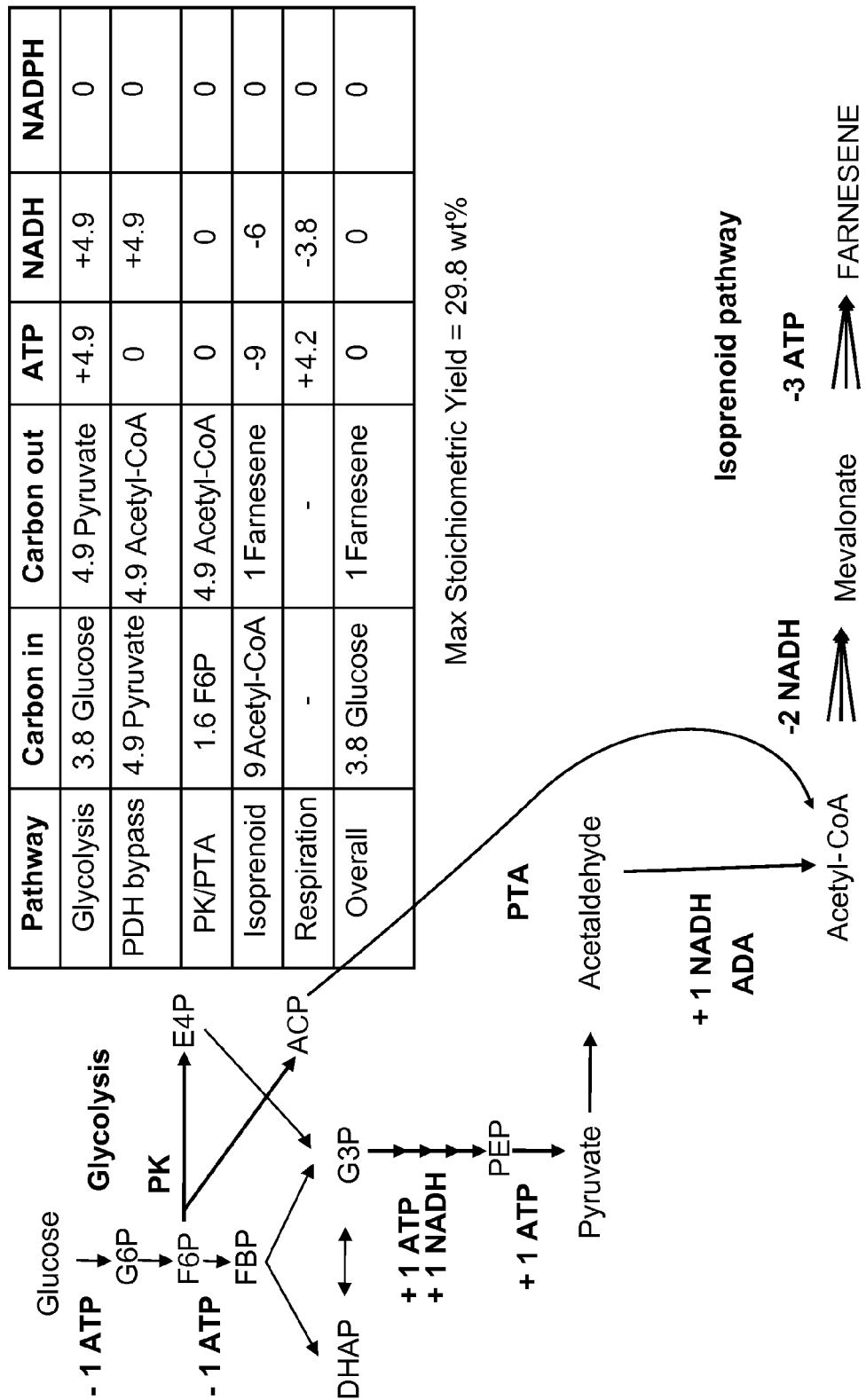
Figure 13:
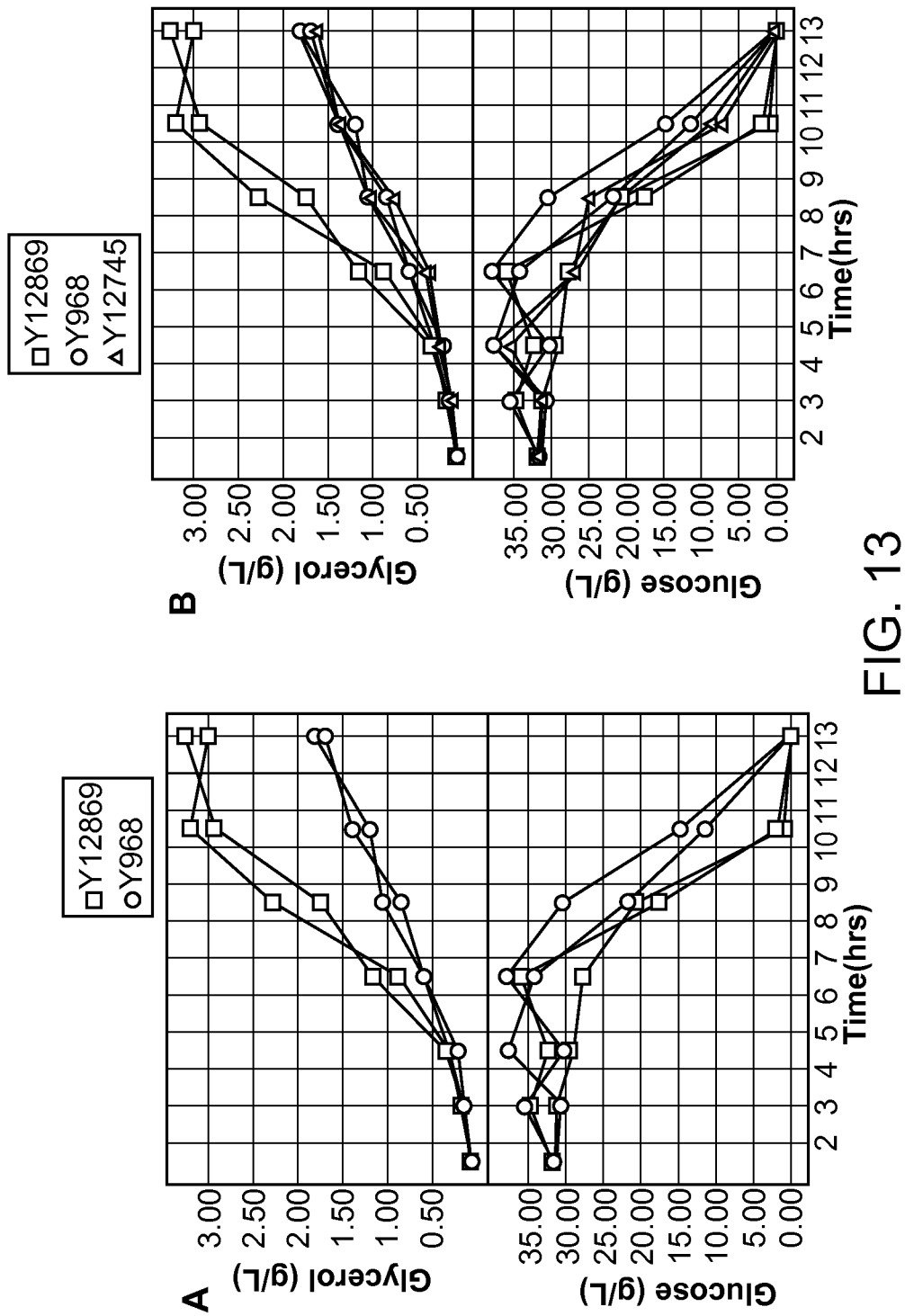

As shown in FIG. 7, additional efficiencies can be gained via the introduction of phosphoketolase (PK) and phosphotransacetylase (PTA) enzymes. PK and PTA catalyze the reactions to convert fructose-6-phosphate (F6P) or xyulose-5-phosphate (X5P) to acetyl-CoA. With these metabolic pathways available, at optimality, the reaction network is able to reach 29.8 wt % mass yield or greater, a significant increase in maximum theoretical yield. This solution involves diverting carbon away from lower glycolysis (G3P→pyruvate), which results in less ATP and NADH generation, both of which are already in excess in a network comprising the ADA and NADH-using HMG-CoA reductase modifications. One benefit of reducing flux through lower glycolysis is that less $CO_2$ is produced in converting pyruvate into acetaldehyde, and thus more carbon can be captured in the end product, thereby increasing the maximum theoretical yield of the network. A second benefit is that less NADH is produced, and therefore significantly less oxygen is needed to reoxidize it. In particular, the oxygen demand at optimality is only 1.84 molecules of $O_2$ per glucose consumed. The redox impact of the addition of PK and PTA to an ADA background is visible even at low yields in the microscale, as illustrated in FIG. 13, where glycerol production returns to wild-type levels.

Thus, provided herein are genetically modified host cells and methods of their use for the production of acetyl-CoA-derived isoprenoids. In one aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate; and (b) a heterologous nucleic acid encoding an acylating acetyl-aldehyde dehydrogenase.

In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an acetyl-CoA:malonyl-CoA acyltransferase (i.e., an acetoacetyl-CoA synthase (AACS)).

In some embodiments, the one or more enzymes of the MEV pathway comprise an NADH-using enzyme that converts HMG-CoA to mevalonate. In some embodiments, the one or more enzymes of the MEV pathway comprise an NADH-using HMG-CoA reductase.

In some embodiments, the genetically modified host cell further comprises a heterologous nucleic acid encoding a phosphoketolase. In some embodiments, the genetically modified host cell further comprises a heterologous nucleic acid encoding a phosphotransacetylase.

In some embodiments, the amino acid sequence of the ADA is at least 80% identical to SEQ ID NO:2. In some embodiments, the amino acid sequence of the acetyl-CoA: malonyl-CoA acyltransferase is at least 80% identical to SEQ ID NO:16. In some embodiments, the amino acid sequence of the NADH-using HMG-CoA reductase is at least 80% identical to SEQ ID NO:20. In some embodiments, the amino acid sequence of the phosphoketolase is at least 80% identical to SEQ ID NO:12. In some embodiments, the amino acid sequence of the phosphotransacetylase is at least 80% identical to SEQ ID NO:14.

In some embodiments, the genetically modified host cell further comprises a functional disruption of one or more enzymes of the native pyruvate dehydrogenase (PDH)-bypass. In some embodiments, the one or more enzymes of the PDH-bypass are selected from acetyl-CoA synthetase 1 (ACS1), acetyl-CoA synthetase 2 (ACS2), and aldehyde dehydrogenase 6 (ALD6). In some embodiments, ACS1 is functionally disrupted. In some embodiments, ACS2 is functionally disrupted. In some embodiments, ALD6 is functionally disrupted. In some embodiments, ACS1 and ACS2 are functionally disrupted. In some embodiments, ACS1, ACS2 and ALD6 are functionally disrupted.

In some embodiments, the genetically modified host cell further comprises a functional disruption of one or more enzymes having alcohol dehydrogenase (ADH) activity. In some embodiments, the one or more enzymes having ADH activity are selected from alcohol dehydrogenase 1 (ADH1), alcohol dehydrogenase 3 (ADH3), alcohol dehydrogenase 4 (ADH4), and alcohol dehydrogenase 5 (ADH5).

In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate. In some embodiments, the one or more enzymes of the MEV pathway are selected from HMG-CoA synthase, mevalonate kinase, phosphomevalonate kinase and mevalonate pyrophosphate decarboxylase.

In some embodiments, the host cell comprises a plurality of heterologous nucleic acids encoding all of the enzymes of the MEV pathway. In some embodiments, the one or more heterologous nucleic acids encoding one or more enzymes of the MEV pathway are under control of a single transcriptional regulator. In some embodiments, the one or more heterologous nucleic acids encoding one or more enzymes of the MEV pathway are under control of multiple heterologous transcriptional regulators.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound. In some embodiments, the enzyme that can modify IPP or a polyprenyl to form an isoprenoid compound is selected from the group consisting of carene synthase, geraniol synthase, linalool synthase, limonene synthase, myrcene synthase, ocimene synthase, α-pinene synthase, β-pinene synthase, γ-terpinene synthase, terpinolene synthase, amorphadiene synthase, α-farnesene synthase, β-farnesene synthase, farnesol synthase, nerolidol synthase, patchouliol synthase, nootkatone synthase, and abietadiene synthase. In some embodiments, the isoprenoid is selected from the group consisting of a hemiterpene, monoterpene, diterpene, triterpene, tetraterpene, sesquiterpene, and polyterpene. In some embodiments, the isoprenoid is a $C_5$-$C_{20}$ isoprenoid. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

In some embodiments, the genetically modified host cell is a yeast cell. In some embodiments, the yeast is *Saccharomyces cerevisiae*.

In another aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate; (b) a heterologous nucleic acid encoding an acetylaldehyde dehydrogenase, acetylating (ADA); (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); (d) a heterologous nucleic acid encoding a phosphoketolase (PK); and (e) a heterologous nucleic acid encoding a phosphoketolase (PTA).

In another aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate, wherein the one or more enzymes comprise a NADH-using HMG-CoA reductase; (b) a heterologous nucleic acid encoding an acetylaldehyde dehydrogenase, acetylating (ADA); and (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6).

In another aspect, provided herein is a genetically modified host cell capable of producing an isoprenoid, the cell comprising: (a) one or more heterologous nucleic acids encoding one or more enzymes of a mevalonate (MEV) pathway for making isopentenyl pyrophosphate, wherein the one or more enzymes comprise a NADH-using HMG-CoA reductase; (b) a heterologous nucleic acid encoding an acetylaldehyde dehydrogenase, acetylating (ADA); (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); (d) a heterologous nucleic acid encoding a phosphoketolase (PK); and (e) a heterologous nucleic acid encoding a phosphoketolase (PTA).

In another aspect, provided herein is genetically modified host cell capable of producing an isoprenoid, the cell comprising: (a) one or more heterologous nucleic acids encoding one or more enzymes of a mevalonate (MEV) pathway for making isopentenyl pyrophosphate, wherein the one or more enzymes comprise an acetyl-CoA:malonyl-CoA acyltransferase; (b) a heterologous nucleic acid encoding acetylaldehyde dehydrogenase, acetylating (ADA); and (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6).

In another aspect, provided herein is a genetically modified host cell capable of producing an isoprenoid, the cell comprising: (a) one or more heterologous nucleic acids encoding a plurality of enzymes of a mevalonate (MEV) pathway for making isopentenyl pyrophosphate, wherein the plurality of enzymes comprise an acetyl-CoA:malonyl-CoA acyltransferase and an NADH-using HMG-CoA reductase; (b) a heterologous nucleic acid encoding an acetylaldehyde dehydrogenase, acetylating (ADA); (c) a functional disruption of at least one enzyme of the native PDH-bypass selected from the group consisting of acetyl-CoA synthetase 1 (ACS1), acetyl-CoA synthetase 2 (ACS2), and aldehyde dehydrogenase 6 (ALD6); (d) a heterologous nucleic acid encoding a phosphoketolase (PK); and (e) a heterologous nucleic acid encoding a phosphoketolase (PTA).

In another aspect, provided herein is a method for producing an isoprenoid, the method comprising: (a) culturing a population of genetically modified yeast cells described herein in a medium with a carbon source under conditions suitable for making said isoprenoid compound; and (b) recovering said isoprenoid compound from the medium.

4. BRIEF DESCRIPTION OF THE FIGURES

FIG. 1 provides a schematic representation of the mevalonate ("MEV") pathway for the production of isopentenyl diphosphate ("IPP").

FIG. 2 provides a schematic representation of the conversion of IPP and dimethylallyl pyrophosphate ("DMAPP") to geranyl pyrophosphate ("GPP"), farnesyl pyrophosphate ("FPP"), and geranylgeranyl pyrophosphate ("GGPP").

FIG. 3 provides a schematic representation of the optimal flow of carbon and the metabolic requirements and yields in the conversion of glucose to farnesene via the mevalonate pathway, wherein cytosolic acetyl-CoA is generated via the "wild-type" PDH-bypass.

FIG. 4 provides a schematic representation of the optimal flow of carbon and the metabolic requirements and yields in the conversion of glucose to farnesene via the mevalonate pathway, wherein cytosolic acetyl-CoA is generated via ADA, and the mevalonate pathway comprises an NADH-using HMGr instead of an NADPH-using HMGr.

FIG. 5 provides a schematic representation of farnesene production from acetyl-CoA, wherein acetoacteyl-CoA (AcAcCoA) is synthesized from malonyl-CoA and acetyl-CoA (AcCoA) by acetoacetyl-CoA synthase (AACS). Malonyl-CoA synthesis requires an energetic input of 1 ATP per molecule of acetyl-CoA converted (catalyzed by acetyl-CoA carboxylase (ACC1)).

FIG. 6 provides a schematic representation of the optimal flow of carbon and the metabolic requirements and yields in the conversion of glucose to farnesene via the mevalonate pathway, wherein cytosolic acetyl-CoA is generated via ADA, the mevalonate pathway comprises an NADH-using HMGr instead of an NADPH-using HMGr, and acetoacteyl-CoA is synthesized from malonyl-CoA and acetyl-CoA by acetoacetyl-CoA synthase.

FIG. 7 provides a schematic representation of the optimal flow of carbon and the metabolic requirements and yields in the conversion of glucose to farnesene via the mevalonate pathway, wherein cytosolic acetyl-CoA is generated via ADA, the mevalonate pathway comprises an NADH-using HMGr instead of an NADPH-using HMGr, and phosphoketolase (PK) and phosphotransacetylase (PTA) catalyze the reactions to convert fructose-6-phosphate (F6P) to acetyl-CoA.

Figure 8:
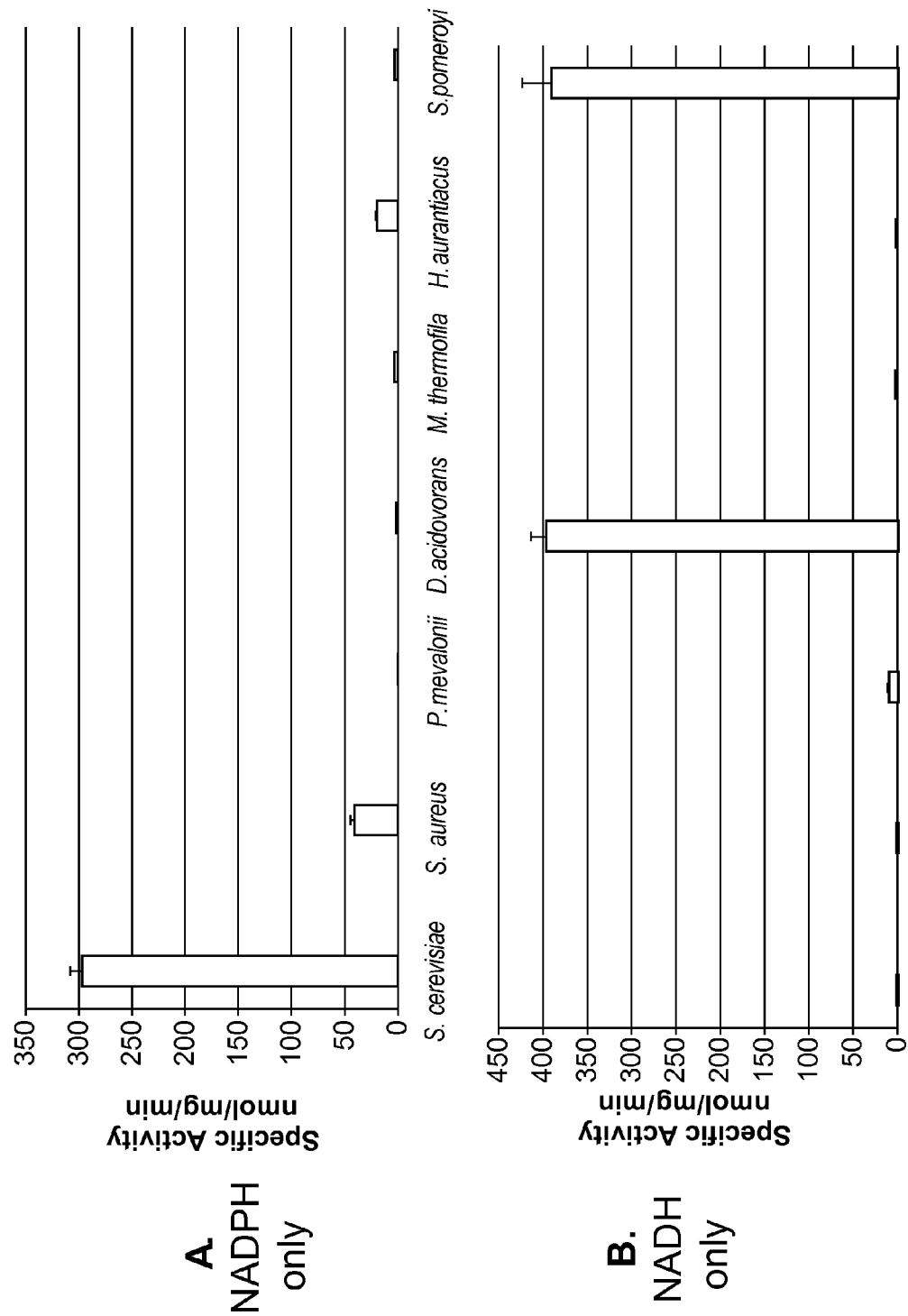

FIG. 8 provides the NADPH-specific or NADH-specific activities (measured as nmol/mg/min) of hydroxymethylglutaryl-CoA reductases from *Sacchormyces cerevisiae* (Sc. tHMG-CoA reductase), *Pseudomonas mevalonii* (Pm.), *Delftia acidovorans* (Da.) and *Silicibacter pomeroyi* (Sp.).

Figure 9:
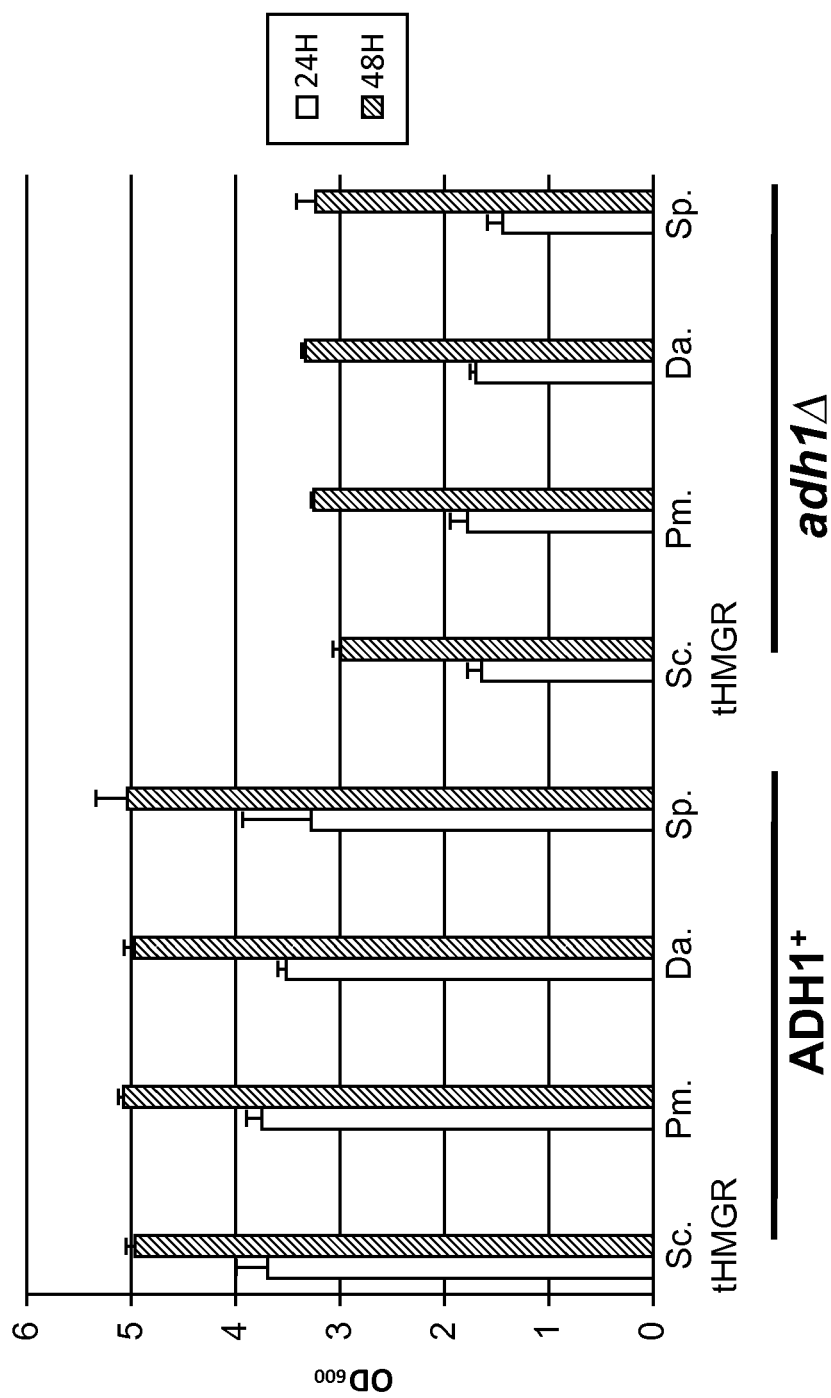

FIG. 9 provides cell densities (measured as $OD_{600}$) after 24 and 48 hours for *S. cerevisiae* (Sc.) strains comprising a heterologous MevT pathway comprising an NADPH-using HMG-CoA reductase (Sc. tHMG-CoA reductase) or an NADH-using HMG-CoA reductase (Pm.—*Pseudomonas mevalonii*; Da.—*Delftia acidovorans*; Sp.—*Silicibacter pomeroyi*) in a wild-type ADH1, and an ADH1 knockout (adh1Δ) background, respectively.

Figure 10:
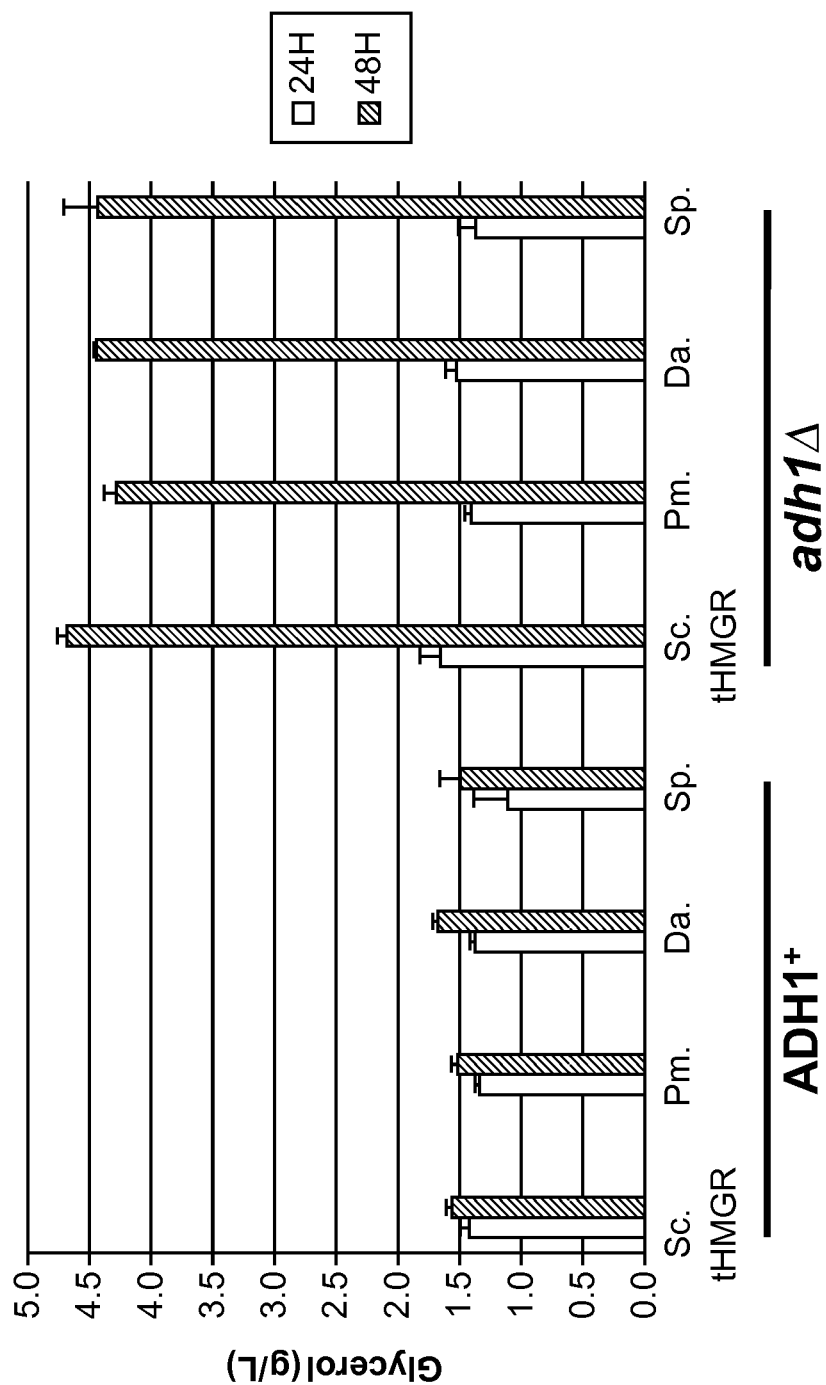

FIG. 10 provides glycerol production (measured as g/L) after 24 and 48 hours for *S. cerevisiae* (Sc.) strains a heterologous MevT pathway comprising comprising an NADPH-using HMG-CoA reductase (Sc. tHMG-CoA reductase) or an NADH-using HMG-CoA reductase (Pm.—*Pseudomonas mevalonii*; Da.—*Delftia acidovorans*; Sp.—*Silicibacter pomeroyi*) in both a wild-type ADH1 and ADH1 knockout background.

Figure 11:
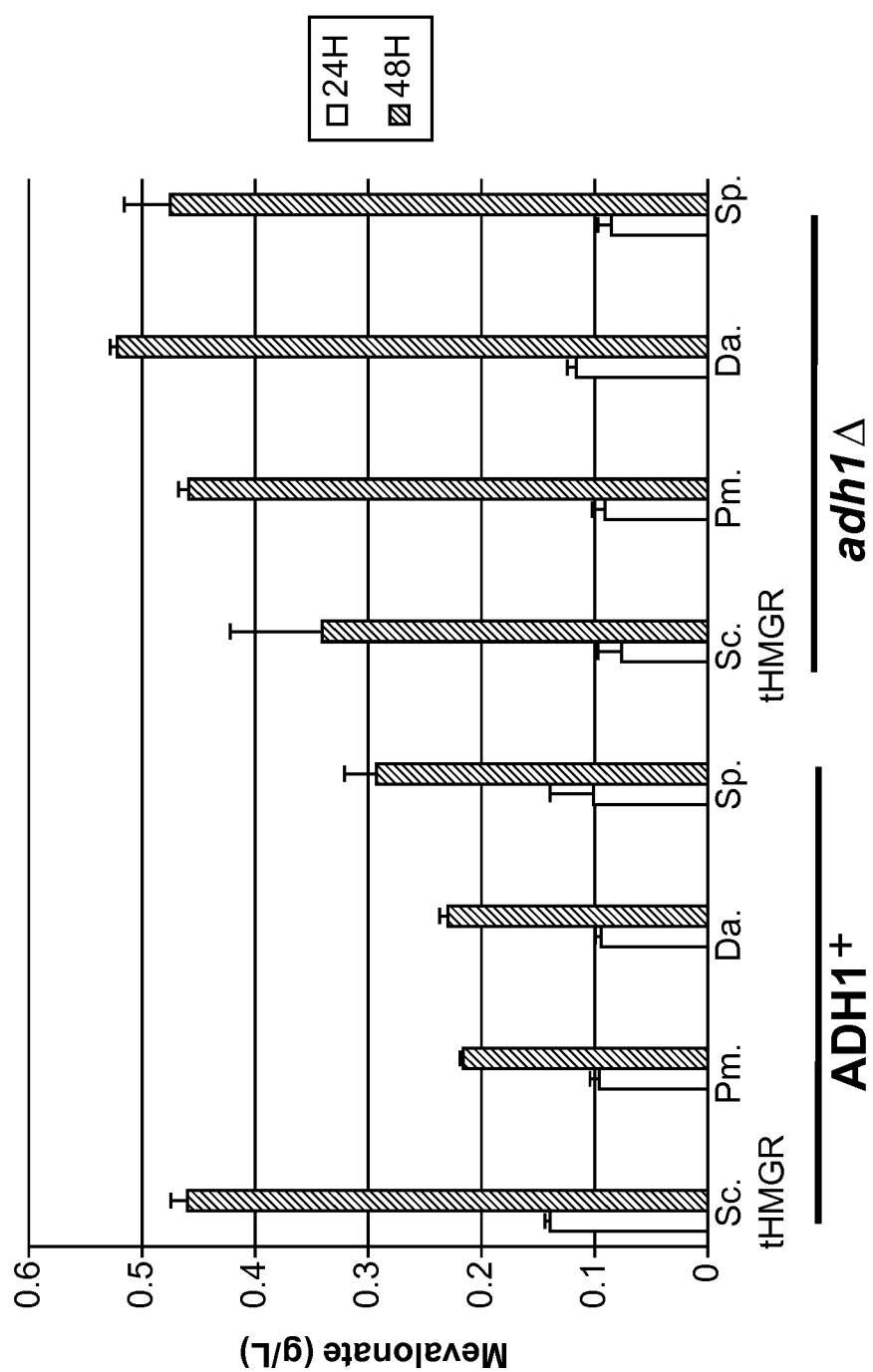

FIG. 11 provides mevlonate production (measured as g/L) after 24 and 48 hours for *S. cerevisiae* (Sc.) strains comprising an NADPH-using HMG-CoA reductase (Sc. tHMG-CoA reductase) or an NADH-using HMG-CoA reductase (Pm.—*Pseudomonas mevalonii*; Da.—*Delftia acidovorans*; Sp.—*Silicibacter pomeroyi*) in both a wild-type ADH1 and ADH1 knockout (adh1Δ) background.

Figure 12:
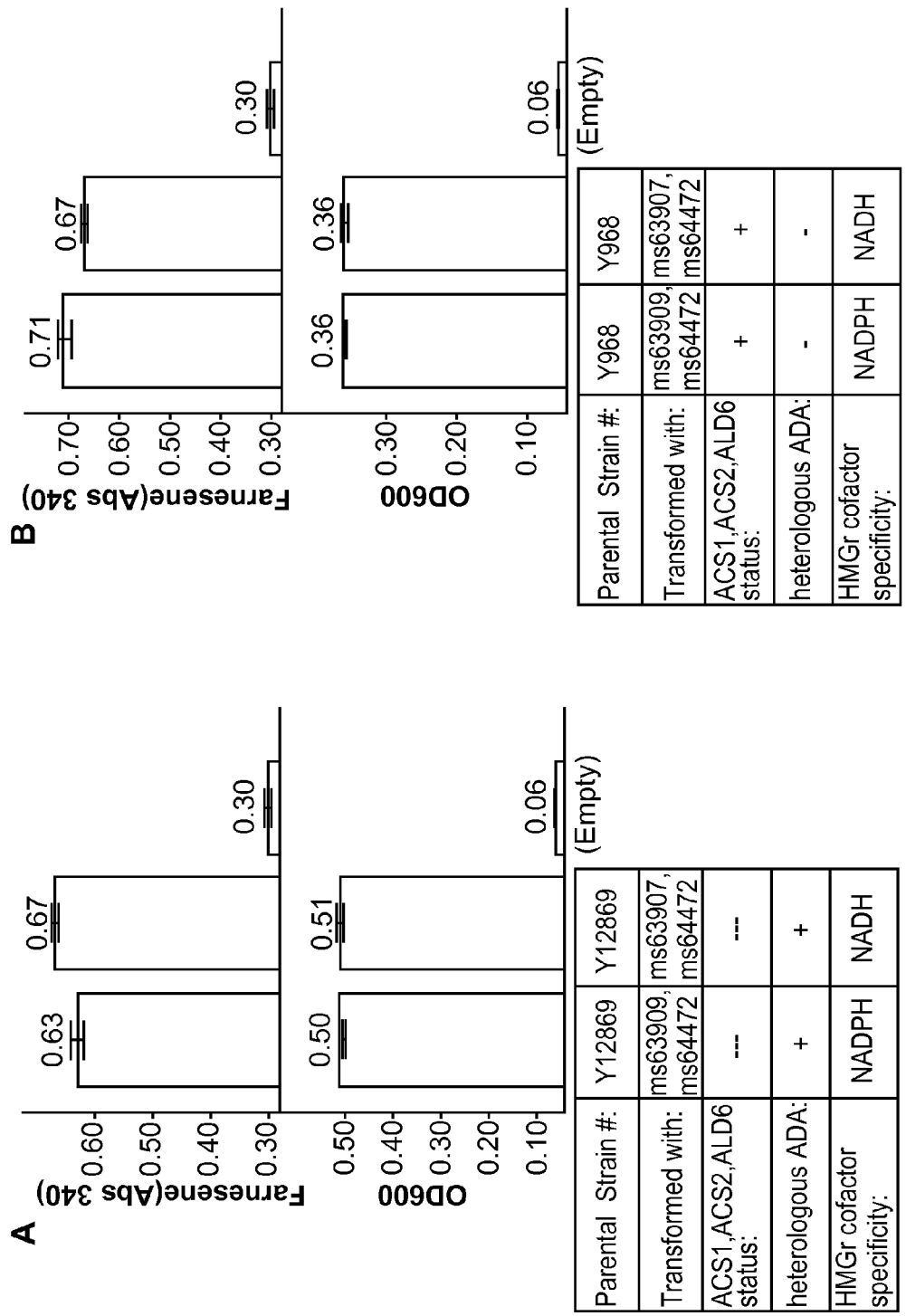

FIG. 12 provides farnesene production and cell densities of *S. cerevisiae* strains comprising: (A) heterologously expressed ADA (Dz.eutE) coupled with acs1Δacs2Δald6Δ and an MEV pathway comprising either an NADPH-using HMG-CoA reductase or an NADH-using HMG-CoA reductase; (B) an intact (wild-type) PDH-bypass and an MEV pathway comprising either an NADPH-using HMG-CoA reductase or an NADH-using HMG-CoA reductase. Columns indicated as "Empty" represent wells with media only (no cells).

FIG. 13 provides glycerol production (top panels) and glucose consumption (lower panels) by: (A) a wild-type strain (Y968); a strain heterologously expressing ADA (Dz.eutE) (Y12869); and (B) a strain heterologously expressing ADA (Dz.eutE), phosphoketolase (PK) and phosphotransacetylase (PTA) (Y12745).

Figure 14:
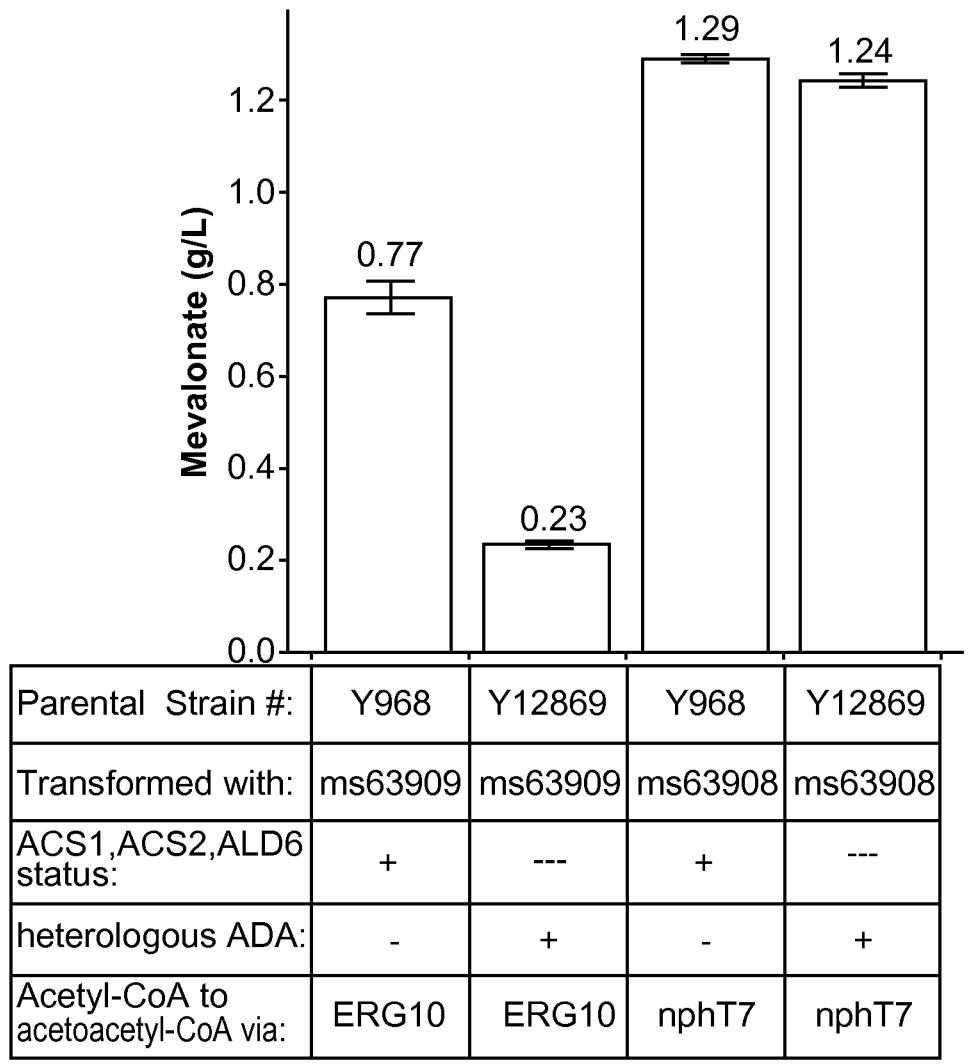

FIG. 14 provides mevalonate production by *S. cerevisiae* strains comprising either an intact (wild-type) PDH-bypass or heterologously expressed ADA (Dz.eutE) coupled with acs1Δacs2Δald6Δ; and an MEV pathway comprising either ERG10 (acetyl-CoA thiolase) or nphT7 (acetoacetyl-CoA synthase).

5. DETAILED DESCRIPTION OF THE EMBODIMENTS

5.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

On the other hand, the term "native" or "endogenous" as used herein with reference to molecules, and in particular enzymes and nucleic acids, indicates molecules that are expressed in the organism in which they originated or are found in nature, independently of the level of expression that can be lower, equal, or higher than the level of expression of the molecule in the native microorganism. It is understood that expression of native enzymes or polynucleotides may be modified in recombinant microorganisms.

As used herein, to "functionally disrupt" or a "functional disruption" e.g., of a target gene, for example, one or more genes of the PDH-bypass, means that the target gene is altered in such a way as to decrease in the host cell the activity of the protein encoded by the target gene. Similarly, to "functionally disrupt" or a "functional disruption" e.g., of a target protein, for example, one or more enzymes of the PDH-bypass, means that the target protein is altered in such a way as to decrease in the host cell the activity of the protein. In some embodiments, the activity of the target protein encoded by the target gene is eliminated in the host cell. In other embodiments, the activity of the target protein encoded by the target gene is decreased in the host cell. Functional disruption of the target gene may be achieved by deleting all or a part of the gene so that gene expression is eliminated or reduced, or so that the activity of the gene product is eliminated or reduced. Functional disruption of the target gene may also be achieved by mutating a regulatory element of the gene, e.g., the promoter of the gene so that expression is eliminated or reduced, or by mutating the coding sequence of the gene so that the activity of the gene product is eliminated or reduced. In some embodiments, functional disruption of the target gene results in the removal of the complete open reading frame of the target gene.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an ADA, heterologous expression of an NADH-using HMG-CoA reductase, heterologous expression of an AACS, heterologous expression of a phosphoketolase, heterologous expression of a phosphotrancacetylase, and heterologous expression of one or more enzymes of the mevalonate pathway.

As used herein, the term "production" generally refers to an amount of an isoprenoid produced by a genetically modified host cell provided herein. In some embodiments, production is expressed as a yield of isoprenoid by the host cell. In other embodiments, production is expressed as a productivity of the host cell in producing the isoprenoid.

As used herein, the term "productivity" refers to production of an isoprenoid by a host cell, expressed as the amount of isoprenoid produced (by weight) per amount of fermentation broth in which the host cell is cultured (by volume) over time (per hour).

As used herein, the term "yield" refers to production of an isoprenoid by a host cell, expressed as the amount of isoprenoid produced per amount of carbon source consumed by the host cell, by weight.

5.2 Genetically Modified Microbes Producing Acetyl-CoA Derived Isoprenoids 5.2.1 Host Cells Host cells useful compositions and methods provided herein include archae, prokaryotic, or eukaryotic cells.

Suitable prokaryotic hosts include, but are not limited to, any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae*, *Pichia pastoris*, *Schizosaccharomyces pombe*, *Dekkera bruxellensis*, *Kluyveromyces lactis* (previously called *Saccharomyces lactis*), *Kluveromyces marxianus*, *Arxula adeninivorans*, or *Hansenula polymorpha* (now known as *Pichia angusta*). In some embodiments, the host microbe is a strain of the genus *Candida*, such as *Candida lipolytica*, *Candida guilliermondii*, *Candida krusei*, *Candida pseudotropicalis*, or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

5.2.2 Heterologous ADA for Acetyl-CoA Production

In one aspect, provided herein is a genetically modified host cell capable of producing an acetyl-CoA derived isoprenoid, the cell comprising one or more heterologous nucleotide sequences encoding acylating acetaldehyde dehydrogenase (alternately referred to as "acetylaldehyde dehydrogenase, acetylating," "acetylaldehyde dehydrogenase, acylating," or ADA (EC 1.2.1.10)).

Proteins capable of catalyzing this reaction that are useful for the compositions and methods provided herein include the following four types of proteins:

(1) Bifunctional proteins that catalyze the reversible conversion of acetyl-CoA to acetaldehyde, and the subsequent reversible conversion of acetaldehyde to ethanol. An example of this type of protein is the AdhE protein in *E. coli* (GenBank No: NP_415757). AdhE appears to be the evolutionary product of a gene fusion. The $NH_2$-terminal region of the AdhE protein is highly homologous to aldehyde:$NAD^+$ oxidoreductases, whereas the COOH-terminal region is homologous to a family of $Fe^{2+}$-dependent ethanol:$NAD^+$ oxidoreductases (Membrillo-Hernandez et al., (2000) *J. Biol. Chem.* 275: 33869-33875). The *E. coli* AdhE is subject to metal-catalyzed oxidation and therefore oxygen-sensitive (Tamarit et al. (1998) *J. Biol. Chem.* 273:3027-32).

(2) Proteins that catalyze the reversible conversion of acetyl-CoA to acetaldehyde in strictly or facultative anaerobic microbes but do not possess alcohol dehydrogenase activity. An example of this type of protein has been reported in *Clostridium kluyveri* (Smith et al. (1980) *Arch. Biochem. Biophys.* 203: 663-675). An ADA has been annotated in the genome of *Clostridium kluyveri* DSM 555 (accession no: EDK33116). A homologous protein AcdH is identified in the genome of *Lactobacillus plantarum* (accession no: NP_784141). Another example of this type of protein is the ald gene product in *Clostridium beijerinckii* NRRL B593 (Toth et al. (1999) *Appl. Environ. Microbiol.* 65: 4973-4980, accession no: AAD31841).

(3) Proteins that are involved in ethanolamine catabolism. Ethanolamine can be utilized both as carbon and nitrogen source by many enterobacteria (Stojiljkovic et al. (1995) *J. Bacteriol.* 177: 1357-1366). Ethanolamine is first converted by ethanolamine ammonia lyase to ammonia and acetaldehyde, subsequently, acetaldehyde is converted by ADA to acetyl-CoA. An example of this type of ADA is the EutE protein in *Salmonella typhimurium* (Stojiljkovic et al. (1995) *J. Bacteriol.* 177: 1357-1366, accession no: AAL21357; see also U18560.1). *E. coli* is also able to utilize ethanolamine (Scarlett et al. (1976) *J. Gen. Microbiol.* 95:173-176) and has an EutE protein (accession no: AAG57564; see also EU897722.1) which is homologous to the EutE protein in *S. typhimurium*.

(4) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) *Biodegradation* 5, 219-236). 4-Hydroxy-2-ketovalerate is first converted by 4-hydroxy-2-ketovalerate aldolase to pyruvate and acetaldehyde, subsequently acetaldehyde is converted by ADA to acetyl-CoA. An example of this type of ADA is the DmpF protein in *Pseudomonas* sp CF600 (accession no: CAA43226) (Shingler et al. (1992) *J. Bacteriol.* 174:711-24). *E. coli* has a homologous MphF protein (Ferrandez et al. (1997) J. Bacteriol. 179: 2573-2581, accession no: NP_414885) to the DmpF protein in *Pseudomonas* sp. CF600.

In some embodiments, an ADA (or nucleic acid sequence encoding such activity) useful for the compositions and methods described herein is selected from the group consisting of *Escherichia coli* adhE, *Entamoeba histolytica* adh2, *Staphylococcus aureus* adhE, *Piromyces* sp.E2 adhE, *Clostridium kluyveri* (EDK33116), *Lactobacillus plantarum* acdH, and *Pseudomonas putida* (YP_001268189), as described in International Publication No. WO 2009/013159, the contents of which are incorporated by reference in their entirety. In some embodiments, the ADA is selected from the group consisting of *Clostridium botulinum* eutE (FR745875.1), *Desulfotalea psychrophila* eutE (CR522870.1), *Acinetobacter* sp. HBS-2 eutE (ABQ44511.2), *Caldithrix abyssi* eutE (ZP_09549576), and *Halorubrum lacusprofundi* ATCC 49239 (YP_002565337.1).

In particular embodiments, the ADA useful for the compositions and methods provided herein is eutE from *Dickeya zeae*. A representative eutE nucleotide sequence of *Dickeya zeae* includes accession number NC_012912.1: 1110476.1111855 and SEQ ID NO: 1 as provided herein. A representative eutE protein sequence of *Dickeya zeae* includes accession number YP_003003316, and SEQ ID NO: 2 as provided herein. ADAs also useful in the compositions and methods provided herein include those molecules which are said to be "derivatives" of any of the ADAs described herein. Such a "derivative" has the following characteristics: (1) it shares substantial homology with any of the ADAs described herein; and (2) is capable of catalyzing the conversion of acetaldehyde to acetyl-CoA. A derivative of an ADA is said to share "substantial homology" with ADA if the amino acid sequences of the derivative is at least 80%, at least 85% and more preferably at least 90%, and most preferably at least 95%, the same as that of any of the ADAs described herein.

5.2.2.1 Methods for Identifying Functional ADAs

In another aspect, provided herein is a screening method for ADAs with elevated in vivo performance. In this screening method, ADAs with elevated in vivo performance are identified by their ability to rescue engineered host cells from cell death. The engineered host cells comprise a heterologous pathway for the production of a cytosolic acetyl-CoA derived secondary metabolite, e.g., an isoprenoid. In some embodiments, the engineered host cells further comprise a functionally disrupted PDH-bypass pathway, and a weakly active ADA, wherein the combined activities of the functionally disrupted PDH-bypass pathway and the weakly active ADA do not produce enough cytosolic acetyl-CoA to meet the requirements for production of both: (1) the cytosolic acetyl-CoA derived secondary metabolite; and (2) the cytosolic acetyl-CoA derived primary metabolites required for cell survival, health, and/or growth. For survival, health, and/or growth, the host cell thus requires an active ADA that enables production of an elevated pool of cytosolic acetyl-CoA.

In some embodiments, the method of screening for ADAs with elevated in vivo performance comprises: (a) expressing a control ADA in a host cell having a functionally disrupted PDH-bypass pathway to produce an elevated level of a cytosolic acetyl-CoA derived secondary metabolite, wherein production of the elevated level of the cytosolic acetyl-CoA derived secondary metabolite reduces the viability of the host cell compared to a parent cell not producing the elevated level of the cytosolic acetyl-CoA derived secondary metabolite; and (b) expressing in the host cell a test ADA instead of the control ADA; whereby an increase in viability of the host cell expressing the test ADA compared to the host cell expressing the control ADA identifies the test ADA as having improved in vivo performance compared to the control ADA.

In some embodiments, production of the elevated level of a cytosolic acetyl-CoA derived secondary metabolite in the host cell is inducible. Induction may occur in response to an inducing agent (e.g., galcatose) or specific growth condition (e.g., growth temperature). When grown in the absence of the inducing agent, the ADA activity of the host cell is sufficient to enable production of the cytosolic acetyl-CoA required by the host cell for survival. However, when grown in the presence of the inducing agent, the ADA activity of the host cell is not sufficient to enable production of both the cytosolic acetyl-CoA required by the host cell for survival and the elevated level of the cytosolic acetyl-CoA derived secondary metabolite. In the latter case, the host cell thus requires for survival a more active ADA that enables production of an elevated pool of cytosolic acetyl-CoA. The production of the cytosolic acetyl-CoA derived secondary metabolite in the host cell may range from about 10% to at least about 1.000-fold, or more, higher than the production of the cytosolic acetyl-CoA derived secondary metabolite in the parent cell.

The reduced viability of the host cell expressing the control ADA compared to the parent cell may range from decreased cell growth to lethality. Thus, in some embodiments, the host cell expressing the control ADA produces a reduced number of progeny cells in a liquid culture or on an agar plate compared to the parent cell. In other embodiments, the host cell expressing the control ADA produces no progeny cells in a liquid culture or on an agar plate compared to the parent cell. Accordingly, the increase in viability of the host cell expressing the test ADA instead of the control ADA may be apparent in liquid culture by a higher number of progeny cells, or on an agar plate by a larger colony size, compared to the number of progeny cells or colony size produced by the host cell expressing the control ADA.

Production of the elevated level of the cytosolic acetyl-CoA derived secondary metabolite in the host cell may be effected by modifying the expression and/or activity of an enzyme involved in the production of the cytosolic acetyl-CoA derived secondary metabolite or its precursors in the host cell. In some such embodiments, the expression and/or activity of an enzyme of the MEV or DXP pathway is modified. In some such embodiments, the expression and/or activity of a HMG-CoA reductase and/or a mevalonate kinase is modified.

The control ADA and test ADA may be naturally occurring ADAs or non-naturally occurring ADAs. In some embodiments, the test ADA is a variant of the control ADA that differs from the control ADA by one or more amino acid substitutions, deletions, and/or additions. In some embodiments, the test ADA comprises identical amino acids as the control ADA but the codons encoding these amino acids differ between the test ADA and the control ADA. In some such embodiments, the codons are optimized for usage in the host cell. In some embodiments, the control ADA and/or test ADA is fused to a pyruvate decarboxylase. In some embodiments, expression of the test ADA is under regulatory control of a strong promoter. In some embodiments, expression of the test ADA is under regulatory control of a medium strength promoter. In some embodiments, expression of the test ADA is under regulatory control of a weak promoter.

The increase in viability of the host cell in the presence of the test ADA may be effected by a test ADA that is more active than the control ADA or by a test ADA that is similarly or less active than the control ADA but that is expressed at a higher level. Identification of test ADAs with increased activity can be accomplished by expressing the control ADA and the test ADA at similar levels in the host cell. This can be accomplished, for example, by placing the nucleotide sequences encoding the control ADA and test ADA in the host cell under the control of the same regulatory elements. In other embodiments in which the method is used, for example, to identify regulatory elements (e.g., promoters) that provide a desired expression level, the test ADA differs from the control ADA not in nucleotide or amino acid sequence but in expression level. In such embodiments, different regulatory elements can be used for the expression of the control ADA and the test ADA, and comparison of host cell viabilities provides information not about the activity of the test ADA but about the strength of the regulatory elements driving the expression of the test ADA.

To prevent a competitive growth situation in which fast growing false positive host cells comprising a growth promoting mutation rather than an improved ADA variant take over a host cell culture, one embodiment of the screening method involves an agar-plate based selection system. In this embodiment, the host cell is plated on an agar plate, and a host cell comprising a test ADA variant with improved in vivo performance is identified by colony growth.

A substantial advantage of the presently disclosed screening method is its simplicity and capacity for high-throughput implementation. ADA variants are identified simply based on cell viability, making other costly and time consuming screening methods virtually unnecessary. Thus, in one embodiment, the method is used to screen a collection of ADA variants (e.g., a library of mutant ADAs) for ADA variants with improved in vivo performance. In such an embodiment, not a single test ADA is expressed in a host cell but a collection of test ADAs are expressed in a collection of host cells. The host cells can then be grown on agar plates, and host cells expressing ADA variants with improved in vivo performance can be identified based on colony growth. In some embodiments, the collection of ADA variants comprises from 2 to 5, from 5 to 10, from 10 to 50, from 50 to 100, from 100 to 500, from 500 to 1,000, from 1,000 to 10,000, from 10,000 to 100,000, from 100,000 to 1,000,000, and more, ADA variants.

Another major advantage of the presently disclosed screening method is its continued capacity to select for better and better ADA variants in an iterative fashion, wherein a test ADA identified in an iteration is used as the control ADA in a subsequent iteration. Such an embodiment requires, however, that at each iteration the production of the cytosolic acetyl-CoA derived secondary metabolite in the host cell is checked and potentially increased (e.g., by increasing or decreasing expression levels of enzymes, adding or subtracting enzymes, increasing or decreasing copy numbers of genes, replacing promoters controlling expression of enzymes, or altering enzymes by genetic mutation) to a level that causes reduced viability when the host cell expresses the new control ADA (i.e., the test ADA of the previous iteration). Alternatively, or in addition, at each iteration, the expression of the control ADA can be reduced (e.g., by decreasing expression of or by using weaker promoters or by reducing the stability of the control ADA transcript or polypeptide) to provide reduced control ADA activity. In the next iteration, a test ADA can then be identified that has yet increased in vivo performance compared to the test ADA of the previous iteration.

Another major advantage of the presently disclosed screening method is that selection for improved ADAs occurs in vivo rather than in vitro. As a result, improvements of multiple enzyme properties that enhance the in vivo performance of the ADA variant can be obtained.

Enzymes developed using the presently disclosed screening method can be subjected to additional means of optional screening including but not limited to a fluorescent screen and/or a direct quantitation of the cytosolic acetyl-CoA derived secondary metabolite by gas chromatography. More specifically, this includes a Nile Red-based high throughput fluorescent assay for measuring production of a sesquiterpene such as farnesene, and a gas chromatography (GC)-based direct quantitation method for measuring the titer of a sesquiterpene such as farnesene. The improved enzymes can also be further improved by genetic engineering methods such as induced mutations and the like. As a result, improvements of multiple enzyme properties that enhance the final enzyme performance are successively accomplished, and the most effective enzyme variants are identified.

5.2.3 Functional Disruption of the PDH-bypass

Acetyl-CoA can be formed in the mitochondria by oxidative decarboxylation of pyruvate catalyzed by the PDH complex. However, due to the inability of S. cerevisiae to transport acetyl-CoA out of the mitochondria, the PDH bypass has an essential role in providing acetyl-CoA in the cytosolic compartment, and provides an alternative route to the PDH reaction for the conversion of pyruvate to acetyl-CoA. The PDH bypass involves the enzymes pyruvate decarboxylase (PDC; EC 4.1.1.1), acetaldehyde dehydrogenase (ACDH; EC 1.2.1.5 and EC 1.2.1.4), and acetyl-CoA synthetase (ACS; EC 6.2.1.1). Pyruvate decarboxylase catalyzes the decarboxylation of pyruvate to acetaldehyde and carbon dioxide. Acetaldehyde dehydrogenase oxidizes acetaldehyde to acetic acid. In S. cerevisiae, the family of aldehyde dehydrogenases contains five members. ALD2 (YMR170c), ALD3 (YMR169c), and ALD6 (YPL061w) correspond to the cytosolic isoforms, while ALD4 (YOR374w) and ALD5 (YER073w) encode the mitochondrial enzyme. The main cytosolic acetaldehyde dehydrogenase isoform is encoded by ALD6. The formation of acetyl-CoA from acetate is catalyzed by ACS and involves hydrolysis of ATP. Two structural genes, ACS1 and ACS2, encode ACS.

In some embodiments, the genetically modified host cell comprises a functional disruption in one or more genes of the PDH-bypass pathway. In some embodiments, disruption of the one or more genes of the PDH-bypass of the host cell results in a genetically modified microbial cell that is impaired in its ability to catalyze one or more of the following reactions: (1) the decarboxylation of pyruvate into acetaldehyde by pyruvate decarboxylase; (2) the conversion of acetaldehyde into acetate by acetaldehyde dehydrogenase; and (3) the synthesis of acetyl-CoA from acetate and CoA by acetyl-CoA synthetase.

In some embodiments, compared to a parent cell, a host cell comprises a functional disruption in one or more genes of the PDH-bypass pathway, wherein the activity of the reduced-function or non-functional PDH-bypass pathway alone or in combination with a weak ADA is not sufficient to support host cell growth, viability, and/or health.

In some embodiments, the activity or expression of one or more endogenous proteins of the PDH-bypass is reduced by at least about 50%. In another embodiment, the activity or expression of one or more endogenous proteins of the PDH-bypass is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction or deletion of the activity or expression of one or more endogenous proteins of the PDH-bypass.

As is understood by those skilled in the art, there are several mechanisms available for reducing or disrupting the activity of a protein, such as a protein of the PDH-bypass, including, but not limited to, the use of a regulated promoter, use of a weak constitutive promoter, disruption of one of the two copies of the gene encoding the protein in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologous gene with lower specific activity, the like or combinations thereof.

In some embodiments, the genetically modified host cell comprises a mutation in at least one gene encoding for a protein of the PDH-bypass, resulting in a reduction of activity of a polypeptide encoded by said gene. In another embodiment, the genetically modified host cell comprises a partial deletion of gene encoding for a protein of the PDH-bypass, resulting in a reduction of activity of a polypeptide encoded by the gene. In another embodiment, the genetically modified host cell comprises a complete deletion of a gene encoding for a protein of the PDH-bypass, resulting in a reduction of activity of a polypeptide encoded by the gene. In yet another embodiment, the genetically modified host cell comprises a modification of the regulatory region associated with the gene encoding a protein of the PDH-bypass, resulting in a reduction of expression of a polypeptide encoded by said gene. In yet another embodiment, the genetically modified host cell comprises a modification of the transcriptional regulator resulting in a reduction of transcription of a gene encoding a protein of the PDH-bypass. In yet another embodiment, the genetically modified host cell comprises mutations in all genes encoding for a protein of the PDH-bypass resulting in a reduction of activity of a polypeptide encoded by the gene(s). In one embodiment, the activity or expression of the protein of the PDH-bypass is reduced by at least about 50%. In another embodiment, the activity or expression of the protein of the PDH-bypass is reduced by at least about 60%, by at least about 65%, by at least about 70%, by at least about 75%, by at least about 80%, by at least about 85%, by at least about 90%, by at least about 95%, or by at least about 99% as compared to a recombinant microorganism not comprising a reduction of the activity or expression of the protein of the PDH-bypass.

In some embodiments, disruption of one or more genes of the PDH-bypass is achieved by using a "disruption construct" that is capable of specifically disrupting a gene of the PDH-bypass upon introduction of the construct into the microbial cell, thereby rendering the disrupted gene non-functional. In some embodiments, disruption of the target gene prevents the expression of a functional protein. In some embodiments, disruption of the target gene results in expression of a non-functional protein from the disrupted gene. In some embodiments, disruption of a gene of the PDH-bypass is achieved by integration of a "disrupting sequence" within the target gene locus by homologous recombination. In such embodiments, the disruption construct comprises a disrupting sequence flanked by a pair of nucleotide sequences that are homologous to a pair of nucleotide sequences of the target gene locus (homologous sequences). Upon replacement of the targeted portion of the target gene by the disruption construct, the disrupting sequence prevents the expression of a functional protein, or causes expression of a non-functional protein, from the target gene.

Disruption constructs capable of disrupting a gene of the PDH-bypass may be constructed using standard molecular biology techniques well known in the art. See, e.g., Sambrook et al., 2001, *Molecular Cloning—A Laboratory Manual*, $3^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY. Parameters of disruption constructs that may be varied in the practice of the present methods include, but are not limited to, the lengths of the homologous sequences; the nucleotide sequence of the homologous sequences; the length of the disrupting sequence; the nucleotide sequence of the disrupting sequence; and the nucleotide sequence of the target gene. In some embodiments, an effective range for the length of each homologous sequence is 50 to 5,000 base pairs. In particular embodiments, the length of each homologous sequence is about 500 base pairs. For a discussion of the length of homology required for gene targeting, see Hasty et al., *Mol Cell Biol* 11:5586-91 (1991). In some embodiments, the homologous sequences comprise coding sequences of the target gene. In other embodiments, the homologous sequences comprise upstream or downstream sequences of the target gene. Is some embodiments, one homologous sequence comprises a nucleotide sequence that is homologous to a nucleotide sequence located 5' of the coding sequence of the target gene, and the other homologous sequence comprises a nucleotide sequence that is homologous to a nucleotide sequence located 3' of the coding sequence of the target gene. In some embodiments, the disrupting sequence comprises a nucleotide sequence encoding a selectable marker that enables selection of microbial cells comprising the disrupting sequence. Thus, in such embodiments, the disruption construct has a dual function, i.e., to functionally disrupt the target gene and to provide a selectable marker for the identification of cells in which the target gene is functionally disrupted. In some embodiments, a termination codon is positioned in-frame with and downstream of the nucleotide sequence encoding the selectable marker to prevent translational read-through that might yield a fusion protein having some degree of activity of the wild type protein encoded by the target gene. In some embodiments, the length of the disrupting sequence is one base pair. Insertion of a single base pair can suffice to disrupt a target gene because insertion of the single base pair in a coding sequence could constitute a frame shift mutation that could prevent expression of a functional protein. In some embodiments, the sequence of the disruption sequence differs from the nucleotide sequence of the target gene located between the homologous sequences by a single base pair. Upon replacement of the nucleotide sequence within the target gene with the disrupting sequence, the single base pair substitution that is introduced could result in a single amino acid substitution at a critical site in the protein and the expression of a non-functional protein. It should be recognized, however, that disruptions effected using very short disrupting sequences are susceptible to reversion to the wild type sequence through spontaneous mutation, thus leading to restoration of PDH-bypass function to the host strain. Accordingly, in particular embodiments, the disrupting sequences are longer than one to a few base pairs. At the other extreme, a disrupting sequence of excessive length is unlikely to confer any advantage over a disrupting sequence of moderate length, and might diminish efficiency of transfection or targeting. Excessive length in this context is many times longer than the distance between the chosen homologous sequences in the target gene. Thus, in certain embodiments, the length for the disrupting sequence can be from 2 to 2,000 base pairs. In other embodiments, the length for the disrupting sequence is a length approximately equivalent to the distance between the regions of the target gene locus that match the homologous sequences in the disruption construct.

In some embodiments, the disruption construct is a linear DNA molecule. In other embodiments, the disruption construct is a circular DNA molecule. In some embodiments, the circular disruption construct comprises a pair of homologous sequences separated by a disrupting sequence, as described above. In some embodiments, the circular disruption construct comprises a single homologous sequence. Such circular disruption constructs, upon integration at the target gene locus, would become linearized, with a portion of the homologous sequence positioned at each end and the remaining segments of the disruption construct inserting into and disrupting the target gene without replacing any of the target gene nucleotide sequence. In particular embodiments, the single homologous sequence of a circular disruption construct is homologous to a sequence located within the coding sequence of the target gene.

Disruption constructs can be introduced into a microbial cell by any method known to one of skill in the art without limitation. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming yeast cells are well known in the art. See Hinnen et al., Proc. Natl. Acad. Sci. USA 75:1292-3 (1978); Cregg et al., Mol.

Cell. Biol. 5:3376-3385 (1985). Exemplary techniques include, but are not limited to, spheroplasting, electroporation, PEG 1000 mediated transformation, and lithium acetate or lithium chloride mediated transformation.

5.2.3.1 ALD4 and ALD6

In some embodiments, one or more genes encoding aldehyde dehydrogenase (ACDH) activity are functionally disrupted in the host cell. In some embodiments, the aldehyde dehydrogenase is encoded by a gene selected from the group consisting of ALD2, ALD3, ALD4, ALD5, ALD6, and homologs and variants thereof.

In some embodiments, the genetically modified host cell comprises a functional disruption of ALD4. Representative ALD4 nucleotide sequences of *Saccharomyces cerevisiae* include accession number NM_001183794, and SEQ ID NO:7 as provided herein. Representative Ald4 protein sequences of *Saccharomyces cerevisiae* include accession number NP_015019.1 and SEQ ID NO:8 as provided herein.

In some embodiments, the genetically modified host cell comprises a functional disruption of cytosolic aldehyde dehydrogenase (ALD6). Ald6p functions in the native PDH-bypass to convert acetaldehyde to acetate. Representative ALD6 nucleotide sequences of *Saccharomyces cerevisiae* include accession number SCU56604, and SEQ ID NO:9 as provided herein. Representative Ald6 protein sequences of *Saccharomyces cerevisiae* include accession number AAB01219 and SEQ ID NO:10 as provided herein.

As would be understood in the art, naturally occurring homologs of aldehyde dehydrogenase in yeast other than *S. cerevisiae* can similarly be inactivated using the methods described herein.

As would be understood by one skilled in the art, the activity or expression of more than one aldehyde dehydrogenase can be reduced or eliminated. In one specific embodiment, the activity or expression of ALD4 and ALD6 or homologs or variants thereof is reduced or eliminated. In another specific embodiment, the activity or expression of ALD5 and ALD6 or homologs or variants thereof is reduced or eliminated. In yet another specific embodiment, the activity or expression of ALD4, ALD5, and ALD6 or homologs or variants thereof is reduced or eliminated. In yet another specific embodiment, the activity or expression of the cytosolically localized aldehyde dehydrogenases ALD2, ALD3, and ALD6 or homologs or variants thereof is reduced or eliminated. In yet another specific embodiment, the activity or expression of the mitochondrially localized aldehyde dehydrogenases, ALD4 and ALD5 or homologs or variants thereof, is reduced or eliminated.

5.2.3.2 ACS1 and ACS2

In some embodiments, one or more genes encoding acetyl-CoA synthetase (ACS) activity are functionally disrupted in the host cell. In some embodiments, the acetyl-CoA synthetase is encoded by a gene selected from the group consisting of ACS1, ACS2, and homologs and variants thereof.

In some embodiments, one or more genes encoding acetyl-CoA synthetase (ACS) activity is functionally disrupted in the host cell. ACS1 and ACS2 are both acetyl-CoA synthetases that can convert acetate to acetyl-CoA. ACS1 is expressed only under respiratory conditions, whereas ACS2 is expressed constitutively. When ACS2 is knocked out, strains are able to grow on respiratory conditions (e.g. ethanol, glycerol, or acetate media), but die on fermentable carbon sources (e.g. sucrose, glucose).

In some embodiments, the genetically modified host cell comprises a functional disruption of ACS1. The sequence of the ACS1 gene of *S. cerevisiae* has been previously described. See, e.g., Nagasu et al., Gene 37 (1-3):247-253 (1985). Representative ACS1 nucleotide sequences of *Saccharomyces cerevisiae* include accession number X66425, and SEQ ID NO:3 as provided herein. Representative Acs1 protein sequences of *Saccharomyces cerevisiae* include accession number AAC04979 and SEQ ID NO:4 as provided herein.

In some embodiments, the genetically modified host cell comprises a functional disruption of ACS2. The sequence of the ACS2 gene of *S. cerevisiae* has been previously described. See, e.g., Van den Berg et al., *Eur. J. Biochem.* 231(3):704-713 (1995). Representative ACS2 nucleotide sequences of *Saccharomyces cerevisiae* include accession number S79456, and SEQ ID NO:5 as provided herein. Representative Acs2 protein sequences of *Saccharomyces cerevisiae* include accession number CAA97725 and SEQ ID NO:6 as provided herein.

As would be understood in the art, naturally occurring homologs of acetyl-CoA synthetase in yeast other than *S. cerevisiae* can similarly be inactivated using the methods described herein.

In some embodiments, the host cell comprises a cytosolic acetyl-coA synthetase activity that can convert acetate to acetyl-CoA under respiratory conditions (i.e., when the host cell is grown in the presence of e.g. ethanol, glycerol, or acetate). In some such embodiments, the host cell is a yeast cell that comprises ACS1 activity. In other embodiments, the host cell compared to a parent cell comprises no or reduced endogenous acetyl-CoA synthetase activity under respiratory conditions. In some such embodiments, the host cell is a yeast cell that compared to a parent cell comprises no or reduced ACS1 activity.

In some embodiments, the host cell comprises a cytosolic acetyl-coA synthetase activity that can convert acetate to acetyl-CoA under non-respiratory conditions (i.e., when the host cell is grown in the presence of fermentable carbon sources (e.g. sucrose, glucose)). In some such embodiments, the host cell is a yeast cell that comprises ACS2 activity. In other embodiments, the host cell compared to a parent cell comprises no or reduced endogenous acetyl-CoA synthetase activity under non-respiratory conditions. In some such embodiments, the host cell is a yeast cell that compared to a parent cell comprises no or reduced ACS2 activity.

5.2.4 Phophoketolase (PK) and Phosphotransacetylase (PTA)

In yeast, acetyl-CoA is biosynthesized from glucose via glycolysis, the tricarboxylic acid (TCA) cycle, oxidative phosphorylation, and pyruvate metabolism. However, in this biosynthetic pathway, $CO_2$ is lost during pyruvate metabolism by pyruvate carboxylase, and in the TCA cycle by pyruvate dehydrogenase and isocitrate dehydrogenase. In an industrial fermentation setting, one benefit of reducing flux through lower glycolysis is that less $CO_2$ is produced in converting pyruvate into acetaldehyde, and thus more carbon can be captured in the end product, thereby increasing the maximum theoretical yield. A second benefit is that less NADH is produced, and therefore significantly less oxygen is needed to reoxidize it. The loss of carbon atoms can theoretically be avoided by bypassing the TCA cycle. This can be accomplished by using phosphoketolase (PK) (enzyme classes EC 4.1.2.9, EC 4.1.2.22) in conjunction with phosphoacetyl-transferase (PTA) (EC 2.3.1.8).

PK and PTA catalyze the reactions to convert fructose-6-phosphate (F6P) or xylulose-5-phosphate (X5P) to acetyl-CoA (FIG. 7). PK draws from the pentose phosphate intermediate xyulose 5-phosphate, or from the upper glycolysis intermediate D-fructose 6-phosphate (F6P); PK splits X5P into glyceraldehyde 3-phosphate (G3P) and acetyl phosphate, or F6P into erythrose 4-phosphate (E4P). PTA then converts the acetyl phosphate into acetyl-CoA. G3P can re-enter lower glycolysis, and E4P can re-enter the pentose phosphate pathway or glycolysis by cycling through the non-oxidative pentose phosphate pathway network of transaldolases and transketolases.

In some embodiments, the genetically modified host cell provided herein comprises a heterologous nucleotide sequence encoding a phosphoketolase. In some embodiments, the phosphoketolase is from *Leuconostoc mesenteroides* (Lee et al., *Biotechnol Lett.* 27(12); 853-858 (2005). Representative phosphoketolase nucleotide sequences of *Leuconostoc mesenteroides* includes accession number AY804190, and SEQ ID NO: 11 as provided herein. Representative phosphoketolase protein sequences of *Leuconostoc mesenteroides* include accession numbers YP_819405, AAV66077.1 and SEQ ID NO: 12 as provided herein. Other useful phosphoketolases include, but are not limited to, those from *Bifidobacterium dentium* ATCC 27678 (ABIX02000002.1:2350400.2352877; EDT46356.1); *Bifidobacterium animalis* (NC_017834.1:1127580.1130057; YP_006280131.1); and *Bifidobacterium pseudolongum* (AY518216.1:988.3465; AAR98788.1).

Phosphoketolases also useful in the compositions and methods provided herein include those molecules which are said to be "derivatives" of any of the phosphoketolases described herein. Such a "derivative" has the following characteristics: (1) it shares substantial homology with any of the phosphoketolases described herein; and (2) is capable of catalyzing the conversion of X5P into glyceraldehyde 3-phosphate (G3P) and acetyl phosphate; or F6P into erythrose 4-phosphate (E4P). A derivative of a phosphoketolase is said to share "substantial homology" with the phosphoketolase if the amino acid sequences of the derivative is at least 80%, and more preferably at least 90%, and most preferably at least 95%, the same as that of the phosphoketolase.

In some embodiments, the genetically modified host cell provided herein comprises a heterologous nucleotide sequence encoding a phosphotransacetylase. In some embodiments, the phosphotransacetylase is from *Clostridium kluyveri*. Representative phosphotransacetylase nucleotide sequences of *Clostridium kluyveri* includes accession number NC_009706.1:1428554.1429555, and SEQ ID NO: 13 as provided herein. Representative phosphotransacetylase protein sequences of *Clostridium kluyveri* include accession number YP_001394780 and SEQ ID NO: 14 as provided herein. Other useful phosphotransacetylases include, but are not limited to, those from *Lactobacillus reuteri* (NC_010609.1:460303.461277; YP_001841389.10); *Bacillus subtilis* (NC_014479.1:3671865.3672836; YP_003868063.1); and *Methanosarcina thermophile* (L23147.1:207.1208; AAA72041.1).

Phosphotransacetylases also useful in the compositions and methods provided herein include those molecules which are said to be "derivatives" of any of the phosphotransacetylases described herein. Such a "derivative" has the following characteristics: (1) it shares substantial homology with any of the phosphotransacetylases described herein; and (2) is capable of catalyzing the conversion of acetyl phosphate into acetyl-CoA. A derivative of a phosphotransacetylase is said to share "substantial homology" with the phosphotransacetylase if the amino acid sequences of the derivative is at least 80%, and more preferably at least 90%, and most preferably at least 95%, the same as that of the phosphotransacetylase.

5.2.5 MEV Pathway

In some embodiments, the host cell comprises one or more heterologous enzymes of the MEV pathway. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate.

In some embodiments, the one or more enzymes of the MEV pathway are selected from the group consisting of acetyl-CoA thiolase, acetoacetyl-CoA synthase, HMG-CoA synthase, HMG-CoA reductase, mevalonate kinase, phosphomevalonate kinase and mevalonate pyrophosphate decarboxylase. In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate. In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound.

5.2.5.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising a heterologous ADA and acetyl-CoA thiolase, the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Thus, in some embodiments, in order to provide a strong pull on acetyl-CoA to drive the forward reaction of ADA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci* USA 107 (25):11265-70 (2010). Representative AACS nucleotide sequences of *Streptomyces* sp. strain CL190 include accession number AB540131.1 and SEQ ID NO:15 as provided herein. Representative AACS protein sequences of *Streptomyces* sp. strain CL190 include accession numbers D7URV0, BAJ10048 and SEQ ID NO:16 as provided herein. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); *Actinoplanes* sp. A40644 (AB113568; BAD07381); *Streptomyces* sp. C(NZ_ACEWO10000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mgl (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthesis said to share "substantial homology" with acetoacetyl-CoA synthase if the amino acid sequences of the derivative is at least 80%, and more preferably at least 90%, and most preferably at least 95%, the same as that of acetoacetyl-CoA synthase.

5.2.5.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

5.2.5.3 Conversion of HMG-CoA to Mevalonate

In some embodiments, the host cell comprises a heterologous nucleotide sequence encoding an enzyme that can convert HMG-CoA into mevalonate, e.g., a HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

TABLE 1

Co-factor specificities for select class II HMG-CoA reductases

| Source | Coenzyme specificity | $K_m^{NADPH}$ (µM) | $K_m^{NADH}$ (µM) |
|---|---|---|---|
| P. mevalonii | NADH | | 80 |
| A. fulgidus | NAD(P)H | 500 | 160 |
| S. aureus | NAD(P)H | 70 | 100 |
| E. faecalis | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii, A. fulgidus* or *S. aureus*. In particular embodiments, the HMG-CoA reductase is capable of only utilizing NADH as a cofactor, e.g., HMG-CoA reductase from *P. mevalonii, S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (E.C. 1.1.1.88), has been previously described. See Beach and Rodwell, *J. Bacteriol.* 171: 2994-3001 (1989). Representative mvaA nucleotide sequences of *Pseudomonas mevalonii* include accession number M24015, and SEQ ID NO: 17 as provided herein. Representative HMG-CoA reductase protein sequences of *Pseudomonas mevalonii* include accession numbers AAA25837, P13702, MVAA_PSEMV and SEQ ID NO: 18 as provided herein.

In some embodiments, the NADH-using HMG-CoA reductase is from *Silicibacter pomeroyi*. Representative HMG-CoA reductase nucleotide sequences of *Silicibacter pomeroyi* include accession number NC_006569.1, and SEQ ID NO: 19 as provided herein. Representative HMG-CoA reductase protein sequences of *Silicibacter pomeroyi* include accession number YP_164994 and SEQ ID NO: 20 as provided herein.

In some embodiments, the NADH-using HMG-CoA reductase is from *Delftia acidovorans*. A representative HMG-CoA reductase nucleotide sequences of *Delftia acidovorans* includes NC_010002 REGION: complement (319980.321269), and SEQ ID NO: 21 as provided herein. Representative HMG-CoA reductase protein sequences of *Delftia acidovorans* include accession number YP_001561318 and SEQ ID NO: 22 as provided herein.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro (see, e.g., Example 1 and Section 6.1.1.3 below), and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171:2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase. Illustrative examples of nucleotide sequences encoding an NADPH-using HMG-CoA reductase include, but are not limited to: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

5.2.5.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

5.2.5.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

5.2.5.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

5.2.5.7 Conversion of IPP to DMAPP

In some embodiments, the host cell further comprises a heterologous nucleotide sequence encoding an enzyme that can convert IPP generated via the MEV pathway into dimethylallyl pyrophopsphate (DMAPP), e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

5.2.5.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×piperita*), (MPI249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFG-GPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides f. lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP 721015; *Streptococcus mutans* UA159).

5.2.5.9 Terpene Synthases

In some embodiments, the host cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP 463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. crispa cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes a ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−)β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include, but are not limited to: (AY693650 from *Oscimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes a α-farnesene synthase. Illustrative examples of suitable nucleotide sequences include, but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include but is not limited to accession number AF024615 from *Menthaxpiperita* (peppermint; gene *Tspa*11), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to accession number AF529266 from *Zea mays* and YDR481c from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of suitable nucleotide sequences include, but are not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

In some embodiments, the host cell produces a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

5.3 Methods of Making Genetically Modified Cells

Also provided herein are methods for producing a host cell that is genetically engineered to comprise one or more of the modifications described above, e.g., one or more nucleic heterologous nucleic acids encoding one or more enzymes selected from ADA, NADH-using HMG-CoA reductase, AACS, PK, PTA, and other mevalonate pathway enzymes. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci.* USA 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the $KAN^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorphs*, *Candida* spp., *Trichosporon* spp., *Yamadazyma* spp., including *Y.* spp. *stipitis*, *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia. coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous ADA genes, proteins, or enzymes, techniques may include, but are not limited to, cloning a gene by PCR using primers based on a published sequence of an ADA gene/enzyme or by degenerate PCR using degenerate primers designed to amplify a conserved region among ADA genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology*, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

5.4 Methods of Producing Isoprenoids

In another aspect, provided herein is a method for the production of an isoprenoid, the method comprising the steps of: (a) culturing a population of any of the genetically modified host cells described herein in a medium with a carbon source under conditions suitable for making an isoprenoid compound; and (b) recovering said isoprenoid compound from the medium.

In some embodiments, the genetically modified host cell comprises one or more modifications selected from the group consisting of: heterologous expression of an ADA, heterologous expression of an NADH-using HMG-CoA reductase, heterologous expression of an AACS, heterologous expression of a phosphoketolase, heterologous expression of a phosphotrancacetylase, and heterologous expression of one or more enzymes of the mevalonate pathway; and the genetically modified host cell produces an increased amount of the isoprenoid compound compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of isoprenoid that is greater than about 10 grams per liter of fermentation medium. In some such embodiments, the isoprenoid is produced in an amount from about 10 to about 50 grams, more than about 15 grams, more than about 20 grams, more than about 25 grams, or more than about 30 grams per liter of cell culture.

In some embodiments, the host cell produces an elevated level of isoprenoid that is greater than about 50 milligrams per gram of dry cell weight. In some such embodiments, the isoprenoid is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1.000-fold, or more, higher than the level of isoprenoid produced by a parent cell, on a per unit volume of cell culture basis.

In some embodiments, the host cell produces an elevated level of isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1.000-fold, or more, higher than the level of isoprenoid produced by the parent cell, on a per unit dry cell weight basis.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1.000-fold, or more, higher than the level of isoprenoid produced by the parent cell, on a per unit volume of cell culture per unit time basis.

In some embodiments, the host cell produces an elevated isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1.000-fold, or more, higher than the level of isoprenoid produced by the parent cell, on a per unit dry cell weight per unit time basis.

In most embodiments, the production of the elevated level of isoprenoid by the host cell is inducible by an inducing compound. Such a host cell can be manipulated with ease in the absence of the inducing compound. The inducing compound is then added to induce the production of the elevated level of isoprenoid by the host cell. In other embodiments, production of the elevated level of isoprenoid by the host cell is inducible by changing culture conditions, such as, for example, the growth temperature, media constituents, and the like.

5.4.1 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing isoprenoids provided herein may be performed in a suitable culture medium (e.g., with or without pantothenate supplementation) in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an isoprenoid can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or isoprenoid production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of isoprenoids. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

5.4.2 Recovery of Isoprenoids

Once the isoprenoid is produced by the host cell, it may be recovered or isolated for subsequent use using any suitable separation and purification methods known in the art. In some embodiments, an organic phase comprising the isoprenoid is separated from the fermentation by centrifugation. In other embodiments, an organic phase comprising the isoprenoid separates from the fermentation spontaneously. In other embodiments, an organic phase comprising the isoprenoid is separated from the fermentation by adding a deemulsifier and/or a nucleating agent into the fermentation reaction. Illustrative examples of deemulsifiers include flocculants and coagulants. Illustrative examples of nucleating agents include droplets of the isoprenoid itself and organic solvents such as dodecane, isopropyl myristrate, and methyl oleate.

The isoprenoid produced in these cells may be present in the culture supernatant and/or associated with the host cells. In embodiments where the isoprenoid is associated with the host cell, the recovery of the isoprenoid may comprise a method of permeabilizing or lysing the cells. Alternatively or simultaneously, the isoprenoid in the culture medium can be recovered using a recovery process including, but not limited to, chromatography, extraction, solvent extraction, membrane separation, electrodialysis, reverse osmosis, distillation, chemical derivatization and crystallization.

In some embodiments, the isoprenoid is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

6. EXAMPLES

6.1 Example 1

Identification and Characterization of NADH-Specific HMG-CoA Reductases

This example describes the identification and characterization of HMG-CoA reductases not previously known to have NADH cofactor specificity.

6.1.1 Materials and Methods 6.1.1.1 Strain Engineering

A wild-type *Saccharomyces cerevisiae* strain, (CEN.PK2, Mat a, ura3⁻, TRP1⁺, leu2⁻, MAL2-8C, SUC2,) was used as a host for the expression of the mevalonate (MevT) pathway (whereby acetyl-CoA thiolase (ERG10) converts acetyl-CoA to acetoacetyl-CoA; HMG-CoA synthase (ERG13) converts acetoacetyl-CoA into HMG-CoA; and HMG-CoA reductase converts HMG-CoA into mevalonate (FIG. 1)).

This strain was transformed with a plasmid encoding either a heterologous class II HMG-CoA reductase derived from *Staphylococcus aureus* (ZP_06815052), *Herpetosiphon aurantiacus* (YP_001546303), *Pseudomonas mevalonii* (P13702), *Delftia acidovorans* (YP_001561318), *Menthanosaeta thermofila* (YP_843364) or *Silicibacter pomeoyri* (YP_164994); or an N-terminally truncated version of the *Saccharomyces cerevisiae* HMG-CoA reductase (tHMG-CoA reductase) (EEU05004). The class II HMG-CoA reductases were codon optimized for yeast expression and chemically synthesized with c-terminal FLAG-HIS tags, with the exception that the *P. mevalonii* HMG-CoA reductase was synthesized with the following additional modifications:

NotI site—GAL1 promotor—NdeI site—[*P. mevalonii* HMG-CoA reductase]—EcoRI site—FLAG tag—HIS tag—STOP codon—PGK1 terminator—NotI site This DNA was cloned into the NotI site of the pBluescript SK+ vector (Stratagene). The yeast Gal7 promoter was PCR amplified using the genomic DNA extract of a wild-type CENPK2 strain as template and using the oligonucleotides YT_164_30_Gal7F (which contains a SacI and a NotI restriction site at 5'-end) and YT_164_30_Gal7R (which contains NdeI restriction site at 3'-end) (see Table 2). The PCR product was cloned onto pCR II-TOPO vector (Invitrogen). Both plasmids were cut using SacI and NotI, and the excised Sc.GAL7 promoter was used to swap the GalI promoter upstream of the *P. mevalonii* HMG-CoA reductase gene. The resulting plasmid and pAM70 (SEQ ID NO:23), a yeast episomal vector pRS426 with a URA3 marker, were both digested with NotI. The plasmid pAM01147 (SEQ ID NO:24) was then constructed by ligating the NotI fragment into the NotI digested site of pAM70. This plasmid was used as a base plasmid to swap the *P. mevalonii* HMG-CoA reductase coding sequence for any HMG-CoA reductase coding sequence of interest (including the yeast tHMG-CoA reductase) by digesting the plasmid with NdeI and EcoRI and ligating a digested HMG-CoA reductase coding sequence of interest having NdeI and EcoRI sites at the 5'- and 3'-ends, respectively. Propagation of plasmid DNA was performed in *Escherichia coli* strain DH5a. Strain Y1389 was then transformed with the plasmids harboring coding sequences for different HMG-CoA reductases, and transformants were selected on CSM media plate without uracil containing 2% glucose. All DNA-mediated transformation into *S. cerevisiae* was conducted using the standard Lithium Acetate procedure as described by Gietz R W and Woods R A, *Guide to Yeast Genetics and Molecular and Cell Biology, Part B*. San Diego, Calif.: Academic Press Inc. pp. 87-96 (2002).

Genomic integration of Sc. acetoacetyl-CoA thiolase (ERG10) and Sc.HMG-CoA Synthase (ERG13) was targeted to the Ga180 locus of the host strain using the integration construct shown below (SEQ ID NO:25).

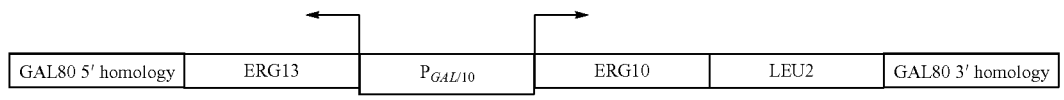

Each component of the integration construct was PCR amplified using 100 ng of Y002 genomic DNA as template. PCR amplification of the upstream GAL80 locus from positions −1000 to −1 was performed with oligonucleotides YT_164_36_001 and YT_164_36_003 (see Table 2). PCR amplification of the yeast ERG10 and ERG13 genes was done using the pair of oligonucleotides YT_164_36_002 and YT_164_36_005 for ERG13 and YT_164_36_006 and YT_164_36_009 for ERG10. The oligonucleotides YT_164_36_004 and YT_164_36_007 were used to amplify the GAL1/10 promoter, while primers YT_164_36_008 and YT_164_36_011 were used to amplify the LEU2 gene. PCR amplification of the downstream GAL80 locus positions 23 to 1000 (after the stop codon) was performed with oligonucleotides YT_164_36_010 and YT_164_36_012. One hundred fmol of each piece of DNA was added in a single tube and assembled by stitching PCR reaction (as described in U.S. Pat. No. 8,221,982, the contents of which are hereby incorporated by reference) using the primers YT_164_36_001 and YT_164_36_012. PCR products having the expected molecular weights were gel purified.

TABLE 2

Primers used for strain engineering

| Primer name | SEQ ID NO: | Primer Sequence |
|---|---|---|
| YT_164_36_001 | SEQ ID NO: 26 | GCCTGTCTACAGGATAAAGACGGG |
| YT_164_36_002 | SEQ ID NO: 27 | TCCCGTTCTTTCCACTCCCGTCTATATATATATCATTGTTATTA |
| YT_164_36_003 | SEQ ID NO: 28 | TAATAACAATGATATATATATAGACGGGAGTGGAAAGAACGGGA |
| YT_164_36_004 | SEQ ID NO: 29 | CCAACAAAGTTTAGTTGAGAGTTTCATTTATATTGAATTTTCAAAAATTCTTAC |
| YT_164_36_005 | SEQ ID NO: 30 | GTAAGAATTTTTGAAAATTCAATATAAATGAAACTCTCAACTAAACTTTGTTGG |
| YT_164_36_006 | SEQ ID NO: 31 | GTCAAGGAGAAAAAACTATAATGTCTCAGAACGTTTACATTGTATCGACTGCCAGAACCC |
| YT_164_36_007 | SEQ ID NO: 32 | GGGTTCTGGCAGTCGATACAATGTAAACGTTCTGAGACATTATAGTTTTTTCTCCTTGAC |
| YT_164_36_008 | SEQ ID NO: 33 | GTGTGCCTTTTGACTTACTTTTACGTTGAGCCATTAGTATCA |
| YT_164_36_009 | SEQ ID NO: 34 | TGATACTAATGGCTCAACGTAAAAGTAAGTCAAAAGGCACAC |
| YT_164_36_010 | SEQ ID NO: 35 | GATATTTCTTGAATCAGGCGCCTTAGACCCCCCAGTGCAGCGAACGTTATAAAAC |
| YT_164_36_011 | SEQ ID NO: 36 | GTTTTTATAACGTTCGCTGCACTGGGGGGTCTAAGGCGCCTGATTCAAGAAATATC |
| YT_164_36_012 | SEQ ID NO: 37 | AAATATGACCCCCAATATGAGAAATTAAGGC |
| YT_164_30_Gal3F | SEQ ID NO: 38 | GAGCTCGCGGCCGCGTACATACCTCTCTCCGTATCCTCGTAATCATTTTCTTGT |
| YT_164_30_Gal3R | SEQ ID NO: 39 | CATATGACTATGTGTTGCCCTACCTTTTTACTTTTATTTTCTCTTT |
| YT_164_30_Gal7F | SEQ ID NO: 40 | GAGCTCGCGGCCGCGTGTCACAGCGAATTCCTCACATGTAGGGACCGAATTGT |
| YT_164_30_Gal7R | SEQ ID NO: 41 | CATATGTTTTGAGGGAATATTCAACTGTTTTTTTTTATCATGTTGA |
| RYSE 0 | SEQ ID NO: 42 | GACGGCACGGCCACGCGTTTAAACCGCC |
| RYSE 19 | SEQ ID NO: 43 | CCCGCCAGGCGCTGGGGTTTAAACACC |

Derivatives of Y1389 transformed with different HMG-CoA reductases (as indicated above) were transformed with the ERG 10/ERG13 integration construct to create the strains listed below in Table 3. Transformants were selected on CSM containing 2% glucose media plate without uracil and leucine. All gene disruptions and replacements were confirmed by phenotypic analysis and colony PCR.

TABLE 3

Strain Description

| Strain # | Descrption | strain # after adh1 Knockout |
|---|---|---|
| Y1431 | MevT with S. cerevisae tHMG-CoA reductase | Y1804 |
| Y1432 | MevT with S. aureus HMG-CoA reductase | |
| Y1433 | MevT with P. mevalonii HMG-CoA reductase | Y1805 |
| Y1435 | MevT with D. acidovorans HMG-CoA reductase | Y1806 |
| Y1436 | MevT with M. thermofila HMG-CoA reductase | |
| Y1486 | MevT with H. aurantiacus HMG-CoA reductase | |
| Y1487 | MevT with S. pomeroyi HMG-CoA reductase | Y1807 |

For strains Y1431, Y1433, Y1435 and Y1487, the ADH1 gene was knocked out using the disruption construct shown below (SEQ ID NO:44):

| ADH1 5' homology | Kan A | ADH1 3' homology |

The disruption construct was generated by the methods of polynucleotide assembly described in U.S. Pat. No. 8,221,982. The ADH1 5' homology region of the integration construct was homologous to positions −563 to −77 of the ADH1 coding sequence, and the ADH1 3' homology region was homologous to positions 87 to 538 (after the stop codon of the ADH1 gene). Primers RYSE 0 and RYSE 19 were used to amplify the product. Strain Y1431, Y1433, Y1435 and Y1487 (Table 2) were transformed with the product, and transformants were selected on YPD media plate containing 2% glucose and G418 (Geneticin). The ADH1 gene disruption was confirmed by phenotypic analysis and colony PCR.

6.1.1.2 Cell Culture

A single colony of a given yeast strain was cultured in 3 ml of Yeast Nitrogen Base (YNB) media with 2% sucrose as an overnight starter culture. The next day, production flasks were prepared with an initial $OD_{600}$ of 0.05 diluted from the starter culture in 40 ml YNB-4% sucrose production culture media in 250 ml disposable PETG sterile flasks (Nalgene). The flasks were incubated at 30° C. by shaking at 250 RPM for the durations indicated below.

6.1.1.3 HMG-CoA Reductase Activity Assay Using Cell-Free Extract

Yeast cells were grown for 48 hours HMG-CoA reductase activity assays (FIG. 8) or 72 hours for mevalonate assays (Table 4) and harvested by centrifugation in a 15 mL Falcon tube for 10 minutes at 4000×g in a swinging bucket rotor JS-5.3 with proper carriage for the Falcon tubes. The cell pellet was resuspended in 1 ml and washed once using cold lysis buffer (100 mM Tris pH 7.0 with Mini, EDTA free protease inhibitor tablet (Roche) added, 1 mM DTT and 1 mM EDTA). The cells were then transferred to a 2 mL plastic screw cap microfuge tube with O ring cap (Fisher Brand 520-GRD) and cells were lysed using disruption beads (Disruption beads, 0.5Mm, Fisher) and a bead beater for 1 minute at 6 M/S. The tubes were immediately placed in an ice water bath for at least 5 minutes. Tubes were spun at a minimum of 8000×g for 20 minutes. The supernatant was then transferred to a new cold tube. Protein concentration was measured using the classic Bradford assay for proteins (Bradford M M A rapid and sensitive method for quantitation of microgram quantities of protein utilizing the principle of protein-dye binding. Anal. Biochem 72, 248-254 (1976)).

For HMG-CoA reducatase assays, the reaction buffer (100 mM phosphate buffer pH 7.0, 100 mM KCl, 1 mM DTT and 1 mM EDTA) was initially pre-incubated in a 96 well plate at 30° C. Either NADH or NADPH at a final concentration of 150 µM, a final concentration of 400 µM HMG-CoA and 5 mM final concentration of DTT was added to a total volume of 190 µl in each well. The assay was initiated by adding ten microliter of cell-free extract diluted to the range of linear activity. The reaction was monitored by measuring the decrease in absorbance of NADPH or NADH at 340 nm using Molecular Devices Spectramax M5 plate reader. The slope of the line of absorbance at 340 nm along with the protein concentration was used to calculate the specific activity of HMGr for each cell free extract.

6.1.1.4 Organic Acids and Alcohol Measurement

Samples for organic acids and alcohols assay were prepared by taking 1 ml of fermentation broth and transferring the samples to a 1.5 ml eppendorf tubes. Samples were spun for 1 min at 13,000 RPM using a table eppendorf centrifuges. The supernatant was then diluted (1:1 v/v) in 15 mM sulfuric acid. The mixture was vortexed and centrifuged for 1 min at 13,000 RPM. The clarified supernatant was transferred to a vial for HPLC analysis.

HPLC analysis was performed for glycerol and mevalonate content using HPLC Thermofisher and by ion exclusion chromatography using Column Waters IC-Pak 7.8 mm×300 mm, 7 µm, 50 Å (Waters) and with refractive index (RI) detection (Thermofisher). Elution was carried out isocratically using a 15 mM sulfuric acid aqueous mobile phase with 0.6 mL/min flow rate.

6.1.2 Results 6.1.2.1 Determination of Cofactor Specificity for Class II HMG-CoA Reductases As shown in FIG. 8, HMG-CoA reductases from D. acidovorans and S. pomeroyi exhibit high specificity for NADH and high specific activity in vitro. These HMG-CoA reductases displayed virtually no specific activity in the presence of NADPH, while specific activity approached 400 nmol/mg/min in the presence of NADH. Similarly, HMG-CoA reductase from P. mevalonii demonstrated selectivity for NADH as a cofactor, consistent with previously published reports. See, e.g., Hedl et al., J. Bacteriol 186(7):1927-1932 (2004). By contrast, HMG-CoA reductases from S. cerevisiae, S. aureus and H. aurantiacus showed no measurable activity in the presence of NADH, and HMG-CoA reductase from M. thermofila showed barely detectable activity in the presence of both NADPH and NADH. These results indicate that HMG-CoA reductases from D. acidovorans and S. pomeroyi are NADH-selective HMG-CoA reductases, similar to the HMG-CoA reductase from P. mevalonii.

In addition, Table 4 indicates that strains comprising a MevT pathway comprising an NADH-using HMG-CoA reductase (from P. mevalonii, D. acidovorans and S. pomeroyi, respectively) produced substantially less mevalonate than strains comprising a MevT pathway comprising an NADPH-using HMG-CoA reductase (from S. cerevisiae, S. aureus and H. aurantiacus, respectively). This suggests that in vivo, an additional source of NADH is required to utilize the full catalytic capacity of NADH-using HMG-CoA reductases towards mevalonate and downstream isoprenoid production.

TABLE 4

Mevalonate production from NADPH-using HMG-CoA reductases vs. NADH-using HMG-CoA reductases

| Source of HMG-CoA reductase | Mevalonate production (g/L) | Co-factor specificity |
|---|---|---|
| S. cerevisiae | 1.11 | NADPH |
| S. aureus | 1.74 | NADPH |
| H. aurantiacus | 1.84 | NADPH |
| P. mevalonii | 0.41 | NADH |
| D. acidovorans | 0.42 | NADH |
| S. pomeoyri | 0.57 | NADH |

6.1.2.2 Increased Intracellular NADH Improves NADH-Using HMG-CoA Reductase Activity As indicated in FIGS. 9-11, mevalonate production is substantially improved in cells comprising a MevT pathway comprising an NADH-using HMG-CoA reductase when a metabolic perturbation is introduced which increases the intracellular concentration of NADH. ADH1 reduces acetaldehyde to ethanol in an NADH-dependent manner. In an adh1Δbackground, host cells suffer reduced growth (FIG. 9) and increased glycerol production (FIG. 10), which is indicative of redox imbalance likely resulting from the accumulation of intracellular NADH. However, while cells comprising a MevT pathway comprising an NADPH-using HMG-CoA reductase (S. cerevisiae (Sc.) tHMG-CoA reductase) display reduced mevalonate production in the adh1Δbackground, cells comprising a MevT pathway comprising an NADH-using HMG-CoA reductase ((from P. mevalonii, D. acidovorans and S. pomeoryi, respectively) display substantial improvements in mevalonate production (FIG. 11), despite also showing signs of redox stress. These data suggest that NADH-using HMG-CoA reductases are able to utilize increased pools of intracellular NADH to boost mevalonate production. These results also suggest that in the absence of an increased intracellular source of NADH, NADH-using HMG-CoA reductases are cofactor limited.

Notably, previous published reports have indicated that the HMG-CoA reductase of P. mevalonii is utilized in the degradation of mevalonate. See Anderson et al., J. Bacteriol., (171 (12):6468-6472 (1989). P. mevalonii is among the few prokaryotes that have been identified as capable of subsisting on mevalonate as its sole carbon source. However, the results presented here demonstrate the unexpected utility of P. mevalonii HMG-CoA reductase for use in a biosynthetic pathway for mevalonate.

6.2 Example 2

Improved Isoprenoid Production and Redox Balancing with Alternate Routes to Acetyl-CoA and Alternate MEV Pathway Enzymes This example demonstrates that mevalonate and downstream isoprenoid production from the MEV pathway can be improved by utilizing alternate routes to cytolsolic acetyl-CoA production, e.g. via the heterologous expression of acetaldehyde dehydrogenase, acetylating (ADA, E.C. 1.2.1.10), in lieu of the wild-type PDH-bypass, and in various combinations with alternate MEV pathway enzymes. These results show that the redox imbalance introduced by the replacement of the NADPH-producing PDH-bypass enzymes with NADH-producing ADA can be alleviated in part by combining ADA expression with an NADH-using HMG-CoA reductase of the MEV pathway, and/or with heterologous expression of phosphoketolase and phosphotrancsacetylasse, which can also provide an additional alternate route to cytosolic acetyl-CoA production. These results further demonstrate that the catalytic capacity of ADA for providing acetyl-CoA substrate to the MEV pathway is substantially improved by providing a thermodynamically favorable downstream conversion of acetyl-CoA to acetoacetyl-CoA, such as that provided by acetyl-CoA:malonyl-CoA acyltransferase.

6.2.1 Materials and Methods
6.2.1.1 Strain Engineering

The strains listed in Table 5 were constructed to determine: (1) the effects on cell growth and heterologous isoprenoid production when ADA is paired with an NADH-using HMG-CoA reductase versus an NADPH-using HMG-CoA reductase; (2) the effect of phosphoketolase and phosphotransacetylase expression on the redox imbalance created by the expression of ADA; and (3) the effect of acetoacetyl-CoA synthase expression on mevalonate levels in strains expressing ADA.

TABLE 5

| Strain Name | Description |
|---|---|
| Y968 | Wildtype CEN.PK2 |
| Y12869 | acs1^ acs2^ ald6^; 2x Dz.eutE |
| Y12746 | acs1^ acs2^ ald6^; 2x Dz.eutE; 3x Lm.PK; 1x Ck.PTA |
| Y12869.ms63908 | Y12869 with construct ms63908 |
| Y12869.ms63909 | Y12869 with construct ms63909 |
| Y968.ms63908 | Y968 with construct ms63908 |
| Y968.ms63909 | Y968 with construct ms63909 |
| Y12869.ms63907.ms64472 | Y12869.ms63907 with construct ms64472 |
| Y12869.ms63909.ms64472 | Y12869.ms63909 with construct ms64472 |
| Y968.ms63907.ms64472 | Y968.ms63907 with construct ms64472 |
| Y968.ms63909.ms64472 | Y968.ms63909 with construct ms64472 |

6.2.1.1.1 Y968

Y968 is wildtype *Saccharomyces cerevisiae* CEN.PK2, Matalpha. The starting strain for Y12869, Y12746, and all of their derivatives, was *Saccharomyces cerevisiae* strain (CEN.PK2, Mat alpha, ura3-52, trp1-289, leu2-3,122, his3^1), Y003. All DNA-mediated transformation into *S. cerevisiae* was conducted using the standard Lithium Acetate procedure as described by Gietz R W and Woods R A, *Guide to Yeast Genetics and Molecular and Cell Biology. Part B*. San Diego, Calif.: Academic Press Inc. pp. 87-96 (2002), and in all cases integration of the constructs were confirmed by PCR amplification of genomic DNA.

6.2.1.1.2 Y12869

Y12869 was generated through three successive integrations into Y003. First, the gene ACS2 was deleted by introducing an integration construct (i2235; SEQ ID NO:45) consisting of the native *S. cerevisiae* LEU2 gene, flanked by sequences consisting of upstream and downstream nucleotide sequences of the ACS2 locus. Upon introduction of a *S. cerevisiae* host cell, this construct can integrate by homologous recombination into the ACS2 locus of the genome, functionally disrupting ACS2 by replacing the ACS2 coding sequence with its integrating sequence. Transformants were plated onto CSM-leu plates containing 2% EtOH as the sole carbon source, and were confirmed by PCR amplification. The resulting strain was Y4940.

Next, ALD6 was deleted and *Dickeya zeae* eutE was introduced in Y4940 with the integration construct (i74804; SEQ ID NO:46) pictured below.

| ALD6US | pTDH3 | Dz.eutE | tTEF2 | TRP1 | ZdEL1 | ƎʇnƏ·zᗡ | ƐHᗡʇd | ALD6DS |

This integration construct comprises a selectable marker (TRP1), as well as two copies a yeast-codon-optimized sequence encoding the gene cutE from *Dickeya zeae* (NCBI Reference Sequence: YP_003003316.1) under control of the TDH3 promoter (840 basepairs upstream of the native *S. cerevisiae* TDH3 coding region), and the TEF2 terminator (508 basepairs downstream of the native *S. cerevisiae* TEF2 coding region). These components are flanked by upstream and downstream nucleotide sequences of the ALD6 locus. Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. The construct was transformed into Y4940, and transformants were selected on CSM-TRP plates with 2% glucose and confirmed by PCR amplification. The resulting strain was 12602.

Next, ACS1 was deleted in Y12602 by introducing an integration construct (i76220; SEQ ID NO:47) consisting of the upstream and downstream nucleotide sequences of ACS1, flanking the native *S. cerevisiae* HIS3 gene under its own promoter and terminator. Transformants were plated onto CSM-his plates containing 2% glucose as the sole carbon source, and were confirmed by PCR amplification. The resulting strain was Y12747.

Next, Y12747 was transformed with a PCR product amplified from the native URA3 sequence. This sequence restores the ura3-52 mutation. See Rose and Winston, *Mol Gen Genet*. 193:557-560 (1984). Transformants were plated onto CSM-ura plates containing 2% glucose as the sole carbon source, and were confirmed by PCR amplification. The resulting strain was Y12869.

6.2.1.1.3 Y12746

Y12746 was generated through three successive integrations into Y4940. First, Y4940 was transformed with the integration construct (i73830; SEQ ID NO:48) pictured below.

| BUD9US | pTDH3 | Lm.PK | tTDH3 | URA3 | tPGK1 | CK.PTA | pTDH3 | BUD9DS |

This integration construct comprises a selectable marker (URA3); a yeast codon-optimized version of phosphoketolase from *Leuconostoc mesenteroides* (NCBI Reference Sequence YP_819405.1) under the TDH3 promoter (870 by upstream of the TDH3 coding sequence) and TDH3 terminator (259 by downstream of the TDH3 coding sequence); a yeast codon-optimized version of *Clostridium kluyveri* phosphotransacetylase (NCBI Reference Sequence: YP_001394780.1) under control of the TDH3 promoter (870 by upstream of the TDH3 coding sequence) and the PGK1 terminator (259 by downstream of the PGK1 coding sequence); flanked by homologous sequences consisting of the upstream and downstream nucleotide sequences of the *S. cerevisiae* BUD9 locus. Upon introduction into a host cell, this construct integrates by homologous recombination into the host cell genome, functionally disrupting BUD9 by replacing the BUD9 coding sequence with its integrating sequence. The construct was assembled using the methods described in U.S. Pat. No. 8,221,982. Transformants were selected on CSM-URA plates with 2% glucose.

The resulting strain was transformed with the construct (i74810; SEQ ID NO:49) shown below.

| ALD6US | pTDH3 | Lm.PK | tTDH3 | TRP1 | tPGK1 | Lm.PK | pTDH3 | ALD6DS |

This construct comprising a selectable marker (TRP1); two copies of phosphoketolase from *Leuconostoc mesenteroides* under the TDH3 promoter (870 by upstream of the TDH3 coding sequence) and TDH3 terminator (259 by downstream of the TDH3 coding sequence); flanked by homologous sequences consisting of the upstream and downstream nucleotide sequences of the ALD6 locus. Upon introduction into a host cell, this construct integrates by homologous recombination into the host cell genome, functionally disrupting ALD6 by replacing the ALD6 coding sequence with its integrating sequence. The construct was assembled using the methods described in U.S. Pat. No. 8,221,982. Transformants were selected on CSM-URA plates with 2% glucose and confirmed by PCR amplification.

Finally, the resulting strain was transformed with the construct (i76221; SEQ ID NO:50) shown below.

| ACS1US | pTDH3 | Dz.eutE | tTEF2 | HIS3 | tTEF2 | Dz.eutE | pTDH3 | ACS1DS |

This construct comprises a selectable marker (HIS3); as well as two copies a yeast-codon-optimized sequence encoding the gene eutE from *Dickeya Zeae* (NCBI Reference Sequence: YP_003003316.1) under control of the TDH3 promoter (840 basepairs upstream of the native *S. cerevisiae* TDH3 coding region) and the TEF2 terminator (508 basepairs downstream of the native *S. cerevisiae* TEF2 coding region). These components are flanked by upstream and downstream nucleotide sequences of the ACS1 locus. Upon introduction into a host cell, this construct integrates by homologous recombination into the host cell genome, functionally disrupting ACS1 by replacing the ACS1 coding sequence with its integrating sequence. The construct was assembled using the methods described in U.S. Pat. No. 8,221,982. Transformants were selected on CSM-HIS plates with 2% glucose and confirmed by PCR amplification. The resulting strain was Y12746.

6.2.1.1.4 ms63907, ms63908, ms63909, and ms64472 Integration Constructs

The ms63907 integration construct (i84022; SEQ ID NO:51) is shown below.

| HO US | GAL4 | Sc.MHGr | tGAL1 | pGAL10 | ERG10 | URA3 | ERG13 | pGAL10 | pGAL1 | Sp.HMGr | HO DS |

This construct comprises nucleotide sequences that encode a selectable marker (URA3); a copy of the native yeast GAL4 transcription factor under its own promoter; two native yeast enzymes of the mevalonate pathway (ERG10 which encodes Acetoacetyl-CoA thiolase, and ERG13, which encodes HMG-CoA synthase), as well as two copies of a yeast codon-optimized version of *Silicibacter pomeroyi* HMG-CoA reductase, all under galactose-inducible promoters (promoters of the *S. cerevisiae* genes GAL1 and GAL10, flanked by homologous sequences consisting of upstream and downstream nucleotide sequences of the *S. cerevisiae* HO endonuclease locus. Upon introduction into a host cell, the ms63907 construct integrates by homologous integration into the host cell genome, functionally disrupting HO by replacing the HO coding sequence with its integrating sequence. The construct was assembled using the methods described in U.S. Pat. No. 8,221,982. Transformants were selected on CSM-URA plates with 2% glucose and confirmed by PCR amplification.

The ms63908 integration construct (i84024; SEQ ID NO:52) is identical to ms63907, with two exceptions: first, ERG10 is replaced by a yeast codon-optimized version of the nphT7 gene of *Streptomyces* sp. CL190 encoding acetyl-CoA:malonyl-CoA acyltransferase (accession no. AB540131.1) fused to the AHP1 terminator (125 by downstream of the AHP1 coding sequence in *S. cerevisiae*); second, the sequences encoding *S. pomeroyi* HMG-CoA reductase are replaced by tHMGr, the truncated HMG1 coding sequence which encodes the native *S. cerevisiae* HMG-CoA reductase.

The ms63909 integration construct (i84026; SEQ ID NO:53) is identical to ms63907, with one exception: the sequences encoding S. pomeroyi HMG-CoA reductase are replaced by tHMGr, the truncated HMG1 coding sequence which encodes the native S. cerevisiae HMG-CoA reductase.

The ms64472 integration construct (i85207; SEQ ID NO:54) is shown below.

with 200 ul of isopropyl alcohol in a 96-well UV plate (Costar 3635), then read on a plate reader for absorbance 222.

6.2.1.4 Quantitation of Optical Density

In a 96-well assay plate, 8 ul of culture was mixed with diluent (20% PEG 200, 20% Ethanol, 2% Triton X-114) and

| GAL80 US | pGAL7 | IDI1 | ERG9 | pGAL1 | pGAL10 | ERG20 | URA3 | ERG8 | pGAL7 | ERG19 | pGAL11 | pGAL1 | ERG12 | GAL80 DS |
|---|---|---|---|---|---|---|---|---|---|---|---|---|---|---|

This construct comprises nucleotide sequences that encode a selectable marker (URA3); five native yeast enzymes of the ergosterol pathway (ERG12 which encodes mevalonate kinase, ERG8 which encodes phosphomevalonate kinase, ERG19 which encodes mevalonate pyrophosphate decarboxylase, IDI1 which encodes dimethylallyl diphosphate isomerase, and ERG20 which encodes farnesyl pyrophosphate synthetase), as well as an evolved, yeast codon-optimized version of Artemisia annua farnesene synthase, all under galactose-inducible promoters (Promoters of the S. cerevisiae genes GAL1, GAL10, and GAL7). These sequences are flanked by homologous sequences consisting of the upstream and downstream nucleotide sequences of GAL80. Upon introduction into a host cell, the ms64472 construct integrates by homologous integration into the host cell genome, functionally disrupting GAL80 by replacing the GAL80 coding sequence with its integrating sequence. The construct was assembled using the methods described in U.S. Pat. No. 8,221,982. Transformants were selected on CSM-URA plates with 2% glucose and confirmed by PCR amplification.

6.2.1.2 Quantitation of Mevalonate

Single colonies were inoculated in wells of a 96-well plate in seed media (15 g/L ammonium sulfate, 8 g/L potassium phosphate, 6.1 g/L magnesium sulfate, 150 mg/L EDTA, 57.5 mg/L zinc sulfate, 4.8 mg/L cobalt chloride, 3.24 mg/L manganese chloride, 5 mg/L copper sulfate, 29.4 mg/L calcium chloride, 27.8 mg/L iron sulfate, 4.8 mg/L sodium molybdate, 0.6 mg/L biotin, 12 mg/L calcium pantothenate, 12 mg/L nicotinic acid, 30 mg/L inositol, 12 mg/L thiamin hydrochloride, 12 mg/L pyridoxine hydrochloride, 0.24 mg/L para-aminobenzoic acid) with 50 mM succinate pH 5.0, and 20 g/L sucrose, and grown at 30 C for three days. Then, 14.4 ul of culture was subcultured into seed media with 50 mM succinate pH 5.0 and 40 g/L galactose, and grown at 30 C for 2 days.

To quantitate secreted mevalonate, whole cell broth was first spun down at 14,000 RPM for 5 min. 10 ul of clarified broth was then incubated with 190 ul of assay buffer (1 mM CoA, 2 mM NAD, purified and lyophilized Pseudomonas mevalonii HMG-CoA reductase at 0.2 mg/ml, purified and lyophilized Pseudomonas mevalonii HMG-CoA lyase at 0.1 mg/ml, 95 mM TrisCl pH8.5, 20 mM MgCl2, and 5 mM DTT). The sample was incubated for 30 minutes at 30 C, then assayed for 340 nM absorbance on a Beckman M5 plate reader. Mevalonate concentration was quantitated by plotting onto a standard curve generated with purified mevalonate.

6.2.1.3 Quantitation of Farnesene

Cultures were first grown as described above. To quantitate farnesene, 600 ul of 2-butoxyethanol was added to 150 ul of whole cell broth in three additions of 200 ul each, with 90 seconds of shaking at 1000 rpm on a 96-well plate shaker between each addition. The samples were then incubated for 40 minutes. 8 ul of the 2-butoxyethanol extract was mixed incubated for 30 minutes at room temperature. The assay plate was vortexed before measuring $OD_{600}$ on a Beckman M5 plate reader.

6.2.1.5 Batch Fermentation

Inoculum cultures of Y967, Y12869, and Y12746 were grown from single colonies in 5 ml of seed media with 50 mM succinate pH 5.0, and 20 g/L sucrose. After 3 days of growth, the precultures were subcultured into 25 ml of seed media with 50 mM succinate pH 5.0 and 40 g/L sucrose to an initial optical density (OD) of 0.1. After 10 hours, the cultures were subcultured again into 50 ml of seed media with 50 mM succinate pH 5.0 and 40 g/L sucrose to an OD of 0.05. Cultures were grown at 30° C. When the OD was approximately 3, the 3 flasks were split in half and spun down and the media was discarded. The cultures were resuspended in 1.5 L seed media with 40 g/L glucose (without succinate) and transferred to the fermentor. Fermentation experiments were performed in a 2 L Biostat B plus vessel (Sartorius, Germany). Stirring was controlled at 1200 rpm and the fermentor was continuously sparged with 0.5 L/min air. The pH was maintained at 5.0 with 14.4 M $NH_4OH$ and the temperature was maintained at 30° C. Roughly every 1.5 hours, a sample was drawn to measure the OD, dry cell weight, and organic acids and sugars.

6.2.2 Results 6.2.2.1 ADA Strains Produce More Isoprenoid when Paired with an NADH-Using HMGr Versus an NADPH-Using HMGr FIG. 12A shows that strain Y12869, comprising a deletion of the PDH-bypass (acs1Δacs2Δald6Δ) and heterologously expressing ADA (Dz.eutE), produces more farnesene when expressing a MEV pathway comprising an NADH-using HMGr (construct ms63907) than a MEV pathway comprising an NADPH-using HMGr (construct ms63909). In contrast, FIG. 12B shows that strain Y968, comprising an intact PDH-bypass, produces more farnesene when paired with an NADPH-using HMGr. These results demonstrate that utilization of ADA for isoprenoid production from the MEV pathway is improved when the MEV pathway comprises an NADH-using HMGr.

6.2.2.2 Expression of ADA Causes a Redox Imbalance which is Alleviated when PK and PTA Share Flux with Glycolysis Native yeast produce two NADH per glucose consumed through glycolysis. When fermented to ethanol, the two NADH are reoxidized to NAD+. However, a fraction of the glucose is converted to biomass rather than fermented to ethanol, resulting in an excess of NADH. This excess NADH is reoxidized to NAD+ through the reduction of dihydroxyacetone phosphate to glycerol 3-phosphate, which is hydrolyzed to glycerol. Strains which use the acylating acetaldehyde dehydrogenase in place of the native PDH-bypass produce NADH instead of NADPH, resulting in a further excess of NADH. For each glucose converted to biomass, a strain which uses ADA in place of the native PDH-bypass produces exactly twice as much NADH, meaning that twice as much glycerol must be produced in order to reoxidize the excess NADH. As shown in FIG. 13A, Y12869 (a strain which uses ADA in the place of the wildtype PDH-bypass) produces twice as much glycerol as Y968 (comprising an intact PDH-bypass) while consuming comparable levels of glucose in a batch glucose fermentation. These results demonstrate that Y12869 is redox imbalanced as predicted by the stoichiometry of the ADA reaction.

The addition of phosphoketolase and phosphotransacetylase to an ADA strain provides an alternative, non-glycolytic route to generating AcCoA from glucose, reducing the NADH produced through glycolysis and improving redox balance. As shown in FIG. 13B, Y12745 (a strain which carries phosphoketolase and phosphotransacetylase in addition to the ADA) produces half as much glycerol as Y12869, while consuming comparable levels of glucose in a batch glucose fermentation.

6.2.2.3 The ATP Savings in an ADA Strain Come at the Cost of Thermodynamic Driving Force, which is Alleviated by a Strong Downstream Pull on Acetyl-CoA The native PDH-bypass reaction for forming Acetyl-CoA is thermodynamically favorable because the reaction is coupled to the hydrolysis of ATP to AMP. In contrast, the acylating acetaldehyde dehydrogenase reaction is not coupled to ATP, and is much closer to equilibrium than the native PDH-bypass reactions for forming Acetyl-CoA. When using then native *S. cerevisiae* pathway genes for producing mevalonate, strains using the ADA produce much less mevalonate than strains using the wildtype PDH-bypass despite comparable kinetic properties of ADA and Ald6 in vitro. As shown in FIG. 14 ($1^{st}$ and 2nd column), mevalonate production in an ADA strain (Y12869.ms63909) is only ~30% that of a wildtype equivalent strain (Y968.ms63909), despite sufficient kinetic capacity measured in vitro. This result reflects the lack of a thermodynamic driving force behind the conversion of acetaldehyde to acetyl-CoA by ADA.

The Erg10 acetyl-CoA thiolase catalyzes the formation of acetoacetyl-CoA from two acetyl-CoA, a reaction that is thermodynamically unfavorable. Acetoacetyl-CoA synthase (i.e., acetyl-CoA:malonyl-CoA acyltransferase), encoded by nphT7, catalyzes the formation of acetoacetyl-CoA from acetyl-CoA and malonyl-CoA, a reaction that is thermodynamically favorable due to the decarboxylation of malonyl-CoA. Putting this thermodynamically favorable reaction directly downstream of AcCoA production provides a thermodynamic driving force that increases the forward activity of ADA. As shown in FIG. 14 ($3^{rd}$ and $4^{th}$ column), when nphT7 is overexpressed in place of ERG10, Y968.ms63908 and Y12869.ms63908 make comparable levels of mevalonate. Moreover, they produce more substantially more mevalonate than equivalent strains which use ERG10 for the first step of the MEV pathway (Y968.ms63909 and Y12869.63909.).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A genetically modified yeast cell capable of producing an isoprenoid, the cell comprising:

(a) a nucleic acid encoding an enzyme that condenses acetyl-CoA with malonyl-CoA to form acetoacetyl-CoA, and optionally one or more heterologous nucleic acids encoding one or more enzymes of a mevalonate (MEV) pathway for making isopentenyl pyrophosphate;

(b) a heterologous nucleic acid encoding an acylating acetylaldehyde dehydrogenase (ADA, EC 1.2.1.10); and (c) a functional disruption of one or more enzymes of the native pyruvate dehydrogenase (PDH)-bypass selected from the group consisting of acetyl-CoA synthetase 1 (ACS1), acetyl-CoA synthetase 2 (ACS2), and aldehyde dehydrogenase 6 (ALD6), wherein the genetically modified yeast cell produces an increased amount of an isoprenoid compound compared to an yeast cell not comprising a nucleic acid encoding an enzyme that condenses acetyl-CoA with malonyl-CoA to form acetoacetyl-CoA.

2. The genetically modified yeast cell of claim 1, wherein the enzyme that condenses acetyl-CoA with malonyl-CoA to form acetoacetyl-CoA is an acetyl-CoA:malonyl-CoA acyltransferase.

3. The genetically modified yeast cell of claim 1, wherein the one or more enzymes of the MEV pathway comprise an NADH-using enzyme that converts 3-hydroxy-3-methylglutaryl-CoA (HMG-CoA) to mevalonate.

4. The genetically modified yeast cell of claim 1, wherein the one or more enzymes of the MEV pathway comprise an NADH-using HMG-CoA reductase (HMGr).

5. The genetically modified yeast cell of claim 1, further comprising a heterologous nucleic acid encoding a phosphoketolase (PK).

6. The genetically modified yeast cell of claim 1, further comprising a heterologous nucleic acid encoding a phosphotransacetylase (PTA).

7. The genetically modified yeast cell of claim 1, wherein ACS1 is functionally disrupted.

8. The genetically modified yeast cell of claim 1, wherein ACS2 is functionally disrupted.

9. The genetically modified yeast cell of claim 1, wherein ALD6 is functionally disrupted.

10. The genetically modified yeast cell of claim 1, wherein ACS1 and ACS2 are functionally disrupted.

11. The genetically modified yeast cell of claim 1, wherein ACS1, ACS2 and ALD6 are functionally disrupted.

12. The genetically modified yeast cell of claim 1, wherein the one or more enzymes of the MEV pathway comprise an enzyme that condenses two molecules of acetyl-CoA to form acetoacetyl-CoA.

13. The genetically modified yeast cell of claim 1, wherein the one or more enzymes of the MEV pathway comprise an enzyme that condenses acetoacetyl-CoA with acetyl-CoA to form HMG-CoA.

14. The genetically modified yeast cell of claim 1, wherein the one or more enzymes of the MEV pathway comprise an NAPDH-using enzyme that converts HMG-CoA to mevalonate.

15. The genetically modified yeast cell of claim 1, wherein the one or more enzymes of the MEV pathway comprise an enzyme that phosphorylates mevalonate to mevalonate 5-phosphate.

16. The genetically modified yeast cell of claim 1, wherein the one or more enzymes of the MEV pathway comprise an enzyme that converts mevalonate 5-phosphate to mevalonate 5-pyrophosphate.

17. The genetically modified yeast cell of claim 1, wherein the one or more enzymes of the MEV pathway comprise an enzyme that converts mevalonate 5-pyrophosphate to isopentenyl pyrophosphate.

18. The genetically modified yeast cell of claim 1, wherein the one or more enzymes of the MEV pathway are selected from HMG-CoA synthase, mevalonate kinase, phosphomevalonate kinase and mevalonate pyrophosphate decarboxylase.

19. The genetically modified yeast cell of claim 1, wherein the cell comprises a plurality of heterologous nucleic acids encoding all of the enzymes of the MEV pathway.

20. The genetically modified yeast cell of claim 1, wherein the one or more heterologous nucleic acids encoding one or more enzymes of the MEV pathway are under control of a single transcriptional regulator.

21. The genetically modified yeast cell of claim 1, further comprising a heterologous nucleic acid encoding an enzyme that can convert isopentenyl pyrophosphate (IPP) into dimethylallyl pyrophosphate (DMAPP).

22. The genetically modified yeast cell of claim 1, further comprising a heterologous nucleic acid encoding an enzyme that can condense IPP and/or DMAPP molecules to form a polyprenyl compound.

23. The genetically modified yeast cell of claim 1, further comprising a heterologous nucleic acid encoding an enzyme that can modify IPP or a polyprenyl to form an isoprenoid compound.

24. The genetically modified yeast cell of claim 23, wherein the enzyme that can modify IPP or a polyprenyl to form an isoprenoid compound is selected from the group consisting of carene synthase, geraniol synthase, linalool synthase, limonene synthase, myrcene synthase, ocimene synthase, α-pinene synthase, β-pinene synthase, γ-terpinene synthase, terpinolene synthase, amorphadiene synthase, α-farnesene synthase, β-farnesene synthase, farnesol synthase, nerolidol synthase, patchouliol synthase, nootkatone synthase, and abietadiene synthase.

25. The genetically modified yeast cell of claim 23, wherein the isoprenoid is selected from the group consisting of a hemiterpene, monoterpene, diterpene, triterpene, tetraterpene, sesquiterpene, and polyterpene.

26. The genetically modified yeast cell of claim 23, wherein the isoprenoid is a $C_5$-$C_{20}$ isoprenoid.

27. The genetically modified yeast cell of claim 23, wherein the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

28. The genetically modified yeast cell of claim 1, wherein the yeast is *Saccharomyces cerevisiae*.

29. A method for producing an isoprenoid comprising:
   (a) culturing a population of the genetically modified yeast cell of claim 1 in a medium with a carbon source under conditions suitable for making said isoprenoid compound; and
   (b) recovering said isoprenoid compound from the medium.

30. The method of claim 29, wherein the genetically modified yeast cell produces an increased amount of an isoprenoid compound compared to the same genetically modified yeast cell not comprising a nucleotide sequence encoding an enzyme that condenses acetyl-CoA with malonyl-CoA to form acetoacetyl-CoA.

* * * * *